(12) United States Patent
Gupta et al.

(10) Patent No.: US 11,572,412 B2
(45) Date of Patent: Feb. 7, 2023

(54) ANTI-SIRP-ALPHA ANTIBODIES

(71) Applicants: Boehringer Ingelheim International GmbH, Ingelheim am Rhein (DE); OSE Immunotherapeutics SA, Nantes (FR)

(72) Inventors: Pankaj Gupta, Scarsdale, NY (US); Priyanka Gupta, Danbury, CT (US); Habte Habtom, LaFayette Hill, PA (US); Yining Huang, Belmont, MA (US); Sandeep Kumar, Ridgefield, CT (US); Kathryn Phoenix, Burlington, CT (US); Kerry-Leigh Ralph, Bethel, CT (US); Wing Pan Kenny Tsang, Bronx, NY (US); Eduardo Sergio Trombetta, Guilford, CT (US)

(73) Assignees: Boehringer Ingelheim International GmbH, Ingelheim am Rhein (DE); OSE Immmnotherapeatics SA, Nantes (FR)

( * ) Notice: Subject to any disclaimer, the term of this patent is extended or adjusted under 35 U.S.C. 154(b) by 0 days.

(21) Appl. No.: 17/831,245

(22) Filed: Jun. 2, 2022

(65) Prior Publication Data
US 2023/0012273 A1    Jan. 12, 2023

Related U.S. Application Data

(60) Provisional application No. 63/339,326, filed on May 6, 2022, provisional application No. 63/325,828, filed on Mar. 31, 2022, provisional application No. 63/197,259, filed on Jun. 4, 2021.

(51) Int. Cl.
C07K 16/28    (2006.01)
A61P 35/00    (2006.01)

(52) U.S. Cl.
CPC .......... *C07K 16/2896* (2013.01); *A61P 35/00* (2018.01); *C07K 2317/21* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,179,337 | A | 12/1979 | Davis et al. |
| 4,301,144 | A | 11/1981 | Iwashita et al. |
| 4,496,689 | A | 1/1985 | Mitra |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 4,816,567 | A | 3/1989 | Cabilly et al. |
| 6,037,454 | A | 3/2000 | Jardieu et al. |
| 6,054,297 | A | 4/2000 | Carter et al. |
| 6,407,213 | B1 | 6/2002 | Carter et al. |
| 11,401,338 | B2 * | 8/2022 | Pons ........................ A61P 15/00 |
| 2010/0215640 | A1 | 8/2010 | Clemmons et al. |
| 2010/0233251 | A1 | 9/2010 | Von Andrian et al. |
| 2012/0039896 | A1 | 2/2012 | Clemmons et al. |
| 2012/0070461 | A1 | 3/2012 | Singh et al. |
| 2014/0141002 | A1 | 5/2014 | Clemmons et al. |
| 2014/0242095 | A1 | 8/2014 | Wang et al. |
| 2019/0359707 | A1 | 11/2019 | Pincetic et al. |

FOREIGN PATENT DOCUMENTS

| | | |
|---|---|---|
| CN | 111995682 A | 11/2020 |
| CN | 112010979 A | 12/2020 |
| CN | 112574310 A | 3/2021 |
| WO | 199005144 A1 | 5/1990 |
| WO | 199013646 A1 | 11/1990 |
| WO | 199632478 A1 | 10/1996 |
| WO | 2005077042 A2 | 8/2005 |
| WO | 2007005874 A2 | 1/2007 |
| WO | 2009131453 A1 | 10/2009 |
| WO | 2010077634 A1 | 7/2010 |
| WO | 2010130053 A1 | 11/2010 |
| WO | 2012092374 A2 | 7/2012 |
| WO | 2012149416 A3 | 1/2013 |
| WO | 2013056352 A1 | 4/2013 |
| WO | 2013079174 A1 | 6/2013 |
| WO | 2015048312 A1 | 4/2015 |
| WO | 2015138600 A3 | 11/2015 |
| WO | 2017178653 A2 | 10/2017 |
| WO | 2018057669 A1 | 3/2018 |
| WO | 2018107058 A1 | 6/2018 |
| WO | 2018190719 A2 | 10/2018 |
| WO | 2018210793 A2 | 11/2018 |
| WO | 2019023347 A1 | 1/2019 |
| WO | 2019073080 A1 | 4/2019 |
| WO | 2019183266 A1 | 9/2019 |
| WO | 2019226973 A1 | 11/2019 |
| WO | 2020013170 A1 | 1/2020 |
| WO | 2020033646 A1 | 2/2020 |
| WO | 2020068752 A1 | 4/2020 |
| WO | 2020099653 A1 | 5/2020 |
| WO | 2020102422 A1 | 5/2020 |
| WO | 2020180811 A1 | 9/2020 |
| WO | 2021032078 A1 | 2/2021 |
| WO | 2021185273 A1 | 9/2021 |

OTHER PUBLICATIONS

Almagro & Fransson, Frontiers in Bioscience 2008; 13:1619-33 (Year: 2008).*
Padlan (Advances in Protein Chemistry, 1996, 49:57-133) (Year: 1996).*
Berglund et al, Protein Science, 2008, 17:606-613 (Year: 2008).*
Corada (Blood, 2001; 97:1679-84) (Year: 2001).*
Kulkarni-Kale et al. Nucleic Acid Research, 2005, 33:W168-W171 (Year: 2005).*

(Continued)

*Primary Examiner* — Meera Natarajan
(74) *Attorney, Agent, or Firm* — Morgan, Lewis & Bockius LLP

(57) ABSTRACT

The present invention relates to anti-SIRPα (Signal regulatory protein alpha) antibodies and antigen-binding fragments thereof for therapeutic and diagnostic methods and compositions using them.

61 Claims, 52 Drawing Sheets
(2 of 52 Drawing Sheet(s) Filed in Color)

Specification includes a Sequence Listing.

(56) References Cited

OTHER PUBLICATIONS

Champiat et al., "Safety, pharmacokinetics, efficacy, and preliminary biomarker data of first-in-class BI 765063, a selective SIRPα inhibitor: Results of monotherapy dose escalation in phase 1 study in patients with advanced solid tumors.", Journal of Clinical Oncology, 2021, vol. 39, No. 15_suppl, p. 2623.
Delord et al., "A Phase 1 Study Evaluating BI 765063, a First in Class Selective Myeloid Sirpa Inhibitor, As Stand-Alone and in Combination with BI 754091, a Programmed Death-1 (PD-1) Inhibitor, in Patients with Advanced Solid Tumours", Blood, 2019, vol. 134, No. Supplement_1, p. 1040.
Gauttier et al., "Selective SIRPα blockade reverses tumor T cell exclusion and overcomes cancer immunotherapy resistance", Journal of Clinical Investigation, 2020, vol. 130, No. 11, pp. 6109-6123.
Kotecki et al., "34th Annual Meeting & Pre-Conference Programs of the Society for Immunotherapy of Cancer (SITC 2019): part 1", Journal for Immunotherapy of Cancer, 2019, vol. 7, No. Suppl 1, p. 428.
Kotecki et al., "983P Phase I dose escalation study in patients (pts) with advanced solid tumours receiving first-in-class BI 765063, a selective signal-regulatory protein a (SIRPα) inhibitor, in combination with ezabenlimab (BI 754091), a programmed cell death protein 1 (PD-1) inhibitor", Annals of Oncology, 2021, vol. 32, pp. S841-S842.
International Search Report for corresponding application PCT/IB2022/055170, dated Sep. 2, 2022.
Mosser, David M., and Justin P. Edwards. "Exploring the full spectrum of macrophage activation." Nature reviews immunology 8.12(2008): 958-969. (Year: 2008).
Myers et al., "Optimal alignments in linear space", CABIOS, 1988, vol. 4, pp. 11-17.
Nicolaou et al., "Calicheamicin ?: A Rationally Designed Molecule with Extremely Potent and Selective DNA Cleaving Properties and Apoptosis Inducing Activity." Angewandte Chemie International Edition in English 33.2 (1994): 183-186.
Nielsen et al., "Alternative Splice Variants of the Human PD-1-Gene", Cell Immunol, 2005, pp. 109-116, vol. 235.
North et al., "A New Clustering of Antibody CDR Loop Conformations", Journal of Molecular Biology, 2011, vol. 406, No. 2, pp. 228-256.
Ochando et al., "Myeloid-derived suppressor cells in transplantation and cancer", Immunol Res., Dec. 2012, 54 (1-3), pp. 275-285.
Oldenborg et al, "Role of CD47 as a Marker of Self on Red Blood Cells", Science Magazine, Jun. 16, 2000, pp. 2051-2054, vol. 288.
Pan et al., "Signal Regulatory Protein [Alpha] is Associated with Tumor-Polarized Macrophages Phenotype Switch and Plays a Pibotal Role in Tumor Progression", Hepatology, Aug. 1, 203, pp. 680-691, vol. 58, No. 2.
Pardoll et al., "The Blockade of Immune Checkpoints in Cancer Immunotherapy", Nature Reviews Cancer, 2012, vol. 12, No. 4.
Peach et al, "Both Extracellular Immunoglobin-Like Domains of CD80 Contains Residues Critical for Binding T-Cell Surface Receptors CTLA-4 and CD28", J. Biol. Chem., 1995, pp. 21181-21187.
Pearson et al., "Improved tools for biological sequence comparison ", Proceedings of the National Academy of Sciences, 1988, vol. 85, No. 8, pp. 2444-2448.
Pluckthun, "The Pharmacology of Monoclonal Antibodies", Handbook of Experimental Pharmacology, 1994, pp. 269-315.
Powles et al, "MPDL3280A {Anti-PD-L 1_ Treatment Leads to Clinical Activity in Metastatic Bladder Cancer", Nature, 2014, vol. 515, No. 7528.
Reichert et al., "The future of antibodies as cancer drugs", Drug Discovery Today, 2012, vol. 17, No. 17-18, pp. 954-963.
Reuter et al., "Diet-induced models for obesity and type 2 diabetes. Drug Discovery Today", Disease Models, vol. 4/1 :3-8 (2007).
Rudikoff et al., "Single amino acid substitution altering antigen-binding specificity." Proceedings of the National Academy of Sciences 79.6 (1982): 1979-1983.
Sakamoto et al., "Anticancer efficacy of monotherapy with antibodies to SIRPa/SIRPß1 mediated by induction of antitumorigenic macrophages", Proceedings of the National Academy of Sciences, 2022, 119.1, pp. 1-10.
Seiffert et al., "Signal-Regulatory Protein ? (SIRP?) but not SIRP? is Involved in T-cell Activation, Binds to CD47 with High Affinity, and is Expressed on Immature CD34+CD38" "Hematopoietic Cells", Blood, May 2001, pp. 2741-2749, vol. 97, No. 9.
Sharma et al., "Immune Checkpoint Targeting in Cancer Therapy: Towards Combination Strategies with Curative Potential", Cell, 2015, pp. 205-214, vol. 161, No. 2.
Sim et al, "Discovery of high affinity, pan allelic, and pan-mammalian reactive antibodies against the myeloid checkpoint receptor SIRPa", MABS, 2019, pp. 1036-1052, vol. 11, No. 6.
Sojar et al., "A chemical method for the deglycosylation of proteins", Archives of Biochemistry and Biophysics, 1987, vol. 259, No. 1, pp. 52-57.
Stefanidakiset al., "Endothelial CD47 interaction with SIRPy is required for human T-cell transendothelial 5 migration under shear flow conditions in vitro", The American Society of Hematology, Blood, Aug. 15, 2008, pp. 1280-1289, vol. 112, No. 4.
Takenaka et al., "Polymorphism in Sira Modulates Engraftment of Human Hematopoietic Stem Cells", Nature Immunology, Nature Publishing Group US, New York, Dec. 1, 2007, vol. 8, No. 12, pp. 1313-1323.
Thotakura et al., "[28] Enzymatic deglycosylation of glycoproteins", Methods in Enzymology, 1987, vol. 138, pp. 350-359.
Topalian et al, "Safety, Activity, and Immune Correlates of Anti-PD-1 Antibody in Cancer", The new England Journal of Medicine, 2012, pp. 2443-2454, vol. 366, No. 26.
Torelli et al., "ADVANCE and ADAM: two algorithms for the analysis of global similarity between homologous informational sequences", Bioinformatics, 1994, vol. 10, No. 1, pp. 3-5.
Treffers et al., "Genetic variation of human neutrophil Fc? receptors and SIRP? in antibody?dependent cellular cytotoxicity towards cancer cells", European Journal of Immunology, 2018, vol. 48, No. 2, pp. 344-354.
Turkbeyler et al., "Prolidase Could Act as a Diagnosis and Treatment Mediator in Lung Fibrosis" Inflammation, vol. 35, No. 5, pp. 1747-1752 (Oct. 2012).
Ueda et al, "Association of the T-Cell Regulatory Gene CTLA4 with Susceptibility to Autoimmune Disease", Nature, 2003, pp. 506-511, vol. 423.
UniProt Sequence Accession Q75144 for PDCD1_HUMAN; retrieved from the internet site https://uniprot.org/uniprot/ on Mar. 26, 2020.
UniProt Sequence Accession P23510 for PDCD1_HUMAN; retrieved from the internet site https://uniprot.org/uniprot/ on Mar. 26, 2020.
UniProt Sequence Accession P33681 for PDCD1_HUMAN; retrieved from the internet site https://uniprot.org/uniprot/ on Mar. 26, 2020.
UniProt Sequence Accession P41273 for PDCD1_HUMAN; retrieved from the internet site https://uniprot.org/uniprot/ on Mar. 26, 2020.
UniProt Sequence Accession P42081 for PDCD1_HUMAN; retrieved from the internet site https://uniprot.org/uniprot/ on Mar. 26, 2020.
UniProt Sequence Accession Q15116 for PDCD1_HUMAN; retrieved from the internet site https://uniprot.org/uniprot/ on Mar. 26, 2020.
UniProt Sequence Accession Q9NZQ7 for PDCD1_HUMAN; retrieved from the internet site https://uniprot.org/uniprot/ on Mar. 26, 2020.
Urlaub et al., "Isolation of Chinese hamster cell mutants deficient in dihydrofolate reductase activity.", Proceedings of the National Academy of Sciences, 1980, vol. 77, No. 7, pp. 4216-4220.
Vargas-Madrazo et al., "An improved model of association for VH-VL immunoglobulin domains: Asymmetries between VH and VL in the packing of some interface residues", Journal of Molecular Recognition, 2003, vol. 16, No. 3, pp. 113-120.
Vinay et al., "Therapeutic Potential of Anti-CD137 (4-18B) Monoclonal Antibodies", Expert Opin. Ther Targets., 2016, pp. 361-373, vol. 20, No. 3.
Wakabayashi et al., "Prevention of metastasis by a polyamine synthesis inhibitor in an animal bone metastasis model", Oncology, 59:75-80 (2000).
Wan et al., "Aberrant Regulation of Synovial TC ell Activation by Soluble Costimulatory molecules in Rheumatoid Arthritis", J_ Immunol, 2006, pp. 8844-8850, vol. 177.

(56) References Cited

OTHER PUBLICATIONS

Wang et al., "Immune Regulation by4-1BB and 4-1 BBL: Complexities and Challenges", Immunol Rev, 2009, pp. 192-215, vol. 229, No. 1.
Weiskopf et al., "Direct SIRPa Blockade Augments Macrophage Responses to Therapeutic Anticancer Antibodies", Blood Journal, Dec. 2014, vol. 124, No. 21.
Willoughby et al., "OX40: Structure and Function—What Questions Remain?", Mol. Immunol, 2017, pp. 13-22, vol. 83.
Wood et al., "Antibody Drug Discovery", Antibody Drug Discovery, 2011, pp. i-xv.
Yanagita et al, "Anti-SIRPa Antibodies as a Potential New Tool for Cancer Immunotherapy", JCI Insight, Jan. 2017, pp. 1-15, vol. 2, No. 1, e89140.
Zak et al., "Structure of the Complex of Human Programmed Death 1, PD-1, and Its Ligand PD-L1", Structure, 2015, pp. 2341-2348, vol. 23, No. 12.
Zapata et al., "Engineering linear F(ab') 2 fragments for efficient production in *Escherichia coli* and enhanced antiproliferative activity", "Protein Engineering, Design and Selection," 1995, vol. 8, No. 10, pp. 1057-1062.
Zhao et al., "CD47-Singal Regulatory Protein—(SIRP) Interactions Form a Barrier for Antibody-Mediated Tumor Cell Destruction", Proceedings of the National Academy of Sciences, Nov. 8, 2011, vol. 108, No. 45, pp. 18342-18347.
Champiat et al., "Abstract 1993: Biomarker analyses from the Phase I clinical trial of the first-in-class SIRPa immune checkpoint inhibitor BI765063 in patients with advanced solid tumors", Cancer Research, 2022, vol. 82, No. 12_Supplement, pp. 1993-1993.
Abdiche et al., "High-Throughput Epitope Binning Assays on Label-Free Array-Based Biosensors Can Yield Exquisite Epitope Discrimination That Facilitates the Selection of Monoclonal Antibodies with Functional Activity", PLOS ONE, 2014, vol. 9, No. 3, pp. e92451.
Ahmed et al., "Intrinsic physicochemical profile of marketed antibody-based biotherapeutics", Proceedings of the National Academy of Sciences, 2021, vol. 118, No. 37, p. e2020577118.
Alblas et al., "Signal Regulatory Protein Ligation Induces Macrophage Nitric Oxide Production Through JAK/STAT and Phosphatidylinositol 3-Kinase/Racl/NAPDH Oxidase/H2O2-Dependent Pathways", Molecular and Cellular Biology, Aug. 15, 2005, vol. 25, No. 16, pp. 7181-7192.
Almagro et al., "Antibody modeling assessment", Proteins: Structure, Function, and Bioinformatics, 2011, vol. 79, No. 11, pp. 3050-3066.
Almagro et al., "Humanization of antibodies.", Frontiers in Bioscience?: A Journal and Virtual Library, 2008, vol. 13, pp. 1619-1633.
Altschul et al., "Basic local alignment search tool", Journal of Molecular Biology, 1990, vol. 215, No. 3, pp. 403-410.
Altschul et al., "Gapped BLAST and PSI-BLAST: a new generation of protein database search programs", Nucleic Acids Research, 1997, vol. 25, No. 17, pp. 3389-3402.
Ansell et al., "Targeting Immune Checkpoints in Lymphoma", Current Opinion in Hematology, 2015, pp. 337-342, vol. 22, No. 4.
Barclay et al., "The Counterbalance Theory for Evolution and Function of Paired Receptors", Immunity, 2008, vol. 29, No. 5, pp. 675-678.
Barclay et al., "The Interaction Between Signal Regulatory Protein Alpha (SIRPa) and CD47: Structure, Function, and Therapeutic Target", Annu Rev Immunol., Nov. 6, 2013, pp. 25-50.
Brahmer et al., "Safety and Activity of Anti-PD-L 1 Antibody in Patients with Advanced Cancer", N Eng J_ Med, 2012, vol. 366, No. 26.
Brennan et al., "Preparation of Bispecific Antibodies by Chemical Recombination of Monoclonal Immunoglobulin G1 Fragments", Science, 1985, vol. 229, No. 4708, pp. 81-83.
Brooke et al., "Human Lymphocytes Interact Directly with CD47 through a Novel Member of the Signal Regulatory Protein (SIRP) Family", The Journal of Immunology, 2004, vol. 173, No. 4, pp. 2562-2570.
Brown et al., "Assessing the binding properties of the anti-PD-1 antibody landscape using label-free biosensors", PLOS ONE, 2020, vol. 15, No. 3, pp. e0229206.
Bruggemann et al., "Production of human antibody repertoires in transgenic mice", Current Opinion in Biotechnology, 1997, vol. 8, No. 4, pp. 455-458.
Carmen et al., "Concepts in antibody phage display", Briefings in Functional Genomics, 2002, vol. 1, No. 2, pp. 189-203.
Carter et al., "High Level *Escherichia coli* Expression and Production of a Bivalent Humanized Antibody Fragment", Bio/Technology, 1992, vol. 10, No. 2, pp. 163-167.
Chao et al., "Response: Mechanisms of targeting CD47-SIRP [alpha] in hematologic malignancies", Blood American Society of Hematology, US, vol. 119, No. 18, May 3, 2012 (May 3, 2012), pp. 4334-4335.
Chothia et al., "Canonical structures for the hypervariable regions of immunoglobulins", Journal of Molecular Biology, 1987, vol. 196, No. 4, pp. 901-917.
Chothia et al., "Domain association in immunoglobulin molecules the packing of variable domains", Journal of Molecular Biology, 1985, vol. 186, No. 3, pp. 651-663.
Clackson et al., "Making antibody fragments using phage display libraries", Nature, 1991, vol. 352, No. 6336, pp. 624-628.
Crepeau et al., "Challenges and Opportunities in Targeting the CD28/CTLA-4 Pathway in Transplantation and Autoimmunity", Expert Opin. Biol. Ther, 2017,pp. 1001-1012, vol. 17, No. 8.
Dahal et al., "Fc?R requirements leading to successful immunotherapy", Immunological Reviews, 2015, vol. 268, No. 1, pp. 104-122.
Edge et al., "Deglycosylation of glycoproteins by liifluoromethanesulfonic acid", Analytical Biochemistry, 1981, vol. 118, No. 1, pp. 131-137.
Gabrilovich et al., (Nat. Rev. Immunol., Mar. 2009, 9(3): 162-174.
Gauttier et al., "Dual Targeting of Adaptive and Innate Immune Checkpoints Induce Potent Memory Anti-Tumor Response". European Journal of Cancer, Jul. 11, 2016, pp. S216-S217, vol. 61, Supplement 1.
Gilbreth et al., "Crystal Structure of the Human 4-1 BB/4-1 BBL Complex", J Biol Chem., 2018, pp. 9880-9891, vol. 293, No. 25.
Girard et al., "CD80 and CD86 IgC Domains are Important for Quaternary Structure, Receptor Binding and Co-Signaling Function", Immunology Letters, 2014.
Graham et al., "Characteristics of a Human Cell Line Transformed by DNA from Human Adenovirus Type 5", Journal of General Virology, 1977, vol. 36, No. 1, pp. 59-72.
Hatherly et al., "The Structure of the Macrophage Signal Regulatory Protein (SIRP) Inhibitory Receptor Reveals a Binding Face Reminiscent of That Used by T Cell Receptors", Journal of Biological Chemistry, Mar. 6, 2007, pp. 14567-14575, vol. 282, No. 19.
Higgins et al., "[22] Using CLUSTAL for multiple sequence alignments", Methods in Enzymology, 1996, vol. 266, pp. 383-402.
Ishida et al., "Induced Expression of PD-1, A Novel Member of the immunoglobulin Gene Superfamily, Upon Programmed Cell Death", EMBO J., 1992, pp. 3887-3895, vol. 11, No. 11.
Jones et al., "The INNs and outs of antibody nonproprietary names", MABS, 2015, vol. 8, No. 1, pp. 1-9.
Justice et al., "Using the mouse to model human disease: increasing validity and reproducibility", Disease, Models & Mechanisms 9:101-103 (2016).
Karlin et al., "Applications and statistics for multiple high-scoring segments in molecular sequences.", Proceedings of the National Academy of Sciences, 1993, vol. 90, No. 12, pp. 5873-5877.
Karlin et al., "Methods for assessing the statistical significance of molecular sequence features by using general scoring schemes.", Proceedings of the National Academy of Sciences, 1990, vol. 87, No. 6, pp. 2264-2268.
Knappik et al., "Fully synthetic human combinatorial antibody libraries (HuCAL) based on modular consensus frameworks and CDRs randomized with trinucleotides 1 1 Edited by I. A. Wilson", Journal of Molecular Biology, 2000, vol. 296, No. 1, pp. 57-86.

(56) References Cited

OTHER PUBLICATIONS

Kohler, "Continuous cultures of fused cells secreting antibody of predefined specificity", Nature, 1975, vol. 256, pp. 495-497.
Lee et al., "Novel Structural Determinants on SIRP Alpha That Mediate Binding to CD47", Journal of Immunology, Jan. 1, 2007, pp. 7741-7750.
Lefranc, "Unique database numberings system for immunogenetic analysis", Immunology Today, 1997, vol. 18, No. 11, pp. 509.
Lin et al., "The PD-1/PD-1L Complex Resembles the Antigen-Binding Fv Domains of Antibodies and T Cell Receptors", PNAS, 2008, pp. 3011-3016, vol. 15, No. 8.
Liu et al., "Functional Elements on SIRPa IgV Domain Mediate Cell Surface Binding to CD47", Journal of Molecular Biology, 2007, vol. 365, No. 3, pp. 680-693.
Liu et al., "Signal Regulatory Protein (SIRPalpha), a Cellular Ligand for CD47, Regulates Neutrophil Transmigration," Journal of Biological Chemistry, Mar. 15, 2002, vol. 277, No. 12, pp. 10028-10036.
Lonberg et al., "Human Antibodies from Transgenic Mice", International Reviews of Immunology, 2009, vol. 13, No. 1, pp. 65-93.
Maier et al., "Assessment of fully automated antibody homology modeling protocols in molecular operating environment", Proteins: Structure, Function, and Bioinformatics, 2014, vol. 82, No. 8, pp. 1599-1610.
Marks et al., "By-passing immunization Human antibodies from V-gene libraries displayed on phage", Journal of Molecular Biology, 1991, vol. 222, No. 3, pp. 581-597.
Mather et al., "Culture of Testicular Cells in Hormone? Supplemented Serum?Free Medium", Annals of the New York Academy of Sciences, 1982, vol. 383, No. 1, pp. 44-68.
Mather, "Establishment and Characterization of Two Distinct Mouse Testicular Epithelial Cell Line", Biology of Reproduction, 1980, vol. 23, No. 1, pp. 243-252.
Morimoto et al., "Single-step purification of F(ab?)2 fragments of mouse monoclonal antibodies (immunoglobulins G1) by hydrophobic interaction high performance liquid chromatography using TSKgel Phenyl-5PW", Journal of Biochemical and Biophysical Methods, 1992, vol. 24, No. 1-2, pp. 107-117.
Morrison et al., "Chimeric human antibody molecules: mouse antigen-binding domains with human constant region domains.", Proceedings of the National Academy of Sciences, 1984, vol. 81, No. 21, pp. 6851-6855.

\* cited by examiner

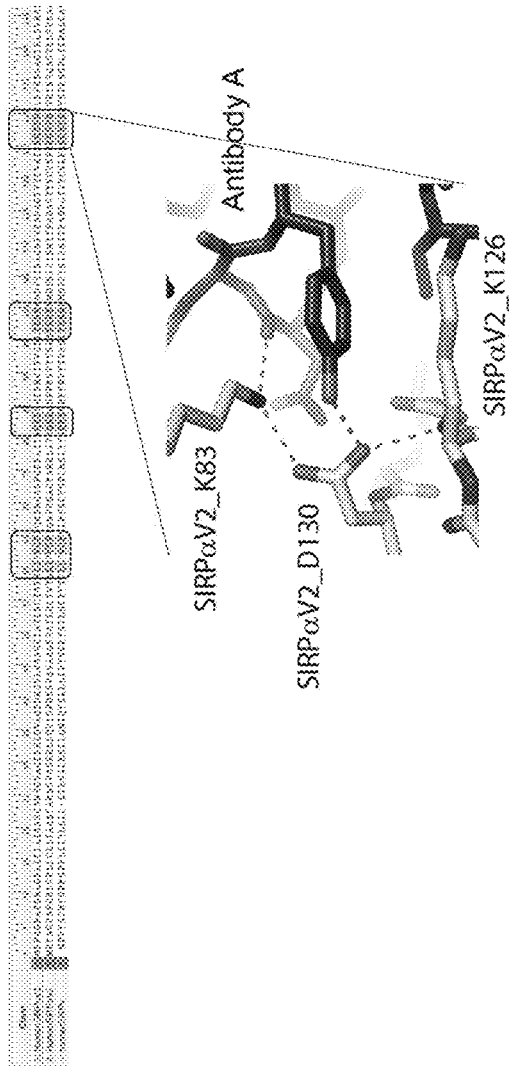
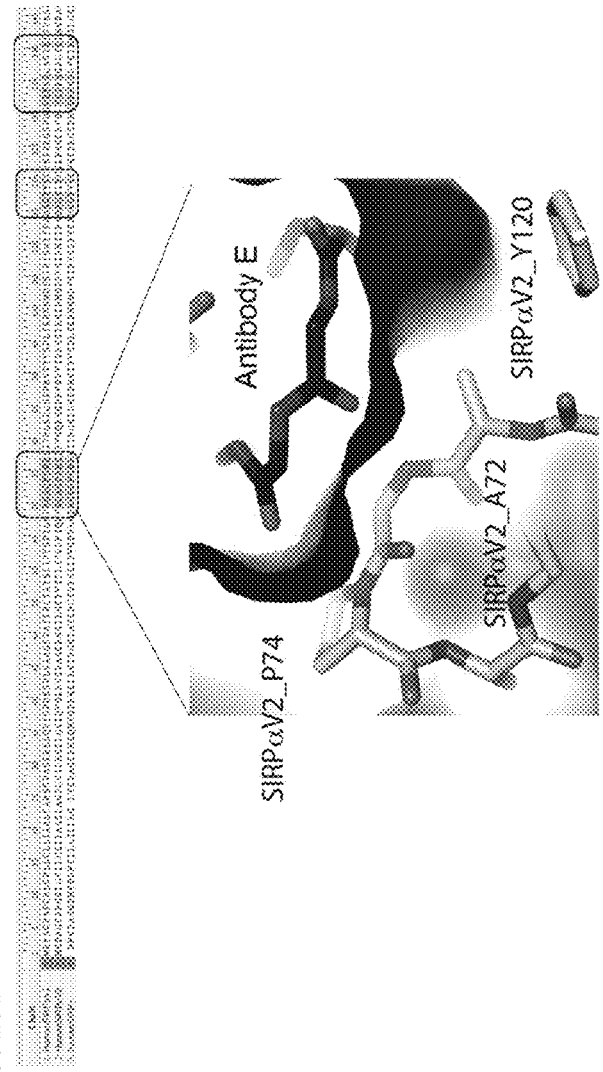
FIG. 26A
FIG. 26B

FIG. 31A 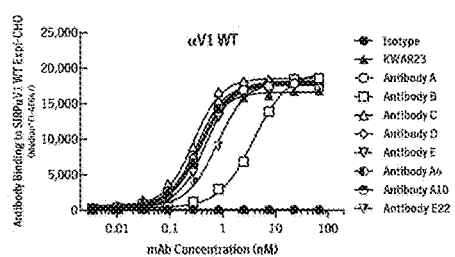 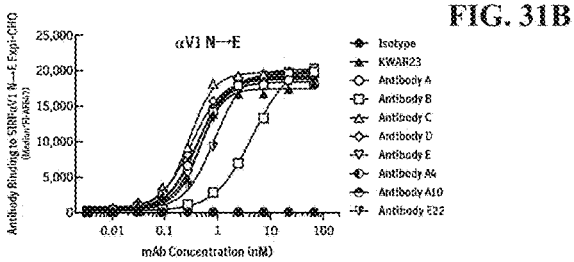 FIG. 31B
FIG. 31C 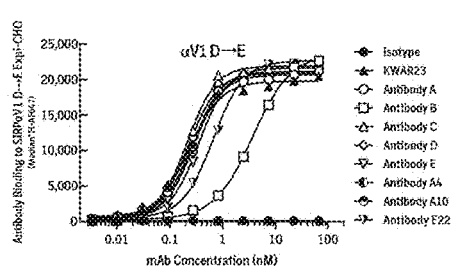 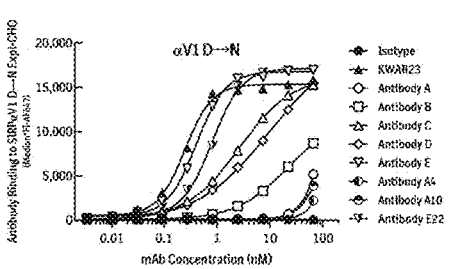 FIG. 31D
FIG. 31E 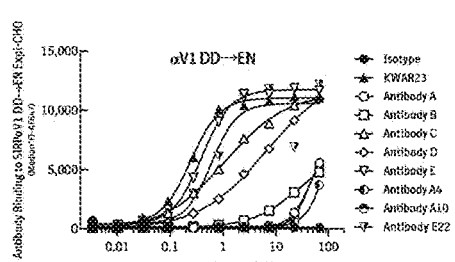 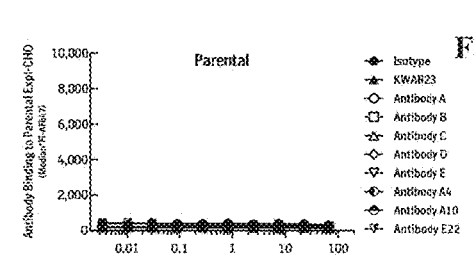 FIG. 31F

FIG. 37A SIRPαV1

FIG. 37B SIRPαV2

FIG. 37C SIRPβ1

FIG. 37D SIRPβL

FIG. 37E SIRPγ

| SIRPαV1 | R | K | G | S | P | D | D | V |
| SIRPαV2 | R | K | G | S | P | D | - | T |
| SIRPβ1  | R | K | G | S | P | D | D | V |
| SIRPβL  | R | K | G | S | P | D | H | V |
| SIRPγ   | R | K | G | S | P | E | N | V |

ANTI-SIRP-ALPHA ANTIBODIES

RELATED APPLICATION DISCLOSURE

The subject application claims the benefit of U.S. Provisional Application No. 63/197,259, filed Jun. 4, 2021, U.S. Provisional Application No. 63/325,828, filed Mar. 31, 2022, and 63/339,326, filed May 6, 2022, each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jun. 2, 2022, is named 105218_03_5011_US_Sequence_Listing.txt and is 463,454 bytes in size.

FIELD OF THE INVENTION

This invention generally relates to anti-SIRPα (Signal regulatory protein alpha) antibodies or antigen-binding fragments thereof for therapeutic and/or diagnostic use. More specifically, the invention relates to anti-SIPRα antibodies or antigen-binding fragments thereof and methods of their use for the treatment of various diseases or disorders, for example, cancer, inflammatory disease, autoimmune disease, respiratory disease, infectious disease, or fibrosis. Pharmaceutical compositions and kits comprising the anti-SIRPα antibodies or antigen-binding fragments thereof are also disclosed.

BACKGROUND OF THE INVENTION

SIRPα is an inhibitory receptor expressed on myeloid cells such as macrophages, neutrophils and subsets of dendritic cells. SIRPα contains three Ig-like domains, a single transmembrane domain, and a cytoplasmic tail with four tyrosine residues which form two typical immunoreceptor tyrosine based inhibitory motifs (ITIMs). The natural ligand for SIRPα is CD47, expressed on many cells including erythrocytes and platelets. Binding of SIRPα to CD47 leads to the phosphorylation of the tyrosine residues in SIRPα intracellular ITIM domain and subsequent recruitment and activation SHP-1 and SHP-2 phosphatases at the cell membrane which can then, by dephosphorylation of downstream targets, regulate cellular functions including phagocytosis or antigen presentation.

The development of an effective SIRPα antagonist is complicated by polymorphisms within the CD47 binding domain. It has been reported that there may be up to ten allelic variants in the general population (Takenaka 2007; *Nat Immunol* 2007 December; 8(12):1313-23. doi: 10.1038/ni1527) and recent studies (Treffers, 2018, *Eur J Immunol.* 2018 February; 48(2):344-354. doi: 10.1002/eji.201747215; *MAbs* August/September 2019; 11(6):1036-1052. doi: 10.1080/19420862.2019.1624123) highlight that two SIRPα variants, V1 and V2, constitute the most prevalent allelic groups: homozygous V1/V1, homozygous V2/V2, and heterozygous V1/V2. These variants differ in 13 out of 118 amino acid residues in the N-terminal immunoglobulin-like domain of SIRPα responsible for CD47 binding. These polymorphic residues are located outside the CD47 binding site and, accordingly, the affinity of CD47 binding to SIRPα variants is similar (Hatherley D, 2008 *Immunity* 2008 Nov. 14; 29(5):675-8. doi: 10.1016/j.immuni.2008.10.004). Consequently, therapeutic targeting of SIRPα in diverse patient population irrespective of SIRPα genotype necessitates pan-allelic antibodies that cross-react with the two major SIRPα alleles (V1 and V2).

In addition to considering polymorphic variants when targeting SIRPα, one also should consider SIRPα's closest relatives, SIRPβ1 and SIRPγ given their high sequence conservation particularly in N-terminal domains. SIRPβ1, like SIRPα is also expressed predominantly on cells of the myeloid lineage, but unlike SIRPα, lacks its own signaling cytoplasmic domain, but harbors a positively charged amino acid residue within the transmembrane region allowing for the stable association with ITAM-containing adapter molecule DAP12 and therefore is presumed to act as an activating receptor. SIRPβ1 does not bind CD47, and its ligands have not been identified. There are at least two isoforms of SIRPβ1 (Liu et al 2007 *J Mol Biol.* 2007 Jan. 19; 365(3): 680-93. doi: 10.1016/j.jmb.2006.09.079; Brooke et al. 2004 *J Immunol.* 2004 Aug. 15; 173(4):2562-70. doi: 10.4049/jimmunol.173.4.2562) that arose through tandem duplication of the gene within the SIRP family gene cluster. SIRPγ is exclusively expressed on T-cells and activated NK cells and does bind to CD47 with 10-fold lower affinity than SIRPα:CD47 interaction. Although it does not have intrinsic signaling capacity, there is reported evidence that it plays a role in T-cell transendothelial migration (TEM) and antigen presentation.

In view of the above, there is a need for pan-allelic anti-SIRPα antibodies capable of blocking the interaction of SIRPα with CD47 and that are selective against SIRPγ to allow for treatment of several types of cancer, inflammatory disease, autoimmune disease, respiratory disease, infectious disease, or fibrosis.

BRIEF SUMMARY OF THE INVENTION

The present invention addresses the above need by providing agents, in particular antibodies or antigen-binding fragments thereof, which bind (e.g., specifically) to SIRPα, in particular human SIRPα. In one aspect of the invention, the antibodies or antigen-binding fragments thereof, block the interaction between SIRPα and CD47. In another aspect of the invention, the antibodies or antigen-binding fragments thereof, block CD47-mediated SIRPα signaling.

The antibodies or antigen-binding fragments thereof of the invention are useful, for example, for the treatment and/or prevention of diseases or disorders that can be alleviated by modulating the interaction between SIRPα and CD47, in particular by blocking CD47-mediated SIRPα signaling. In one aspect of the invention, the antibodies or antigen-binding fragments thereof, are useful, for example for the treatment of cancer, inflammatory disease, autoimmune disease, respiratory disease, infectious disease or fibrosis, preferably cancer.

The invention provides an anti-SIRPα antibody or antigen-binding fragments thereof, having one or more of the properties described herein below.

In one aspect of the invention, the anti-SIRPα antibody or antigen-binding fragment thereof binds specifically to SIRPα, in particular human SIRPα or cynomolgus monkey SIRPα, more particularly human SIRPα. In one aspect, the anti-SIRPα antibody or antigen-binding fragment thereof binds to the V1 and/or V2 alleles of human SIRPα. In one aspect of the invention, the anti-SIRPα antibody or antigen-binding fragment thereof does not bind (e.g., there is no detectable binding or the anti-SIRPα antibody or antigen-binding fragment thereof binds with a $K_D$ of 1 μM or greater)

to SIRPγ, in particular cynomolgus monkey SIRPγ or human SIRPγ, more particularly human SIRPγ. In one aspect of the invention, the anti-SIRPα antibody or antigen-binding fragment thereof, does not bind (e.g., there is no detectable binding or the anti-SIRPα antibody or antigen-binding fragment thereof binds with a $K_D$ of 1 μM or greater) to rabbit, mouse, rat, or dog SIRPα.

In one aspect of the invention, the anti-SIRPα antibody or antigen-binding fragment thereof blocks the binding of CD47 to SIRPα, in particular human SIRPα or cynomolgus monkey SIRPα, more particularly human SIRPα. In one aspect of the invention, the anti-SIRPα antibody or antigen-binding fragment thereof blocks the binding of CD47 to human SIRPα-V1 and SIRPα-V2. In one aspect of the invention, the anti-SIRPα antibody or antigen-binding fragment thereof blocks CD47-mediated SIRPα signaling. In one aspect of the invention, the anti-SIRPα antibody or antigen-binding fragment thereof enhances phagocytosis by macrophages and/or dendritic cells. In one aspect of the invention, the anti-SIRPα antibody or antigen-binding fragment thereof enhances antibody dependent cellular phagocytosis (ADCP), in combination with a tumor targeting agent, in particular a tumor targeting antibody. In one aspect of the invention, the anti-SIRPα antibody or antigen-binding fragment thereof enhances phagocytosis of tumor cells by macrophages and/or dendritic cells. In one aspect of the invention, the anti-SIRPα antibody or antigen-binding fragment thereof blocks inhibition of T-cell proliferation. In one aspect of the invention, the anti-SIRPα antibody or antigen-binding fragment thereof has favorable pharmacokinetic properties. In one aspect of the invention, an anti-SIRPα antibody or antigen-binding fragment thereof has favorable biophysical properties, for example yield, quality, stability or solubility.

In one aspect of the invention, an anti-SIRPα antibody or an antigen-binding fragment thereof comprises:

a) a heavy chain variable region comprising the amino acid sequence of SEQ ID NO: 33 (H-CDR1); the amino acid sequence of SEQ ID NO: 34 (H-CDR2); and the amino acid sequence of SEQ ID NO: 35 (H-CDR3), and
   a light chain variable region comprising the amino acid sequence of SEQ ID NO: 36 or SEQ ID NO: 37 (L-CDR1); the amino acid sequence of SEQ ID NO: 38 (L-CDR2); and the amino acid sequence of SEQ ID NO: 39 (L-CDR3),
or
b) a heavy chain variable region comprising the amino acid sequence of SEQ ID NO: 1 or SEQ ID NO: 223 (H-CDR1); the amino acid sequence of SEQ ID NO: 2, SEQ ID NO: 3, SEQ ID NO: 4, SEQ ID NO: 5 or SEQ ID NO: 224 (H-CDR2); and the amino acid sequence of SEQ ID NO: 6 (H-CDR3); and
   a light chain variable region comprising the amino acid sequence of SEQ ID NO: 7, SEQ ID NO: 8, SEQ ID NO: 9 or SEQ ID NO: 225 (L-CDR1); the amino acid sequence of SEQ ID NO: 10, SEQ ID NO: 11 or SEQ ID NO: 226 (L-CDR2); and the amino acid sequence of SEQ ID NO: 12 or SEQ ID NO: 227 (L-CDR3),
or
c) a heavy chain variable region comprising the amino acid sequence of SEQ ID NO: 52 (H-CDR1); the amino acid sequence of SEQ ID NO: 53 (H-CDR2); and the amino acid sequence of SEQ ID NO: 54 (H-CDR3); and
   a light chain variable region comprising the amino acid sequence of SEQ ID NO: 55 (L-CDR1); the amino acid sequence of SEQ ID NO: 56 (L-CDR2); and the amino acid sequence of SEQ ID NO: 57 (L-CDR3),
or
d) a heavy chain variable region comprising the amino acid sequence of SEQ ID NO: 33 (H-CDR1); the amino acid sequence of SEQ ID NO: 70 (H-CDR2); and the amino acid sequence of SEQ ID NO: 71 (H-CDR3); and
   a light chain variable region comprising the amino acid sequence of SEQ ID NO: 36 (L-CDR1); the amino acid sequence of SEQ ID NO: 72 (L-CDR2); and the amino acid sequence of SEQ ID NO: 39 (L-CDR3),
or
e) a heavy chain variable region comprising the amino acid sequence of SEQ ID NO: 262 (H-CDR1); the amino acid sequence of SEQ ID NO: 87 (H-CDR2); and the amino acid sequence of SEQ ID NO: 88 (H-CDR3); and
   a light chain variable region comprising the amino acid sequence of SEQ ID NO: 36 (L-CDR1); the amino acid sequence of SEQ ID NO: 72 (L-CDR2); and the amino acid sequence of SEQ ID NO: 89 (L-CDR3).

In one aspect of the invention, an anti-SIRPα antibody or an antigen-binding fragment thereof comprises:

a) a heavy chain variable region comprising the amino acid sequence of SEQ ID NO: 33 (H-CDR1); the amino acid sequence of SEQ ID NO: 34 (H-CDR2); the amino acid sequence of SEQ ID NO: 35 (H-CDR3); and a light chain variable region comprising the amino acid sequence of SEQ ID NO:233, wherein amino acids X1=D or G and X2=L or A (L-CDR1); the amino acid sequence of SEQ ID NO: 38, (L-CDR2); the amino acid sequence of SEQ ID NO: 39 (L-CDR3), or
b) a heavy chain variable region comprising the amino acid sequence of SEQ ID NO: 228(H-CDR1), wherein amino acids X1=N or D; the amino acid sequence of SEQ ID NO:229, wherein X1=Y or D, X2=N or T, X3=N or Q, and X4=S or P (H-CDR2); the amino acid sequence of SEQ ID NO: 6 (H-CDR3); and a light chain variable region comprising the amino acid sequence of SEQ ID NO:230, wherein X1=K or R, X2=N or T, X3=G or A and X4=N, A or T (L-CDR1); the amino acid sequence of SEQ ID NO:231, wherein X1=L, Q or G and X2=N or S (L-CDR2); the amino acid sequence of SEQ ID NO:232, wherein X1=M or G (L-CDR3).

In one aspect of the invention, an anti-SIRPα antibody or an antigen-binding fragment thereof comprises a heavy chain variable region comprising the amino acid sequence of any one of SEQ ID NOS: 100, 110, 111, 112, 113, 114, 115, 116, or 117; and a light chain variable region comprising the amino acid sequence of any one of SEQ ID NOS: 105, 125, or 126.

In a further aspect, an anti-SIRPα antibody or an antigen-binding fragment thereof of the present invention comprises a heavy chain variable region comprising the amino acid sequence of any one of SEQ ID NOS: 104, 118, 119, 120, 121, 122, 123, 124 or 221; and a light chain variable region comprising the amino acid sequence of any one of SEQ ID NOS: 109, 127, 128, 129, 130 or 222.

In one aspect of the invention, an anti-SIRPα antibody or an antigen-binding fragment thereof comprises a heavy chain variable region comprising the amino acid sequence of any one of SEQ ID NOS: 100, 101, 102, 103, or 104; and a light chain variable region comprising the amino acid sequence of any one of SEQ ID NOS: 105, 106, 107, 108, or 109.

In one aspect of the invention, an anti-SIRPα antibody or an antigen-binding fragment thereof comprises:

a) a heavy chain variable region comprising the amino acid sequence of SEQ ID NO: 100; and a light chain variable region comprising the amino acid sequence of SEQ ID NO: 105; or b) a heavy chain variable region comprising the amino acid sequence of SEQ ID NO: 110; and a light chain variable region comprising the amino acid sequence of SEQ ID NO: 125; or
c) a heavy chain variable region comprising the amino acid sequence of SEQ ID NO: 111; and a light chain variable region comprising the amino acid sequence of SEQ ID NO: 125; or
d) a heavy chain variable region comprising the amino acid sequence of SEQ ID NO: 112; and a light chain variable region comprising the amino acid sequence of SEQ ID NO: 125; or
e) a heavy chain variable region comprising the amino acid sequence of SEQ ID NO: 113; and a light chain variable region comprising the amino acid sequence of SEQ ID NO: 125; or
f) a heavy chain variable region comprising the amino acid sequence of SEQ ID NO: 114; and a light chain variable region comprising the amino acid sequence of SEQ ID NO: 125; or
g) a heavy chain variable region comprising the amino acid sequence of SEQ ID NO: 115; and a light chain variable region comprising the amino acid sequence of SEQ ID NO: 125; or
h) a heavy chain variable region comprising the amino acid sequence of SEQ ID NO: 116; and a light chain variable region comprising the amino acid sequence of SEQ ID NO: 125; or
i) a heavy chain variable region comprising the amino acid sequence of SEQ ID NO: 117; and a light chain variable region comprising the amino acid sequence of SEQ ID NO: 125; or
j) a heavy chain variable region comprising the amino acid sequence of SEQ ID NO: 111; and a light chain variable region comprising the amino acid sequence of SEQ ID NO: 126; or
k) a heavy chain variable region comprising the amino acid sequence of SEQ ID NO: 112; and a light chain variable region comprising the amino acid sequence of SEQ ID NO: 126; or
l) a heavy chain variable region comprising the amino acid sequence of SEQ ID NO: 113; and a light chain variable region comprising the amino acid sequence of SEQ ID NO: 126; or
m) a heavy chain variable region comprising the amino acid sequence of SEQ ID NO: 114; and a light chain variable region comprising the amino acid sequence of SEQ ID NO: 126; or
n) a heavy chain variable region comprising the amino acid sequence of SEQ ID NO: 115; and a light chain variable region comprising the amino acid sequence of SEQ ID NO: 126; or
o) a heavy chain variable region comprising the amino acid sequence of SEQ ID NO: 116; and a light chain variable region comprising the amino acid sequence of SEQ ID NO: 126; or
p) a heavy chain variable region comprising the amino acid sequence of SEQ ID NO: 117; and a light chain variable region comprising the amino acid sequence of SEQ ID NO: 126.

In one aspect of the invention, an anti-SIRPα antibody or an antigen-binding fragment thereof comprises:
a) a heavy chain variable region comprising the amino acid sequence of SEQ ID NO: 104; and a light chain variable region comprising the amino acid sequence of SEQ ID NO: 109; or
b) a heavy chain variable region comprising the amino acid sequence of SEQ ID NO: 118; and a light chain variable region comprising the amino acid sequence of SEQ ID NO: 127; or
c) a heavy chain variable region comprising the amino acid sequence of SEQ ID NO: 118; and a light chain variable region comprising the amino acid sequence of SEQ ID NO: 128; or
d) a heavy chain variable region comprising the amino acid sequence of SEQ ID NO: 119; and a light chain variable region comprising the amino acid sequence of SEQ ID NO: 127; or
e) a heavy chain variable region comprising the amino acid sequence of SEQ ID NO: 119; and a light chain variable region comprising the amino acid sequence of SEQ ID NO: 129; or
f) a heavy chain variable region comprising the amino acid sequence of SEQ ID NO: 120; and a light chain variable region comprising the amino acid sequence of SEQ ID NO: 127; or
g) a heavy chain variable region comprising the amino acid sequence of SEQ ID NO: 120; and a light chain variable region comprising the amino acid sequence of SEQ ID NO: 129; or
h) a heavy chain variable region comprising the amino acid sequence of SEQ ID NO: 121; and a light chain variable region comprising the amino acid sequence of SEQ ID NO: 127; or
i) a heavy chain variable region comprising the amino acid sequence of SEQ ID NO: 122; and a light chain variable region comprising the amino acid sequence of SEQ ID NO: 127; or
j) a heavy chain variable region comprising the amino acid sequence of SEQ ID NO: 118; and a light chain variable region comprising the amino acid sequence of SEQ ID NO: 130; or
k) a heavy chain variable region comprising the amino acid sequence of SEQ ID NO: 121; and a light chain variable region comprising the amino acid sequence of SEQ ID NO: 129; or
l) a heavy chain variable region comprising the amino acid sequence of SEQ ID NO: 122; and a light chain variable region comprising the amino acid sequence of SEQ ID NO: 129; or
m) a heavy chain variable region comprising the amino acid sequence of SEQ ID NO: 119; and a light chain variable region comprising the amino acid sequence of SEQ ID NO: 130; or
n) a heavy chain variable region comprising the amino acid sequence of SEQ ID NO: 123; and a light chain variable region comprising the amino acid sequence of SEQ ID NO: 127; or
o) a heavy chain variable region comprising the amino acid sequence of SEQ ID NO: 120; and a light chain variable region comprising the amino acid sequence of SEQ ID NO: 130; or
p) a heavy chain variable region comprising the amino acid sequence of SEQ ID NO: 123; and a light chain variable region comprising the amino acid sequence of SEQ ID NO: 129; or
q) a heavy chain variable region comprising the amino acid sequence of SEQ ID NO: 121; and a light chain variable region comprising the amino acid sequence of SEQ ID NO: 130; or r) a heavy chain variable region comprising the amino acid sequence of SEQ ID NO: 122; and a light chain variable region comprising the amino acid sequence of SEQ ID NO: 130; or
s) a heavy chain variable region comprising the amino acid sequence of SEQ ID NO: 124; and a light chain variable region comprising the amino acid sequence of SEQ ID NO: 129; or
t) a heavy chain variable region comprising the amino acid sequence of SEQ ID NO: 124; and a light chain variable region comprising the amino acid sequence of SEQ ID NO: 127; or
u) a heavy chain variable region comprising the amino acid sequence of SEQ ID NO: 123; and a light chain variable region comprising the amino acid sequence of SEQ ID NO: 130; or
v) a heavy chain variable region comprising the amino acid sequence of SEQ ID NO: 124; and a light chain variable region comprising the amino acid sequence of SEQ ID NO: 130; or
w) a heavy chain variable region comprising the amino acid sequence of SEQ ID NO: 221; and a light chain variable region comprising the amino acid sequence of SEQ ID NO: 222.

In one aspect of the invention, an anti-SIRPα antibody or an antigen-binding fragment thereof comprises:
a) a heavy chain variable region comprising the amino acid sequence of SEQ ID NO: 100; and a light chain variable region comprising the amino acid sequence of SEQ ID NO: 105; or
b) a heavy chain variable region comprising the amino acid sequence of SEQ ID NO: 101; and a light chain variable region comprising the amino acid sequence of SEQ ID NO: 106; or
c) a heavy chain variable region comprising the amino acid sequence of SEQ ID NO: 102; and a light chain variable region comprising the amino acid sequence of SEQ ID NO: 107; or
d) a heavy chain variable region comprising the amino acid sequence of SEQ ID NO: 103; and a light chain variable region comprising the amino acid sequence of SEQ ID NO: 108; or
e) a heavy chain variable region comprising the amino acid sequence of SEQ ID NO: 104; and a light chain variable region comprising the amino acid sequence of SEQ ID NO: 109.

In one aspect of the invention, an anti-SIRPα antibody comprises a heavy chain comprising the amino acid sequence of any one of SEQ ID NO: 131, 138, 139, 140, 141, 142, 143, 144, 145, 146, 148, 149, 150, 151 or 152; and a light chain comprising the amino acid sequence of any one of SEQ ID NO: 174, 181, 182, 183, 184, 185, 186, 187, 188, 189, 190, 191, 192, 193, 194, 195 or 218.

In a further aspect, an anti-SIRPα antibody of the invention comprises:
a) a heavy chain comprising the amino acid sequence of SEQ ID NO: 131; and a light chain comprising the amino acid sequence of SEQ ID NO: 174; or
b) a heavy chain comprising the amino acid sequence of SEQ ID NO: 138; and a light chain comprising the amino acid sequence of SEQ ID NO: 121; or
c) a heavy chain comprising the amino acid sequence of SEQ ID NO: 139; and a light chain comprising the amino acid sequence of SEQ ID NO: 182; or
d) a heavy chain comprising the amino acid sequence of SEQ ID NO: 140; and a light chain comprising the amino acid sequence of SEQ ID NO: 183; or
e) a heavy chain comprising the amino acid sequence of SEQ ID NO: 141; and a light chain comprising the amino acid sequence of SEQ ID NO: 184; or
f) a heavy chain comprising the amino acid sequence of SEQ ID NO: 142; and a light chain comprising the amino acid sequence of SEQ ID NO: 185; or
g) a heavy chain comprising the amino acid sequence of SEQ ID NO: 143; and a light chain comprising the amino acid sequence of SEQ ID NO: 186; or
h) a heavy chain comprising the amino acid sequence of SEQ ID NO: 144; and a light chain comprising the amino acid sequence of SEQ ID NO: 187; or
i) a heavy chain comprising the amino acid sequence of SEQ ID NO: 145; and a light chain comprising the amino acid sequence of SEQ ID NO: 188; or
j) a heavy chain comprising the amino acid sequence of SEQ ID NO: 146; and a light chain comprising the amino acid sequence of SEQ ID NO: 189; or
k) a heavy chain comprising the amino acid sequence of SEQ ID NO: 147; and a light chain comprising the amino acid sequence of SEQ ID NO: 190; or
l) a heavy chain comprising the amino acid sequence of SEQ ID NO: 148; and a light chain comprising the amino acid sequence of SEQ ID NO: 191; or
m) a heavy chain comprising the amino acid sequence of SEQ ID NO: 149; and a light chain comprising the amino acid sequence of SEQ ID NO: 192; or
n) a heavy chain comprising the amino acid sequence of SEQ ID NO: 150; and a light chain comprising the amino acid sequence of SEQ ID NO: 193; or
o) a heavy chain comprising the amino acid sequence of SEQ ID NO: 151; and a light chain comprising the amino acid sequence of SEQ ID NO: 194; or
p) a heavy chain comprising the amino acid sequence of SEQ ID NO: 152; and a light chain comprising the amino acid sequence of SEQ ID NO: 195; or
q) a heavy chain comprising the amino acid sequence of SEQ ID NO: 217; and a light chain comprising the amino acid sequence of SEQ ID NO: 218.

In one aspect of the invention, an anti-SIRPα antibody comprises a heavy chain comprising the amino acid sequence of any one of SEQ ID NO: 135, 153, 154, 155, 156, 157, 158, 159, 160, 161, 162, 163, 164, 165, 166, 167, 168, 169, 170, 171, 172, 173 or 219; and a light chain comprising the amino acid sequence of any one of SEQ ID NO: 178, 196, 197, 198, 199, 200, 201, 202, 203, 204, 205, 206, 207, 208, 209, 210, 211, 212, 213, 214, 215, 216 or 220.

In one aspect of the invention, an anti-SIRPα antibody comprises:
a) a heavy chain comprising the amino acid sequence of SEQ ID NO: 135; and a light chain comprising the amino acid sequence of SEQ ID NO: 178; or
b) a heavy chain comprising the amino acid sequence of SEQ ID NO: 153; and a light chain comprising the amino acid sequence of SEQ ID NO: 196; or
c) a heavy chain comprising the amino acid sequence of SEQ ID NO: 154; and a light chain comprising the amino acid sequence of SEQ ID NO: 197; or
d) a heavy chain comprising the amino acid sequence of SEQ ID NO: 155; and a light chain comprising the amino acid sequence of SEQ ID NO: 198; or
e) a heavy chain comprising the amino acid sequence of SEQ ID NO: 156; and a light chain comprising the amino acid sequence of SEQ ID NO: 199; or
f) a heavy chain comprising the amino acid sequence of SEQ ID NO: 157; and a light chain comprising the amino acid sequence of SEQ ID NO: 200; or g) a heavy chain comprising the amino acid sequence of SEQ ID NO: 158; and a light chain comprising the amino acid sequence of SEQ ID NO: 201; or
h) a heavy chain comprising the amino acid sequence of SEQ ID NO: 159; and a light chain comprising the amino acid sequence of SEQ ID NO: 202; or
i) a heavy chain comprising the amino acid sequence of SEQ ID NO: 160; and a light chain comprising the amino acid sequence of SEQ ID NO: 203; or
j) a heavy chain comprising the amino acid sequence of SEQ ID NO: 161; and a light chain comprising the amino acid sequence of SEQ ID NO: 204; or
k) a heavy chain comprising the amino acid sequence of SEQ ID NO: 162; and a light chain comprising the amino acid sequence of SEQ ID NO: 205; or
l) a heavy chain comprising the amino acid sequence of SEQ ID NO: 163; and a light chain comprising the amino acid sequence of SEQ ID NO: 206; or
m) a heavy chain comprising the amino acid sequence of SEQ ID NO: 164; and a light chain comprising the amino acid sequence of SEQ ID NO: 207; or
n) a heavy chain comprising the amino acid sequence of SEQ ID NO: 165; and a light chain comprising the amino acid sequence of SEQ ID NO: 208; or
o) a heavy chain comprising the amino acid sequence of SEQ ID NO: 166; and a light chain comprising the amino acid sequence of SEQ ID NO: 209; or
p) a heavy chain comprising the amino acid sequence of SEQ ID NO: 167; and a light chain comprising the amino acid sequence of SEQ ID NO: 210; or
q) a heavy chain comprising the amino acid sequence of SEQ ID NO: 168; and a light chain comprising the amino acid sequence of SEQ ID NO: 211; or
r) a heavy chain comprising the amino acid sequence of SEQ ID NO: 169; and a light chain comprising the amino acid sequence of SEQ ID NO: 212; or
s) a heavy chain comprising the amino acid sequence of SEQ ID NO: 170; and a light chain comprising the amino acid sequence of SEQ ID NO: 213; or
t) a heavy chain comprising the amino acid sequence of SEQ ID NO: 171; and a light chain comprising the amino acid sequence of SEQ ID NO: 214; or
u) a heavy chain comprising the amino acid sequence of SEQ ID NO: 172; and a light chain comprising the amino acid sequence of SEQ ID NO: 215; or
v) a heavy chain comprising the amino acid sequence of SEQ ID NO: 173; and a light chain comprising the amino acid sequence of SEQ ID NO: 216; or
w) a heavy chain comprising the amino acid sequence of SEQ ID NO: 219; and a light chain comprising the amino acid sequence of SEQ ID NO: 220.

In one aspect of the invention, an anti-SIRPα antibody comprises a heavy chain comprising the amino acid sequence of any one of SEQ ID NO: 131, 133, 134, 137 or 135; and a light chain comprising the amino acid sequence of any one of SEQ ID NO:174, 176, 177, 180, or 178.

In one aspect of the invention, an anti-SIRPα antibody comprises:
a) a heavy chain comprising the amino acid sequence of SEQ ID NO: 131; and a light chain comprising the amino acid sequence of SEQ ID NO: 174; or
b) a heavy chain comprising the amino acid sequence of SEQ ID NO: 133; and a light chain comprising the amino acid sequence of SEQ ID NO: 176; or
c) a heavy chain comprising the amino acid sequence of SEQ ID NO: 134; and a light chain comprising the amino acid sequence of SEQ ID NO: 177; or
d) a heavy chain comprising the amino acid sequence of SEQ ID NO: 137; and a light chain comprising the amino acid sequence of SEQ ID NO: 180; or
e) a heavy chain comprising the amino acid sequence of SEQ ID NO: 135; and a light chain comprising the amino acid sequence of SEQ ID NO: 178.

In one aspect of the invention, the anti-SIRPα antibody or antigen-binding fragment thereof, is a human antibody or antigen-binding fragment thereof. In one aspect of the invention, the anti-SIRPα antibody or antigen-binding fragment thereof, is a monoclonal antibody. In one aspect of the invention, the anti-SIRPα antibody is a full-length antibody. In one aspect of the invention, the anti-SIRPα antibody or fragment thereof, is a human monoclonal antibody, for example a full-length human monoclonal antibody.

In a one aspect of the invention, the anti-SIRPα antibody, or an antigen-binding fragment thereof, comprises a heavy chain variable region having at least 90%, at least 95%, at least 98%, or at least 99% identity to the amino acid sequences of SEQ ID NO: 100, 110, 111, 112, 113, 114, 115, 116, or 117 and a light chain variable region having at least 90%, at least 95%, at least 98%, or at least 99% identity to the amino acid sequences of SEQ ID NO: 105, 125, or 126. In a further aspect of the invention, the antibody or antigen-binding fragment thereof that comprises a heavy chain variable region having at least 90%, at least 95%, at least 98%, or at least 99% identity to the amino acid sequences of SEQ ID NO: 100, 110, 111, 112, 113, 114, 115, 116, or 117 and a light chain variable region having at least 90%, at least 95%, at least 98%, or at least 99% identity to the amino acid sequences of SEQ ID NO: 105, 125, or 126 specifically binds to SIRPα. In a one aspect of the invention, the anti-SIRPα antibody, or an antigen-binding fragment thereof, comprises a heavy chain variable region having at least 90%, at least 95%, at least 98%, or at least 99% identity to the amino acid sequences of SEQ ID NO: 104, 118, 119, 120, 121, 122, 123, 124, or 221 and a light chain variable region having at least 90%, at least 95%, at least 98%, or at least 99% identity to the amino acid sequences of SEQ ID NO: 109, 127, 128, 129, 130, or 222. In a further aspect of the invention, the antibody or antigen-binding fragment thereof that comprises a heavy chain variable region having at least 90%, at least 95%, at least 98%, or at least 99% identity to the amino acid sequences of SEQ ID NO: 104, 118, 119, 120, 121, 122, 123, 124, or 221 and a light chain variable region having at least 90%, at least 95%, at least 98%, or at least 99% identity to the amino acid sequences of SEQ ID NO: 109, 127, 128, 129, 130, or 222 specifically binds to SIRPα. In one aspect of the invention, the anti-SIRPα antibody, or an antigen-binding fragment thereof, comprises a heavy chain variable region having at least 90%, at least 95%, at least 98%, or at least 99% identity to the amino acid sequences of SEQ ID NO: 101, 102 or 103 and a light chain variable region having at least 90%, at least 95%, at least 98%, or at least 99% identity to the amino acid sequences of SEQ ID NO: 106, 107, 108. In a further aspect of the invention, the antibody or antigen-binding fragment thereof that comprises a heavy chain variable region having at least 90%, at least 95%, at least 98%, or at least 99% identity to the amino acid sequences of SEQ ID NO: 101, 102 or 103 and a light chain variable region having at least 90%, at least 95%, at least 98%, or at least 99% identity to the amino acid sequences of SEQ ID NO: 106, 107, 108 specifically binds to SIRPα.

In one aspect of the invention, the anti-SIRPα antibody, or an antigen-binding fragment thereof, comprises a heavy chain constant region from an antibody selected from the group consisting of IgG1, IgG2, IgG3, IgG4, IgM, IgA and IgE, for example human IgG1, IgG2, IgG3, IgG4, IgM, IgA or IgE, more particularly, human IgG1, IgG2, IgG3, IgG4.

In one aspect of the invention, the anti-SIRPα antibody or an antigen-binding fragment thereof comprises a heavy chain constant region, wherein the heavy chain constant region is of an IgG4 with a S241P substitution. In one aspect of the invention, the anti-SIRPα antibody or an antigen-binding fragment thereof comprises a heavy chain lacking a C-terminal lysine residue.

In one aspect of the invention, the anti-SIRPα antibody or an antigen-binding fragment thereof comprises a heavy chain constant region wherein the heavy chain constant region is of an IgG1 with L234A and L235A substitutions.

In one aspect of the invention, the anti-SIRPα antibody or antigen-binding fragment thereof comprises a light chain constant region selected from the group consisting of a kappa and a lambda light chain.

In one aspect of the invention, the anti-SIRPα antibody or antigen-binding fragment thereof, is optionally administered in combination with an additional therapeutic agent. The additional therapeutic agent may be a chemotherapeutic agent, an anti-PD-1 or PD-L1 antibody, an anti-CTLA4 antibody, a T-cell engager, a CD137-agonist-anti-FAP bispecific antibody, a tumor-targeting antibody, a VEGF-ANG2 bispecific antibody, a STING agonist, a MDM2 antagonist, or radiation therapy.

In one aspect, the anti-SIRPα antibody or an antigen-binding fragment thereof is administered in combination with an anti-PD-1 antibody, for example, nivolumab, pembrolizumab, pidilizumab, ezabenlimab, or atezolizumab. In a further aspect, the anti-SIRPα antibody or an antigen-binding fragment thereof is administered in combination with an anti-PD-L1 antibody including, for example, avelumab or durvalumab.

In one aspect, the anti-SIRPα antibody or antigen-binding fragment thereof is administered in combination with a tumor targeting antibody, for example an antibody that targets HER2 (e.g., trastuzumab), EGFR (e.g., cetuximab, panitumumab), CD20 (e.g., rituximab, ofatumumab), or CD52 (e.g., alemtuzumab).

In one aspect, the anti-SIRPα antibody or antigen-binding fragment thereof is administered in combination with two therapeutic agents. In a further aspect, the anti-SIRPα antibody or antigen-binding fragment thereof is administered in combination with an anti-PD-1 antibody (e.g., nivolumab, pembrolizumab, pidilizumab, ezabenlimab, or atezolizumab), or an anti-PD-L1 antibody (e.g., avelumab or durvalumab) and a tumor targeting antibody, for example and antibody that targets HER2 (e.g., trastuzumab), EGFR (e.g., tetuximab, panitumumab), CD20 (e.g., rituximab, ofatumumab), or CD52 (e.g., alemtuzumab).

In one aspect of the invention, the antibody or antigen-binding fragment thereof recognizes a specific linear or conformational "SIRPα epitope" on a SIRPα protein comprising the amino acid sequence set forth in any one of SEQ ID NOs: 240-252. In one aspect of the invention, the antibody or antigen-binding fragment thereof recognizes a specific linear or conformational "SIRPα epitope" on a SIRPα protein comprising the amino acid sequence set forth in any one of SEQ ID NOs: 253-260 and 264, in particular any one or more of SEQ ID NOS: 256 and 257. In one aspect of the invention the antibody or antigen-binding fragment thereof binds to a SIRPα epitope comprising the amino acids; LEU 60, ILE 61, VAL 63, GLY 64, PRO 65, GLN 82, LYS 83, GLU 84, THR 97, LYS 98, ARG 99, GLU 100, LYS 126, GLY 127, SER 128, PRO 129 and ASP 130 as set forth in SEQ ID NO: 266. In one aspect of the invention the antibody or antigen-binding fragment thereof binds to a SIRPα epitope comprising the amino acids LEU 60, ILE 61, VAL 63, GLY 64, PRO 65, GLN 82, LYS 83, GLU 84, THR 97, LYS 98, ARG 99, ASN 100, LYS 126, GLY 127, SER 128, PRO 129 and ASP 130 as set forth in SEQ ID NO: 265. In another aspect of the invention, the antibody or antigen-binding fragment thereof binds to the SIRPα epitope comprising the amino acid ASP130. In another aspect, the antibody or antigen-binding fragment thereof binds to a SIRPα epitope comprising any one or more of SEQ ID NO; 253, SEQ ID NO: 254, SEQ ID NO: 255, SEQ ID NO: 264, and SEQ ID NO: 256, in particular SEQ ID NO: 256.

In one aspect of the invention the antibody or antigen-binding fragment thereof binds to the SIRPα epitope comprising the amino acids ARG 70, GLY 71, ALA 72, GLY 73, PRO 74, ALA 75, ARG 76, GLU 77, ALA 114, ALA 116, GLY 117, THR 118, TYR 120, THR 131, GLU 132, PHE 133, SER 135 and GLU 140 as set forth in SEQ ID NO: 266. In one aspect of the invention the antibody or antigen-binding fragment thereof binds to a SIRPα epitope comprising the amino acids ARG 70, GLY 71, ALA 72, GLY 73, PRO 74, GLY 75, ARG 76, GLU 77, ALA 114, ALA 116, GLY 117, THR 118, TYR 120, VAL 132, GLU 133, PHE 134, SER 136 and GLU 141 as set forth in SEQ ID NO: 265. In another aspect of the invention, the antibody or antigen-binding fragment thereof binds to the SIRPα epitope comprising the amino acid ALA72. In another aspect, the antibody or antigen-binding fragment thereof binds to a SIRPα epitope comprising any one or more of SEQ ID NO: 257, SEQ ID NO: 258, SEQ ID NO: 259 and SEQ ID NO:260, in particular SEQ ID NO: 257. In another aspect of the invention, the antibody or antigen-binding fragment thereof blocks binding of any of Antibody A-E to SIRPα.

In another aspect, the antibody or antigen-binding fragment thereof exhibits comparable binding to (e.g., less than a 10-fold difference in affinity for) the modified SIRPαV1 polypeptide sequence of SEQ ID NO: 269 or 270, compared to its binding to the SIRPαV1 polypeptide of SEQ ID NO: 268, which optionally is measured at room temperature. Preferably the antibody or antigen-binding fragment thereof is antibody A, A4, A10, or an antigen-binding fragment thereof.

In another aspect, the antibody or antigen-binding fragment thereof exhibits reduced binding affinity for (e.g., at least a 10-fold reduction in affinity for) the modified SIRPαV1 polypeptide sequence of SEQ ID NO: 271 or 272, compared to its binding to the SIRPαV1 polypeptide of SEQ ID NO: 268, which optionally is measured at room temperature. Preferably the antibody or antigen-binding fragment thereof is antibody A, A4, A10, or an antigen-binding fragment thereof.

In another aspect, the antibody or antigen-binding fragment thereof exhibits comparable binding to (e.g., less than a 10-fold difference in affinity for) the modified SIRPαV2 polypeptide sequence of SEQ ID NO: 274 or 275, compared to its binding to the SIRPαV2 polypeptide of SEQ ID NO: 273, which optionally is measured at room temperature. Preferably the antibody or antigen-binding fragment thereof is antibody A, A4, A10, or an antigen-binding fragment thereof.

In another aspect, the antibody or antigen-binding fragment thereof exhibits reduced binding affinity for (e.g., at least a 10-fold reduction in affinity for) the modified SIRPβ1 polypeptide sequence of SEQ ID NO: 277, compared to its binding to the SIRPβ1 polypeptide of SEQ ID NO: 276, which optionally is measured at room temperature. Preferably the antibody or antigen-binding fragment thereof is antibody A, A4, A10, or an antigen-binding fragment thereof.

In another aspect, the antibody or antigen-binding fragment thereof exhibits binding to the modified polypeptide sequence of SEQ ID NO: 279, which optionally is measured at room temperature. Preferably the antibody or antigen-binding fragment thereof is antibody A, A4, A10, or an antigen-binding fragment thereof.

In another aspect, the antibody or antigen-binding fragment thereof exhibits binding to the modified polypeptide sequence of SEQ ID NO: 282 or 283, which optionally is measured at room temperature. Preferably the antibody or antigen-binding fragment thereof is antibody A, A4, A10, or an antigen-binding fragment thereof.

In one aspect, the anti-SIRPα antibody or antigen-binding fragment thereof exhibits comparable binding affinity for human SIRPαV1 and SIRPαV2, such as less than 10-fold difference (preferably less than 5-fold difference) in the binding affinity ($K_D$) for human SIRPαV1 and SIRPαV2, which optionally is measured at room temperature.

In one aspect, the present invention provides an anti-SIRPα antibody or antigen-binding fragment thereof that competes for binding to V1-SIRPα and/or V2-SIRPα, with an anti-SIRPα antibody or antigen-binding fragment thereof of the invention. In one aspect, the present invention provides an anti-SIRPα antibody or antigen-binding fragment thereof that competes for binding to V1-SIRPα and/or V2 SIRPα, with an antibody comprising a heavy chain variable region comprising the amino acid sequence of any one of SEQ ID NOS: 100, 110, 111, 112, 113, 114, 115, 116, or 117 and a light chain variable region comprising the amino acid sequence of any one of SEQ ID NOS: 105, 125, or 126; or an antibody comprising a heavy chain comprising the amino acid sequence of any one of SEQ ID NO: 131,138,139, 140, 141, 142, 143, 144, 145, 146, 147, 148, 149, 150, 151, 152, or 217 and a light chain comprising the amino acid sequence of any one of SEQ ID NO: 174, 181, 182, 183, 184, 185, 186, 187, 188, 189, 190, 191, 192, 193, 194, 195, 218.

In one aspect, the present invention provides an anti-SIRPα antibody or antigen-binding fragment thereof that competes for binding to V1-SIRPα and/or V2-SIRPα, with an anti-SIRPα antibody or antigen-binding fragment thereof of the invention. In one aspect, the present invention provides an anti-SIRPα antibody or antigen-binding fragment thereof that competes for binding to V1-SIRPα and/or V2 SIRPα, with an antibody comprising a heavy chain variable region comprising the amino acid sequence of any one of SEQ ID NOS: 104, 118, 119, 120, 121, 122, 123, 124, or 221 and a light chain variable region comprising the amino acid sequence of any one of SEQ ID NOS: 109, 127, 128, 129, 130, or 222; or an antibody comprising a heavy chain comprising the amino acid sequence of any one of SEQ ID NO: 135, 153, 154, 156, 157, 158, 159, 160, 161, 162, 163, 164, 165, 166, 167, 168, 169, 170, 171, 172, 173, or 219 and a light chain comprising the amino acid sequence of any one of SEQ ID NO: 178, 196, 197, 198, 199, 200, 201, 202, 203, 204, 205, 206, 207, 208, 209, 210, 211, 212, 213, 214, 215, 216, or 220.

In one aspect, the invention provides a pharmaceutical composition comprising an anti-SIRPα antibody or antigen-binding fragment thereof as described above, and a pharmaceutically acceptable excipient, optionally in combination with one or more (e.g., one or two) additional therapeutic agents. In a further embodiment, the additional therapeutic agent is a chemotherapeutic agent, an anti-PD-1 or PD-L1 antibody, an anti-CTLA4 antibody, a T cell engager, a CD137-agonist-anti-FAP bispecific antibody, a tumor-targeting antibody, a VEGF-ANG2 bispecific antibody, a STING agonist, or a MDM2 antagonist.

In one aspect, the invention provides an anti-SIRPα antibody or antigen-binding fragment thereof as described above for use as a medicament or in the preparation of a medicament.

In one aspect, the invention provides a method of treating a SIRPα pathway disorder comprising administering to a subject in need thereof a pharmaceutically effective amount of the anti-SIRPα antibody or antigen-binding fragment thereof as described above. In one aspect, the invention provides an anti-SIRPα antibody or antigen-binding fragment thereof as described above for use in treating a SIRPα pathway disorder. In one aspect, the invention provides the use of the anti-SIRPα antibody or antigen-binding fragment thereof as described above in manufacture of a medicament for treating a SIRPα pathway disorder.

In one aspect, the invention provides a method of modulating the interaction between SIRPα and CD47 in a subject (e.g., a human) comprising administering to the subject a composition comprising an anti-SIRPα antibody or the antigen-binding fragment as described above in an amount sufficient to block the CD47-mediated SIRPα signaling in the subject. In one embodiment, the invention provides an anti-SIRPα antibody or the antigen-binding fragment as described above for use in modulating the interaction between SIRPα and CD47 in a subject. In one embodiment, the invention provides the use of an anti-SIRPα antibody or the antigen-binding fragment as described above in the manufacture of a medicament for modulating the interaction between SIRPα and CD47 in a subject.

In one embodiment, the invention provides a method of enhancing phagocytosis comprising administering to a subject a composition comprising an anti-SIRPα antibody or the antigen-binding fragment as described above in an amount sufficient to block the CD47-mediated SIRPα signaling. In one embodiment, the invention provides an anti-SIRPα antibody or the antigen-binding fragment as described above for use in enhancing phagocytosis by macrophages and/or dendritic cells in a subject. In one embodiment, the invention provides an anti-SIRPα antibody or the antigen-binding fragment as described above for use in enhancing phagocytosis of tumor cells by macrophages and/or dendritic cells in a subject. In one embodiment, the present invention provides the use of an anti-SIRPα antibody or the antigen-binding fragment as described above in the manufacture of a medicament for a subject. In one aspect of the invention, the invention provides a method of enhancing antibody dependent cellular phagocytosis (ADCP), in combination with a tumor targeting agent, preferably a tumor targeting antibody, the method comprising administering to a subject a composition comprising an anti-SIRPα antibody or the antigen-binding fragment as described above in an amount sufficient to block the CD47-mediated SIRPα signaling in combination with a tumor targeting agent, preferably a tumor targeting antibody, more preferably a tumor targeting antibody that targets HER2 (e.g., trastuzumab), EGFR (e.g., cetuximab, panitumumab), CD20 (e.g., rituximab, ofatumumab) CD52 (e.g., alemtuzumab).

In one embodiment, in a method above, in an anti-SIRPα antibody or antigen-binding fragment thereof for use above, or in the use of an anti-SIRPα antibody or antigen-binding fragment thereof above, the disease is selected from the group consisting of cancer, inflammatory disease, autoimmune disease, respiratory disease, infectious disease or fibrosis.

In one embodiment, in the method above, in the anti-SIRPα antibody or antigen-binding fragment thereof for use above, or in the use of the anti-SIRPα antibody or antigen-binding fragment thereof above, the antibody or antigen-binding fragment thereof is administered by a parenteral route, intravenous route, or subcutaneous route of administration.

In one embodiment, the invention provides an isolated polynucleotide encoding a heavy chain variable region amino and/or a light chain variable region as described above.

In one embodiment, the invention provides an isolated polynucleotide encoding a heavy chain and/or a light chain as described above.

In one embodiment, the invention provides an isolated polynucleotide encoding a heavy chain variable region comprising the amino acid sequence of any one of SEQ ID NOs: 100, 101, 102, 103, 104, 105, 110, 111, 112, 113, 114, 115, 116, 117, 104, 118, 119, 120, 121, 122, 123, 124, or 221.

In one embodiment, the invention provides an isolated polynucleotide encoding a light chain variable region comprising the amino acid sequence of any one of SEQ ID NOs: 105, 106, 107, 108, 109, 125, 126, 109, 127, 128, 129, 130, or 222.

In one embodiment, the invention provides an isolated polynucleotide encoding a heavy chain variable region comprising the amino acid sequence of any one of SEQ ID NOs: 100, 101, 102, 103, 104, 105, 110, 111, 112, 113, 114, 115, 116, 117, 104, 118, 119, 120, 121, 122, 123, 124, or 221; and an isolated polynucleotide encoding a light chain variable region comprising the amino acid sequence of any one of SEQ ID NOs: 105, 106, 107, 108, 109, 125, 126, 109, 127, 128, 129, 130, or 222.

In one embodiment, the invention provides an isolated polynucleotide encoding a heavy chain region comprising the amino acid sequence of any one of SEQ NO: 131, 138, 139, 140, 141, 142, 143, 144, 145, 146, 147, 148, 149, 150, 151, 152, 217, 135, 153, 154, 156, 157, 158, 159, 160, 161, 162, 163, 164, 165, 166, 167, 168, 169, 170, 171, 172, 173, 219, 133, 134, 137, 132, or 136.

In one embodiment, the invention provides an isolated polynucleotide encoding of a light chain region comprising the amino acid sequence of any one any one of SEQ NO: 174, 181, 182, 183, 184, 185, 186, 187, 188, 189, 190, 191, 192, 193, 194, 195, 218, 178, 196, 197, 198, 199, 200, 201, 202, 203, 204, 205, 206, 207, 208, 209, 210, 211, 212, 213, 214, 215, 216, 220, 176, 177, 180, 175, or 179.

In one embodiment, the invention provides an isolated polynucleotide encoding a heavy chain region comprising the amino acid sequence of any one of SEQ NO: 131, 138, 139, 140, 141, 142, 143, 144, 145, 146, 147, 148, 149, 150, 151, 152, 217, 135, 153, 154, 156, 157, 158, 159, 160, 161, 162, 163, 164, 165, 166, 167, 168, 169, 170, 171, 172, 173, 219, 133, 134, 137, 132, or 136; and an isolated polynucleotide encoding of a light chain region comprising the amino acid sequence of any one any one of SEQ NO: 174, 181, 182, 183, 184, 185, 186, 187, 188, 189, 190, 191, 192, 193, 194, 195, 218, 178, 196, 197, 198, 199, 200, 201, 202, 203, 204, 205, 206, 207, 208, 209, 210, 211, 212, 213, 214, 215, 216, 220, 176, 177, 180, 175, or 179.

In one embodiment, the invention provides an expression vector comprising a polynucleotide as described above.

In one embodiment, the invention provides an expression vector comprising a polynucleotide encoding a heavy chain variable region comprising the amino acid sequence of any one of SEQ ID NOs: 100, 101, 102, 103, 104, 105, 110, 111, 112, 113, 114, 115, 116, 117, 104, 118, 119, 120, 121, 122, 123, 124, or 221.

In one embodiment, the invention provides an expression vector comprising a polynucleotide encoding a light chain variable region comprising the amino acid sequence of any one of SEQ ID NOs: 105, 106, 107, 108, 109, 125, 126, 109, 127, 128, 129, 130, or 222.

In one embodiment, the invention provides an expression vector comprising a polynucleotide encoding a heavy chain variable region comprising the amino acid sequence of any one of SEQ ID NOs: 100, 101, 102, 103, 104, 105, 110, 111, 112, 113, 114, 115, 116, 117, 104, 118, 119, 120, 121, 122, 123, 124, or 221; and a polynucleotide encoding a light chain variable region comprising the amino acid sequence of any one of SEQ ID NOs: 105, 106, 107, 108, 109, 125, 126, 109, 127, 128, 129, 130, or 222.

In one embodiment, the invention provides an expression vector comprising a polynucleotide encoding a heavy chain region comprising the amino acid sequence of any one of SEQ NO: 131, 138, 139, 140, 141, 142, 143, 144, 145, 146, 147, 148, 149, 150, 151, 152, 217, 135, 153, 154, 156, 157, 158, 159, 160, 161, 162, 163, 164, 165, 166, 167, 168, 169, 170, 171, 172, 173, 219, 133, 134, 137, 132, or 136.

In one embodiment, the invention provides an expression vector comprising a polynucleotide encoding of a light chain region comprising the amino acid sequence of any one any one of SEQ NO: 174, 181, 182, 183, 184, 185, 186, 187, 188, 189, 190, 191, 192, 193, 194, 195, 218, 178, 196, 197, 198, 199, 200, 201, 202, 203, 204, 205, 206, 207, 208, 209, 210, 211, 212, 213, 214, 215, 216, 220, 176, 177, 180, 175, or 179.

In one embodiment, the invention provides an expression vector comprising a polynucleotide encoding a heavy chain region comprising the amino acid sequence of any one of SEQ NO: 131, 138, 139, 140, 141, 142, 143, 144, 145, 146, 147, 148, 149, 150, 151, 152, 217, 135, 153, 154, 156, 157, 158, 159, 160, 161, 162, 163, 164, 165, 166, 167, 168, 169, 170, 171, 172, 173, 219, 133, 134, 137, 132, or 136; and a polynucleotide encoding of a light chain region comprising the amino acid sequence of any one any one of SEQ NO: 174, 181, 182, 183, 184, 185, 186, 187, 188, 189, 190, 191, 192, 193, 194, 195, 218, 178, 196, 197, 198, 199, 200, 201, 202, 203, 204, 205, 206, 207, 208, 209, 210, 211, 212, 213, 214, 215, 216, 220, 176, 177, 180, 175, or 179.

In one embodiment, the invention provides a host cell comprising an expression vector as described above. In one embodiment, the host cell is a mammalian cell.

In one embodiment, the invention provides a method of manufacturing an antibody or antigen-binding fragment thereof comprising the steps of:
  culturing a host cell comprising an expression vector comprising an isolated polynucleotide encoding a heavy chain variable region as described above and an expression vector comprising polynucleotide encoding light chain variable region as described above under conditions that allow formation of an antibody or antigen-binding fragment thereof comprising both the heavy and light chain variable region, and
  recovering said antibody or antigen-binding fragment thereof.

In one embodiment, the invention provides a method of manufacturing an antibody or antigen-binding fragment thereof comprising the steps of:
  culturing a host cell comprising an expression vector comprising an isolated polynucleotide encoding a heavy chain as described above and comprising a polynucleotide encoding light chain as described above under conditions that allow formation of an antibody or antigen-binding fragment thereof comprising both the heavy and light chain variable region; and recovering said antibody or antigen-binding fragment thereof.

In one embodiment, a method above further comprises the step of purifying the antibody or antigen-binding fragment thereof. In one embodiment, a method above further comprises the step of formulating the antibody or antigen-binding fragment thereof into a pharmaceutical composition. Also provided herein are pharmaceutical formulations comprising an anti-SIRPα antibody or an antigen-binding fragment thereof as disclosed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The summary, as well as the following detailed description, is further understood when read in conjunction with the appended drawings. For the purpose of illustrating the disclosed compositions, methods, and kits there are shown in the drawings exemplary embodiments of methods and kits; however, these should not be limited to the specific embodiments disclosed.

FIG. 1A. Antibody binding to parental CHO cells. FIG. 1B. Antibody binding to CHO cells expressing full-length human SIRPαV1 (NP_542970.1). FIG. 1C. Antibody binding to CHO cells expressing full-length human SIRPαV2-expressing CHO cells (CAA71403.1).

FIG. 2A. Antibody binding to U-937 human monocytic cell line. FIG. 2B. Antibody binding to THP-1 human monocytic cell line.

16D). Solid, dashed, and dotted lines indicate antibody molecules engineered on hIgG1 (LALA), hIgG4P, hIgG1 (K322A) backbones, respectively.

Figure 17A:
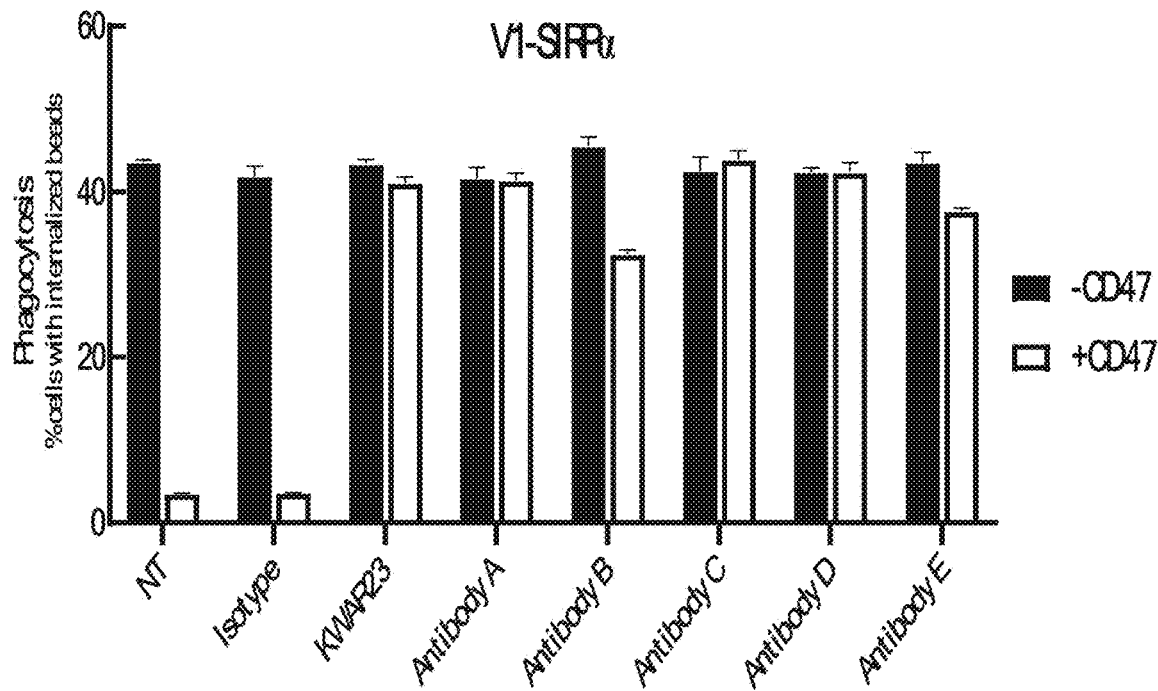
Figure 17B:
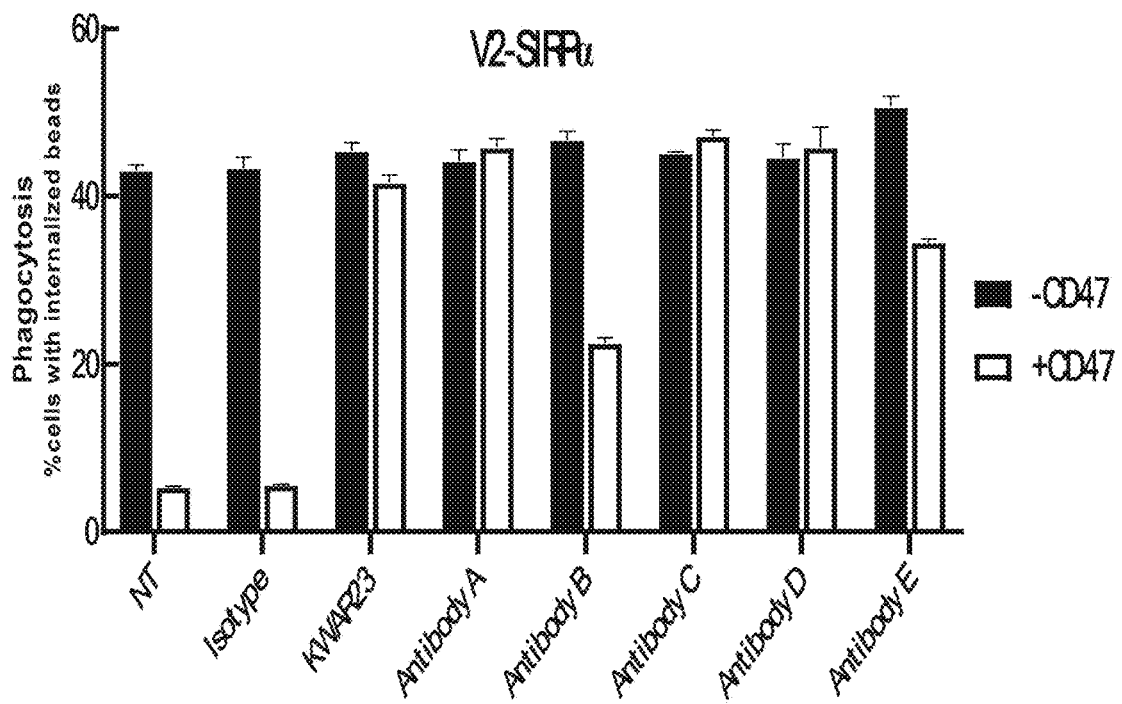

FIG. 17A and FIG. 17B are series of histograms showing that CD47-mediated inhibition of phagocytosis by human monocytic cell lines can be restored by anti-SIRPα antibodies. Anti-SIRPα antibodies restore (FIG. 17A) V1- and (FIG. 17B) V2-SIRPα expressing U937$^{SIRPα\ KO}$ cell's ability to phagocytize CD47-coated beads.

Figure 18A:
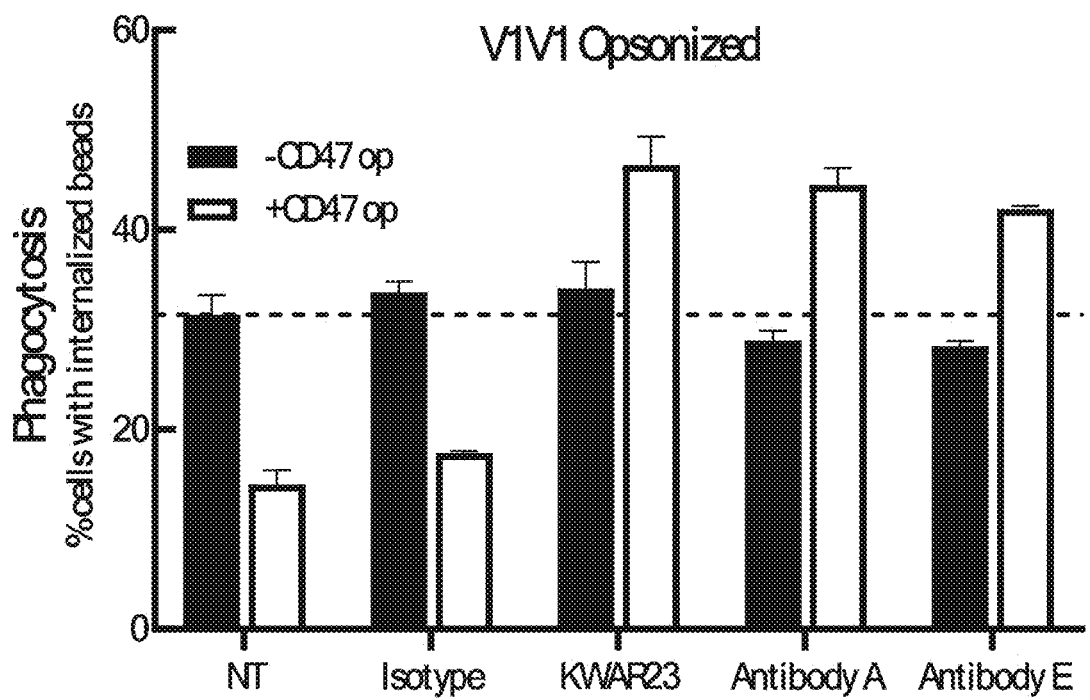
Figure 18B:
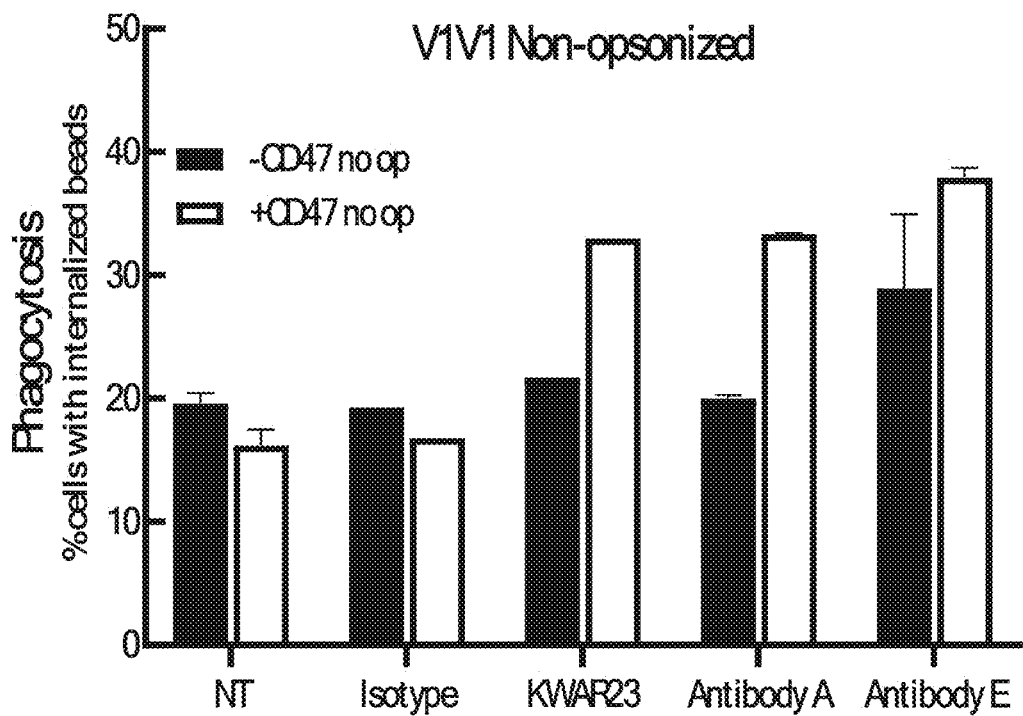
Figure 18C:
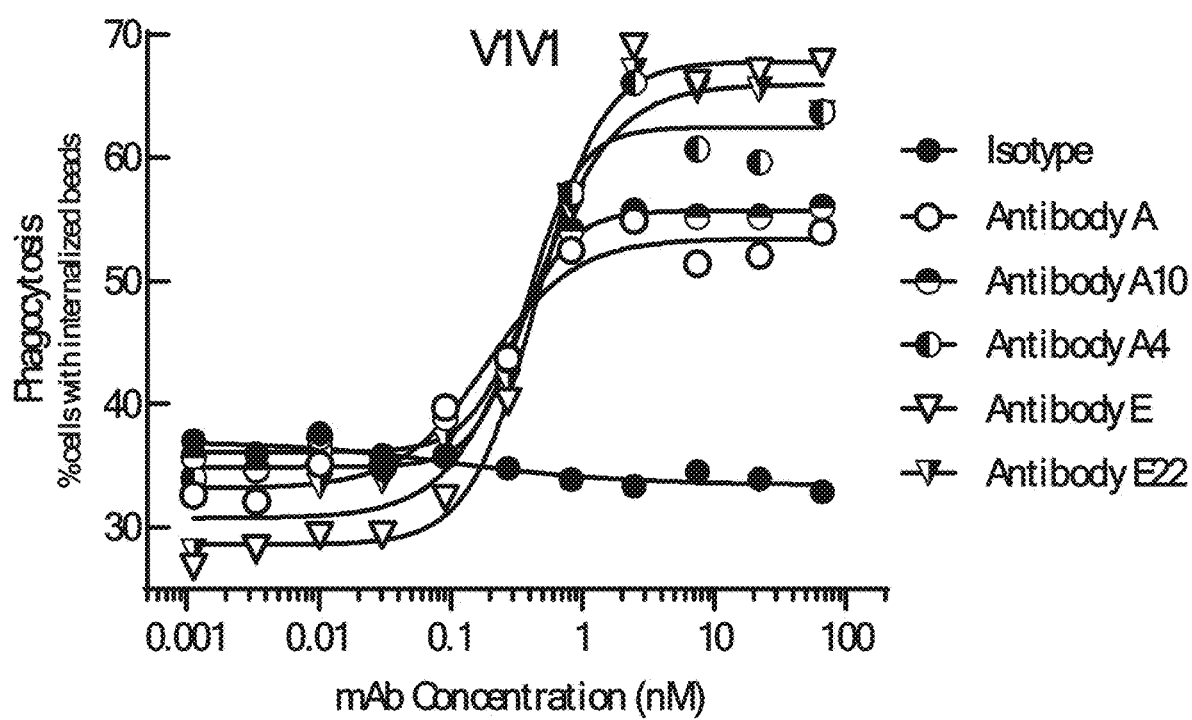

FIGS. 18A-18O are series of histograms and a graph demonstrating that anti-SIRPα antibodies restore CD47-mediated inhibition of phagocytosis by primary human macrophages derived from donors homozygous for V1-SIRPα allele. FIG. 18A. SIRPα antagonists restore monocyte-derived macrophage ability to phagocytize opsonized CD47-coated beads. FIG. 18B. SIRPα antagonists enhance monocyte-derived macrophage ability to phagocytize non-opsonized CD47-coated beads. FIG. 18C. SIRPα antagonists dose-dependently restores monocyte-derived macrophage ability to phagocytize opsonized CD47-coated beads.

Figure 19A:
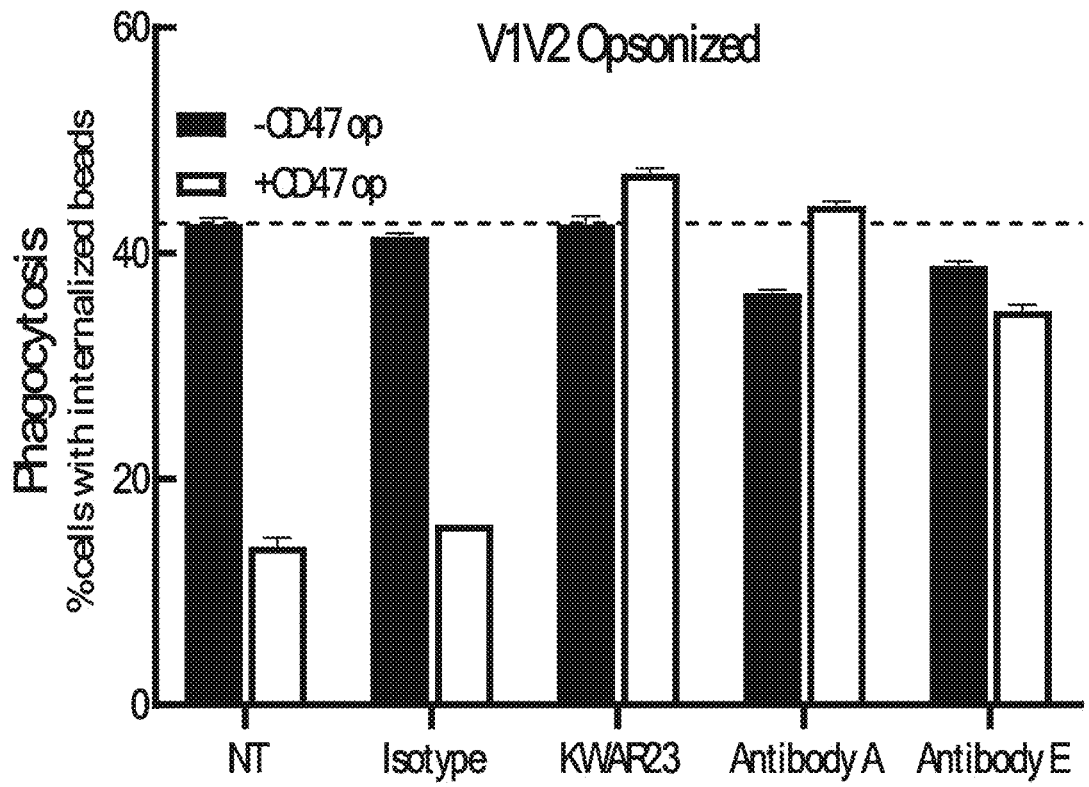
Figure 19B:
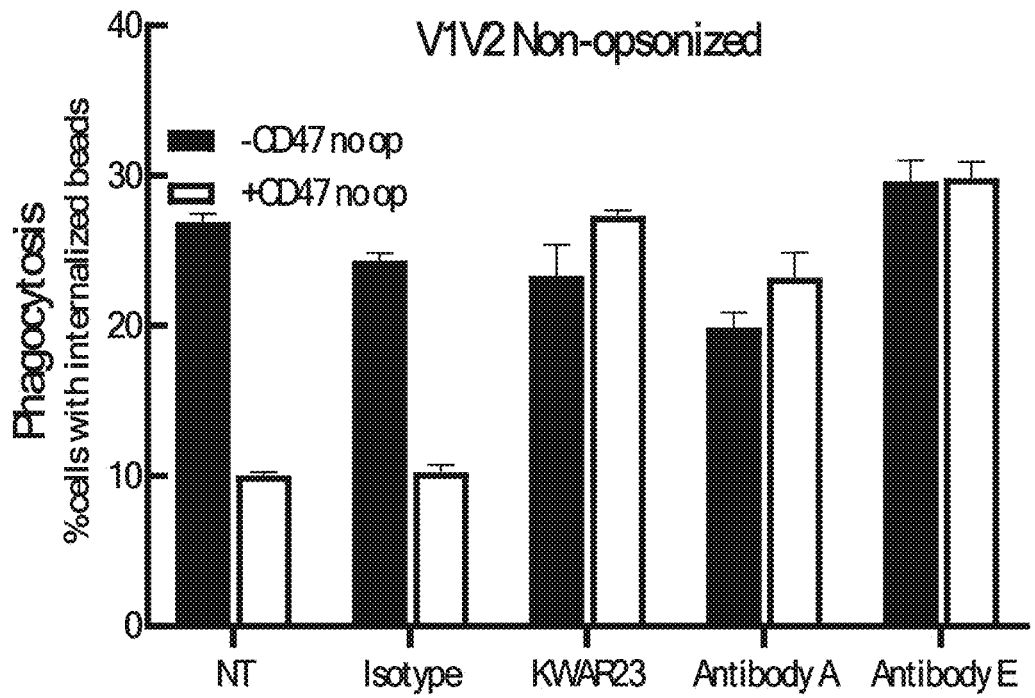
Figure 19C:
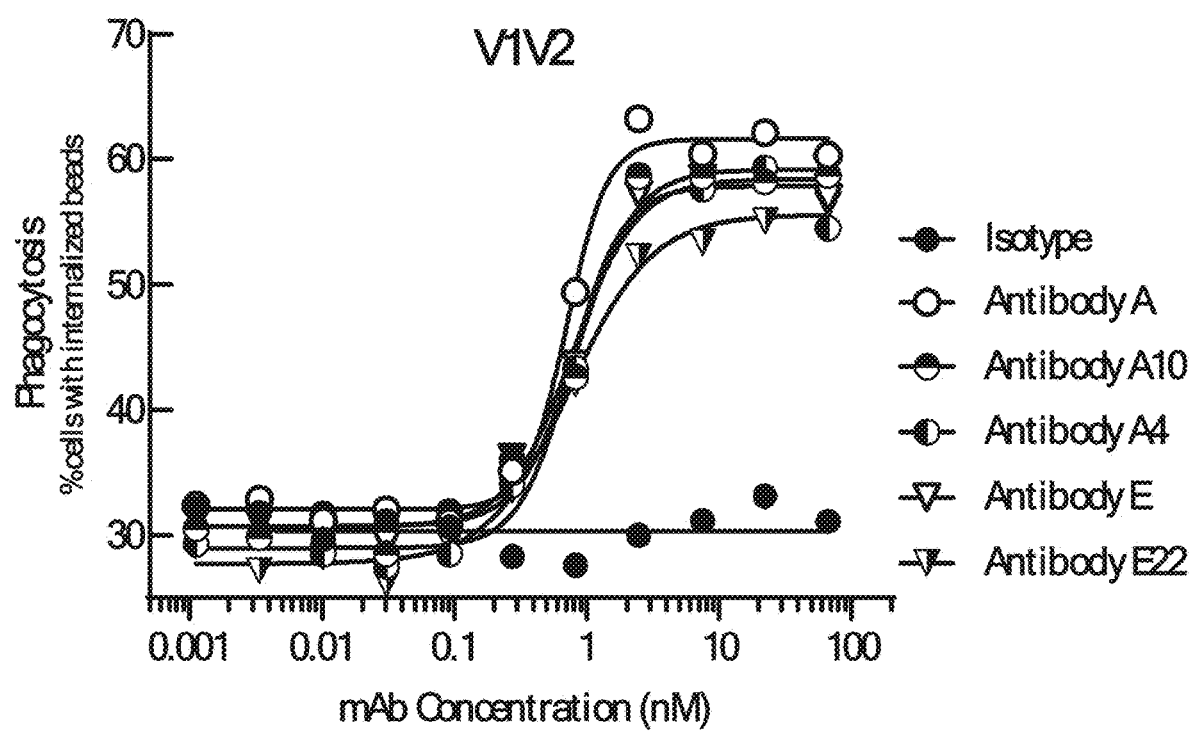

FIGS. 19A-19C are series of histograms and a graph demonstrating that anti-SIRPα antibodies restore CD47-mediated inhibition of phagocytosis by primary human macrophages derived from donors heterozygous for V1- and V2-SIRPα allele. FIG. 19A. SIRPα antagonists restore monocyte-derived macrophage ability to phagocytize opsonized CD47-coated beads. FIG. 19B. SIRPα antagonists restore monocyte-derived macrophage ability to phagocytize non-opsonized CD47-coated beads. FIG. 19C. SIRPα antagonists dose-dependently restores monocyte-derived macrophage ability to phagocytize opsonized CD47-coated beads.

Figure 20A:
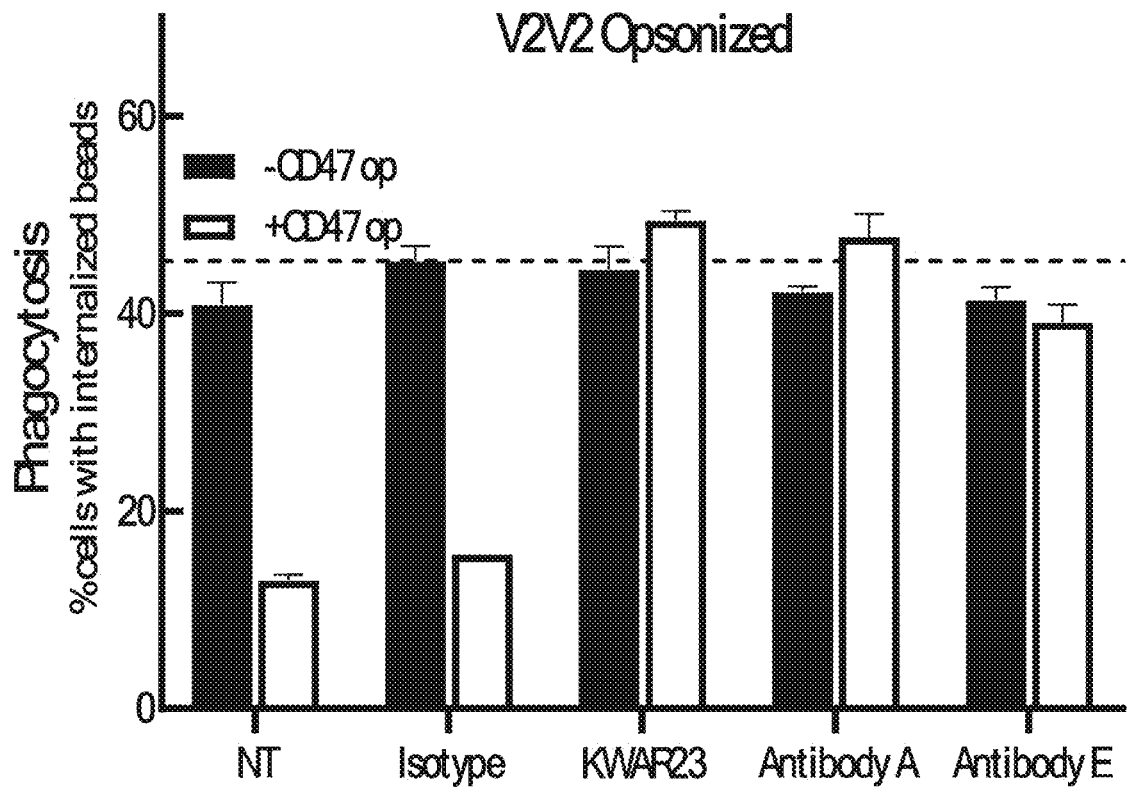
Figure 20B:
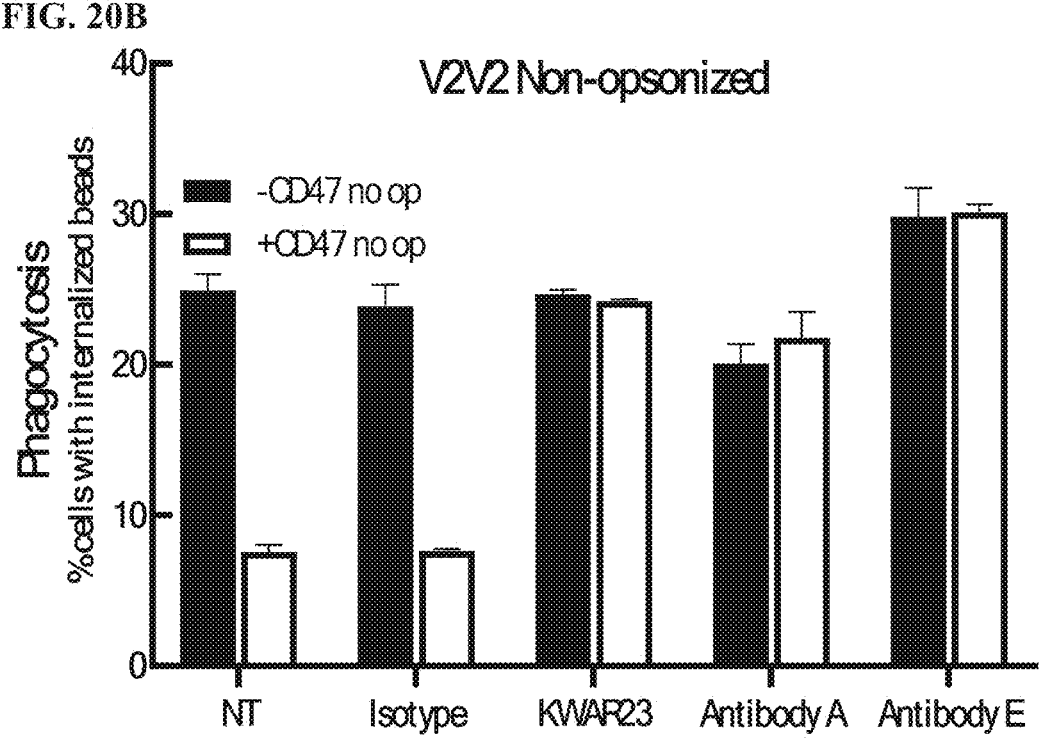
Figure 20C:
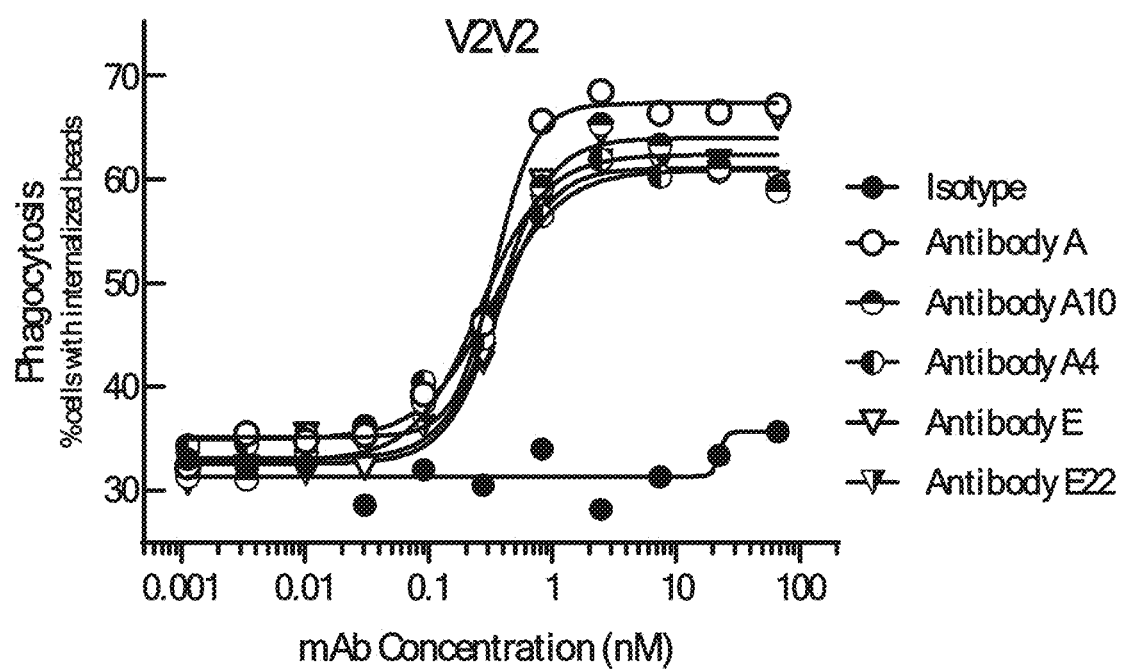

FIGS. 20A-20C are series of histograms and a graph demonstrating that anti-SIRPα antibodies restore CD47-mediated inhibition of phagocytosis by primary human macrophages derived from donors homozygous for V2-SIRPα allele. FIG. 20A. SIRPα antagonists restore monocyte-derived macrophage ability to phagocytize opsonized CD47-coated beads. FIG. 20B. SIRPα antagonists restore monocyte-derived macrophage ability to phagocytize non-opsonized CD47-coated beads. FIG. 20C. SIRPα antagonists dose-dependently restores monocyte-derived macrophage ability to phagocytize opsonized CD47-coated beads.

Figure 21A:
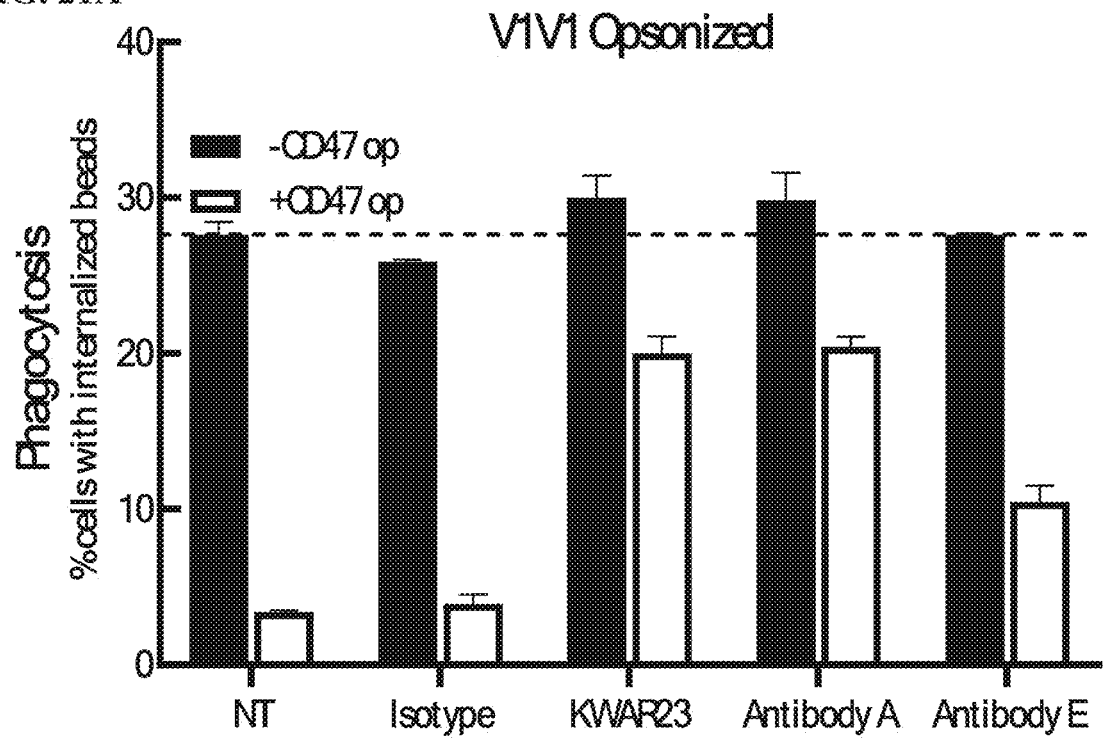
Figure 21B:
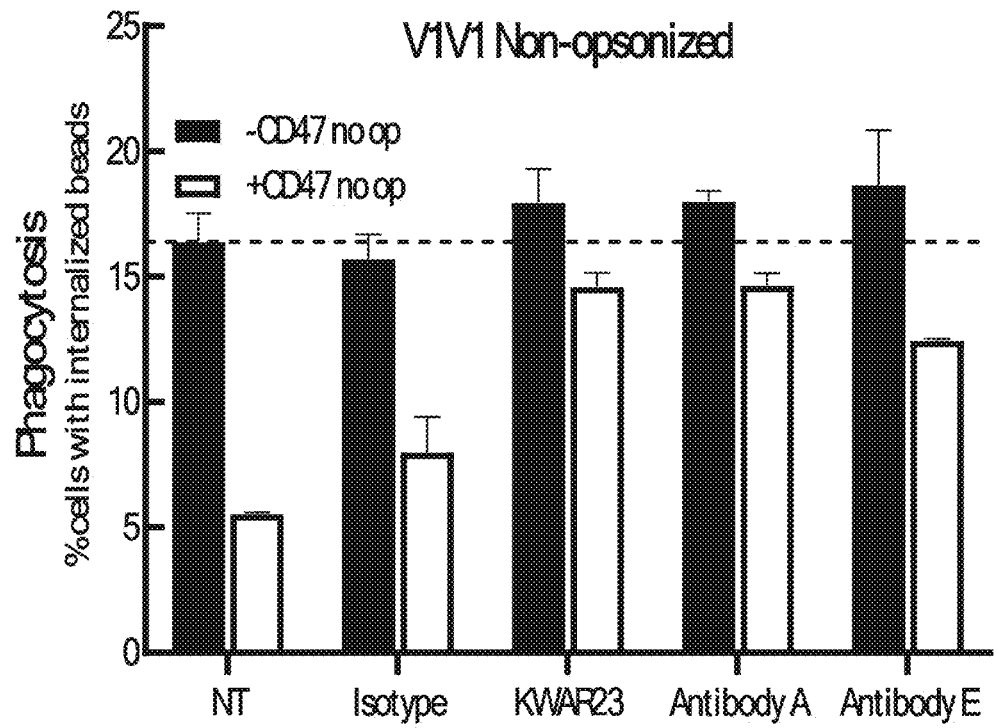

FIG. 21A and FIG. 21B are series of histograms showing that anti-SIRPα antibodies restore CD47-mediated inhibition of phagocytosis by primary human dendritic cells derived from donors homozygous for V1-SIRPα allele. FIG. 21A. SIRPα antagonists restore monocyte-derived dendritic cells' ability to phagocytize opsonized CD47-coated beads. FIG. 21B. SIRPα antagonists restore monocyte-derived dendritic cells' ability to phagocytize non-opsonized CD47-coated beads.

Figure 22A:
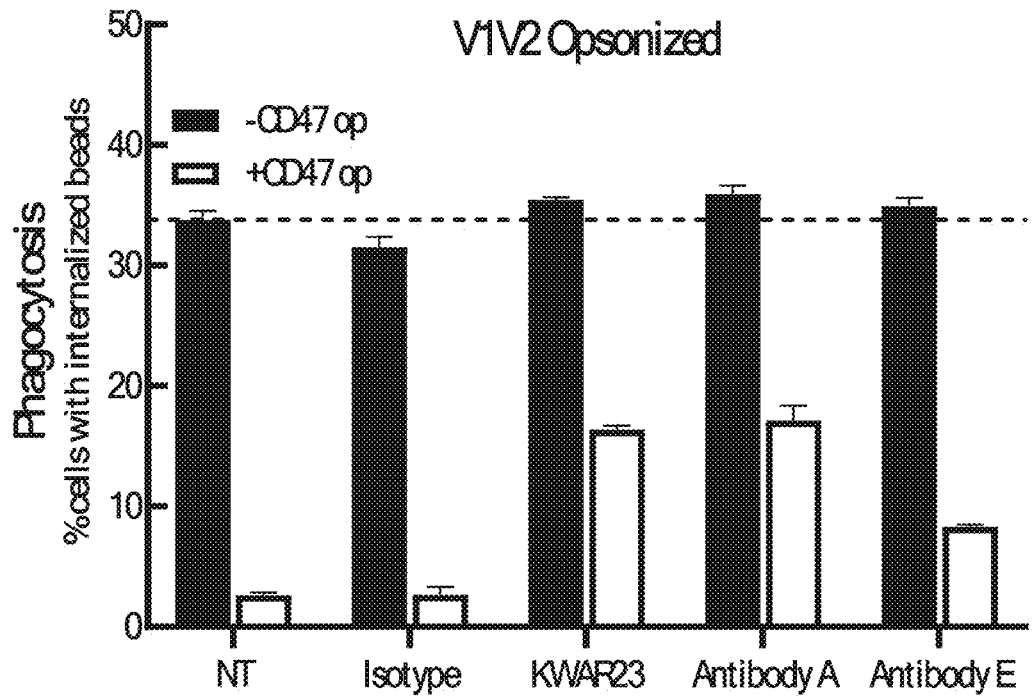
Figure 22B:
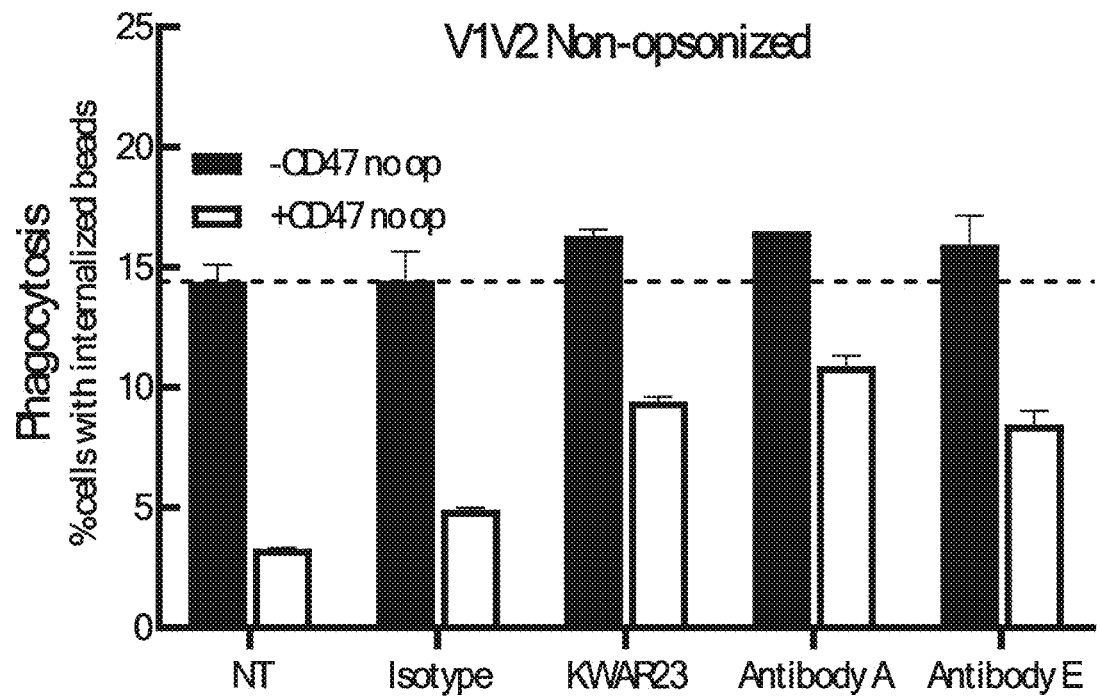

FIG. 22A and FIG. 22B are series of histograms showing that anti-SIRPα antibodies restore CD47-mediated inhibition of phagocytosis by primary human dendritic cells derived from donors heterozygous for V1- and V2-SIRPα allele. FIG. 22A. SIRPα antagonists restore monocyte-derived dendritic cells' ability to phagocytize opsonized CD47-coated beads. FIG. 22B. SIRPα antagonists restore monocyte-derived dendritic cells' ability to phagocytize non-opsonized CD47-coated beads.

Figure 23A:
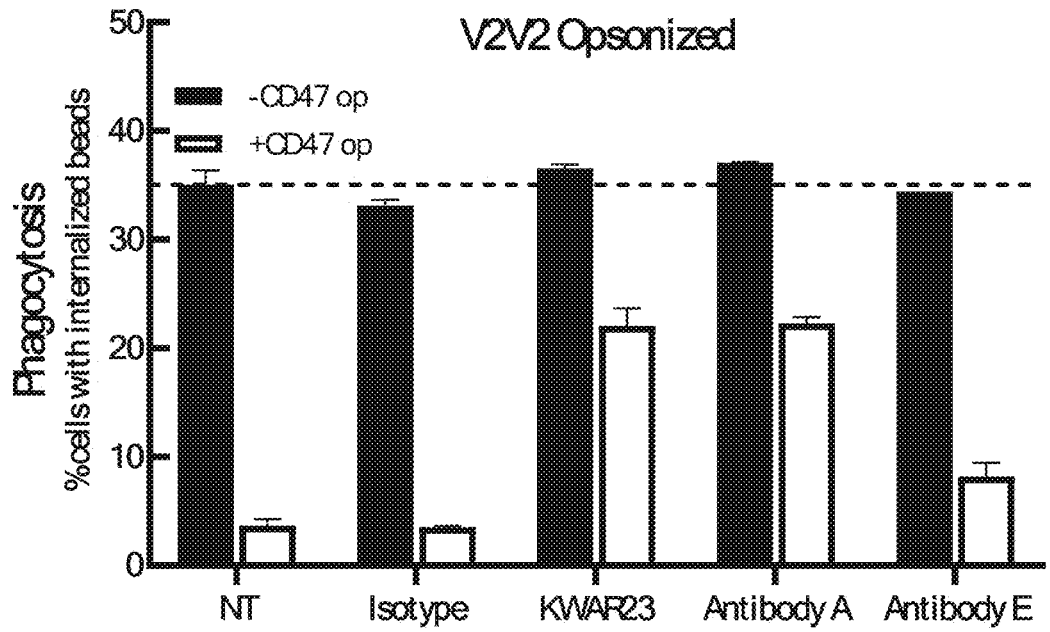
Figure 23B:
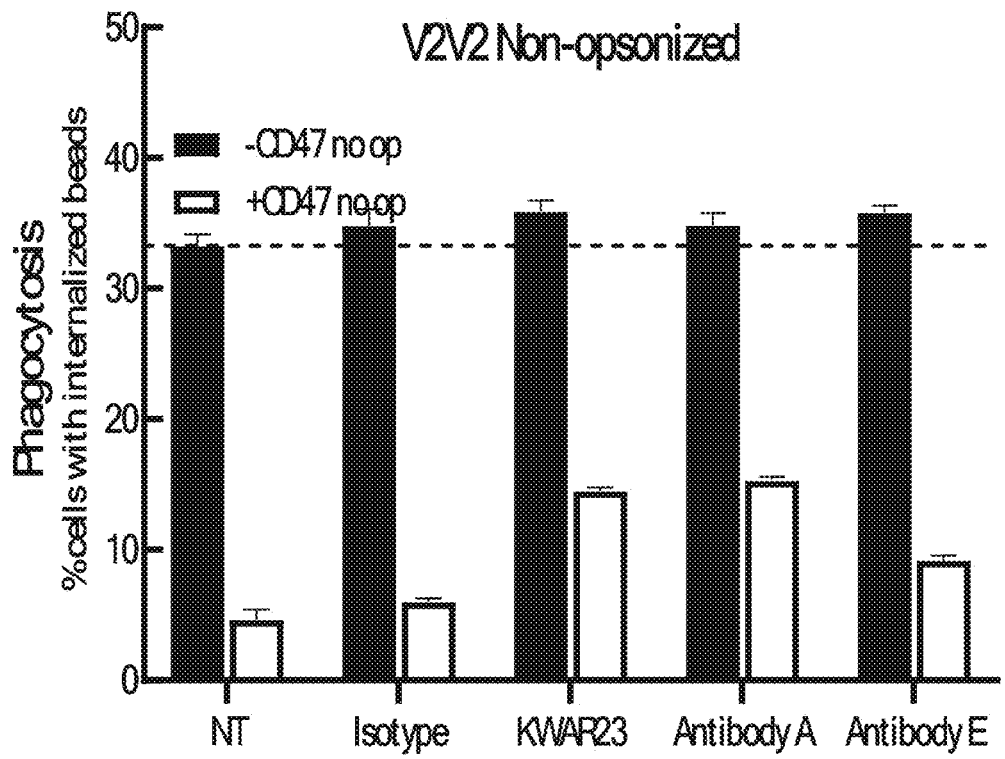

FIG. 23A and FIG. 23B are series of histograms showing that anti-SIRPα antibodies restore CD47-mediated inhibition of phagocytosis by primary human dendritic cells derived from donors homozygous for V2-SIRPα allele. FIG. 23A. SIRPα antagonists restore monocyte-derived dendritic cells' ability to phagocytize opsonized CD47-coated beads. FIG. 23B. SIRPα antagonists restore monocyte-derived dendritic cells' ability to phagocytize non-opsonized CD47-coated beads.

Figure 24A:
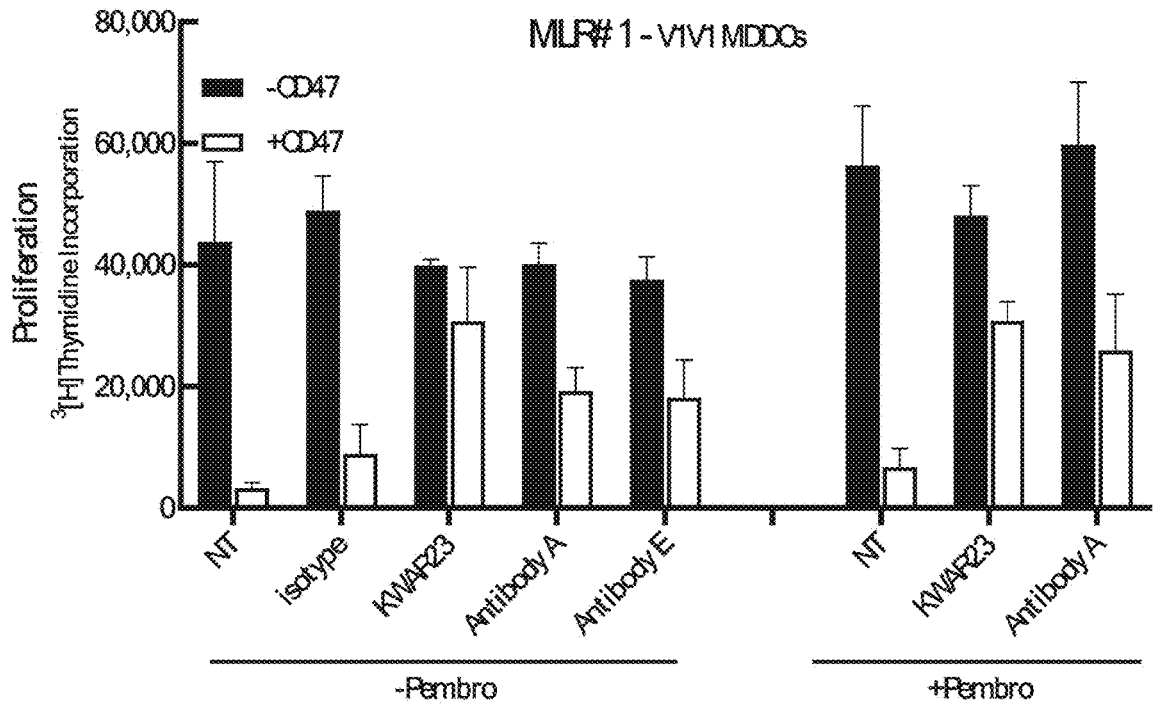
Figure 24B:
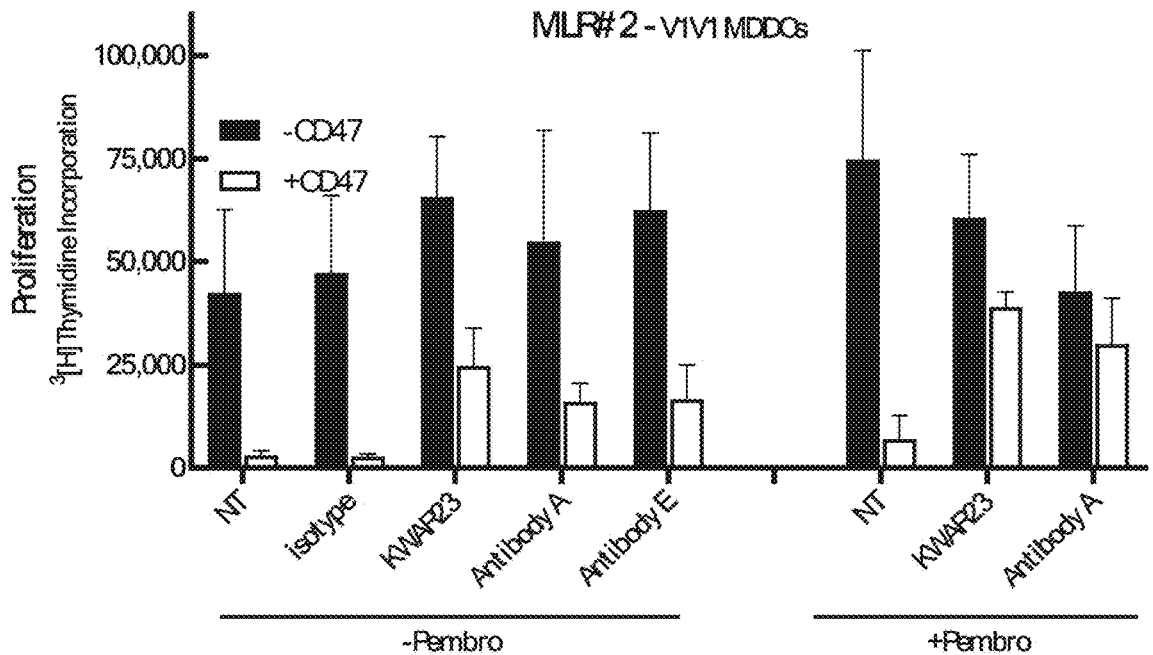

FIG. 24A and FIG. 24B are series of histograms showing that anti-SIRPα antibodies restore human CD47-mediated inhibition of MLR. Human CD47-Fc mediated immunosuppression of MLR partially restored by anti-SIRPα mAb alone or in combination with anti-PD1 antagonist, pembrolizumab (FIG. 24A and FIG. 24B).

Figure 25A:
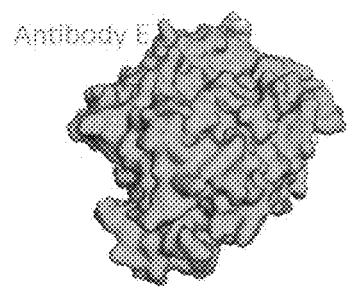
Figure 25B:
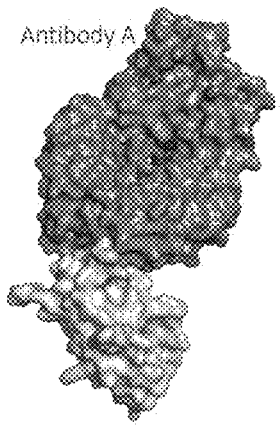
Figure 25C:
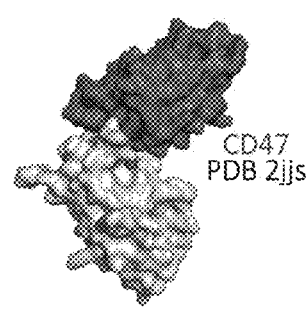
Figure 25D:
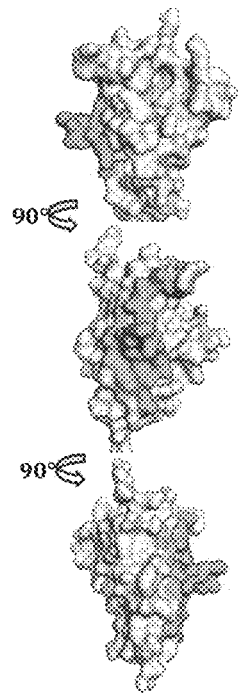
Figure 25E:
Figure 25F:
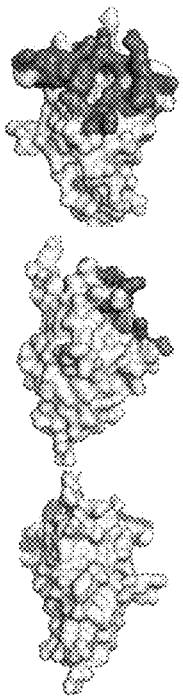

FIGS. 25A-25F are series of images depicting the epitopes recognized by anti-SIRPα antibodies. Structures of Fab fragments of Antibody E (FIG. 25A) or Antibody A (FIG. 25B) bound to domain 1 of the extracellular domain of human SIRPα-V2 (residues 1 to 115). FIG. 25C. Structure of CD47 (in dark grey) bound to domain 1 of the extracellular domain of human SIRPα-V2 (PDB: 2JJS). FIGS. 25D-25F: structure of domain 1 of the extracellular domain of human SIRPα-V2 highlighting the residues contacted by the Fab fragment of Antibody E (FIG. 25D), by the Fab fragment of Antibody A (FIG. 25E), or human CD47 (FIG. 25F).

FIG. 26A and FIG. 26B are series of images depicting epitopes of Antibody A::SIRPα_V2 complex and Antibody E::SIRPα_V2 complex based on crystal structures. FIG. 26A depicts SIRPαV2 shown in light grey as stick representation and residues of Antibody A shown in dark grey by atom type. SIRPαV1 residues comprising atoms in a distance <4.5 Å to Fab fragments of Antibody A are marked and extended by column to the sequences of SIRPαV1 and SIRPγ, aligned by sequence with the program MOE. The interaction of SIRPαV2 D130 is highlighted as a major difference to SIRPγ, where this residue is a glutamate. FIG. 26B depicts SIRPαV2 shown in light grey as stick representation and residues and surface of Antibody E shown in dark grey by atom type. SIRPαV1 residues comprising atoms in a distance <4.5 Å to Fab fragments of Antibody E are marked and extended by column to the sequences of SIRPαV1 and SIRPγ aligned by sequence with the program MOE. The interaction of SIRPαV2 A72 is highlighted as a major difference to SIRPγ, where this residue is comprised of the larger amino acid valine.

Figure 27A:
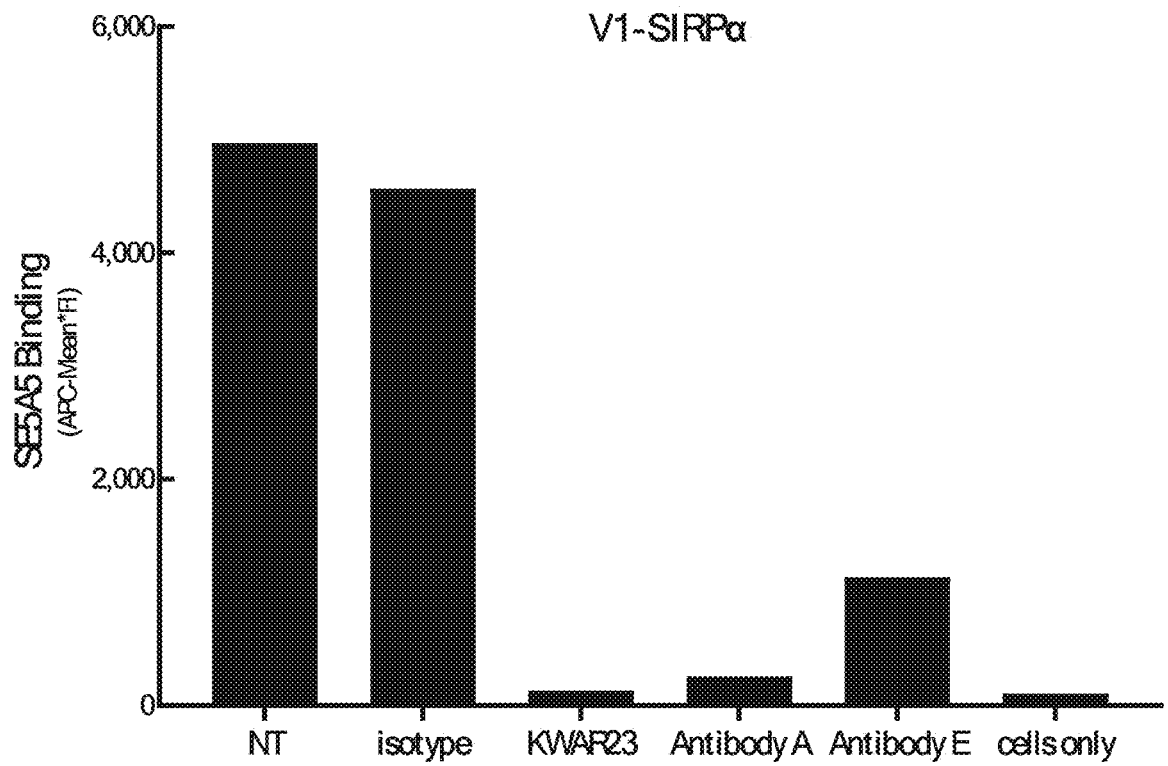
Figure 27B:
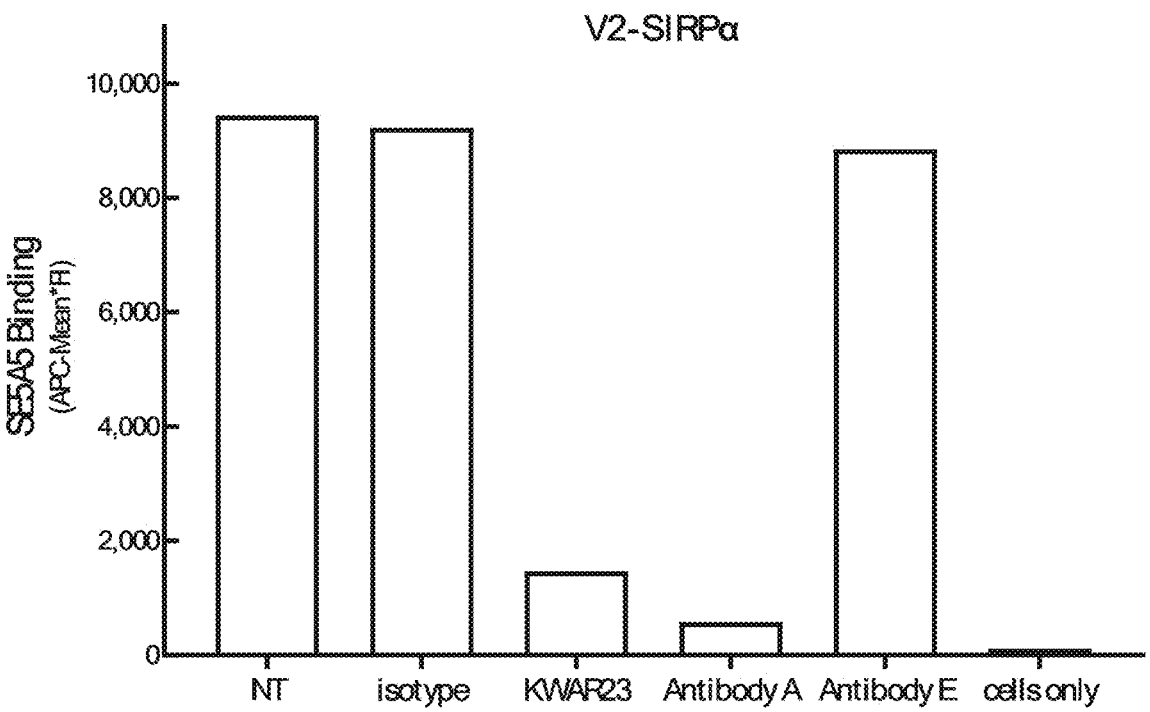

FIG. 27A and FIG. 27B, are series of histograms showing that anti-SIRPα antibodies block binding of SE5A5 to V1- or V2-expressing U-937 cells. Blockade of anti-SIRPα mAb, SE5A5, binding to (FIG. 27A) V1- or (FIG. 27B) V2-SIRPα expressing U-937 cells by anti-SIRPα antibodies.

Figure 28A:
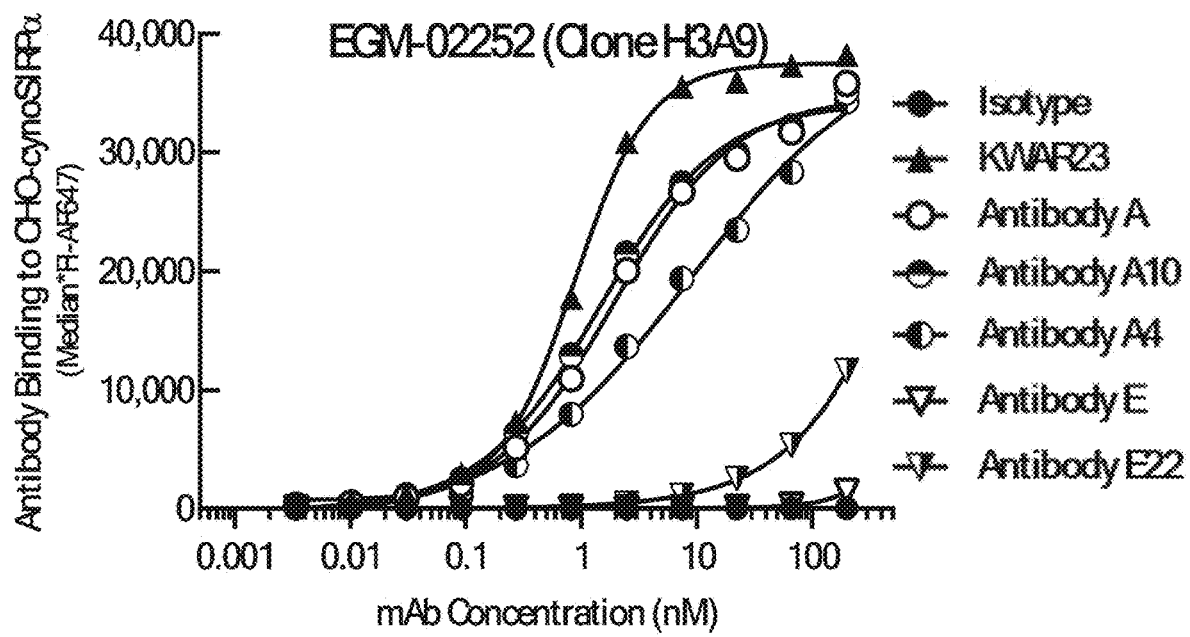
Figure 28B:
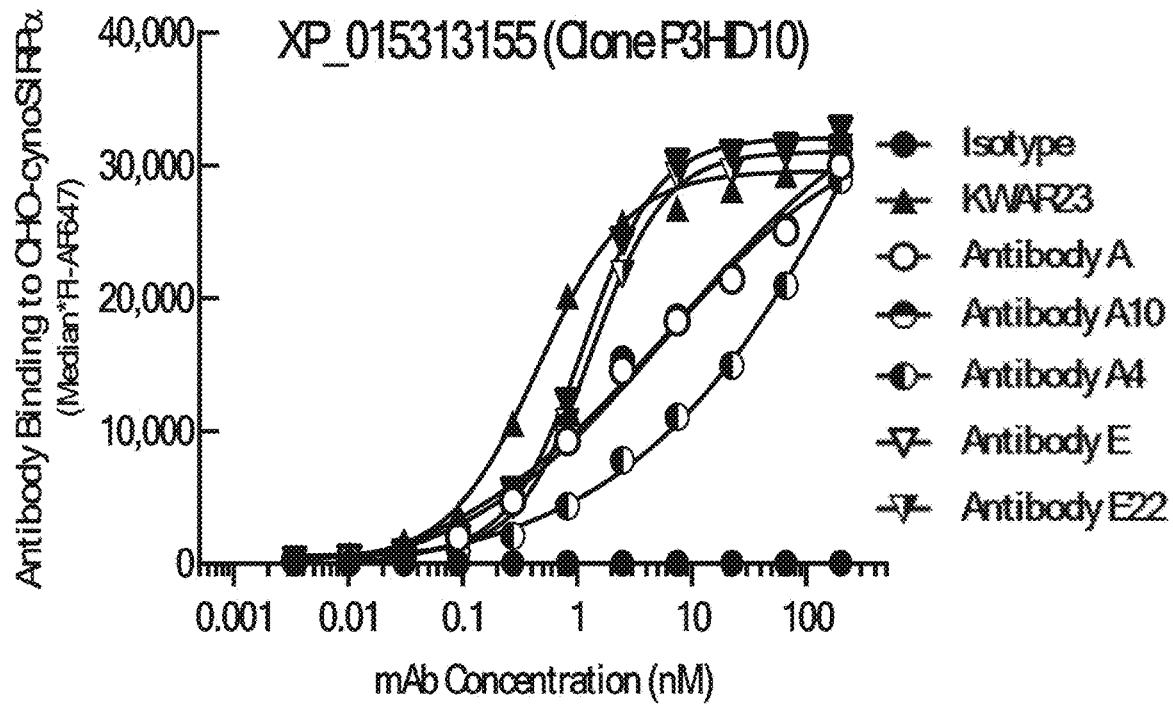
Figure 28C:
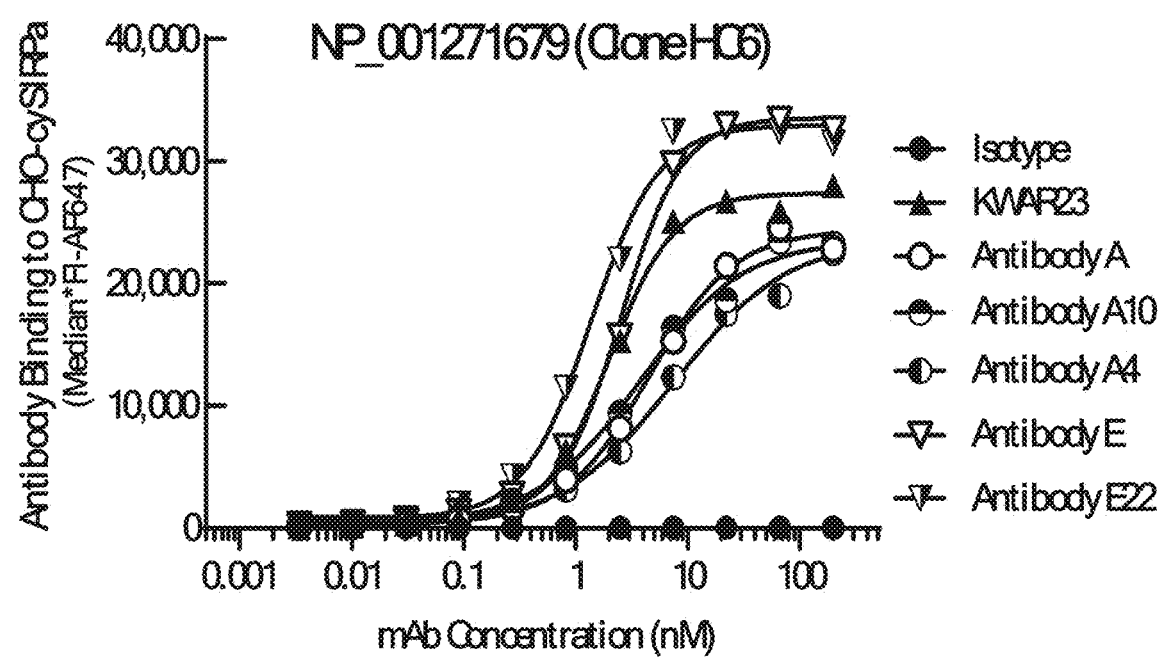

FIGS. 28A-28C are series of graphs depicting the binding of antibodies to full-length cyno SIRPα expressed on CHO cells. FIG. 28A. Antibody binding to CHO cells expressing full-length cyno SIRPα (EGM-02252, clone H3A9). FIG. 28B. Antibody binding to CHO cells expressing full-length cyno SIRPα (XP_015313155, clone P3HD10). FIG. 28C. Antibody binding to CHO cells expressing full-length cyno SIRPα (NP_001271679, clone HC6).

Figure 29A:
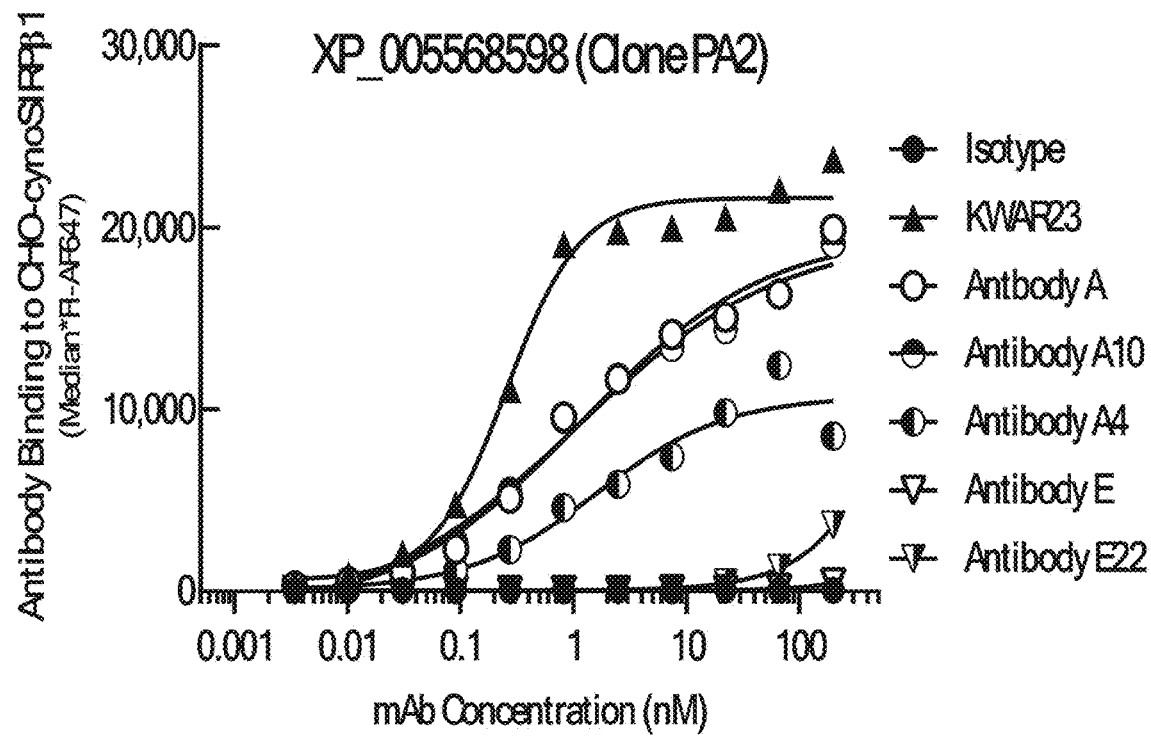
Figure 29B:
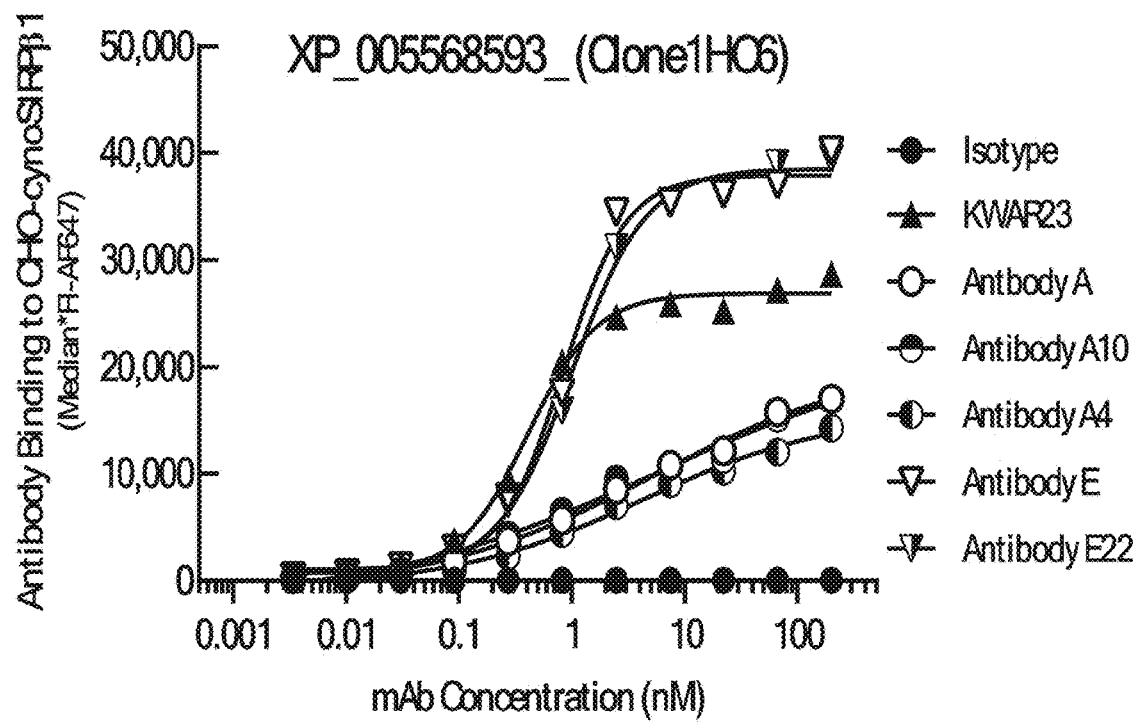

FIG. 29A and FIG. 29B are series of graphs depicting the binding of antibodies to full-length cyno SIRPβ1 expressed on CHO cells. FIG. 29A. Antibody binding to CHO cells expressing full-length cyno SIRPβ1 (XP_005568598, clone PA2). FIG. 29B. Antibody binding to CHO cells expressing full-length cyno SIRP β1v3 (XP_005568593, clone 1HC6).

Figure 30:
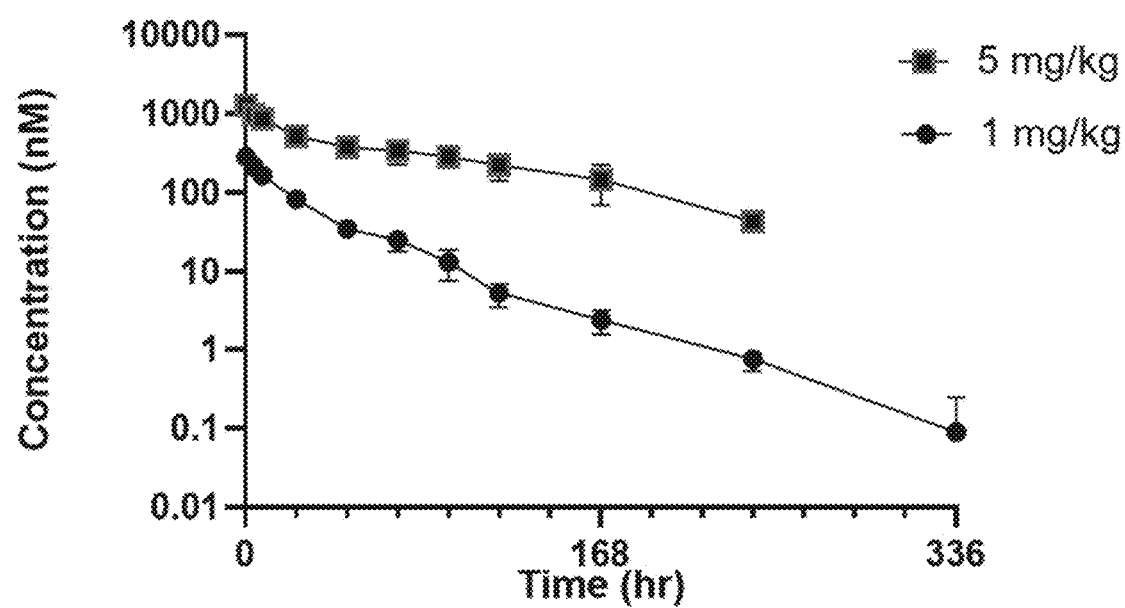

FIG. 30. Mean (SD) serum concentration-time profiles of Antibody A10 following IV administration in cynomolgus monkey at 5 mg/kg (filled squares) or 1 mg/kg (filled circles).

FIGS. 31A-31F show binding of antibodies to full-length human V1-SIRPα with various amino acid point mutations expressed on Expi-CHO cells. Results are shown for cells expressing full-length wild-type human SIRPαV1 (FIG. 31A), SIRPαV1 N→E (FIG. 31B), SIRPαV1 D→E (FIG. 31C), SIRPαV1 D→N (FIG. 31D), SIRPαV1 DD→EN (FIG. 31E), and parental CHO cells (FIG. 31F).

Figure 32A:
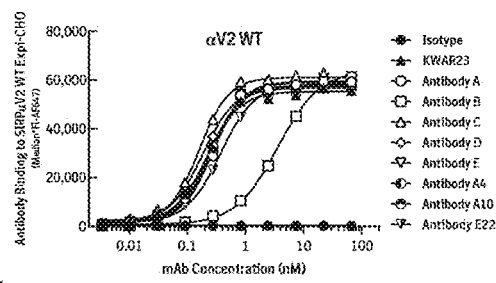
Figure 32B:
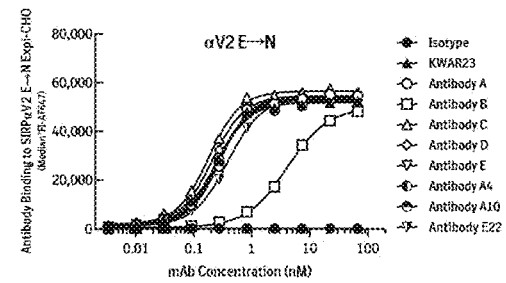
Figure 32C:
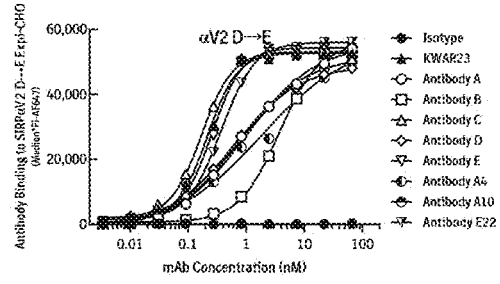

FIGS. 32A-32C show binding of antibodies to full-length human V2-SIRPα with various amino acid point mutations expressed on Expi-CHO cells. Results are shown for cells expressing full-length wild-type human SIRPαV2 (FIG. 32A), SIRPαV2 E→N (FIG. 32B), and SIRPαV2 D→E (FIG. 32C).

Figure 33A:
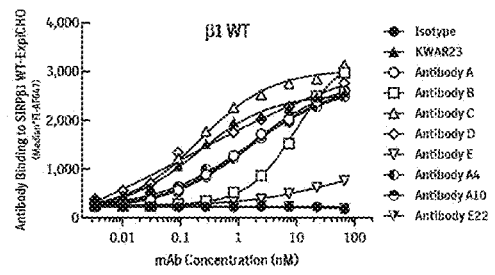
Figure 33B:
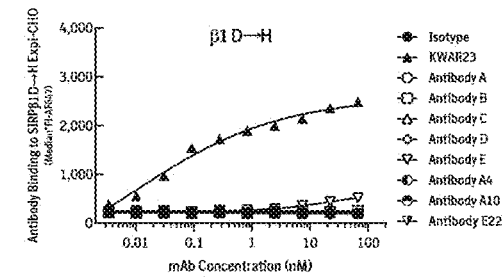

FIG. 33A and FIG. 33B show binding of antibodies to full-length human SIRPβ1 with an amino acid point mutation expressed on Expi-CHO cells. Results are shown for cells expressing full length wild-type human SIRPβ1 (FIG. 33A) and SIRPβ1 DH (FIG. 33B).

Figure 34A:
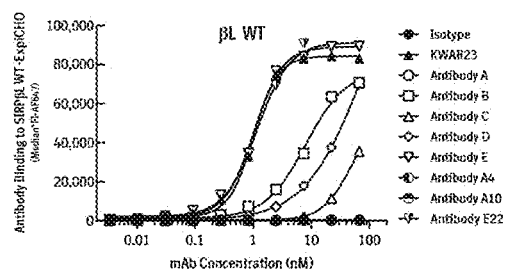
Figure 34B:
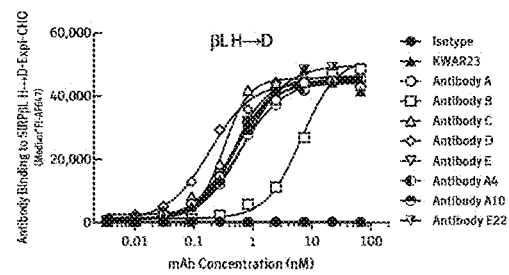

FIG. 34A and FIG. 34B show of antibodies to full-length human SIRPβL with an amino acid point mutation expressed on Expi-CHO cells. Results are shown for cells expressing wild-type SIRPβL (FIG. 34A) or SIRPβL H→D (FIG. 34B).

Figure 35A:
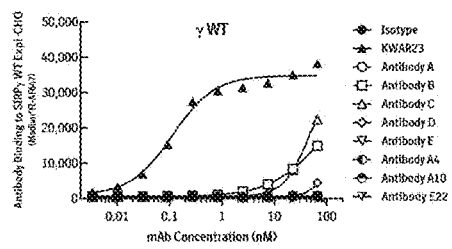
Figure 35B:
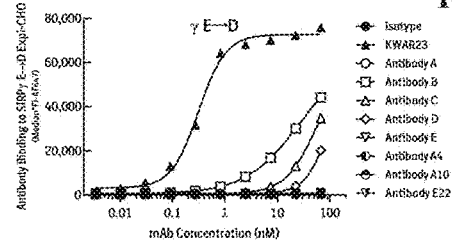
Figure 35C:
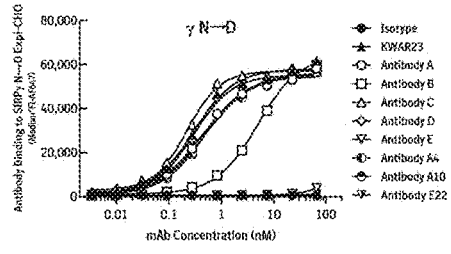
Figure 35D:
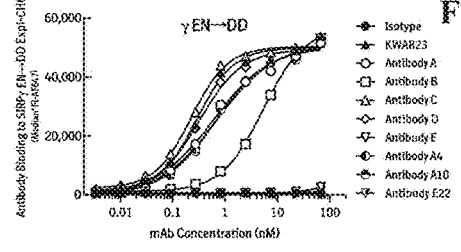

FIGS. 35A-35D show binding of antibodies to full-length human SIRPγ with various amino acid point mutations expressed on Expi-CHO cells. Results are shown for cells expressing full-length wild-type human SIRPγ (FIG. 35A), SIRPγ ED (FIG. 35B), SIRPγ ND (FIG. 35C), and SIRPγ EN→DD (FIG. 35D).

Figure 36A:
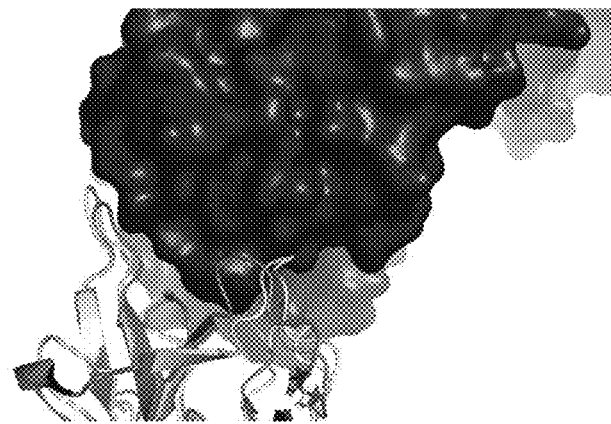

FIG. 36A. Loops of SIRPαV1 (light grey, as observed in pdbID: 4CMM), SIRPαV2 (grey, as observed in the crystal structure in complex with Antibody A) both as shown as a schematic, and Antibody A (surface in dark grey, as observed in the crystal structure in complex with SIRPαV1).

Figure 36B:
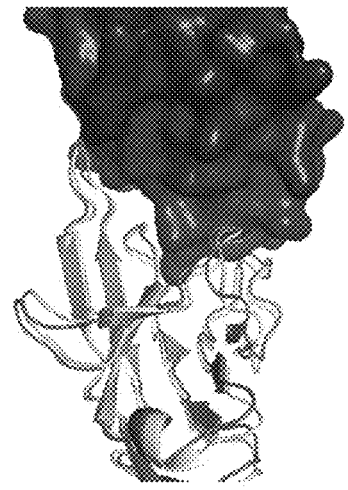
Figure 37F:
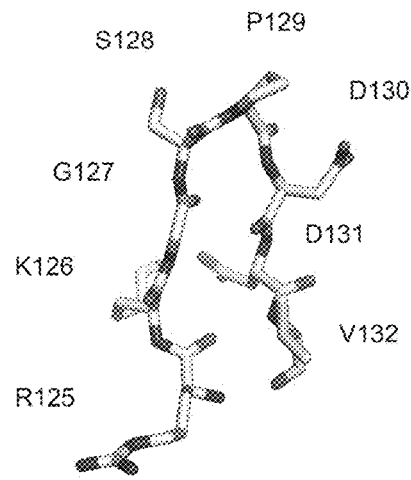
Figure 37F:
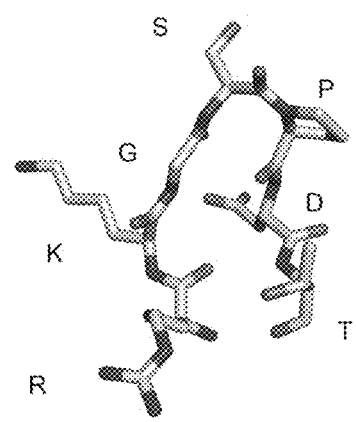
Figure 37F:
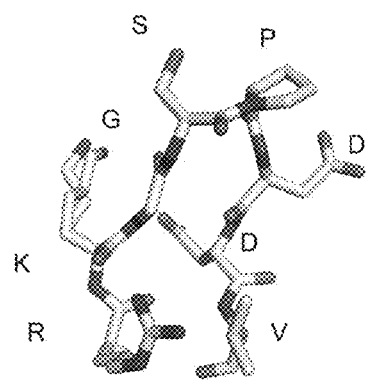
Figure 37F:
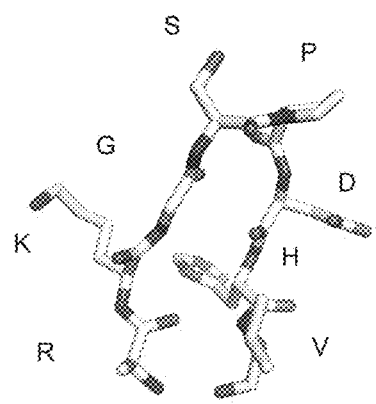
Figure 37F:
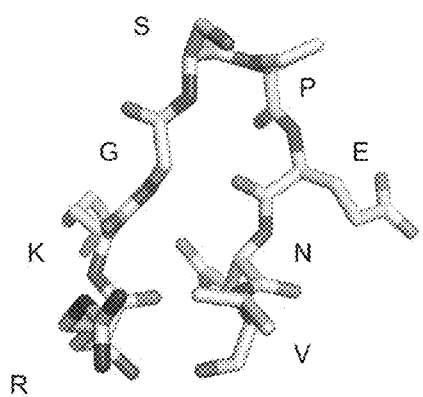

FIG. 36B. Loops of SIRPαV1 (light grey, as observed in pdbID: 4CMM), SIRPαV2 (grey, as observed in the crystal structure in complex with CD47 pdbID: 2JJS) both as shown as a schematic, and CD47 (surface in dark grey, as observed in the crystal structure in complex with SIRPαV1).

FIGS. 37A-37F. Loops of SIRP variants (light grey, color coded by atom type): conformation observed for (FIG. 37A) SIRPαV1 (pdbID: 4CMM), with numbering according to uniprot ID: P78324. (FIG. 37B) SIRPαV2 (as observed in the crystal structure in complex with Antibody A). (FIG. 37C) SIRPβ1 (pdbID: 2JJU). (FIG. 37D) SIRPβL (pdbID: 2JJV). (FIG. 37E) SIRPγ (pdbID: 2JJVV). (FIG. 37F) Comparison of sequence motifs in the respective loop, with amino acid differences from SIRPαV1 that correlate with significant loss in binding being DD→EN in case of SIRPγ and D→H in case of SIRPβL.

DETAILED DESCRIPTION OF THE INVENTION

This invention relates to anti-SIRPα antibodies or antigen-binding fragments thereof. The present invention addresses the need for treatments of conditions modulated by the CD47-mediated SIRPα signaling. In one aspect, the anti-SIRPα antibodies or antigen-binding fragments thereof of the invention are for diagnostic and/or therapeutic use, for example in a subject in need thereof such as a human.

In one aspect of the invention, the anti-SIRPα antibody or antigen-binding fragment thereof specifically binds to SIRPα, in particular human or cynomolgus monkey SIRPα, more particularly human SIRPα. In one aspect, the anti-SIRPα antibody or antigen-binding fragment thereof binds to the V1 and/or V2 alleles of human SIRPα. In one aspect of the invention, the anti-SIRPα antibody or antigen-binding fragment thereof does not bind to SIRPγ, in particular cynomolgus monkey or human SIRPγ, more particularly human SIRPγ. In one aspect of the invention, the anti-SIRPα antibody or antigen-binding fragment thereof, does not bind to rabbit, mouse, rat, or dog SIRPα.

In one aspect of the invention, the anti-SIRPα antibody or antigen-binding fragment thereof has an $EC_{50}$ of 0.1 to 100 nM, 0.1 to 50 nM, 0.1 to 25 nM, 0.1 to 10 nM, or 0.1 to 5 nM. In a further aspect of the invention, the anti-SIRPα antibody or antigen-binding fragment thereof has an $EC_{50}$ of 0.1 nM, 0.2 nM, 0.3 nM, 0.4 nM, 0.5 nM, 0.6 nM, 0.7 nM, 0.8 nM, 0.9 nM, 1 nM, 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, or 25 nM. The $EC_{50}$ may be determined by any method known in the art including for example those set forth in the Examples.

In one aspect of the invention, the anti-SIRPα antibody or antigen-binding fragment thereof has an $IC_{50}$ of 0.01 to 100 nM, 0.01 to 50 nM, 0.01 to 25 nM, 0.01 to 10 nM, or 0.01 to 5 nM. In a further aspect of the invention, the anti-SIRPα antibody or antigen-binding fragment thereof has an $IC_{50}$ of 0.01 nM, 0.02 nM, 0.03 nM, 0.04 nM, 0.05 nM, 0.06 nM, 0.07 nM, 0.08 nM, 0.09 nM, 0.1 nM, 0.2 nM, 0.3 nM, 0.4 nM, 0.5 nM, 0.6 nM, 0.7 nM, 0.8 nM, 0.9 nM, 1 nM, 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, or 25 nM. The $IC_{50}$ may be determined by any method known in the art including for example those set forth in the Examples.

In one aspect of the invention, the anti-SIRPα antibody or antigen-binding fragment thereof, binds to human SIRPα-V1 and SIRPα-V2 at a high affinity. In one aspect of the invention, the anti-SIRPα antibody or antigen-binding fragment thereof, binds to human SIRPα-V1 (e.g., human SIRPα-V1 comprising the amino acid sequence set forth in SEQ ID NO:240) at a high affinity, for example at an affinity of 20 nM or less, for example 10 nM or less, for example 5 nM of less, for example 1 nM or less. In one aspect of the invention, the anti-SIRPα antibody or antigen-binding fragment thereof, binds to human SIRPα-V2 (e.g., human SIRPα-V2 comprising the amino acid sequence set forth in SEQ ID NO:241) at a high affinity, for example at an affinity of 20 nM or less, for example 10 nM or less, for example 5 nM of less, for example 1 nM or less. In another aspect of the invention, the anti-SIRPα antibody or antigen-binding fragment thereof, binds to cynomolgus monkey SIRPα. In another aspect of the invention, the anti-SIRPα antibody or antigen-binding fragment thereof, binds to cynomolgus monkey SIRPα (e.g., cynomolgus monkey SIRPα comprising the amino acid sequence set forth in SEQ ID NO:247) at an affinity of 400 nM or less, 300 nM or less, 250 nM or less, 200 or less, 100 nM or less, or 50 nM or less. In another aspect of the invention, the anti-SIRPα antibody or antigen-binding fragment thereof binds to cynomolgus monkey SIRPα (e.g., cynomolgus monkey SIRPα comprising the amino acid sequence set forth in SEQ ID NO:248) at an affinity of 400 nM or less, 300 nM or less, 200 nM or less, or 50 nM or less. In another aspect of the invention, the anti-SIRPα antibody or antigen-binding fragment thereof binds to cynomolgus monkey SIRPα (e.g., cynomolgus monkey SIRPα comprising the amino acid sequence set forth in SEQ ID NO:249) at an affinity of 400 nM or less, 300 nM or less, 200 nM or less, or 50 nM or less.

In one aspect of the invention, the anti-SIRPα antibody or antigen-binding fragment thereof does not bind to SIRPγ, for example at an affinity of 1 μM or greater. In one aspect of the invention, the anti-SIRPα antibody or antigen-binding fragment thereof does not bind to human SIRPγ, for example does not bind to human SIRPγ at an affinity of greater than 1 µM or greater. In one aspect of the invention, the anti-SIRPα antibody or antigen-binding fragment thereof does not bind to cynomolgus monkey SIRPγ, for example does not bind to cynomolgus monkey SIRPγ at an affinity of 1 µM or greater.

In one aspect, an anti-SIRPα antibody or antigen-binding fragment thereof of the invention blocks the interaction between SIRPα and CD47. In a further aspect, an anti-SIRPα antibody or antigen-binding fragment thereof of the invention blocks CD47-mediated SIRPα signaling. In some aspects, the antibody of the invention blocks the binding of CD47 to SIRPα, whereby it decreases CD47-mediated SIRPα signaling by at by at least 80%, by at least 85%, by at least 90%, or by at least 95% when compared with a comparator antibody control or in the absence of an anti-SIRPα antibody or antigen-binding fragment of the invention. In an embodiment, the comparator antibody control comprises a heavy chain variable region comprising the amino acid sequence of any one of SEQ ID NOs: 100, 101, 102, 103, 104, 105, 110, 111, 112, 113, 114, 115, 116, 117, 104, 118, 119, 120, 121, 122, 123, 124, or 221; and a light chain variable region comprising the amino acid sequence of any one of SEQ ID NOs: 105, 106, 107, 108, 109, 125, 126, 109, 127, 128, 129, 130, or 222; or a heavy chain region comprising the amino acid sequence of any one of SEQ NO: 131,138,139, 140, 141, 142, 143, 144, 145, 146, 147, 148, 149, 150, 151, 152, 217, 135,153, 154, 156, 157, 158, 159, 160, 161, 162, 163, 164, 165, 166, 167, 168, 169, 170, 171, 172, 173, 219, 133, 134, 137, 132, or 136; and a light chain region comprising the amino acid sequence of any one any one of SEQ NO: 174, 181, 182, 183, 184, 185, 186, 187, 188, 189, 190, 191, 192, 193, 194, 195, 218, 178, 196, 197, 198, 199, 200, 201, 202, 203, 204, 205, 206, 207, 208, 209, 210, 211, 212, 213, 214, 215, 216, 220, 176, 177, 180, 175, or 179.

Whether a binding domain specifically binds to a target can be tested with various methods known in the art. These methods include, Surface Plasmon Resonance or ELISA to detect binding of antibodies to purified proteins, or flow cytometry to detect binding of antibodies to cells. The ability of an antibody to block binding of CD47 can be measured by detecting purified soluble CD47 interaction with SIRPα-expressing cells. Alternatively, the blocking activity of an antibody can be measured by assessing SIRPα phosphorylation and recruitment of SHP-1 phosphatase. The blocking activity of an anti-SIRPα antibody can also be evaluated by the capacity to restore the inhibition of phagocytosis caused by CD47. Methods for determining antibody specificity and affinity by competitive inhibition are known in the art.

In one aspect, the present invention provides an anti-SIRPα antibody, in particular a monoclonal anti-SIRPα antibody, for example a human monoclonal anti-SIRPα antibody, or a full-length human monoclonal antibody.

In one aspect, an anti-SIRPα antibody or antigen-binding fragment thereof of the present invention has favorable pharmacokinetic properties. In one aspect, an anti-SIRPα antibody of the present invention has favorable biophysical properties, for example yield, quality, stability or solubility.

Antibodies

The generalized structure of antibodies or immunoglobulin is well known to those of skill in the art, these molecules are heterotetrametric glycoproteins, typically of about 150, 000 daltons, composed of two identical light (L) chains and two identical heavy (H) chains. Each light chain is covalently linked to a heavy chain by one disulfide bond to form a heterodimer, and the heterotrimeric molecule is formed through a covalent disulfide linkage between the two identical heavy chains of the heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the amino-terminus a variable domain ($V_H$=variable heavy chain), followed by three or four constant domains ($C_{H1}$, $C_{H2}$, $C_{H3}$, and $C_{H4}$), as well as a hinge region between $C_{H1}$ and $C_{H2}$. Each light chain has two domains, an amino-terminal variable domain ($V_L$=variable light chain) and a carboxy-terminal constant domain ($C_L$). The $V_L$ domain associates non-covalently with the $V_H$ domain, whereas the $C_L$ domain is commonly covalently linked to the $C_{H1}$ domain via a disulfide bond. Particular amino acid residues are believed to form an interface between the light and heavy chain variable domains (Chothia et al., 1985, J. Mol. Biol. 186:651-663, Vargas-Madrazo E, Paz-Garcia E. J Mol Recognit. 2003; 16(3):113-120). The variable domains are also referred herein as variable regions, and the constant domains as constant regions.

Certain domains within the variable domains differ extensively between different antibodies i.e., are "hypervariable." These hypervariable domains contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: Sequences of Proteins of Immunological Interest, 5th Ed. Public Health Service, National Institutes of Health, Bethesda, Md., whereas HVLs are structurally defined according to the three-dimensional structure of the variable domain, as described by Chothia and Lesk, 1987, J. Mol. Biol. 196: 901-917. Where these two methods result in slightly different identifications of a CDR, the structural definition is preferred. As defined by Kabat, CDR-L1 is positioned at about residues 24-34, CDR-L2, at about residues 50-56, and CDR-L3, at about residues 89-97 in the light chain variable domain; CDR-H1 is positioned at about residues 31-35, CDR-H2 at about residues 50-65, and CDR-H3 at about residues 95-102 in the heavy chain variable domain. IMGT and NORTH provide alternative definitions of the CDRs (see, Lefranc M P. Unique database numbering system for immunogenetic analysis. Immunol Today (1997) 18:509; and North B, Lehmann A, Dunbrack R L J. A new clustering of antibody CDR loop conformations. J Mol Biol. (2011) 406:228-56). Additionally, CDRs may be defined per the Chemical Computing Group (CCG) numbering (Almagro et al., Proteins 2011; 79:3050-3066 and Maier et al, Proteins 2014; 82:1599-1610). The CDR1, CDR2, CDR3 of the heavy and light chains therefore define the unique and functional properties specific for a given antibody.

The three CDRs within each of the heavy and light chains are separated by framework regions (FR), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains into close proximity to each other as well as to the CDRs from the other chain. The resulting conformation contributes to the antigen binding site (see Kabat et al., 1991, NIH Publ. No. 91-3242, Vol. I, pages 647-669), although not all CDR residues are necessarily directly involved in antigen binding. Those skilled in the art can routinely determine which residues comprise a particular CDR given the variable region amino acid sequence of the antibody. The CDR1, CDR2, CDR3 of the heavy and light chains therefore define the unique and functional properties specific for a given antibody.

FR residues and Ig constant domains are generally not directly involved in antigen binding but contribute to antigen binding and/or mediate antibody effector function. Some FR residues are thought to have a significant effect on antigen binding in at least three ways: by noncovalently binding directly to an epitope, by interacting with one or more CDR residues, and by affecting the interface between the heavy and light chains. The constant domains are not directly involved in antigen binding but mediate various Ig effector functions, such as participation of the antibody in antibody-dependent cellular cytotoxicity (ADCC), complement-dependent cytotoxicity (CDC) and antibody-dependent cellular phagocytosis (ADCP).

The light chains of vertebrate immunoglobulins are assigned to one of two clearly distinct classes, kappa (κ) and lambda (λ), based on the amino acid sequence of the constant domain. By comparison, the heavy chains of mammalian immunoglobulins are assigned to one of five major classes, according to the sequence of the constant domains: IgA, IgD, IgE, IgG, and IgM. IgG and IgA are further divided into subclasses (isotypes), e.g., $IgG_1$, $IgG_2$, $IgG_3$, $IgG_4$, $IgA_1$, and $IgA_2$, respectively. The heavy chain constant domains that correspond to the different classes of immunoglobulins are called α, δ, ε, γ, and μ, respectively. The subunit structures and three-dimensional configurations of the classes of native immunoglobulins are well known.

Definitions

The terms, "antibody", and "anti-SIRPα antibody", are used herein interchangeably and encompass monoclonal antibodies (including full length monoclonal antibodies), multispecific antibodies (e.g., bispecific antibodies), antibodies with minor modifications such as N- or C-terminal truncations and antibody fragments such as variable domains and other portions of antibodies that exhibit a desired biological activity, e.g., SIRPα binding.

The term "monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation that may be present. Monoclonal antibodies typically bind one antigenic epitope. A bispecific monoclonal antibody binds two distinct antigenic epitopes. A monoclonal antibody may be monospecific or multispecific such as bispecific, monovalent, bivalent or multivalent. It should be understood that monoclonal antibodies can be made by any technique or methodology known in the art; including e.g., the hybridoma method (Kohler et al., 1975, Nature 256:495), or recombinant DNA methods known in the art (see, e.g., U.S. Pat. No. 4,816,567), or methods of isolation of monoclonal recombinantly produced using phage antibody libraries, using techniques described in Clackson et al., 1991, Nature 352: 624-628, and Marks et al., 1991, J. Mol. Biol. 222: 581-597.

Chimeric antibodies consist of the heavy and light chain variable regions of an antibody from one species (e.g., a non-human mammal such as a mouse) and the heavy and light chain constant regions of another species (e.g., human) antibody and can be obtained by linking the DNA sequences encoding the variable regions of the antibody from the first species (e.g., mouse) to the DNA sequences for the constant regions of the antibody from the second (e.g. human) species and transforming a host with an expression vector containing the linked sequences to allow it to produce a chimeric antibody. Alternatively, the chimeric antibody also could be one in which one or more regions or domains of the heavy and/or light chain is identical with, homologous to, or a variant of the corresponding sequence in a monoclonal antibody from another immunoglobulin class or isotype, or from a consensus or germline sequence. Chimeric antibodies can include fragments of such antibodies, provided that the antibody fragment exhibits the desired biological activity of its parent antibody, for example binding to the same epitope (see, e.g., U.S. Pat. No. 4,816,567; and Morrison et al., 1984, Proc. Natl. Acad. Sci. USA 81: 6851-6855).

The terms "antibody fragment", "antigen-binding fragment", "anti-SIRPα antibody fragment", "anti-SIRPα antibody fragment", "engineered anti-SIRPα antibody fragment" refer to a portion of a full length anti-SIRPα antibody, in which a variable region or a functional capability is retained, for example, SIRPα binding. Examples of antibody fragments include, but are not limited to, a Fab, Fab', $F(ab')_2$, Fd, Fv, scFv and scFv-Fc fragment, a diabody, a linear antibody, a single-chain antibody, a minibody, a diabody formed from antibody fragments, and multispecific antibodies formed from antibody fragments.

Antibody fragments can be obtained for example by treating full-length antibodies treated with enzymes such as papain or pepsin to generate useful antibody fragments. Papain digestion is used to produce two identical antigen-binding antibody fragments called "Fab" fragments, each with a single antigen-binding site, and a residual "Fc" fragment. The Fab fragment also contains the constant domain of the light chain and the $C_{H1}$ domain of the heavy chain. Pepsin treatment yields a $F(ab')_2$ fragment that has two antigen-binding sites and is still capable of cross-linking antigen.

Another example of antibody fragments according to the invention are Fab' fragments. Fab' fragments differ from Fab fragments by the presence of additional residues including one or more cysteines from the antibody hinge region at the C-terminus of the $C_{H1}$ domain. $F(ab')_2$ antibody fragments are pairs of Fab' fragments linked by cysteine residues in the hinge region. Other chemical couplings of antibody fragments are also known.

A "Fv" fragment contains a complete antigen-recognition and binding site consisting of a dimer of one heavy and one light chain variable domain in tight, non-covalent association. In this configuration, the three CDRs of each variable domain interact to define an antigen-biding site on the surface of the $V_H$-$V_L$ dimer. Collectively, the six CDRs confer antigen-binding specificity to the antibody.

Antibody fragments may also include "single-chain Fv" or "scFv" fragments. A "single-chain Fv" or "scFv" antibody fragment is a single chain Fv variant comprising the $V_H$ and $V_L$ domains of an antibody where the domains are present in a single polypeptide chain. The single chain Fv is capable of recognizing and binding antigen. The scFv polypeptide may optionally also contain a polypeptide linker positioned between the $V_H$ and $V_L$ domains in order to facilitate formation of a desired three-dimensional structure for antigen binding by the scFv (see, e.g., Pluckthun, 1994, In The Pharmacology of monoclonal Antibodies, Vol. 113, Rosenburg and Moore eds., Springer-Verlag, New York, pp. 269-315).

Antibody fragments may also form tandem Fd segments, which comprise a pair of tandem Fd segments ($V_H$-$C_{H1}$-$V_H$-$C_{H1}$) to form a pair of antigen binding regions. These "linear antibodies" can be bispecific or monospecific as described in, for example, Zapata et al. 1995, Protein Eng. 8(10):1057-1062.

The term "human antibody" as used herein includes antibodies or fragments thereof derived from human germline immunoglobulin sequences. The term "human antibody" is not intended to include antibodies in which CDR sequences derived from the germline of another (mammalian) species, such as a mouse, rat or rabbit, have been grafted onto human framework sequences. Thus, as used herein, the term "human antibody" refers to an antibody or fragment thereof in which every part of the protein (e.g., CDR, framework, CL, CH domains (e.g., CH1, CH2, CH3), hinge, VL, VH) is substantially non-immunogenic in humans, with only minor sequence changes or variations as further described herein below.

Technologies for creating such a "human antibody" have been described and include without being limiting phage display or use of transgenic animals (www. Ablexis.com/technology-alivamab.php; WO 90/05144; D. Marks, H. R. Hoogenboom, T. P. Bonnert, J. McCafferty, A. D. Griffiths and G. Winter (1991) "By-passing immunisation. Human antibodies from V-gene libraries displayed on phage." J. Mol. Biol., 222, 581-597; Knappik et al., J. Mol. Biol. 296: 57-86, 2000; S. Carmen and L. Jermutus, "Concepts in antibody phage display". Briefings in Functional Genomics and Proteomics 2002 1(2):189-203; Lonberg N, Huszar D. "Human antibodies from transgenic mice". Int Rev Immunol. 1995; 13(1):65-93; Bruggemann M, Taussig M J. "Production of human antibody repertoires in transgenic mice". Curr Opin Biotechnol. 1997 August; 8(4):455-8).

Thus, a human antibody is distinct from e.g., a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes.

In one aspect, an anti-SIRPα antibody of the invention is a humanized antibody or antibody fragment thereof. A humanized antibody or a humanized antibody fragment is a specific type of chimeric antibody which includes an immunoglobulin amino acid sequence variant, or fragment thereof, which is capable of binding to a predetermined antigen and which, comprises one or more FRs having substantially the amino acid sequence of a human immunoglobulin and one or more CDRs having substantially the amino acid sequence of a non-human immunoglobulin. This non-human amino acid sequence often referred to as an "import" sequence is typically taken from an "import" antibody domain, particularly a variable domain. In general, a humanized antibody includes at least the CDRs or HVLs of a non-human antibody, inserted between the FRs of a human heavy or light chain variable domain. Methods of humanization of antibodies are for example described by Almagro et al., (2008) Frontiers in Bioscience 13, 1619-1633, or in WO12092374 A2.

The chimeric, humanized or human antibodies or antigen-binding fragments thereof of the present invention may further be engineered. Such engineering includes without limitation the removal or exchange of undesired amino acids, for example to reduce immunogenicity in humans, or to avoid deamidation, undesirable charges or lipophilicity or non-specific binding. Such removal or exchange of undesired amino acids can, for example, be introduced by random or site-specific mutagenesis in vitro or by somatic mutation in vivo. Moreover, in connection with chimeric or humanized antibodies, it will be understood that certain mouse FR residues may be retained in an antibody or fragment thereof.

In one aspect, an anti-SIRPα antibody comprises substantially all of at least one, and typically two, variable domains (such as contained, for example, in Fab, Fab', F(ab')2, Fabc, and Fv fragments). In another aspect, an anti-SIRPα antibody also includes at least a portion of an immunoglobulin Fc region, typically that of a human immunoglobulin. Ordinarily, the antibody will contain both the light chain as well as at least the variable domain of a heavy chain. The antibody also may include one or more of the $C_{H1}$, hinge, $C_{H2}$, $C_{H3}$, and/or $C_{H4}$ regions of the heavy chain, as appropriate.

In one aspect, an anti-SIRPα antibody can be selected from any class of immunoglobulins, including IgM, IgG, IgD, IgA and IgE, and any isotype, including $I_{gG1}$, $IgG_2$, $IgG_3$, $IgG_4$, $IgA_1$ and $IgA_2$. An alternative anti-SIRPα antibody can comprise sequences from more than one immunoglobulin class or isotype, and selecting particular modified or unmodified constant domains to optimize desired effector functions is within the ordinary skill in the art.

For example, the Fc region of an antibody mediates its serum half-life and effector functions, such as complement-dependent cytotoxicity (CDC), antibody-dependent cellular cytotoxicity (ADCC) and antibody-dependent cell phagocytosis (ADCP). Fc engineering can be employed to optimize antibody properties suited to the pharmacology activity required of them. Where such cytotoxic activity is not desirable, such as targeting an immune cell in the treatment of cancer, the constant domain may be of isotype with reduced effector function, such as IgG4, and/or be modified with known modifications that reduce effector function. Where such cytotoxic activity is desirable, such as for destruction of a targeted tumor cell, the constant domain may be of isotype with increased effector function and/or be modified with known modifications to increase effector function. Several mutations are known to either reduce or increase effector function. See, e.g., "*The future of antibodies as cancer drugs*" Janice M Reichert, Eugen Dhimolea, Drug Discov Today (2012) September; 17(17-18):954-63—PMID: 22561895, "*Antibody Drug Discovery*" (Volume 4 of Molecular medicine and medicinal chemistry) Clive R. Wood, World Scientific, 2012 ISBN 1848166281, 9781848166288; "*FcγR requirements leading to successful immunotherapy*" Immunol Rev. (2015) November; 268(1): 104-22—PMID: 26497516.

In one aspect, the constant domain of an antibody of the present invention is IgG4Pro, which has one replacement mutation (Ser228Pro) that prevents Fab-arm exchanging. In another aspect, the constant domain of an antibody of the present invention is IgG1, which has two mutations in the constant region, Leu234Ala and Leu235Ala to reduce effector function.

The FRs and CDRs, or HVLs, of an engineered anti-SIRPα antibody or antigen-binding fragment thereof need not correspond precisely to the parental sequences. For example, a parental sequence may be altered (e.g., mutagenized) by substitution, insertion or deletion such that the resulting amino acid residue is no longer identical to the original residue in the corresponding position in either parental sequence but the antibody nevertheless retains the function of binding to SIRPα. Such alteration typically will not be extensive and will be conservative alterations. Usually, at least 75% of the engineered antibody residues will correspond to those of the parental sequences, more often at least 90%, and most frequently greater than 95%, or greater than 98% or greater than 99%.

Immunoglobulin residues that affect the interface between heavy and light chain variable regions ("the $V_L$-$V_H$ interface") are those that affect the proximity or orientation of the two chains with respect to one another. Certain residues that may be involved in interchain interactions include $V_L$ residues 34, 36, 38, 44, 46, 87, 89, 91, 96, and 98 and $V_H$ residues 35, 37, 39, 45, 47, 91, 93, 95, 100, and 103 (utilizing the numbering system set forth in Kabat et al., Sequences of Proteins of Immunological Interest (National Institutes of Health, Bethesda, Md., 1987)). U.S. Pat. No. 6,407,213 also discusses that residues such as $V_L$ residues 43 and 85, and $V_H$ residues 43 and 60 also may be involved in this interaction. While these residues are indicated for human IgG only, they are applicable across species. Important antibody residues that are reasonably expected to be involved in interchain interactions are selected for substitution into the consensus sequence.

The terms "consensus sequence" and "consensus antibody" refer to an amino acid sequence which comprises the most frequently occurring amino acid residue at each location in all immunoglobulins of any particular class, isotype, or subunit structure, e.g., a human immunoglobulin variable domain. The consensus sequence may be based on immunoglobulins of a particular species or of many species. A "consensus" sequence, structure, or antibody is understood to encompass a consensus human sequence as described in certain embodiments, and to refer to an amino acid sequence which comprises the most frequently occurring amino acid residues at each location in all human immunoglobulins of any particular class, isotype, or subunit structure. Thus, the consensus sequence contains an amino acid sequence having at each position an amino acid that is present in one or more known immunoglobulins, but which may not exactly duplicate the entire amino acid sequence of any single immunoglobulin. The variable region consensus sequence is not obtained from any naturally produced antibody or immunoglobulin. Kabat et al., 1991, Sequences of Proteins of Immunological Interest, 5th Ed. Public Health Service, National Institutes of Health, Bethesda, Md., and variants thereof. The FRs of heavy and light chain consensus sequences, and variants thereof, provide useful sequences for the preparation of human or humanized anti-SIRPα antibodies. See, for example, U.S. Pat. Nos. 6,037,454 and 6,054,297.

An "isolated" antibody is one that has been identified and separated and/or recovered from a component of its natural environment or from a cell culture from which it was expressed. An isolated antibody or antibody fragment may have one or more co- or post-translational modifications that arise during production, purification, and/or storage of the antibody or antibody fragment. Contaminant components of the antibody's natural environment are those materials that may interfere with diagnostic or therapeutic uses of the antibody, and can be enzymes, hormones, or other proteinaceous or non-proteinaceous solutes. In one aspect, the antibody will be purified to at least greater than 95% isolation by weight of antibody, for example purified to at least greater than 95%, 96%, 97%, 98%, or 99%.

An isolated antibody includes an antibody in situ within recombinant cells in which it is produced, since at least one component of the antibody's natural environment will not be present. Ordinarily however, an isolated antibody will be prepared by at least one purification step in which the recombinant cellular material is removed.

"Multispecific" refers to a protein, such as an antibody, that specifically binds two or more distinct antigens or two or more distinct epitopes within the same antigen.

"Bispecific" refers to a protein, such as an antibody, that specifically binds two distinct antigens or two distinct epitopes within the same antigen.

In some embodiments, the antibody that specifically binds SIRPα or the antigen-binding fragment thereof of the invention is a bispecific antibody. In some embodiments, the antibody or the antigen-binding fragment thereof of the invention is a multispecific antibody. The monospecific antibodies that specifically bind SIRPα provided herein may be engineered into bispecific antibodies, which are also encompassed within the scope of the invention.

Full-length bispecific antibodies may be generated for example using Fab arm exchange (e.g., half-molecule exchange, exchanging one heavy chain-light chain pair) between two monospecific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond.

Bispecific antibodies may also be generated using designs such as the Triomab/Quadroma (Trion Pharma/Fresenius Biotech), Knob-in-Hole (Genentech), CrossMAbs (Roche) and the electrostatically-induced CH3 interaction (Chugai, Amgen, NovoNordisk, Oncomed), the LUZ-Y (Genentech), the Strand Exchange Engineered Domain body (SEEDbody) (EMD Serono), the Biclonic (Merus) and as DuoBody® Products (Genmab A/S).

As used herein, the terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length after gaps are introduced within the sequences, as appropriate (e.g., excluding additional sequence extending beyond the sequences being compared). For example, when variable region sequences are compared, the leader and/or constant domain sequences are not considered. For sequence comparisons between two sequences, a "corresponding" CDR refers to a CDR in the same location in both sequences (e.g., CDR-H1 of each sequence).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the N BLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

A "chemotherapeutic agent" is a chemical compound useful in the treatment of cancer. Examples of such chemotherapeutic agents include alkylating agents such a thiotepa and cyclosphosphamide; alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethylenethiophosphoramide, and trimethylolomelamine; acetogenins (especially bullatacin and bullatacinone); camptothecin (including the synthetic analogue topotecan); bryostatin; callystatin; CC-1065 (including its adozelesin, carzelesin, and bizelesin synthetic analogues); cryptophycines (particularly cryptophycin 1 and cryptophycin 8); dolastatin, auristatins, (including analogues monomethyl-auristatin E and monomethyl-auristatin F); duocarmycin (including the synthetic analogues, KW-2189 and CBI-TMI); eleutherobin; pancratistatin; sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine; trofosfamide, uracil mustard; nitrosureas such as carmustine, chlorozotocin, fotemustine, lomustine, nimustine, ranimustine; antibiotics such as the enediyne antibiotics (e.g., calicheamicin, especially calichemicin gamma1I and calicheamicin phi11, see for example, Agnew, Chem. Intl. Ed. Engl., 33:183-186; dynemicin, including dynemicin A; bisphosphonates, such as clodronate; esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (Adriamycin™) (including morpholino-doxorubicin, cyanomorpholino-doxorubicin, 2-pyrrolino-doxorubicin, and deoxydoxorubicin), epirubucin, esorubicin, idarubicin, marcellomycin, mitomycins such as mitomycin C, mycophenolic acid, nogalamycin, olivomycins, peplomycin, potfiromycin, puromycine, quelamycin, rodorubicin, streptonigrin, streptozocin, tubercidin, ubenimex, zinostatin, zorubicin; anti-metabolites such a methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adranals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; democolcine; diaziquone; elfomithine; elliptinium acetate; an epothilone; etoglucid; gallium nitrate; hydroxyurea; lentinan; lonidamine; maytansinoids such as maytansine and ansamitocins; mitoguazone, mitoxantrone; mopidamol; nitracrine; pentostatin; phenamet; pirarubicin; losoxantrone; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitabronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitoxantrone; vincristine; vinorelbine Navelbine™); novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids, or derivatives of any of the above. Also included in this definition are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston™); aromatase inhibitors that inhibit the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprolide, and goserelin; and pharmaceutically acceptable salts, acids, or derivatives of any of the above. Any one or more of these agents may be conjugated to the human antibodies or antigen-binding fragments thereof of the present invention to provide a useful therapeutic agent for the treatment of various diseases and/or disorders.

For diagnostic as well as therapeutic monitoring purposes, the antibodies or antigen-binding fragment thereof of the invention also may be conjugated to a label, either a label alone or a label and an additional second agent (prodrug, chemotherapeutic agent and the like). A label, as distinguished from the other second agents refers to an agent that is a detectable compound or composition and it may be conjugated directly or indirectly to an anti-SIRPα antibody or antigen-binding fragment thereof of the present invention. The label may itself be detectable (e.g., radioisotope labels or fluorescent labels) or, in the case of an enzymatic label, may catalyze chemical alteration of a substrate compound or composition that is detectable. Labeled anti-SIRPα antibodies or antigen-binding fragments thereof can be prepared and used in various applications including in vitro and in vivo diagnostics.

In various aspects of the present invention one or more domains of the anti-SIRPα antibodies or antigen-binding fragments thereof will be recombinantly expressed. Such recombinant expression may employ one or more control sequences, i.e., polynucleotide sequences necessary for expression of an operably linked coding sequence in a particular host organism. The control sequences suitable for use in prokaryotic cells include, for example, promoter, operator, and ribosome binding site sequences. Eukaryotic control sequences include, but are not limited to, promoters, polyadenylation signals, and enhancers. These control sequences can be utilized for expression and production of anti-SIPRα antibodies or antigen-binding fragments thereof in prokaryotic and eukaryotic host cells.

A nucleic acid sequence is "operably linked" when it is placed into a functional relationship with another nucleic acid sequence. For example, a nucleic acid presequence or secretory leader is operably linked to a nucleic acid encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers are optionally contiguous. Linking can be accomplished by ligation at convenient restriction sites. If such sites do not exist, synthetic oligonucleotide adaptors or linkers can be used.

As used herein, the expressions "cell", "cell line", and "cell culture" are used interchangeably and all such designations include the progeny thereof. Thus, "transformants" and "transformed cells" include the primary subject cell and cultures derived therefrom without regard for the number of transfers, which may for example have been transfected with one or more expression vectors encoding one or more amino acids sequences of an antibody or antigen-binding fragment thereof of the present invention.

The term "mammal" for purposes of treatment according to the invention refers to any animal classified as a mammal, including humans, domesticated and farm animals, and zoo, sports, or pet animals, such as dogs, horses, cats, cows, and the like. Preferably, the mammal is a human.

A "disorder", as used herein, is any condition that would benefit from treatment with an anti-SIRPα antibody or antigen-binding fragment thereof described herein. This includes chronic and acute disorders or diseases including those pathological conditions that predispose the mammal to the disorder in question. Non-limiting examples or disorders to be treated herein include inflammatory, angiogenic, autoimmune and immunologic disorders, respiratory disorders, cancer, hematological malignancies, benign and malignant tumors, leukemias and lymphoid malignancies.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia.

As used herein, the term "SIRPα pathway disorder" or "SIRPα pathway disease" refers to a condition, which can be alleviated by modulating the interaction between SIRPα and CD47, in particular by inhibiting the SIRPα/CD47 signaling. A "SIRPα pathway disorder" or "SIRPα pathway disease" includes myeloid associated diseases where SIRPα is expressed. A "SIRPα pathway disorder" or "SIRPα pathway disease" also includes conditions characterized by reduced phagocytosis by macrophages and/or dendritic cells that express SIRPα increased immune response is desired.

Examples of SIRPα pathway disorders are cancer, inflammatory disease, autoimmune disease, respiratory disease, infectious disease or fibrosis. Examples of cancers include hematological cancer (e.g. leukemia, lymphoma, myeloma, e.g. multiple myeloma), and a metastatic lesion. Further examples include solid tumor cancers. Examples of solid tumors include malignancies, e.g. sarcomas and carcinomas, e.g. adenocarcinomas of the various organ systems, such as those affecting the lung, breast, ovarian, lymphoid, gastrointestinal (e.g. colon), anal, genitals and genitourinary tract (e.g. renal, urothelial, bladder cells, prostate), pharynx, CNS (e.g. brain, neural or glial cells), head and neck, skin (e.g. melanoma), and pancreas, as well as adenocarcinomas which include malignancies such as colon cancers, rectal cancer, renal-cell carcinoma, liver cancer, gastric cancers, non-small cell lung cancer, cancer of the small intestine and cancer of the esophagus. The cancer may be at an early, intermediate, late stage or metastatic cancer.

In some embodiments, the cancer is chosen from a lung cancer (e.g. NSCLC (e.g. a NSCLC with squamous and/or non-squamous histology, or a NSCLC adenocarcinoma)), a melanoma (e.g. an advanced melanoma), a renal cancer (e.g. a renal cell carcinoma), a liver cancer, hepatocellular carcinoma, a myeloma (e.g. a multiple myeloma), a prostate cancer, a breast cancer (e.g. a breast cancer that does not express one, two or all of estrogen receptor, progesterone receptor, or HER2/neu, e.g. a triple negative breast cancer), a colorectal cancer, a pancreatic cancer, a head and neck cancer (e.g. head and neck squamous cell carcinoma (HN-SCC), anal cancer, gastro-esophageal cancer, thyroid cancer, cervical cancer, a lymphoproliferative disease (e.g. a post-transplant lymphoproliferative disease) or a hematological cancer, T-cell lymphoma, B-cell lymphoma, a non-Hodgkin lymphoma, or a leukemia (e.g. a myeloid leukemia or a lymphoid leukemia).

In some embodiments, the cancer is chosen from a carcinoma (e.g. advanced or metastatic carcinoma), melanoma or a lung carcinoma, e.g. a NSCLC.

In some embodiments, the cancer is chosen from a pancreatic cancer, prostate cancer, breast cancer, colorectal cancer, lung cancer, glioblastoma, renal cancer, preferably pancreatic cancer, prostate cancer, breast cancer, colorectal cancer or lung cancer.

In some embodiments, the cancer is pancreatic cancer, lung cancer, breast cancer, melanoma, colorectal cancer, ovarian cancer, gastric cancer, thyroid cancer, liver cancer or prostate cancer.

The terms "specifically binds" or "specific binding" in the context of a binding agent, e.g., an antibody or antigen-binding fragment thereof, refers to a binding agent that associates more frequently, more rapidly, with greater duration, with greater affinity, with greater avidity or with some combination of the above, to an antigen or an epitope within the antigen than with an unrelated antigen. In certain embodiments, an antibody or antigen-binding fragment thereof specifically binds to an antigen or epitope within an antigen with a $K_D$ of about 0.1 mM or less, preferably less than about 1 μM. Because of the sequence identity between homologous proteins in different species, or variants of a protein within a single species, specific binding can include an antibody or antigen-binding fragment thereof that recognizes a protein in more than one species (e.g., human SIRPα and cyno SIRPα). It is understood that, in certain embodiments, an antibody or antigen-binding fragment thereof that specifically binds a first protein may or may not specifically bind a second protein. As such, "specific binding" does not necessarily require (although it can include) exclusive binding, i.e. binding to a single protein. Thus, an antibody or antigen-binding fragment thereof may, in certain embodiments, specifically bind more than one protein.

Methods for determining whether two molecules specifically bind a protein are described herein or a known in the art and include, for example, equilibrium dialysis, surface plasmon resonance, and the like. In one embodiment, specific binding is characterized by a $K_D$ of about $1 \times 10^{-7}$ M (100 nM) or less according to the affinity binding method described in the Examples section herein. In another embodiment, specific binding is characterized by a $K_D$ of about $5 \times 10^{-8}$ M (50 nM) or less according to the affinity binding method described in the Examples section herein. In another embodiment, specific binding is characterized by a $K_D$ of about $1 \times 10^{-8}$ M (10 nM) or less according to the affinity binding method described in the Examples section herein. In another embodiment, specific binding is characterized by a $K_D$ of about $5 \times 10^{-9}$ M (5 nM) or less according to the affinity binding method described in the Examples section herein.

The term "subcutaneous administration" refers to introduction of a drug, for example an anti-SIRPα antibody or antigen-binding fragment thereof of the invention, under the skin of a subject such as an animal or human patient, preferable within a pocket between the skin and underlying tissue, by relatively slow, sustained delivery from a drug receptacle. Pinching or drawing the skin up and away from underlying tissue may create the pocket.

The term "subcutaneous infusion" refers to introduction of a drug, for example an anti-SIRPα antibody or antigen-binding fragment thereof of the invention, under the skin of a subject, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the subject, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of a subject, where bolus drug delivery is less than approximately 15 minutes; in another aspect, less than 5 minutes, and in still another aspect, less than 60 seconds. In yet even another aspect, administration is within a pocket between the skin and underlying tissue, where the pocket may be created by pinching or drawing the skin up and away from underlying tissue. For example, "subcutaneous bolus" refers to the administration of an anti-SIRPα antibody or antigen-binding fragment thereof of the invention to a subject in less than approximately 15 minutes; in another aspect, less than 5 minutes, and in still another aspect, less than 60 seconds The term "therapeutically effective amount" is used to refer to an amount of an anti-SIRPα antibody or antigen-binding fragment thereof that relieves or ameliorates one or more of the symptoms of the disorder being treated. In doing so, it is that amount that has a beneficial patient outcome. Efficacy can be measured in conventional ways, depending on the condition to be treated.

The terms "treatment" and "therapy" and the like, as used herein, are meant to include therapeutic as well as prophylactic, or suppressive measures for a disease or disorder leading to any clinically desirable or beneficial effect, including but not limited to alleviation or relief of one or more symptoms, regression, slowing or cessation of progression of the disease or disorder. Thus, for example, the term treatment includes the administration of an anti-SIRPα antibody or antigen-binding fragment thereof prior to or following the onset of a symptom of a disease or disorder thereby preventing or removing one or more signs of the disease or disorder. As another example, the term includes the administration of an anti-SIRPα antibody or antigen-binding fragment thereof after clinical manifestation of the disease to combat the symptoms of the disease. Further, administration of an anti-SIRPα antibody or antigen-binding fragment thereof after onset and after clinical symptoms have developed where administration affects clinical parameters of the disease or disorder, such as the degree of tissue injury or the amount or extent of metastasis, whether or not the treatment leads to amelioration of the disease, comprises "treatment" or "therapy" as used herein. Moreover, as long as the compositions of the invention either alone or in combination with another therapeutic agent alleviate or ameliorate at least one symptom of a disorder being treated as compared to that symptom in the absence of use of the anti-SIRPα antibody or antigen-binding fragment thereof composition or antigen-binding fragment thereof, the result should be considered an effective treatment of the underlying disorder regardless of whether all the symptoms of the disorder are alleviated or not.

The term "package insert" is used to refer to instructions customarily included in commercial packages of therapeutic products, that contain information about the indications, usage, administration, contraindications and/or warnings concerning the use of such therapeutic products.

Antibodies

Described and disclosed herein are anti-SIRPα antibodies, in particular human anti-SIRPα antibodies, as well as compositions and articles of manufacture comprising anti-SIRPα antibodies of the present invention. Also described are antigen-binding fragments of an anti-SIRPα antibody. The anti-SIRPα antibodies and antigen-binding fragments thereof can be used in the treatment of a variety of diseases or disorders, in particular diseases or disorders characterized by modulation of CD47-mediated SIRPα signaling. An anti-SIRPα antibody and an antigen-binding fragment thereof each include at least a portion that specifically recognizes a SIRPα epitope.

The epitopes are most commonly proteins, short oligopeptides, oligopeptide mimics (e.g., organic compounds that mimic antibody binding properties of the SIRPα antigen), or combinations thereof. The minimum size of a peptide or polypeptide epitope for an antibody is thought to be about four to five amino acids. Peptide or polypeptide epitopes contain for example at least seven amino acids or for example at least nine amino acids or for example between about 15 to about 20 amino acids. Since an antibody can recognize an antigenic peptide or polypeptide in its tertiary form, the amino acids comprising an epitope need not be contiguous, and in some cases, may not even be on the same peptide chain. Epitopes may be determined by various techniques known in the art, such as X-ray crystallography, Hydrogen/Deuterium Exchange Mass Spectrometry (HXMS), site-directed mutagenesis, alanine scanning mutagenesis, and peptide screening methods.

The generation of anti-SIRPα antibodies and their characterization is described in the Examples. CDRs of representative anti-SIRPα antibodies of the present invention are disclosed in Tables 1-25 below. Heavy Chain CDR-1, CDR-2, CDR3 (HCDR1-3) and Light Chain CDR-1, CDR-2, CDR3 (L-CDR1-3) are provided according to the numbering systems according to Kabat, CCG, Chothia, IMGT, and North.

TABLE 1

KABAT NOMENCLATURE

Antibody E, E1-E22

| | KABAT SEQ | SEQ ID NO: | |
|---|---|---|---|
| HCDR1 | NYYWS | 1 | |
| HCDR1-h | DYYWS | 223 | |
| HCDR2 | FIYYNGRTFYNS SLKS | 2 | |
| HCDR2-h | FIYYNGRTFYNPSLKS | 3 | |
| HCDR2-h | FIYDNGRTFYNPSLKS | 4 | |
| HCDR2-h | FIYYTGRTFYNPSLKS | 5 | |
| HCR2-h | FIYYNGRTFYQS SLKS | 224 | |
| HCDR3 | VRAYSGIGLDGTDV | 6 | |
| LCDR1 | KSSQSLLYSNGYNYLD | 7 | |
| LCDR1-h | KSSQSLLYSNGYAYLD | 8 | |
| LCDR1-h | KSSQSLLYSNAYNYLD | 9 | |
| LCR1-h | RSSQSLLYSTGYTYLD | 225 | |
| LCDR2 | LGSNRAS | 10 | |
| LCDR2-h | QGSNRAS | 11 | |
| LCDR2-h | GGSSRAS | 226 | |
| LCDR3 | MQALQTPLT | 12 | |
| LCDR3-h | GQALQTPLT | 227 | |
| HCDR1-Consensus | X1YYWS | 228 | wherein X1 = N or D |
| HCDR2-Consensus | FIYX1X2GRTFYX3X4SLKS | 229 | wherein X1 = Y or D; X2 = N or T; X3 = N or Q; X4 = S or P |
| LCDR1-Consensus | X1SSQSLLYSX2X3YX4YLD | 230 | wherein X1 = K or R; X2 = N or T; X3 = G or A; X4 = N, A or T |
| LCDR2-Consensus | X1GSX2RAS | 231 | wherein X1 = L, Q or G; X2 = N or S |
| LCDR3-Consensus | X1QALQTPLT | 232 | wherein X1 = M or G |

TABLE 2

IMGT NOMENCLATURE

Antibody E, E1-E22

| | IMGT SEQ | SEQ ID NO: |
|---|---|---|
| HCDR1 | GGSIRNYY | 13 |
| HCDR2 | IYYNGRT | 14 |
| HCDR2-h | IYDNGRT | 15 |
| HCDR2-h | IYYTGRT | 16 |
| HCDR3 | ARVRAYSGIGLDGTDV | 17 |
| LCDR1 | QSLLYSNGYNY | 18 |
| LCDR1-h | QSLLYSNGYAY | 19 |
| LCDR1-h | QSLLYSNAYNY | 20 |
| LCDR2 | LGS | 21 |
| LCDR2-h | QGS | 22 |
| LCDR3 | MQALQTPLT | 12 |

TABLE 3

CCG NOMENCLATURE

Antibody E, E1-E22

| | CCG SEQ | SEQ ID NO: |
|---|---|---|
| HCDR1 | GGSIRNYYWS | 23 |
| HCDR2 | FIYYNGRTFYNSSLKS | 2 |
| HCDR2-h | FIYYNGRTFYNPSLKS | 3 |

TABLE 3-continued

CCG NOMENCLATURE

Antibody E, E1-E22

| | CCG SEQ | SEQ ID NO: |
|---|---|---|
| HCDR2-h | FIYDNGRTFYNPSLKS | 4 |
| HCDR2-h | FIYYTGRTFYNPSLKS | 5 |
| HCDR3 | VRAYSGIGLDGTDV | 6 |
| LCDR1 | KSSQSLLYSNGYNYLD | 7 |
| LCDR1-h | KSSQSLLYSNGYAYLD | 8 |
| LCDR1-h | KSSQSLLYSNAYNYLD | 9 |
| LCDR2 | LGSNRAS | 10 |
| LCDR2-h | QGSNRAS | 11 |
| LCDR3 | MQALQTPLT | 12 |

TABLE 4

CHOTHIA NOMENCLATURE

Antibody E, E1-E22

| | CHOTHIA SEQ | SEQ ID NO: |
|---|---|---|
| HCDR1 | GGSIRNY | 261 |
| HCDR2 | YNGR | 24 |
| HCDR2-h | YDNGR | 25 |
| HCDR2-h | YYTGR | 26 |
| HCDR3 | VRAYSGIGLDGTDV | 6 |
| LCDR1 | KSSQSLLYSNGYNYLD | 7 |
| LCDR1-h | KSSQSLLYSNGYAYLD | 8 |
| LCDR1-h | KSSQSLLYSNAYNYLD | 9 |
| LCDR2 | LGSNRAS | 10 |
| LCDR2-h | QGSNRAS | 11 |
| LCDR3 | MQALQTPLT | 12 |

TABLE 5

NORTH NOMENCLATURE

Antibody E, E1-E22

| | NORTH SEQ | SEQ ID NO: |
|---|---|---|
| HCDR1 | TVSGGSIRNYYWS | 27 |
| HCDR2 | FIYYNGRTF | 28 |
| HCDR2-h | FIYDNGRTF | 29 |
| HCDR2-h | FIYYTGRTF | 30 |
| HCDR3 | ARVRAYSGIGLDGTDV | 17 |
| LCDR1 | KSSQSLLYSNGYNYLD | 7 |
| LCDR1-h | KSSQSLLYSNGYAYLD | 8 |
| LCDR1-h | KSSQSLLYSNAYNYLD | 9 |
| LCDR2 | YLGSNRAS | 31 |
| LCDR2-h | YQGSNRAS | 32 |
| LCDR3 | MQALQTPLT | 12 |

TABLE 6

KABAT NOMENCLATURE

Antibody A, A1-A16

| | KABAT SEQ | SEQ ID NO: |
|---|---|---|
| HCDR1 | SYDMH | 33 |
| HCDR2 | AIGTAGDTYYTGSVKG | 34 |
| HCDR3 | GGVWDDAFDI | 35 |
| LCDR1 | RASQDINNYLA | 36 |
| LCDR1-h | RASQGINNYAA | 37 |
| LCDR2 | TASSLHS | 38 |
| LCDR3 | QQYVSYPYT | 39 |
| LCDR1-Consensus | RASQX1INNYX2A | 233 wherein X1 = D or G; X2 = L or A |

TABLE 7

IMGT NOMENCLATURE

Antibody A, A1-A16

| | IMGT SEQ | SEQ ID NO: |
|---|---|---|
| HCDR1 | GFTLSSYD | 40 |
| HCDR2 | IGTAGDT | 41 |
| HCDR3 | VRGGVWDDAFDI | 42 |
| LCDR1 | QDINNY | 43 |
| LCDR1-h | QGINNY | 44 |
| LCDR2 | TAS | 45 |
| LCDR3 | QQYVSYPYT | 39 |

TABLE 8

CCG NOMENCLATURE

Antibody A, A1-A16

| | CCG SEQ | SEQ ID NO: |
|---|---|---|
| HCDR1 | GFTLSSYDMH | 46 |
| HCDR2 | AIGTAGDTYYTGSVKG | 34 |
| HCDR3 | GGVWDDAFDI | 35 |
| LCDR1 | RASQDINNYLA | 36 |
| LCDR1-h | RASQGINNYAA | 37 |
| LCDR2 | TASSLHS | 38 |
| LCDR3 | QQYVSYPYT | 39 |

TABLE 9

CHOTHIA NOMENCLATURE

Antibody A, A1-A16

| | CHOTHIA SEQ | SEQ ID NO: |
|---|---|---|
| HCDR1 | GFTLSSY | 47 |
| HCDR2 | GTAGD | 48 |
| HCDR3 | GGVWDDAFDI | 35 |
| LCDR1 | RASQDINNYLA | 36 |
| LCDR1-h | RASQGINNYAA | 37 |
| LCDR2 | TASSLHS | 38 |
| LCDR3 | QQYVSYPYT | 39 |

TABLE 10

NORTH NOMENCLATURE

Antibody A, A1-A16

| | NORTH SEQ | SEQ ID NO: |
|---|---|---|
| HCDR1 | AASGFTLSSYDMH | 49 |
| HCDR2 | AIGTAGDTY | 50 |
| HCDR3 | VRGGVWDDAFDI | 42 |
| LCDR1 | RASQDINNYLA | 36 |
| LCDR1-h | RASQGINNYAA | 37 |
| LCDR2 | YTASSLHS | 51 |
| LCDR3 | QQYVSYPYT | 39 |

TABLE 11

KABAT NOMENCLATURE

Antibody B

| | KABAT SEQ | SEQ ID NO: |
|---|---|---|
| HCDR1 | GNYMH | 52 |
| HCDR2 | WINPNSGGTNYAQKFQG | 53 |
| HCDR3 | GSGWYENYYYYGMDV | 54 |

TABLE 11-continued

KABAT NOMENCLATURE

Antibody B

| KABAT SEQ | | SEQ ID NO: |
|---|---|---|
| LCDR1 | RASQGISSWLA | 55 |
| LCDR2 | AESSLQS | 56 |
| LCDR3 | QQANSFPLT | 57 |

TABLE 12

IMGT NOMENCLATURE

Antibody B

| | IMGT SEQ | SEQ ID NO: |
|---|---|---|
| HCDR1 | GYTFTGNY | 58 |
| HCDR2 | INPNSGGT | 59 |
| HCDR3 | VSGSGWYENYYYYGMDV | 60 |
| LCDR1 | QGISSW | 61 |
| LCDR2 | AES | 62 |
| LCDR3 | QQANSFPLT | 57 |

TABLE 13

CCG NOMENCLATURE

Antibody B

| | CCG SEQ | SEQ ID NO: |
|---|---|---|
| HCDR1 | GFTFSSYDMH | 63 |
| HCDR2 | WINPNSGGTNYAQKFQG | 53 |
| HCDR3 | GSGWYENYYYYGMDV | 54 |
| LCDR1 | RASQGISSWLA | 55 |
| LCDR2 | AESSLQS | 56 |
| LCDR3 | QQANSFPLT | 57 |

TABLE 14

CHOTHIA NOMENCLATURE

Antibody B

| | CHOTHIA SEQ | SEQ ID NO: |
|---|---|---|
| HCDR1 | GYTFTGN | 64 |
| HCDR2 | NPNSGG | 65 |
| HCDR3 | GSGWYENYYYYGMDV | 54 |
| LCDR1 | RASQGISSWLA | 55 |
| LCDR2 | AESSLQS | 56 |
| LCDR3 | QQANSFPLT | 57 |

TABLE 15

NORTH NOMENCLATURE

Antibody B

| | NORTH SEQ | SEQ ID NO: |
|---|---|---|
| HCDR1 | KASGYTFTGNYMH | 66 |
| HCDR2 | WINPNSGGTN | 67 |
| HCDR3 | VSGSGWYENYYYYGMDV | 68 |
| LCDR1 | RASQGISSWLA | 55 |
| LCDR2 | YAESSLQS | 69 |
| LCDR3 | QQANSFPLT | 57 |

TABLE 16

KABAT NOMENCLATURE

Antibody C

| | KABAT SEQ | SEQ ID NO: |
|---|---|---|
| HCDR1 | SYDMH | 33 |
| HCDR2 | VIGIAGDTYYPGSVKG | 70 |
| HCDR3 | GGSWDDAFDI | 71 |
| LCDR1 | RASQDINNYLA | 36 |
| LCDR2 | TASSLQS | 72 |
| LCDR3 | QQYVSYPYT | 39 |

TABLE 17

IMGT NOMENCLATURE

Antibody C

| | IMGT SEQ | SEQ ID NO: |
|---|---|---|
| HCDR1 | GFTFSSYD | 73 |
| HCDR2 | IGIAGDT | 74 |
| HCDR3 | ARGGSWDDAFDI | 75 |
| LCDR1 | QDINNY | 43 |
| LCDR2 | TAS | 45 |
| LCDR3 | QQYVSYPYT | 39 |

TABLE 18

CCG NOMENCLATURE

Antibody C

| | CCG SEQ | SEQ ID NO: |
|---|---|---|
| HCDR1 | GFTFSSYDMH | 76 |
| HCDR2 | VIGIAGDTYYPGSVKG | 77 |
| HCDR3 | GGSWDDAFDI | 78 |
| LCDR1 | RASQDINNYLA | 36 |
| LCDR2 | TASSLQS | 79 |
| LCDR3 | QQYVSYPYT | 39 |

TABLE 19

CHOTHIA NOMENCLATURE

Antibody C

| | CHOTHIA SEQ | SEQ ID NO: |
|---|---|---|
| HCDR1 | GFTFSSY | 80 |
| HCDR2 | GIAGD | 81 |
| HCDR3 | GGSWDDAFDI | 82 |
| LCDR1 | RASQDINNYLA | 36 |

TABLE 19-continued

CHOTHIA NOMENCLATURE

| | Antibody C | |
|---|---|---|
| | CHOTHIA SEQ | SEQ ID NO: |
| LCDR2 | TASSLQS | 79 |
| LCDR3 | QQYVSYPYT | 39 |

TABLE 20

NORTH NOMENCLATURE

| | Antibody C | |
|---|---|---|
| | NORTH SEQ | SEQ ID NO: |
| HCDR1 | AASGFTFSSYDMH | 83 |
| HCDR2 | VIGIAGDTY | 84 |
| HCDR3 | ARGGSWDDAFDI | 85 |
| LCDR1 | RASQDINNYLA | 36 |
| LCDR2 | YTASSLQS | 86 |
| LCDR3 | QQYVSYPYT | 39 |

TABLE 21

KABAT NOMENCLATURE

| | Antibody D | |
|---|---|---|
| | KABAT SEQ | SEQ ID NO: |
| HCDR1 | SFDMH | 262 |
| HCDR2 | TIGIAGDTYFPGSVKG | 87 |
| HCDR3 | GGNWDDALDI | 88 |
| LCDR1 | RASQDINNYLA | 36 |
| LCDR2 | TASSLQS | 72 |
| LCDR3 | QQYNTYPYT | 89 |

TABLE 22

IMGT NOMENCLATURE

| | Antibody D | |
|---|---|---|
| | IMGT SEQ | SEQ ID NO: |
| HCDR1 | GFTFSSFD | 263 |
| HCDR2 | IGIAGDT | 74 |
| HCDR3 | ARGGNWDDALDI | 90 |
| LCDR1 | QDINNY | 43 |
| LCDR2 | TAS | 45 |
| LCDR3 | QQYNTYPYT | 89 |

TABLE 23

CCG NOMENCLATURE

| | Antibody D | |
|---|---|---|
| | CCG SEQ | SEQ ID NO: |
| HCDR1 | GFTFSSFDMH | 91 |
| HCDR2 | TIGIAGDTYFPGSVKG | 92 |
| HCDR3 | GGNWDDALDI | 93 |
| LCDR1 | RASQDINNYLA | 36 |
| LCDR2 | TASSLQS | 79 |
| LCDR3 | QQYNTYPYT | 89 |

TABLE 24

CHOTHIA NOMENCLATURE

| | Antibody D | |
|---|---|---|
| | CHOTHIA SEQ | SEQ ID NO: |
| HCDR1 | GFTFSSF | 94 |
| HCDR2 | GIAGD | 81 |
| HCDR3 | GGNWDDALDI | 95 |
| LCDR1 | RASQDINNYLA | 36 |
| LCDR2 | TASSLQS | 79 |
| LCDR3 | QQYNTYPYT | 89 |

TABLE 25

NORTH NOMENCLATURE

| | Antibody D | |
|---|---|---|
| | NORTH SEQ | SEQ ID NO: |
| HCDR1 | AASGFTFSSFDMH | 96 |
| HCDR2 | TIGIAGDTY | 97 |
| HCDR3 | ARGGNWDDALDI | 98 |
| LCDR1 | RASQDINNYLA | 99 |
| LCDR2 | YTASSLQS | 86 |
| LCDR3 | QQYNTYPYT | 89 |

Anti-SIRPα Antibody Sequences

Heavy and light chain variable regions of representative anti-SIRPα antibodies of the present invention are disclosed in Tables 26-27 below.

TABLE 26

Heavy Chain Variable Region (VH) Amino Acid Sequences

>Antibody A (SEQ ID NO: 100)
EVQLVESGGGLVQPGGSLRLSCAASGFTLS<u>SYDMH</u>WVRQATGKGLEWVS<u>A</u>
<u>IGTAGDTYYTGSVKG</u>RFTISRENAKNSLYLQMNSLRAGDTAVYYCVR<u>GGV</u>
<u>WDDAFDI</u>WGQGTMVTSS TABLE 26-continued Heavy Chain Variable Region (VH) Amino Acid Sequences >Antibody B
(SEQ ID NO: 101)
QVQLVQSGAEVKKPGASVKVSCKASGYTFTGNYMHWVRQAPGQGLEWMGW
INPNSGGTNYAQKFQGRVTMTRDTSISTAYMELSRLRSDDTAVYYCVSGS
GWYENYYYYGMDVWGQGTTVTVSS >Antibody C
(SEQ ID NO: 102)
EVQLVESGGGLVQPGGSLRLSCAASGFTFSSYDMHWVRQATGKGLEWVSV
IGIAGDTYYPGSVKGRFTISRENAKNSLYLQMNSLRVGDTAVYYCARGGS
WDDAFDIWGQGTMVTVSS >Antibody D
(SEQ ID NO: 103)
EVQLVESGGGLVQPGGSLRLSCAASGFTFSSFDMHWVRQPTGKGLEWVST
IGIAGDTYFPGSVKGRFTISRENAKNSLYLQMNSLRAGDTAVYYCARGGN
WDDALDIWGQGTMVTVSS >Antibody E
(SEQ ID NO: 104)
QVQLQESGPGLVRPSETLSLTCTVSGGSIRNYYWSWIRQPPGKGLEWIGF
IYYNGRTFYNSSLKSRVTISLDMSMNQFSLKMTSVTAADTAVYYCARVRA
YSGIGLDGTDVWGQGTTVTVSSARFTVDKSSSTAYMQFSSLTSEDTAVYF
CARSGPYSYYAGGYALDYWGQGTSVTVSS

TABLE 27

Light Chain Variable Region Amino Acid Sequences

>Antibody A
(SEQ ID NO: 105)
DIQMTQSPSSLSASVGDRVTITCRASQDINNYLAWFQQKPGKAPKSLIYT
ASSLHSGVPSKFSGSGSGTDFTLTISSLQPEDFATYYCQQYVSYPYTFGQ
GTKLEIK >Antibody B
(SEQ ID NO: 106)
DIQMTQSPSSVSASVGDRVTITCRASQGISSWLAWYQQKPGKAPKLLIYA
ESSLQSGVPSRFSGSGSGTDFTLTISSLQPEDFATYYCQQANSFPLTFGG
GTKVEIK >Antibody C
(SEQ ID NO: 107)
DIQMTQSPSSLSASIGDKVTITCRASQDINNYLAWFQQKPGKAPKSLIYT
ASSLQSGVPSKFSGSGSGTDFTLTISSLQPEDFATYYCQQYVSYPYTFGQ
GTKLEIK >Antibody D
(SEQ ID NO: 108)
DIQMTQSPSSLSASVGDRVTITCRASQDINNYLAWFQQKPGKAPKSLIYT
ASSLQSGVPSKFSGSGSGTDFTLTISSLQPEDFATYYCQQYNTYPYTFGQ
GTKLEIK >Antibody E
(SEQ ID NO: 109)
DIVMTQSPLSLPVTPGEPASISCKSSQSLLYSNGYNYLDWYLQRPGQSPQ
LLIYLGSNRASGVPDRFSGSGSGTDFTLKISRVEAEDVGVFYCMQALQTP
LTFGGGTKVEIK Representative anti-SIRPα antibodies of the present invention have the light and/or heavy chain variable regions sequences as set forth in Tables 28 or 29.

TABLE 28

Heavy Chain Variable Region (VH) Amino Acid Sequences

| CLONE NAME | VH SEQUENCE | SEQ ID NO: |
|---|---|---|
| Antibody A1<br>Antibody A9 | EVQLVESGGGLVQPGGSLRLSCAASGFTLSSYDMHWV<br>RQAPGKGLEWVSAIGTAGDTYYTGSVKGRFTISRENAK<br>NSLYLQMNSLRADDTAVYYCVRGGVWDDAFDIWGQG<br>TMVTVSS | 110 |
| Antibody A2<br>Antibody A10<br>Antibody A11 | EVQLVESGGGLVQPGGSLRLSCAASGFTLSSYDMHWV<br>RQATGKGLEWVSAIGTAGDTYYTGSVKGRFTISRENAK<br>NSLYLQMNSLRAADTAVYYCVRGGVWDDAFDIWGQG<br>TMVTVSS | 111 |
| Antibody A3<br>Antibody A12 | EVQLVESGGGLVQPGGSLRLSCAASGFTLSSYDMHWV<br>RQATGKGLEWVSAIGTAGDTYYTGSVKGRFTISRENAK<br>NSLYLQMNSLRASDTAVYYCVRGGVWDDAFDIWGQG<br>TMVTVSS | 112 |
| Antibody A4<br>Antibody A13 | EVQLVESGGGLVQPGGSLRLSCAASGFTLSSYDMHWV<br>RQAPGKGLEWVSAIGTAGDTYYTGSVKGRFTISRENAK<br>NSLYLQMNSLRAADTAVYYCVRGGVWDDAFDIWGQG<br>TMVTVSS | 113 |
| Antibody A5<br>Antibody A14 | EVQLVESGGGLVQPGGSLRLSCAASGFTLSSYDMHWV<br>RQAPGKGLEWVSAIGTAGDTYYTGSVKGRFTISRENAK<br>NSLYLQMNSLRASDTAVYYCVRGGVWDDAFDIWGQG<br>TMVTVSS | 114 |
| Antibody A6<br>Antibody A15 | EVQLVESGGGLVQPGGSLRLSCAASGFTLSSYDMHWV<br>RQAPGKGLEWVSAIGTAGDTYYTGSVKGRFTISRENAK<br>NSLYLQMNSLRAEDTAVYYCVRGGVWDDAFDIWGQG<br>TMVTVSS | 115 |
| Antibody A7 | EVQLVESGGGLVQPGGSLRLSCAASGFTLSSYDMHWV<br>RQATGKGLEWVSAIGTAGDTYYTGSVKGRFTISRENAK<br>NSLYLQMNSLRAGDTAVYYCVRGGVWDDAFDIWGQG<br>TMVTVSS | 116 |

TABLE 28-continued

Heavy Chain Variable Region (VH) Amino Acid Sequences

| CLONE NAME | VH SEQUENCE | SEQ ID NO: |
| --- | --- | --- |
| Antibody A8<br>Antibody A16 | EVQLVESGGGLVQPGGSLRLSCAASGFTLSSYDMHWV<br>RQAPGKGLEWVSAIGTAGDTYYTGSVKGRFTISRENAK<br>NSLYLQMNSLRAGDTAVYYCVRGGVWDDAFDIWGQG<br>TMVTVSS | 117 |
| Antibody E1<br>Antibody E2<br>Antibody E9 | QVQLQESGPGLVRPSETLSLTCTVSGGSIRNYYWSWIR<br>QPPGKGLEWIGFIYYNGRTFYNPSLKSRVTISLDMSINQ<br>FSLKMTSVTAADTAVYYCARVRAYSGIGLDGTDVWGQ<br>GTTVTVSS | 118 |
| Antibody E3<br>Antibody E4<br>Antibody E12 | QVQLQESGPGLVRPSETLSLTCTVSGGSIRNYYWSWIR<br>QPPGKGLEWIGFIYYNGRTFYNPSLKSRVTISLDMSKN<br>QFSLKMTSVTAADTAVYYCARVRAYSGIGLDGTDVWG<br>QGTTVTVSS | 119 |
| Antibody E5<br>Antibody E6<br>Antibody E14 | QVQLQESGPGLVRPSETLSLTCTVSGGSIRNYYWSWIR<br>QPPGKGLEWIGFIYYNGRTFYNPSLKSRVTISLDKSKNQ<br>FSLKMTSVTAADTAVYYCARVRAYSGIGLDGTDVWGQ<br>GTTVTVSS | 120 |
| Antibody E7<br>Antibody E10<br>Antibody E16 | QVQLQESGPGLVRPSETLSLTCTVSGGSIRNYYWSWIR<br>QPPGKGLEWIGFIYYNGRTFYNPSLKSRVTISLDTSKNQ<br>FSLKMTSVTAADTAVYYCARVRAYSGIGLDGTDVWGQ<br>GTTVTVSS | 121 |
| Antibody E8<br>Antibody E11<br>Antibody E17 | QVQLQESGPGLVRPSETLSLTCTVSGGSIRNYYWSWIR<br>QPPGKGLEWMGFIYDNGRTFYNPSLKSRVTISLDMSM<br>NQFSLKMTSVTAADTAVYYCARVRAYSGIGLDGTDVW<br>GQGTTVTVSS | 122 |
| Antibody E13<br>Antibody E15<br>Antibody E20 | QVQLQESGPGLVRPSETLSLTCTVSGGSIRNYYWSWIR<br>QPPGKGLEWIGFIYYTGRTFYNPSLKSRVTISLDMSINQ<br>FSLKMTSVTAADTAVYYCARVRAYSGIGLDGTDVWGQ<br>GTTVTVSS | 123 |
| Antibody E18<br>Antibody E19<br>Antibody E21 | QVQLQESGPGLVRPSETLSLTCTVSGGSIRNYYWSWIR<br>QPPGKGLEWIGFIYYTGRTFYNPSLKSRVTISLDMSKN<br>QFSLKMTSVTAADTAVYYCARVRAYSGIGLDGTDVWG<br>QGTTVTVSS | 124 |
| Antibody E22 | QVQLQESGPGLVKPSETLSLTCTVSGGSIRDYYWSWIR<br>QPPGKGLEWIGFIYYNGRTFYQSSLKSRVTISLDTSKNQ<br>FSLKMTSVTAADTAVYYCARVRAYSGIGLDGTDVWGQ<br>GTTVTVSS | 221 |

TABLE 29

Light Chain Variable Region (VL) Amino Acid Sequences

| CLONE NAME | VL SEQUENCE | SEQ ID NO: |
| --- | --- | --- |
| Antibody A1<br>Antibody A2<br>Antibody A3<br>Antibody A4<br>Antibody A5<br>Antibody A6<br>Antibody A7<br>Antibody A8 | DIQMTQSPSSLSASVGDRVTITCRASQGINNYAAWFQQ<br>KPGKAPKSLIYTASSLHSGVPSKFSGSGSGTDFTLTISS<br>LQPEDFATYYCQQYVSYPYTFGQGTKLEIK | 125 |
| Antibody A9<br>Antibody A10<br>Antibody A11<br>Antibody A12<br>Antibody A13<br>Antibody A14<br>Antibody A15<br>Antibody A16 | DIQMTQSPSSLSASVGDRVTITCRASQDINNYLAWFQQ<br>KPGKAPKSLIYTASSLHSGVPSKFSGSGSGTDFTLTISS<br>LQPEDFATYYCQQYVSYPYTFGQGTKLEIK | 126 |

TABLE 29-continued

Light Chain Variable Region (VL) Amino Acid Sequences

| CLONE NAME | VL SEQUENCE | SEQ ID NO: |
|---|---|---|
| Antibody E1<br>Antibody E3<br>Antibody E5<br>Antibody E7<br>Antibody E8<br>Antibody E13<br>Antibody E19 | DIVMTQSPLSLPVTPGEPASISCKSSQSLLYSNGYAYLD<br>WYLQRPGQSPQLLIYQGSNRASGVPDRFSGSGSGTDF<br>TLKISRVEAEDVGVFYCMQALQTPLTFGGGTKVEIK | 127 |
| Antibody E2 | DIVMTQSPLSLPVTPGEPASISCKSSQSLLYSNGYAYLD<br>WYLQRPGQSPQLLIYLGSNRASGVPDRFSGSGSGTDF<br>TLKISRVEAEDVGVYYCMQALQTPLTFGGGTKVEIK | 128 |
| Antibody E4<br>Antibody E6<br>Antibody E10<br>Antibody E11<br>Antibody E15<br>Antibody E18 | DIVMTQSPLSLPVTPGEPASISCKSSQSLLYSNGYAYLD<br>WYLQRPGQSPQLLIYLGSNRASGVPDRFSGSGSGTDF<br>TLKISRVEAEDVGVYYCMQALQTPLTFGGGTKVEIK | 129 |
| Antibody E9<br>Antibody E12<br>Antibody E14<br>Antibody E16<br>Antibody E17<br>Antibody E20<br>Antibody E21 | DIVMTQSPLSLPVTPGEPASISCKSSQSLLYSNAYNYLD<br>WYLQRPGQSPQLLIYLGSNRASGVPDRFSGSGSGTDF<br>TLKISRVEAEDVGVYYCMQALQTPLTFGGGTKVEIK | 130 |
| Antibody E22 | DIVMTQSPLSLPVTPGEPASISCRSSQSLLYSTGYTYLD<br>WYLQRPGQSPQLLIYGGSSRASGVPDRFSGSGSGTDF<br>TLKISRVEAEDVGVFYCGQALQTPLTFGQGTKVEIK | 222 |

Representative anti-SIRPα antibodies of the present invention may comprise a heavy and/or light chain as set forth in Tables 30 or 31 below.

TABLE 30

| FULL LENGTH HC SEQUENCES OF ANTI-SIRPα ANTIBODIES. | | |
|---|---|---|
| Antibody | Sequence | SEQ ID NO: |
| Antibody A | EVQLVESGGGLVQPGGSLRLSCAASGFTLSSYDMHWVRQATGKGLE<br>WVSAIGTAGDTYYTGSVKGRFTISRENAKNSLYLQMNSLRAGDTAVY<br>YCVRGGVWDDAFDIWGQGTMVTVSSASTKGPSVFPLAPSSKSTSG<br>GTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 131 |
| Antibody F | EVQLVESGGGLVQPGGSLRLSCAASGFTLSSYDMHWVRQATGKGLE<br>WVSAIGTAGDTYYTGSVKGRFTISRENAKNSLYLQMNSLRAGDTAVY<br>YCVRGGVWDDAFDIWGQGTMVTVSSASTKGPSVFPLAPCSRSTSES<br>TAALGCLVKDYFPEPVTVSWNSGALTSGVHTFPAVLQSSGLYSLSSVV<br>TVPSSSLGTKTYTCNVDHKPSNTKVDKRVESKYGPPCPPCPAPEFLGG<br>PSVFLFPPKPKDTLMISRTPEVTCVVVDVSQEDPEVQFNWYVDGVE<br>VHNAKTKPREEQFNSTYRVVSVLTVLHQDWLNGKEYKCKVSNKGLP<br>SSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFS<br>CSVMHEALHNHYTQKSLSLSLG | 132 |
| Antibody B | QVQLVQSGAEVKKPGASVKVSCKASGYTFTGNYMHWVRQAPGQG<br>LEWMGWINPNSGGTNYAQKFQGRVTMTRDTSISTAYMELSRLRSD<br>DTAVYYCVSGSGWYENYYYYGMDVWGQGTTVTVSSASTKGPSVFP<br>LAPSSKSTSGGTAALGCLVKDYFPEPVTVSWNSGALTSGVHTFPAVL<br>QSSGLYSLSSVVTVPSSSLGTQTYICNVNHKPSNTKVDKRVEPKSCDK<br>THTCPPCPAPEAAGGPSVFLFPPKPKDTLMISRTPEVTCVVVDVSHE<br>DPEVKFNWYVDGVEVHNAKTKPREEQYNSTYRVVSVLTVLHQDWL<br>NGKEYKCKVSNKALPAPIEKTISKAKGQPREPQVYTLPPSREEMTKNQ<br>VSLTCLVKGFYPSDIAVEWESNGQPENNYKTTPPVLDSDGSFFLYSKL<br>TVDKSRWQQGNVFSCSVMHEALHNHYTQKSLSLSPG | 133 |

TABLE 30-continued

FULL LENGTH HC SEQUENCES OF ANTI-SIRPα ANTIBODIES.

| Antibody | Sequence | SEQ ID NO: |
|---|---|---|
| Antibody C | EVQLVESGGGLVQPGGSLRLSCAASGFTFSSYDMHWVRQATGKGLE WVSVIGIAGDTYYPGSVKGRFTISRENAKNSLYLQMNSLRVGDTAVY YCARGGSWDDAFDIWGQGTMVTVSSASTKGPSVFPLAPSSKSTSGG TAALGCLVKDYFPEPVTVSWNSGALTSGVHTFPAVLQSSGLYSLSSVV TVPSSSLGTQTYICNVNHKPSNTKVDKRVEPKSCDKTHTCPPCPAPEA AGGPSVFLFPPKPKDTLMISRTPEVTCVVVDVSHEDPEVKFNWYVD GVEVHNAKTKPREEQYNSTYRVVSVLTVLHQDWLNGKEYKCKVSNK ALPAPIEKTISKAKGQPREPQVYTLPPSREEMTKNQVSLTCLVKGFYPS DIAVEWESNGQPENNYKTTPPVLDSDGSFFLYSKLTVDKSRWQQGN VFSCSVMHEALHNHYTQKSLSLSPG | 134 |
| Antibody E | QVQLQESGPGLVRPSETLSLTCTVSGGSIRNYYWSWIRQPPGKGLE WIGFIYYNGRTFYNSSLKSRVTISLDMSMNQFSLKMTSVTAADTAVY YCARVRAYSGIGLDGTDVWGQGTTVTVSSASTKGPSVFPLAPSSKST SGGTAALGCLVKDYFPEPVTVSWNSGALTSGVHTFPAVLQSSGLYSL SSVVTVPSSSLGTQTYICNVNHKPSNTKVDKRVEPKSCDKTHTCPPCP APEAAGGPSVFLFPPKPKDTLMISRTPEVTCVVVDVSHEDPEVKFNW YVDGVEVHNAKTKPREEQYNSTYRVVSVLTVLHQDWLNGKEYKCKV SNKALPAPIEKTISKAKGQPREPQVYTLPPSREEMTKNQVSLTCLVKG FYPSDIAVEWESNGQPENNYKTTPPVLDSDGSFFLYSKLTVDKSRWQ QGNVFSCSVMHEALHNHYTQKSLSLSPG | 135 |
| Antibody G | QVQLQESGPGLVRPSETLSLTCTVSGGSIRNYYWSWIRQPPGKGLE WIGFIYYNGRTFYNSSLKSRVTISLDMSMNQFSLKMTSVTAADTAVY YCARVRAYSGIGLDGTDVWGQGTTVTVSSASTKGPSVFPLAPCSRST SESTAALGCLVKDYFPEPVTVSWNSGALTSGVHTFPAVLQSSGLYSLS SVVTVPSSSLGTKTYTCNVDHKPSNTKVDKRVESKYGPPCPPCPAPEF LGGPSVFLFPPKPKDTLMISRTPEVTCVVVDVSQEDPEVQFNWYVD GVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPS DIAVEWESNGQPENNYKTTPPVLDSDGSFFLYSRLTVDKSRWQEGN VFSCSVMHEALHNHYTQKSLSLSLG | 136 |
| Antibody D | EVQLVESGGGLVQPGGSLRLSCAASGFTFSSFDMHWVRQPTGKGLE WVSTIGIAGDTYFPGSVKGRFTISRENAKNSLYLQMNSLRAGDTAVY YCARGGNWDDALDIWGQGTMVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 137 |
| Antibody A1 | EVQLVESGGGLVQPGGSLRLSCAASGFTLSSYDMHWVRQAPGKGLE WVSAIGTAGDTYYTGSVKGRFTISRENAKNSLYLQMNSLRADDTAVY YCVRGGVWDDAFDIWGQGTMVTVSSASTKGPSVFPLAPSSKSTSGG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 138 |
| Antibody A2 | EVQLVESGGGLVQPGGSLRLSCAASGFTLSSYDMHWVRQATGKGLE WVSAIGTAGDTYYTGSVKGRFTISRENAKNSLYLQMNSLRAADTAVY YCVRGGVWDDAFDIWGQGTMVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 139 |
| Antibody A3 | EVQLVESGGGLVQPGGSLRLSCAASGFTLSSYDMHWVRQATGKGLE WVSAIGTAGDTYYTGSVKGRFTISRENAKNSLYLQMNSLRASDTAVY YCVRGGVWDDAFDIWGQGTMVTVSSASTKGPSVFPLAPSSKSTSGG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 140 |

TABLE 30-continued

FULL LENGTH HC SEQUENCES OF ANTI-SIRPα ANTIBODIES.

| Antibody | Sequence | SEQ ID NO: |
|---|---|---|
| Antibody A4 | EVQLVESGGGLVQPGGSLRLSCAASGFTLSSYDMHWVRQAPGKGLE WVSAIGTAGDTYYTGSVKGRFTISRENAKNSLYLQMNSLRAADTAVY YCVRGGVWDDAFDIWGQGTMVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 141 |
| Antibody A5 | EVQLVESGGGLVQPGGSLRLSCAASGFTLSSYDMHWVRQAPGKGLE WVSAIGTAGDTYYTGSVKGRFTISRENAKNSLYLQMNSLRASDTAVY YCVRGGVWDDAFDIWGQGTMVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 142 |
| Antibody A6 | EVQLVESGGGLVQPGGSLRLSCAASGFTLSSYDMHWVRQAPGKGLE WVSAIGTAGDTYYTGSVKGRFTISRENAKNSLYLQMNSLRAEDTAVY YCVRGGVWDDAFDIWGQGTMVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 143 |
| Antibody A7 | EVQLVESGGGLVQPGGSLRLSCAASGFTLSSYDMHWVRQATGKGLE WVSAIGTAGDTYYTGSVKGRFTISRENAKNSLYLQMNSLRAGDTAVY YCVRGGVWDDAFDIWGQGTMVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 144 |
| Antibody A8 | EVQLVESGGGLVQPGGSLRLSCAASGFTLSSYDMHWVRQAPGKGLE WVSAIGTAGDTYYTGSVKGRFTISRENAKNSLYLQMNSLRAGDTAVY YCVRGGVWDDAFDIWGQGTMVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 145 |
| Antibody A9 | EVQLVESGGGLVQPGGSLRLSCAASGFTLSSYDMHWVRQAPGKGLE WVSAIGTAGDTYYTGSVKGRFTISRENAKNSLYLQMNSLRADDTAVY YCVRGGVWDDAFDIWGQGTMVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 146 |
| Antibody A10 | EVQLVESGGGLVQPGGSLRLSCAASGFTLSSYDMHWVRQATGKGLE WVSAIGTAGDTYYTGSVKGRFTISRENAKNSLYLQMNSLRAADTAVY YCVRGGVWDDAFDIWGQGTMVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 147 |

TABLE 30-continued

FULL LENGTH HC SEQUENCES OF ANTI-SIRPα ANTIBODIES.

| Antibody | Sequence | SEQ ID NO: |
|---|---|---|
| Antibody A11 | EVQLVESGGGLVQPGGSLRLSCAASGFTLSSYDMHWVRQATGKGLE<br>WVSAIGTAGDTYYTGSVKGRFTISRENAKNSLYLQMNSLRAADTAVY<br>YCVRGGVWDDAFDIWGQGTMVTVSSASTKGPSVFPLAPCSRSTSES<br>TAALGCLVKDYFPEPVTVSWNSGALTSGVHTFPAVLQSSGLYSLSSVV<br>TVPSSSLGTKTYTCNVDHKPSNTKVDKRVESKYGPPCPPCPAPEFLGG<br>PSVFLFPPKPKDTLMISRTPEVTCVVVDVSQEDPEVQFNWYVDGVE<br>VHNAKTKPREEQFNSTYRVVSVLTVLHQDWLNGKEYKCKVSNKGLP<br>SSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFS<br>CSVMHEALHNHYTQKSLSLSLG | 217 |
| Antibody A12 | EVQLVESGGGLVQPGGSLRLSCAASGFTLSSYDMHWVRQATGKGLE<br>WVSAIGTAGDTYYTGSVKGRFTISRENAKNSLYLQMNSLRASDTAVY<br>YCVRGGVWDDAFDIWGQGTMVTVSSASTKGPSVFPLAPSSKSTSG<br>GTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 148 |
| Antibody A13 | EVQLVESGGGLVQPGGSLRLSCAASGFTLSSYDMHWVRQAPGKGLE<br>WVSAIGTAGDTYYTGSVKGRFTISRENAKNSLYLQMNSLRAADTAVY<br>YCVRGGVWDDAFDIWGQGTMVTVSSASTKGPSVFPLAPSSKSTSG<br>GTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 149 |
| Antibody A14 | EVQLVESGGGLVQPGGSLRLSCAASGFTLSSYDMHWVRQAPGKGLE<br>WVSAIGTAGDTYYTGSVKGRFTISRENAKNSLYLQMNSLRASDTAVY<br>YCVRGGVWDDAFDIWGQGTMVTVSSASTKGPSVFPLAPSSKSTSG<br>GTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 150 |
| Antibody A15 | EVQLVESGGGLVQPGGSLRLSCAASGFTLSSYDMHWVRQAPGKGLE<br>WVSAIGTAGDTYYTGSVKGRFTISRENAKNSLYLQMNSLRAEDTAVY<br>YCVRGGVWDDAFDIWGQGTMVTVSSASTKGPSVFPLAPSSKSTSG<br>GTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 151 |
| Antibody A16 | EVQLVESGGGLVQPGGSLRLSCAASGFTLSSYDMHWVRQAPGKGLE<br>WVSAIGTAGDTYYTGSVKGRFTISRENAKNSLYLQMNSLRAGDTAVY<br>YCVRGGVWDDAFDIWGQGTMVTVSSASTKGPSVFPLAPSSKSTSG<br>GTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 152 |
| Antibody E1 | QVQLQESGPGLVRPSETLSLTCTVSGGSIRNYYWSWIRQPPGKGLE<br>WIGFIYYNGRTFYNPSLKSRVTISLDMSINQFSLKMTSVTAADTAVYY<br>CARVRAYSGIGLDGTDVWGQGTTVTVSSASTKGPSVFPLAPSSKSTS<br>GGTAALGCLVKDYFPEPVTVSWNSGALTSGVHTFPAVLQSSGLYSLS<br>SVVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 153 |

TABLE 30-continued

FULL LENGTH HC SEQUENCES OF ANTI-SIRPα ANTIBODIES.

| Antibody | Sequence | SEQ ID NO: |
|---|---|---|
| Antibody E2 | QVQLQESGPGLVRPSETLSLTCTVSGGSIRNYYWSWIRQPPGKGLE WIGFIYYNGRTFYNPSLKSRVTISLDMSINQFSLKMTSVTAADTAVYY CARVRAYSGIGLDGTDVWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 154 |
| Antibody E3 | QVQLQESGPGLVRPSETLSLTCTVSGGSIRNYYWSWIRQPPGKGLE WIGFIYYNGRTFYNPSLKSRVTISLDMSKNQFSLKMTSVTAADTAVYY CARVRAYSGIGLDGTDVWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 155 |
| Antibody E4 | QVQLQESGPGLVRPSETLSLTCTVSGGSIRNYYWSWIRQPPGKGLE WIGFIYYNGRTFYNPSLKSRVTISLDMSKNQFSLKMTSVTAADTAVYY CARVRAYSGIGLDGTDVWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 156 |
| Antibody E5 | QVQLQESGPGLVRPSETLSLTCTVSGGSIRNYYWSWIRQPPGKGLE WIGFIYYNGRTFYNPSLKSRVTISLDKSKNQFSLKMTSVTAADTAVYY CARVRAYSGIGLDGTDVWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 157 |
| Antibody E6 | QVQLQESGPGLVRPSETLSLTCTVSGGSIRNYYWSWIRQPPGKGLE WIGFIYYNGRTFYNPSLKSRVTISLDKSKNQFSLKMTSVTAADTAVYY CARVRAYSGIGLDGTDVWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 158 |
| Antibody E7 | QVQLQESGPGLVRPSETLSLTCTVSGGSIRNYYWSWIRQPPGKGLE WIGFIYYNGRTFYNPSLKSRVTISLDTSKNQFSLKMTSVTAADTAVYY CARVRAYSGIGLDGTDVWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 159 |
| Antibody E8 | QVQLQESGPGLVRPSETLSLTCTVSGGSIRNYYWSWIRQPPGKGLE WMGFIYDNGRTFYNPSLKSRVTISLDMSMNQFSLKMTSVTAADTAV YYCARVRAYSGIGLDGTDVWGQGTTVTVSSASTKGPSVFPLAPSSKS TSGGTAALGCLVKDYFPEPVTVSWNSGALTSGVHTFPAVLQSSGLYS LSSVVTVPSSSLGTQTYICNVNHKPSNTKVDKRVEPKSCDKTHTCPPC PAPEAAGGPSVFLFPPKPKDTLMISRTPEVTCVVVDVSHEDPEVKFN WYVDGVEVHNAKTKPREEQYNSTYRVVSVLTVLHQDWLNGKEYKC KVSNKALPAPIEKTISKAKGQPREPQVYTLPPSREEMTKNQVSLTCLV KGFYPSDIAVEWESNGQPENNYKTTPPVLDSDGSFFLYSKLTVDKSR WQQGNVFSCSVMHEALHNHYTQKSLSLSPG | 160 |

TABLE 30-continued

FULL LENGTH HC SEQUENCES OF ANTI-SIRPα ANTIBODIES.

| Antibody | Sequence | SEQ ID NO: |
|---|---|---|
| Antibody E9 | QVQLQESGPGLVRPSETLSLTCTVSGGSIRNYYWSWIRQPPGKGLE<br>WIGFIYYNGRTFYNPSLKSRVTISLDMSINQFSLKMTSVTAADTAVYY<br>CARVRAYSGIGLDGTDVWGQGTTVTVSSASTKGPSVFPLAPSSKSTS<br>GGTAALGCLVKDYFPEPVTVSWNSGALTSGVHTFPAVLQSSGLYSLS<br>SVVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 161 |
| Antibody E10 | QVQLQESGPGLVRPSETLSLTCTVSGGSIRNYYWSWIRQPPGKGLE<br>WIGFIYYNGRTFYNPSLKSRVTISLDTSKNQFSLKMTSVTAADTAVYY<br>CARVRAYSGIGLDGTDVWGQGTTVTVSSASTKGPSVFPLAPSSKSTS<br>GGTAALGCLVKDYFPEPVTVSWNSGALTSGVHTFPAVLQSSGLYSLS<br>SVVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 162 |
| Antibody E11 | QVQLQESGPGLVRPSETLSLTCTVSGGSIRNYYWSWIRQPPGKGLE<br>WMGFIYDNGRTFYNPSLKSRVTISLDMSMNQFSLKMTSVTAADTAV<br>YYCARVRAYSGIGLDGTDVWGQGTTVTVSSASTKGPSVFPLAPSSKS<br>TSGGTAALGCLVKDYFPEPVTVSWNSGALTSGVHTFPAVLQSSGLYS<br>LSSVVTVPSSSLGTQTYICNVNHKPSNTKVDKRVEPKSCDKTHTCPPC<br>PAPEAAGGPSVFLFPPKPKDTLMISRTPEVTCVVVDVSHEDPEVKFN<br>WYVDGVEVHNAKTKPREEQYNSTYRVVSVLTVLHQDWLNGKEYKC<br>KVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSR<br>WQQGNVFSCSVMHEALHNHYTQKSLSLSPG | 163 |
| Antibody E12 | QVQLQESGPGLVRPSETLSLTCTVSGGSIRNYYWSWIRQPPGKGLE<br>WIGFIYYNGRTFYNPSLKSRVTISLDMSKNQFSLKMTSVTAADTAVYY<br>CARVRAYSGIGLDGTDVWGQGTTVTVSSASTKGPSVFPLAPSSKSTS<br>GGTAALGCLVKDYFPEPVTVSWNSGALTSGVHTFPAVLQSSGLYSLS<br>SVVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 164 |
| Antibody E13 | QVQLQESGPGLVRPSETLSLTCTVSGGSIRNYYWSWIRQPPGKGLE<br>WIGFIYYTGRTFYNPSLKSRVTISLDMSINQFSLKMTSVTAADTAVYYC<br>ARVRAYSGIGLDGTDVWGQGTTVTVSSASTKGPSVFPLAPSSKSTSG<br>GTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 165 |
| Antibody E14 | QVQLQESGPGLVRPSETLSLTCTVSGGSIRNYYWSWIRQPPGKGLE<br>WIGFIYYNGRTFYNPSLKSRVTISLDKSKNQFSLKMTSVTAADTAVYY<br>CARVRAYSGIGLDGTDVWGQGTTVTVSSASTKGPSVFPLAPSSKSTS<br>GGTAALGCLVKDYFPEPVTVSWNSGALTSGVHTFPAVLQSSGLYSLS<br>SVVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 166 |
| Antibody E15 | QVQLQESGPGLVRPSETLSLTCTVSGGSIRNYYWSWIRQPPGKGLE<br>WIGFIYYTGRTFYNPSLKSRVTISLDMSINQFSLKMTSVTAADTAVYC<br>ARVRAYSGIGLDGTDVWGQGTTVTVSSASTKGPSVFPLAPSSKSTSG<br>GTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 167 |

TABLE 30-continued

FULL LENGTH HC SEQUENCES OF ANTI-SIRPα ANTIBODIES.

| Antibody | Sequence | SEQ ID NO: |
| --- | --- | --- |
| Antibody E16 | QVQLQESGPGLVRPSETLSLTCTVSGGSIRNYYWSWIRQPPGKGLE<br>WIGFIYYNGRTFYNPSLKSRVTISLDTSKNQFSLKMTSVTAADTAVYY<br>CARVRAYSGIGLDGTDVWGQGTTVTVSSASTKGPSVFPLAPSSKSTS<br>GGTAALGCLVKDYFPEPVTVSWNSGALTSGVHTFPAVLQSSGLYSLS<br>SVVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 168 |
| Antibody E17 | QVQLQESGPGLVRPSETLSLTCTVSGGSIRNYYWSWIRQPPGKGLE<br>WMGFIYDNGRTFYNPSLKSRVTISLDMSMNQFSLKMTSVTAADTAV<br>YYCARVRAYSGIGLDGTDVWGQGTTVTVSSASTKGPSVFPLAPSSKS<br>TSGGTAALGCLVKDYFPEPVTVSWNSGALTSGVHTFPAVLQSSGLYS<br>LSSVVTVPSSSLGTQTYICNVNHKPSNTKVDKRVEPKSCDKTHTCPPC<br>PAPEAAGGPSVFLFPPKPKDTLMISRTPEVTCVVVDVSHEDPEVKFN<br>WYVDGVEVHNAKTKPREEQYNSTYRVVSVLTVLHQDWLNGKEYKC<br>KVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSR<br>WQQGNVFSCSVMHEALHNHYTQKSLSLSPG | 169 |
| Antibody E18 | QVQLQESGPGLVRPSETLSLTCTVSGGSIRNYYWSWIRQPPGKGLE<br>WIGFIYYTGRTFYNPSLKSRVTISLDMSKNQFSLKMTSVTAADTAVYY<br>CARVRAYSGIGLDGTDVWGQGTTVTVSSASTKGPSVFPLAPSSKSTS<br>GGTAALGCLVKDYFPEPVTVSWNSGALTSGVHTFPAVLQSSGLYSLS<br>SVVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 170 |
| Antibody E19 | QVQLQESGPGLVRPSETLSLTCTVSGGSIRNYYWSWIRQPPGKGLE<br>WIGFIYYTGRTFYNPSLKSRVTISLDMSKNQFSLKMTSVTAADTAVYY<br>CARVRAYSGIGLDGTDVWGQGTTVTVSSASTKGPSVFPLAPSSKSTS<br>GGTAALGCLVKDYFPEPVTVSWNSGALTSGVHTFPAVLQSSGLYSLS<br>SVVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 171 |
| Antibody E20 | QVQLQESGPGLVRPSETLSLTCTVSGGSIRNYYWSWIRQPPGKGLE<br>WIGFIYYTGRTFYNPSLKSRVTISLDMSINQFSLKMTSVTAADTAVYC<br>ARVRAYSGIGLDGTDVWGQGTTVTVSSASTKGPSVFPLAPSSKSTSG<br>GTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 172 |
| Antibody E21 | QVQLQESGPGLVRPSETLSLTCTVSGGSIRNYYWSWIRQPPGKGLE<br>WIGFIYYTGRTFYNPSLKSRVTISLDMSKNQFSLKMTSVTAADTAVYY<br>CARVRAYSGIGLDGTDVWGQGTTVTVSSASTKGPSVFPLAPSSKSTS<br>GGTAALGCLVKDYFPEPVTVSWNSGALTSGVHTFPAVLQSSGLYSLS<br>SVVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 173 |

TABLE 30-continued

FULL LENGTH HC SEQUENCES OF ANTI-SIRPα ANTIBODIES.

| Antibody | Sequence | SEQ ID NO: |
|---|---|---|
| Antibody E22 | QVQLQESGPGLVKPSETLSLTCTVSGGSIRDYYWSWIRQPPGKGLE WIGFIYYNGRTFYQSSLKSRVTISLDTSKNQFSLKMTSVTAADTAVYY CARVRAYSGIGLDGTDVWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 219 |

TABLE 31

FULL LENGTH LC SEQUENCES OF ANTI-SIRP-α ANTIBODIES.

| Antibody | Sequence | SEQ ID NO: |
|---|---|---|
| Antibody A | DIQMTQSPSSLSASVGDRVTITCRASQDINNYLAWFQQKPGKAPKSL IYTASSLHSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 174 |
| Antibody F | DIQMTQSPSSLSASVGDRVTITCRASQDINNYLAWFQQKPGKAPKSL IYTASSLHSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 175 |
| Antibody B | DIQMTQSPSSVSASVGDRVTITCRASQGISSWLAWYQQKPGKAPKL LIYAESSLQSGVPSRFSGSGSGTDFTLTISSLQPEDFATYYCQQANSFP LTFGGGTKVEIKRTVAAPSVFIFPPSDEQLKSGTASVVCLLNNFYPREA KVQWKVDNALQSGNSQESVTEQDSKDSTYSLSSTLTLSKADYEKHKV YACEVTHQGLSSPVTKSFNRGEC | 176 |
| Antibody C | DIQMTQSPSSLSASIGDKVTITCRASQDINNYLAWFQQKPGKAPKSLI YTASSLQSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 177 |
| Antibody E | DIVMTQSPLSLPVTPGEPASISCKSSQSLLYSNGYNYLDWYLQRPGQS PQLLIYLGSNRASGVPDRFSGSGSGTDFTLKISRVEAEDVGVFYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 178 |
| Antibody G | DIVMTQSPLSLPVTPGEPASISCKSSQSLLYSNGYNYLDWYLQRPGQS PQLLIYLGSNRASGVPDRFSGSGSGTDFTLKISRVEAEDVGVFYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 179 |
| Antibody D | DIQMTQSPSSLSASVGDRVTITCRASQDINNYLAWFQQKPGKAPKSL IYTASSLQSGVPSKFSGSGSGTDFTLTISSLQPEDFATYYCQQYNTYPY TFGQGTKLEIKRTVAAPSVFIFPPSDEQLKSGTASVVCLLNNFYPREAK VQWKVDNALQSGNSQESVTEQDSKDSTYSLSSTLTLSKADYEKHKVY ACEVTHQGLSSPVTKSFNRGEC | 180 |
| Antibody A1 | DIQMTQSPSSLSASVGDRVTITCRASQGINNYAAWFQQKPGKAPKS LIYTASSLHSGVPSKFSGSGSGTDFTLTISSLQPEDFATYYCQQYVSYPY TFGQGTKLEIKRTVAAPSVFIFPPSDEQLKSGTASVVCLLNNFYPREAK VQWKVDNALQSGNSQESVTEQDSKDSTYSLSSTLTLSKADYEKHKVY ACEVTHQGLSSPVTKSFNRGEC | 181 |
| Antibody A2 | DIQMTQSPSSLSASVGDRVTITCRASQGINNYAAWFQQKPGKAPKS LIYTASSLHSGVPSKFSGSGSGTDFTLTISSLQPEDFATYYCQQYVSYPY TFGQGTKLEIKRTVAAPSVFIFPPSDEQLKSGTASVVCLLNNFYPREAK VQWKVDNALQSGNSQESVTEQDSKDSTYSLSSTLTLSKADYEKHKVY ACEVTHQGLSSPVTKSFNRGEC | 182 |

TABLE 31-continued

FULL LENGTH LC SEQUENCES OF ANTI-SIRP-α ANTIBODIES.

| Antibody | Sequence | SEQ ID NO: |
|---|---|---|
| Antibody A3 | DIQMTQSPSSLSASVGDRVTITCRASQGINNYAAWFQQKPGKAPKS LIYTASSLHSGVPSKFSGSGSGTDFTLTISSLQPEDFATYYCQQYVSYPY TFGQGTKLEIKRTVAAPSVFIFPPSDEQLKSGTASVVCLLNNFYPREAK VQWKVDNALQSGNSQESVTEQDSKDSTYSLSSTLTLSKADYEKHKVY ACEVTHQGLSSPVTKSFNRGEC | 183 |
| Antibody A4 | DIQMTQSPSSLSASVGDRVTITCRASQGINNYAAWFQQKPGKAPKS LIYTASSLHSGVPSKFSGSGSGTDFTLTISSLQPEDFATYYCQQYVSYPY TFGQGTKLEIKRTVAAPSVFIFPPSDEQLKSGTASVVCLLNNFYPREAK VQWKVDNALQSGNSQESVTEQDSKDSTYSLSSTLTLSKADYEKHKVY ACEVTHQGLSSPVTKSFNRGEC | 184 |
| Antibody A5 | DIQMTQSPSSLSASVGDRVTITCRASQGINNYAAWFQQKPGKAPKS LIYTASSLHSGVPSKFSGSGSGTDFTLTISSLQPEDFATYYCQQYVSYPY TFGQGTKLEIKRTVAAPSVFIFPPSDEQLKSGTASVVCLLNNFYPREAK VQWKVDNALQSGNSQESVTEQDSKDSTYSLSSTLTLSKADYEKHKVY ACEVTHQGLSSPVTKSFNRGEC | 185 |
| Antibody A6 | DIQMTQSPSSLSASVGDRVTITCRASQGINNYAAWFQQKPGKAPKS LIYTASSLHSGVPSKFSGSGSGTDFTLTISSLQPEDFATYYCQQYVSYPY TFGQGTKLEIKRTVAAPSVFIFPPSDEQLKSGTASVVCLLNNFYPREAK VQWKVDNALQSGNSQESVTEQDSKDSTYSLSSTLTLSKADYEKHKVY ACEVTHQGLSSPVTKSFNRGEC | 186 |
| Antibody A7 | DIQMTQSPSSLSASVGDRVTITCRASQGINNYAAWFQQKPGKAPKS LIYTASSLHSGVPSKFSGSGSGTDFTLTISSLQPEDFATYYCQQYVSYPY TFGQGTKLEIKRTVAAPSVFIFPPSDEQLKSGTASVVCLLNNFYPREAK VQWKVDNALQSGNSQESVTEQDSKDSTYSLSSTLTLSKADYEKHKVY ACEVTHQGLSSPVTKSFNRGEC | 187 |
| Antibody A8 | DIQMTQSPSSLSASVGDRVTITCRASQGINNYAAWFQQKPGKAPKS LIYTASSLHSGVPSKFSGSGSGTDFTLTISSLQPEDFATYYCQQYVSYPY TFGQGTKLEIKRTVAAPSVFIFPPSDEQLKSGTASVVCLLNNFYPREAK VQWKVDNALQSGNSQESVTEQDSKDSTYSLSSTLTLSKADYEKHKVY ACEVTHQGLSSPVTKSFNRGEC | 188 |
| Antibody A9 | DIQMTQSPSSLSASVGDRVTITCRASQDINNYLAWFQQKPGKAPKSL IYTASSLHSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 189 |
| Antibody A10 | DIQMTQSPSSLSASVGDRVTITCRASQDINNYLAWFQQKPGKAPKSL IYTASSLHSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 190 |
| Antibody A11 | DIQMTQSPSSLSASVGDRVTITCRASQDINNYLAWFQQKPGKAPKSL IYTASSLHSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 218 |
| Antibody A12 | DIQMTQSPSSLSASVGDRVTITCRASQDINNYLAWFQQKPGKAPKSL IYTASSLHSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 191 |
| Antibody A13 | DIQMTQSPSSLSASVGDRVTITCRASQDINNYLAWFQQKPGKAPKSL IYTASSLHSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 192 |
| Antibody A14 | DIQMTQSPSSLSASVGDRVTITCRASQDINNYLAWFQQKPGKAPKSL IYTASSLHSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 193 |

TABLE 31-continued

FULL LENGTH LC SEQUENCES OF ANTI-SIRP-α ANTIBODIES.

| Antibody | Sequence | SEQ ID NO: |
|---|---|---|
| Antibody A15 | DIQMTQSPSSLSASVGDRVTITCRASQDINNYLAWFQQKPGKAPKSL IYTASSLHSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 194 |
| Antibody A16 | DIQMTQSPSSLSASVGDRVTITCRASQDINNYLAWFQQKPGKAPKSL IYTASSLHSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 195 |
| Antibody E1 | DIVMTQSPLSLPVTPGEPASISCKSSQSLLYSNGYAYLDWYLQRPGQS PQLLIYQGSNRASGVPDRFSGSGSGTDFTLKISRVEAEDVGVFYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 196 |
| Antibody E2 | DIVMTQSPLSLPVTPGEPASISCKSSQSLLYSNGYAYLDWYLQRPGQS PQLLIYLGSNRASGVPDRFSGSGSGTDFTLKISRVEAEDVGVYYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 197 |
| Antibody E3 | DIVMTQSPLSLPVTPGEPASISCKSSQSLLYSNGYAYLDWYLQRPGQS PQLLIYQGSNRASGVPDRFSGSGSGTDFTLKISRVEAEDVGVFYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 198 |
| Antibody E4 | DIVMTQSPLSLPVTPGEPASISCKSSQSLLYSNGYAYLDWYLQRPGQS PQLLIYLGSNRASGVPDRFSGSGSGTDFTLKISRVEAEDVGVYYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 199 |
| Antibody E5 | DIVMTQSPLSLPVTPGEPASISCKSSQSLLYSNGYAYLDWYLQRPGQS PQLLIYQGSNRASGVPDRFSGSGSGTDFTLKISRVEAEDVGVFYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 200 |
| Antibody E6 | DIVMTQSPLSLPVTPGEPASISCKSSQSLLYSNGYAYLDWYLQRPGQS PQLLIYLGSNRASGVPDRFSGSGSGTDFTLKISRVEAEDVGVYYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 201 |
| Antibody E7 | DIVMTQSPLSLPVTPGEPASISCKSSQSLLYSNGYAYLDWYLQRPGQS PQLLIYQGSNRASGVPDRFSGSGSGTDFTLKISRVEAEDVGVFYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 202 |
| Antibody E8 | DIVMTQSPLSLPVTPGEPASISCKSSQSLLYSNGYAYLDWYLQRPGQS PQLLIYQGSNRASGVPDRFSGSGSGTDFTLKISRVEAEDVGVFYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 203 |
| Antibody E9 | DIVMTQSPLSLPVTPGEPASISCKSSQSLLYSNAYNYLDWYLQRPGQS PQLLIYLGSNRASGVPDRFSGSGSGTDFTLKISRVEAEDVGVYYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 204 |
| Antibody E10 | DIVMTQSPLSLPVTPGEPASISCKSSQSLLYSNGYAYLDWYLQRPGQS PQLLIYLGSNRASGVPDRFSGSGSGTDFTLKISRVEAEDVGVYYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 205 |

TABLE 31-continued

FULL LENGTH LC SEQUENCES OF ANTI-SIRP-α ANTIBODIES.

| Antibody | Sequence | SEQ ID NO: |
| --- | --- | --- |
| Antibody E11 | DIVMTQSPLSLPVTPGEPASISCKSSQSLLYSNGYAYLDWYLQRPGQS PQLLIYLGSNRASGVPDRFSGSGSGTDFTLKISRVEAEDVGVYYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 206 |
| Antibody E12 | DIVMTQSPLSLPVTPGEPASISCKSSQSLLYSNAYNYLDWYLQRPGQS PQLLIYLGSNRASGVPDRFSGSGSGTDFTLKISRVEAEDVGVYYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 207 |
| Antibody E13 | DIVMTQSPLSLPVTPGEPASISCKSSQSLLYSNGYAYLDWYLQRPGQS PQLLIYQGSNRASGVPDRFSGSGSGTDFTLKISRVEAEDVGVFYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 208 |
| Antibody E14 | DIVMTQSPLSLPVTPGEPASISCKSSQSLLYSNAYNYLDWYLQRPGQS PQLLIYLGSNRASGVPDRFSGSGSGTDFTLKISRVEAEDVGVYYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 209 |
| Antibody E15 | DIVMTQSPLSLPVTPGEPASISCKSSQSLLYSNGYAYLDWYLQRPGQS PQLLIYLGSNRASGVPDRFSGSGSGTDFTLKISRVEAEDVGVYYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 210 |
| Antibody E16 | DIVMTQSPLSLPVTPGEPASISCKSSQSLLYSNAYNYLDWYLQRPGQS PQLLIYLGSNRASGVPDRFSGSGSGTDFTLKISRVEAEDVGVYYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 211 |
| Antibody E17 | DIVMTQSPLSLPVTPGEPASISCKSSQSLLYSNAYNYLDWYLQRPGQS PQLLIYLGSNRASGVPDRFSGSGSGTDFTLKISRVEAEDVGVYYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 212 |
| Antibody E18 | DIVMTQSPLSLPVTPGEPASISCKSSQSLLYSNGYAYLDWYLQRPGQS PQLLIYLGSNRASGVPDRFSGSGSGTDFTLKISRVEAEDVGVYYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 213 |
| Antibody E19 | DIVMTQSPLSLPVTPGEPASISCKSSQSLLYSNGYAYLDWYLQRPGQS PQLLIYQGSNRASGVPDRFSGSGSGTDFTLKISRVEAEDVGVFYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 214 |
| Antibody E20 | DIVMTQSPLSLPVTPGEPASISCKSSQSLLYSNAYNYLDWYLQRPGQS PQLLIYLGSNRASGVPDRFSGSGSGTDFTLKISRVEAEDVGVYYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 215 |
| Antibody E21 | DIVMTQSPLSLPVTPGEPASISCKSSQSLLYSNAYNYLDWYLQRPGQS PQLLIYLGSNRASGVPDRFSGSGSGTDFTLKISRVEAEDVGVYYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 216 |
| Antibody E22 | DIVMTQSPLSLPVTPGEPASISCRSSQSLLYSTGYTYLDWYLQRPGQS PQLLIYGGSSRASGVPDRFSGSGSGTDFTLKISRVEAEDVGVFYCGQA LQTPLTFGQGTKVEIKRTVAAPSVFIFPPSDEQLKSGTASVVCLLNNFY PREAKVQWKVDNALQSGNSQESVTEQDSKDSTYSLSSTLTLSKADYE KHKVYACEVTHQGLSSPVTKSFNRGEC | 220 |

Representative anti-SIRPα antibodies of the present invention may comprise a heavy and/or light chain constant region as set forth in Tables 32 or 33 below.

99% identical to the amino acid sequences disclosed in Tables 26-29 provided that the antibody or fragments thereof retain binding to SIRPα-V1 and/or SIRPα-V2.

TABLE 32

EXAMPLE HC AND LC SEQUENCES OF THE CONSTANT REGIONS OF ANTI-SIRPα ANTIBODIES.

| Antibody | Sequence | SEQ ID NO: |
|---|---|---|
| IgG1-HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRE EMTKNQVSLTCLVKGFYPSDIAVEWESNGQPENNYKTTPPVLDSDG SFFLYSKLTVDKSRWQQGNVFSCSVMHEALHNHYTQKSLSLSPGK | 234 |
| IgG1-LC | RTVAAPSVFIFPPSDEQLKSGTASVVCLLNNFYPREAKVQWKVDNAL QSGNSQESVTEQDSKDSTYSLSSTLTLSKADYEKHKVYACEVTHQGLS SPVTKSFNRGEC | 235 |
| IgG4-HC | ASTKGPSVFPLAPCSRSTSESTAALGCLVKDYFPEPVTVSWNSGALTS GVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVV DVSQEDPEVQFNWYVDGVEVHNAKTKPREEQFNSTYRVVSVLTVLH QDWLNGKEYKCKVSNKGLPSSIEKTISKAKGQPREPQVYTLPPSQEE MTKNQVSLTCLVKGFYPSDIAVEWESNGQPENNYKTTPPVLDSDGS FFLYSRLTVDKSRWQEGNVFSCSVMHEALHNHYTQKSLSLSLGK | 236 |
| IgG4-LC | RTVAAPSVFIFPPSDEQLKSGTASVVCLLNNFYPREAKVQWKVDNAL QSGNSQESVTEQDSKDSTYSLSSTLTLSKADYEKHKVYACEVTHQGLS SPVTKSFNRGEC | 237 |
| IgG1-KO-HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPEAAGGPSVFLFPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPREPQVYTLPPS REEMTKNQVSLTCLVKGFYPSDIAVEWESNGQPENNYKTTPPVLDS DGSFFLYSKLTVDKSRWQQGNVFSCSVMHEALHNHYTQKSLSLSPG K | 238 |
| IgG1-KO-LC | RTVAAPSVFIFPPSDEQLKSGTASVVCLLNNFYPREAKVQWKVDNAL QSGNSQESVTEQDSKDSTYSLSSTLTLSKADYEKHKVYACEVTHQGLS SPVTKSFNRGEC | 239 |

Amino Acid Sequence Variants

Variant anti-SIRPα antibodies and antibody fragments thereof can be engineered based on a set of CDRs depicted in Tables 1-25. It is to be understood that in the variant anti-SIRPα antibodies and antibody fragments the amino acid sequence of the CDRs remain unchanged or have minimal changes (e.g., 1-5 changes), but the surrounding regions, e.g., FR regions can be engineered. Amino acid sequence variants of the anti-SIRPα antibody can be prepared by introducing appropriate nucleotide changes into the anti-SIRPα antibody DNA, or by peptide synthesis. Such variants include, for example, deletions from, and/or insertions into and/or substitutions of, residues within the amino acid sequences of the anti-SIRPα antibodies of the examples herein. Any combination of deletions, insertions, and substitutions is made to arrive at the final construct, provided that the final construct possesses the desired characteristics. The amino acid changes also may alter post-translational processes of the human or variant anti-SIRPα antibody, such as changing the number or position of glycosylation sites.

In some embodiments, the present invention includes anti-SIRPα antibodies or antibody fragments thereof having a variable heavy chain and a variable light chain, wherein the variable heavy chain amino acid sequence and the variable light chain amino acid sequence are at least at least 90%, at least 92.5%, at least 95%, at least 98%, or at least 99% identical to the amino acid sequences disclosed in Tables 26-29 provided that the antibody or fragments thereof retain binding to SIRPα-V1 and/or SIRPα-V2.

In some embodiments, the present invention includes anti-SIRPα antibodies or antibody fragments thereof having a variable heavy chain and a variable light chain, wherein the variable heavy chain amino acid sequence and the variable light chain amino acid sequence are at least 80%, at least 85%, at least 90%, at least 92.5%, at least 95%, at least 98%, or at least 99% identical to the amino acid sequences of SEQ ID Nos: 100, 101, 102, 103, 110, 111, 112, 113, 114, 115, 116, 117, 104, 118, 119, 120, 121, 122, 123, 124, or 221, and SEQ ID Nos: 105, 106, 107, 108,109, 126, 127, 128, 129, 130, or 222, respectively.

In some embodiments, the present invention includes anti-SIRPα antibodies having a heavy chain and a light chain, wherein the heavy chain amino acid sequence and the light chain amino acid sequence are at least 95%, at least 98%, or at least 99% identical to the amino acid sequences disclosed in Tables 30 and 31 provided that the antibody or fragments thereof retain binding to SIRPα-V1 and/or SIRPα-V2.

In some embodiments, the anti-SIRPα antibodies or antibody fragments thereof comprise a variable heavy chain sequence that comprises an amino acid sequence with at least about 95%, about 96%, about 97%, about 98%, or about 99%, sequence identity to the amino acid sequence set forth in SEQ ID NOs: 100, 101, 102, 103, 110, 111, 112, 113, 114, 115, 116, 117, 104, 118, 119, 120, 121, 122, 123, 124, or 221. In other embodiments, the anti-SIRPα antibodies or antibody fragments thereof retains the binding and/or functional activity of an anti-SIRPα antibody or antibody fragment thereof that comprises the variable heavy chain sequence of SEQ ID NOs: 100, 101, 102, 103, 110, 111, 112, 113, 114, 115, 116, 117, 104, 118, 119, 120, 121, 122, 123, 124, or 221. In still further embodiments, the anti-SIRPα antibodies or antibody fragments thereof comprise the variable heavy chain sequence of SEQ ID NOs: 100, 101, 102, 103, 110, 111, 112, 113, 114, 115, 116, 117, 104, 118, 119, 120, 121, 122, 123, 124, or 221 and have one or more conservative amino acid substitutions, e.g., 1, 2, 3, 4, 5, 1-2, 1-3, 1-4 or 1-5 conservative amino acid substitutions in the heavy chain variable sequence. In yet further embodiments, the one or more conservative amino acid substitutions fall within one or more framework regions in SEQ ID NOs: 100, 101, 102, 103, 110, 111, 112, 113, 114, 115, 116, 117, 104, 118, 119, 120, 121, 122, 123, 124, or 221 (based on the numbering system of Kabat).

In some embodiments, the anti-SIRPα antibody or antibody fragment thereof comprises a variable heavy chain sequence with at least about 95%, about 96%, about 97%, about 98%, or about 99% sequence identity to the anti-SIRPα heavy chain variable region sequence set forth in 100, 101, 102, 103, 110, 111, 112, 113, 114, 115, 116, 117, 104, 118, 119, 120, 121, 122, 123, 124, or 221 comprises one or more conservative amino acid substitutions in a framework region (based on the numbering system of Kabat), and retains the binding and/or functional activity of an anti-SIRPα antibody or antibody fragment thereof that comprises a variable heavy chain sequence as set forth in SEQ ID NOs: 100, 101, 102, 103, 110, 111, 112, 113, 114, 115, 116, 117, 104, 118, 119, 120, 121, 122, 123, 124, or 221 and a variable light chain sequence as set forth in SEQ ID NOs: 105, 106, 107, 108,109, 126, 127, 128, 129, 130, or 222.

In some embodiments, the anti-SIRPα antibodies or antibody fragments thereof comprise a variable light chain sequence that comprises an amino acid sequence with at least about 95%, about 96%, about 97%, about 98%, or about 99%, sequence identity to the amino acid sequence set forth in SEQ ID NOs: 105, 106, 107, 108,109, 126,127, 128, 129, 130, or 222. In other embodiments, the anti-SIRPα antibodies or antibody fragments thereof retains the binding and/or functional activity of an anti-SIRPα antibody or antibody fragment thereof that comprises the variable light chain sequence of SEQ ID NOs: 105, 106, 107, 108,109, 126, 127, 128, 129, 130, or 222. In still further embodiments, the anti-SIRPα antibodies or antibody fragments thereof comprise the variable light chain sequence of SEQ ID NOs: 105, 106, 107, 108,109, 126, 127, 128, 129, 130, or 222 and have one or more conservative amino acid substitutions, e.g., 1, 2, 3, 4, 5, 1-2, 1-3, 1-4 or 1-5 conservative amino acid substitutions in the light chain variable sequence. In yet further embodiments, the one or more conservative amino acid substitutions fall within one or more framework regions in SEQ ID NOs: 105, 106, 107, 108,109, 127, 128, 129, 130, or 222 (based on the numbering system of Kabat).

In some embodiments, the anti-SIRPα antibody or antibody fragment thereof comprises a variable light chain sequence with at least about 95%, about 96%, about 97%, about 98%, or about 99% sequence identity to the anti-SIRPα light chain variable region sequence set forth in SEQ ID NOs: 105, 106, 107, 108,109, 126, 127, 128, 129, 130, or 222 comprises one or more conservative amino acid substitutions in a framework region (based on the numbering system of Kabat), and retains the binding and/or functional activity of an anti-SIRPα antibody or antibody fragment thereof that comprises a variable heavy chain sequence as set forth in SEQ ID NOs: 100, 101, 102, 103, 110, 111, 112, 113, 114, 115, 116, 117, 104, 118, 119, 120, 121, 122, 123, 124, or 221 and a variable light chain sequence as set forth in SEQ ID NOs: 105, 106, 107, 108,109, 126, 127, 128, 129, 130, or 222.

In some embodiments, the present invention includes anti-SIRPα antibodies or antigen-binding fragments thereof having an amino acid substitution. These variants have at least one amino acid residue in the anti-SIRPα antibody or antigen-binding fragment thereof removed and a different residue inserted in its place. The sites of greatest interest for substitutional mutagenesis include the hypervariable regions, but FR alterations are also contemplated. Conservative substitutions are shown in Table 33 under the heading of "preferred substitutions". If such substitutions result in a change in biological activity, then more substantial changes, denominated "exemplary substitutions", or as further described below in reference to amino acid classes, may be introduced and the products screened.

TABLE 33

Exemplary amino acid substitutions

| Original Residue Exemplary Substitutions | | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gin | asp |
| Gly (G) | ala | ala |
| His (H) | arg; asn; gln; lys; | arg |
| Ile (I) | leu; val; met; ala; phe; norleucine | leu |
| Leu (L) | ile; norleucine; val; met; ala; phe | ile |
| Lys (K) | arg; gln; asn | arg |
| Met (M) | leu; phe; ile | leu |
| Phe (F) | tyr; leu; val; ile; ala; | tyr |
| Pro (P) | ala | ala |
| Ser (S) | thr | thr |
| Thr (T) | ser | ser |
| Trp (W) | tyr; phe | tyr |
| Tyr (Y) | phe; trp; thr; ser | phe |
| Val (V) | leu; ile; met; phe ala; norleucine; | leu |

In protein chemistry, it is generally accepted that the biological properties of the antibody can be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the anti-SIRPα antibody or antigen-binding fragment thereof also may be substituted, generally with serine, to improve the oxidative stability of the molecule, prevent aberrant crosslinking, or provide for established points of conjugation to a cytotoxic or cytostatic compound. Conversely, cysteine bond(s) may be added to the antibody or antigen-binding fragment thereof to improve its stability (particularly where the antibody is an antibody fragment such as an Fv fragment).

Another type of amino acid variant of the antibody involves altering the original glycosylation pattern of the antibody. The term "altering" in this context means deleting one or more carbohydrate moieties found in the antibody, and/or adding one or more glycosylation sites that were not previously present in the antibody. For example, an antibody may comprise an amino acid substitution at position 297 of the human IgG1 heavy chain to abrogate oligosaccharyl-transferase enzyme complex-mediated glycosylation by replacing the asparagine 297 (e.g. N297A, N297G).

In some aspects, the present invention includes nucleic acid molecules that encode the amino acid sequence variants of the anti-SIRPα antibodies or antigen-binding fragments thereof described herein. Nucleic acid molecules encoding amino acid sequence variants of an anti-SIRPα antibody or antigen-binding fragment thereof are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-SIRPα antibody or antigen-binding fragment thereof. For example, nucleic acid molecules according to the invention also encompass nucleic acid molecules which hybridize under stringent conditions to nucleic acid molecules as disclosed herein, whereby the term "stringent conditions" within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C.

In certain embodiments, the anti-SIRPα antibody is an antibody fragment. There are techniques that have been developed for the production of antibody fragments. Fragments can be derived via proteolytic digestion of intact antibodies (see, e.g., Morimoto et al., 1992, Journal of Biochemical and Biophysical Methods 24:107-117; and Brennan et al., 1985, Science 229:81). Alternatively, the fragments can be produced directly in recombinant host cells. For example, Fab'-SH fragments can be directly recovered from E. coli and chemically coupled to form F(ab')$_2$ fragments (see, e.g., Carter et al., 1992, Bio/Technology 10:163-167). By another approach, F(ab')$_2$ fragments can be isolated directly from recombinant host cell culture. Other techniques for the production of antibody fragments will be apparent to a skilled practitioner.

In one aspect, the anti-SIRPα antibodies and antigen-binding fragments thereof can include modifications, such as glycosylation, oxidation, or deamidation.

In certain embodiments, it may be desirable to use an anti-SIRPα antibody fragment, rather than an intact antibody. It may be desirable to modify the antibody fragment in order to increase its serum half-life. This can be achieved, for example, by incorporation of a salvage receptor binding epitope into the antibody fragment. In one method, the appropriate region of the antibody fragment can be altered (e.g., mutated), or the epitope can be incorporated into a peptide tag that is then fused to the antibody fragment at either end or in the middle, for example, by DNA or peptide synthesis (see, e.g., WO 96/32478). For example, antibody fragments of the invention may also be fused to human serum albumin to increase the serum half-life, if the use of a full-length IgG scaffold is undesirable. Such fusion proteins of the antibody fragment with human serum albumin may be advantageous in situations in which two different antibody fragments need to be fused to increase avidity, or to generate a bispecific binding protein with extended serum half-life (see e.g. WO 05/077042 A2).

Removal of any carbohydrate moieties present on the antibody can be accomplished chemically or enzymatically. Chemical deglycosylation is described by Hakimuddin et al., 1987, Arch. Biochem. Biophys. 259:52 and by Edge et al., 1981, Anal. Biochem., 118:131. Enzymatic cleavage of carbohydrate moieties on antibodies can be achieved by the use of a variety of endo- and exo-glycosidases as described by Thotakura et al., 1987, Meth. Enzymol 138:350.

Another type of useful modification comprises linking the antibody to one of a variety of nonproteinaceous polymers, e.g., polyethylene glycol, polypropylene glycol, or polyoxyalkylenes, in the manner set forth in one or more of U.S. Pat. Nos. 4,640,835, 4,496,689, 4,301,144, 4,670,417, 4,791,192 and 4,179,337.

Biophysical Properties

In one aspect, the present invention provides an anti-SIRPα antibody or antigen-binding fragment thereof having one or more favorable biophysical properties. In one aspect, a human anti-SIRPα antibody or antigen-binding fragment thereof of the present invention is present in at least 90% monomer form, or in at least 92% monomer form, or in at least 95% monomer form, or in at least 96% monomer form, or in at least 97% monomer form, or in at least 98% monomer form, or in at least 99% monomer form in a buffer. In a further aspect, a human anti-SIRPα antibody or antigen-binding fragment thereof of the present invention remains in at least 90% monomer form, or in at least 92% monomer form, or in at least 95% monomer form, or in at least 96% monomer form, or in at least 97% monomer form, or in at least 98% monomer form, or in at least 99% monomer form in a buffer for one week, one month, or for four months. Said percentage of monomer may be determined after one or more purification steps are performed, e.g., Protein A purification optionally followed by cation exchange chromatography. Said percentage of monomer may be determined following a low pH treatment, e.g., pH 3.5 treatment. Said percentage of monomer may be determined following one week, one month, or four months in a buffer at room temperature, e.g., 25° C., or an elevated temperature, e.g., 40° C.

In another aspect, an anti-SIRPα antibody or antigen-binding fragment thereof of the invention is stable at high concentrations.

In another aspect, an anti-SIRPα antibody or antigen-binding fragment thereof of the invention has low viscosity.

Epitope Binding

In another aspect, the invention relates to an antibody or antigen-binding fragment thereof that recognizes a specific linear and/or conformational "SIRPα antigen epitope" and "SIRPα epitope".

As used herein, the terms "SIRPα antigen epitope" and "SIRPα epitope" refer to a molecule (e.g., a peptide) or a fragment of a molecule capable of binding to an anti-SIRPα antibody or antigen-binding fragment thereof. These terms further include, for example, a SIRPα antigenic determinant recognized by any of the antibodies or antibody fragments of the present invention or key points of contact between the molecule and antibody.

SIRPα antigen epitopes can be included in proteins, protein fragments, peptides or the like. The epitopes are most commonly proteins, short oligopeptides, oligopeptide mimics (e.g., organic compounds that mimic antibody binding properties of the SIRPα antigen), or combinations thereof.

In one aspect of the invention, the antibody or antigen-binding fragment thereof recognizes a specific linear or conformational "SIRPα epitope" on a SIRPα protein comprising the amino acid sequence set forth in any one of SEQ ID NOs: 240-252. In one aspect of the invention, the antibody or antigen-binding fragment thereof recognizes a specific linear or conformational "SIRPα epitope" on a SIRPα protein comprising the amino acid sequence set forth in any one of SEQ ID NOs: 253-260 and 264, in particular any one or more of SEQ ID NOS: 256 and 257. In one aspect of the invention the antibody or antigen-binding fragment thereof binds to a SIRPα epitope comprising the amino acids; LEU 60, ILE 61, VAL 63, GLY 64, PRO 65, GLN 82, LYS 83, GLU 84, THR 97, LYS 98, ARG 99, GLU 100, LYS 126, GLY 127, SER 128, PRO 129 and ASP 130 as set forth in SEQ ID NO: 266. In one aspect of the invention the antibody or antigen-binding fragment thereof binds to a SIRPα epitope comprising the amino acids LEU 60, ILE 61, VAL 63, GLY 64, PRO 65, GLN 82, LYS 83, GLU 84, THR 97, LYS 98, ARG 99, ASN 100, LYS 126, GLY 127, SER 128, PRO 129 and ASP 130 as set forth in SEQ ID NO: 265. In another aspect of the invention, the antibody or antigen-binding fragment thereof binds to the SIRPα epitope comprising the amino acid ASP130. In another aspect, the antibody or antigen-binding fragment thereof binds to a SIRPα epitope comprising any one or more of SEQ ID NO; 253, SEQ ID NO: 254, SEQ ID NO: 255, SEQ ID NO: 264, and SEQ ID NO: 256, in particular SEQ ID NO: 256.

In one aspect of the invention the antibody or antigen-binding fragment thereof binds to the SIRPα epitope comprising the amino acids ARG 70, GLY 71, ALA 72, GLY 73, PRO 74, ALA 75, ARG 76, GLU 77, ALA 114, ALA 116, GLY 117, THR 118, TYR 120, THR 131, GLU 132, PHE 133, SER 135 and GLU 140 as set forth in SEQ ID NO: 266. In one aspect of the invention the antibody or antigen-binding fragment thereof binds to a SIRPα epitope comprising the amino acids ARG 70, GLY 71, ALA 72, GLY 73, PRO 74, GLY 75, ARG 76, GLU 77, ALA 114, ALA 116, GLY 117, THR 118, TYR 120, VAL 132, GLU 133, PHE 134, SER 136 and GLU 141 as set forth in SEQ ID NO: 265. In another aspect of the invention, the antibody or antigen-binding fragment thereof binds to the SIRPα epitope comprising the amino acid ALA72. In another aspect, the antibody or antigen-binding fragment thereof binds to a SIRPα epitope comprising any one or more of SEQ ID NO: 257, SEQ ID NO: 258, SEQ ID NO: 259 and SEQ ID NO:260, in particular SEQ ID NO: 257. In another aspect of the invention, the antibody or antigen-binding fragment thereof blocks binding of any of Antibody A-E to SIRPα.

In a further embodiment, the epitope is present on a SIRPα protein set forth in Table 34 or 35 below.

TABLE 34

Sequences of SIRP proteins

| Protein | Sequence (Extracellular Domain) | SEQ ID NO: |
|---|---|---|
| Human SIRPαV1 (NP_542970.1) | EEELQVIQPDKSVLVAAGETATLRCTATSLIPVGPIQWFR GAGPGRELIYNQKEGHFPRVTTVSDLTKRNNMDFSIRIG NITPADAGTYYCVKFRKGSPDDVEFKSGAGTELSVRAKPS APVVSGPAARATPQHTVSFTCESHGFSPRDITLKWFKNG NELSDFQTNVDPVGESVSYSIHSTAKVVLTREDVHSQVIC EVAHVTLQGDPLRGTANLSETIRVPPTLEVTQQPVRAEN QVNVTCQVRKFYPQRLQLTWLENGNVSRTETASTVTEN KDGTYNWMSWLLVNVSAHRDDVKLTCQVEHDGQPAV SKSHDLKVSAHPKEQGSNTAAENTGSNERNIYGGSG | 240 |
| Human SIRPαV2 (CAA71403.1) | EEELQVIQPDKSVSVAAGESAILHCTVTSLIPVGPIQWFRG AGPARELIYNQKEGHFPRVTTVSESTKRENMDFSISISNIT PADAGTYYCVKFRKGSPDTEFKSGAGTELSVRAKPSAPVV SGPAARATPQHTVSFTCESHGFSPRDITLKWFKNGNELS DFQTNVDPVGESVSYSIHSTAKVVLTREDVHSQVICEVAH VTLQGDPLRGTANLSETIRVPPTLEVTQQPVRAENQVNV TCQVRKFYPQRLQLTWLENGNVSRTETASTVTENKDGTY NWMSWLLVNVSAHRDDVKLTCQVEHDGQPAVSKSHDL KVSAHPKEQGSNTAAENTGSNERNIYGGSG | 241 |
| Human SIRPβ1 (NP_006056.2). | EDELQVIQPEKSVSVAAGESATLRCAMTSLIPVGPIMWFR GAGAGRELIYNQKEGHFPRVTTVSELTKRNNLDFSISISNI TPADAGTYYCVKFRKGSPDDVEFKSGAGTELSVRAKPSAP VVSGPAVRATPEHTVSFTCESHGFSPRDITLKWFKNGNEL SDFQTNVDPAGDSVSYSIHSTARVVLTRGDVHSQVICEIA HITLQGDPLRGTANLSEAIRVPPTLEVTQQPMRAENQAN VTCQVSNFYPRGLQLTWLENGNVSRTETASTLIENKDGT YNWMSWLLVNTCAHRDDVVLTCQVEHDGQQAVSKSY ALEISAHQKEHGSDITHEAALAPTAPLGGSG | 242 |
| Human SIRPβL/SIRPβ1v3 (NP_001129316.1) | EEELQVIQPDKSISVAAGESATLHCTVTSLIPVGPIQWFRG AGPGRELIYNQKEGHFPRVTTVSDLTKRNNMDFSIRISNI TPADAGTYYCVKFRKGSPDHVEFKSGAGTELSVRAKPSAP VVSGPAARATPQHTVSFTCESHGFSPRDITLKWFKNGNE LSDFQTNVDPAGDSVSYSIHSTAKVVLTREDVHSQVICEV AHVTLQGDPLRGTANLSETIRVPPTLEVTQQPVRAENQV NVTCQVRKFYPQRLQLTWLENGNVSRTETASTLTENKDG TYNWMSWLLVNVSAHRDDVKLTCQVEHDGQPAVSKSH DLKVSAHPKEQGSNTAPGPALASAAPLGGSG | 243 |

TABLE 34-continued

Sequences of SIRP proteins

| Protein | Sequence (Extracellular Domain) | SEQ ID NO: |
|---|---|---|
| human SIRPγ (NP_061026.2) | EEELQMIQPEKLLLVTVGKTATLHCTVTSLLPVGPVLWFR GVGPGRELIYNQKEGHFPRVTTVSDLTKRNNMDFSIRISSI TPADVGTYYCVKFRKGSPENVEFKSGPGTEMALGAKPSA PVVLGPAARTTPEHTVSFTCESHGFSPRDITLKWFKNGNE LSDFQTNVDPTGQSVAYSIRSTARVVLDPWDVRSQVICE VAHVTLQGDPLRGTANLSEAIRVPPTLEVTQQPMRVGN QVNVTCQVRKFYPQSLQLTWSENGNVCQRETASTLTEN KDGTYNWTSWFLVNISDQRDDVVLTCQVKHDGQLAVS KRLALEVTVHQKDQSSDATP | 244 |
| Human CD47 (NP_942088) | WQPPLLFNKTKSVEFTFGNDTVVIPCFVTNMEAQNTTEV YVKWKFKGRDIYTFDGQANKSTVPTDFSSAKIEVSQLLKG DASLKMDKSDAVSHTGNYTCEVTELTREGETIIELKYRVVS | 245 |
| Mouse SIRPα (NP_031573) | KELKVTQPEKSVSVAAGDSTVLNCTLTSLLPVGPIKWYRG VGQSRLLIYSFTGEHFPRVTNVSDATKRNNMDFSIRISNV TPEDAGTYYCVKFQKGPSEPDTEIQSGGGTEVYVLAKPSP PEVSGPADRGIPDQKVNFTCKSHGFSPRNITLKWFKDGQ ELHHLETTVNPSGKNVSYNISSTVRVVLNSMDVHSKVICE VAHITLDRSPLRGIANLSNFIRVSPTVKVTQQSPTSMNQV NLTCRAERFYPEDLQLIWLENGNVSRNDTPKNLTKNTDG TYNYTSLFLVNSSAHREDVVFTCQVKHDQQPAITRNHTV LGLAHSSDQGSMQTFPGNNATHNWN | 246 |
| CySIRPα NP_001271679 | EEELQVIQPEKSVSVAAGDSATLNCTVSSLIPVGPIQWFR GAGPGRELIYNLKEGHFPRVTAVSDPTKRNNMDFSIRISN ITPADAGTYYCVKFRKGSPDVELKSGAGTELSVRAKPSAP VVSGPAVRATAEHTVSFTCESHGFSPRDITLKWFKNGNEL SDVQTNVDPAGKSVSYSIRSTARVLLTRRDVHSQVICEVA HVTLQGDPLRGTANLSEAIRVPPFLEVTQQSMRADNQV NVTCQVTKFYPQRLQLTWLENGNVSRTEMASALPENKD GTYNWTSWLLVNSAHRDDVKLTCQVEHDGQPAVNKS FSVKVSAHPKEQGSNTAAENTGTNERNIYGGSG | 247 |
| CySIRPα EGM_02252 | EEELQVIQPEKSVSVAAGESATLNCTATSLIPVGPIQWFR GVGPGRELIYHQKEGHFPRVTPVSDPTKRNNMDFSIRISN ITPADAGTYYCVKFRKGSPDVELKSGAGTELSVRAKPSAP VVSGPAVRATAEHTVSFTCESHGFSPRDITLKWFKNGNEL SDFQTNVDPAGKSVSYSIRSTARVVLTRRDVHSQVICEVA HVTLQGDPLRGTANLSEAIRVPPFLEFTQQSMRADNQV NVTCQVMKFYPQRLQLTWLENGNVSRTEMASALPENK DGTYNWTSWLLVNVSAHRDDVKLTCQVEHDGQPAVNK SFSVKVSAHPKEQGSNTAAENTGTNERNIYGGSG | 248 |
| CySIRPα XP_015313155 | EEELQVIQPEKSVSVAAGDSATLNCTVSSLIPVGPIQWFR GAGPGRELIYNLKEGHFPRVTPVSDPTKRNNMDFSIRISN ITPADAGTYYCVKFRKGSPDVELKSGAGTELSVRAKPSAP VVSGPAVRATAEHTVSFTCESHGFSPRDITLKWFKNGNEL SDFQTNVDPAGKSVSYSIRSTARVVLTRRDVHSQVICEVA HVTLQGDPLRGTANLSEAIRVPPFLEVTQQSMRADNQV NVTCQVTKFYPQRLQLTWLENGNVSRTEMASALPENKD GTYNWTSWLLVNVSAHRDDVKLTCQVEHDGQPAVNKS FSVKVSAHPKEQGSNTAAENTGTNERNIYGGSG | 249 |
| Cyno SIRPβ1v3 XP_005568593 | EEELQVIQPEKSVSVTAGESATLNCTVTSLIPVGPIQWFRG AGPGRELIYNLKEGHFPRVTTVLDPTKRNNMDFSIHISNIT PADAGTYYCVKFRKGSPDVELKSGAGTELSVRAKPSAPVV SGPTARATPEHTVSFTCESHGFSPRDITLKWFKNGNELSD FQTNVDPAGKSVSYSIRSTARVVLTRRDVHSQVICEVAHV TLQGDPLRGTANLSEAIRVPPTLEVFQRPMRAENQVNVT CQVRKFYPQRLLLTWLENGNVSQTETASTLTENKDGTYN WRSWLLVNTCAHRDGVVLTCQVEHDGQPAVSKSHALE VSAHQKEQCSDTTSGPVLAPTAPLGGSG | 250 |
| Cyno SIRPβ1 XP_005568598 | EEELQVIQPEKSISVAAGESATLNCTVTSLIPVGPIQWFRG VGPGRELIFNLQEGHFPRVTPVSDPTKRNNMDFSILISSIT PADAGTYYCVKFRKGSPDVELKSGAGTELSVRAKPSAPVV SGPAVRATAEHTVSFTCESHGFSPRDITLKWFKNGNELSD FQTSVDPAGKSVSYSIRSTARVVLTRRDVHSQVICEVAHV TLQGDPLRGTANLSEAIRVPPFLEVTQQSMRAENQANIT CQVSNFYPQRLLLTWLENGNVSQTETASTLTENKDGTYN WTSWLLVNICAHRDDVVLTCQVKHDGQPAVSKSHTLEIS AHQKEQDSDVTHGLALAPTAPLGGSG | 251 |

TABLE 34-continued

Sequences of SIRP proteins

| Protein | Sequence (Extracellular Domain) | SEQ ID NO: |
|---|---|---|
| Cyno SIRPγ XP_005568591 | EEELQMIQPEKLLLVAVGESATLNCTVTSLLPVGPVLWFR GVGPGRELIYNQKEGHFPRVTTVSDLTKRNNMDFSIRISSI TPADAGTYYCVKFRKGSPENVEFKSGPGTEMALRAKPSA PVVSGPAARATPEHTVSFTCKSHGFSPRDITLKWFKNGN ELSDFQTNVDPAGQSVSYSIRSTARVVLAPWDVRSQVTC EVAHVTLQGDPLRGTANLSEAIRVPPTLEVTQQPMRAG NQVNITYQVRNFYPQNLQLTWLENGNVCRTETASTLTEN KDGTYNWTSWLLVNTSDQRDDVVLTCQVKHDGQLAVN KSLVLEVSAHQKDQSSDATHGGSG | 252 |

TABLE 35

Sequences of SIRPα epitopes

| Protein | Sequence | SEQ ID NO: |
|---|---|---|
| Human SIRPαV1 or V2 | LIPVGP | 253 |
| Human SIRPαV1 or V2 | QKE | 254 |
| Human SIRPαV1 | TKRN | 255 |
| Human SIRPαV2 | TKRE | 264 |
| Human SIRPαV1 or V2 | KGSPD | 256 |
| Human SIRPαV1 or V2 | RGAGPGRE | 257 |
| Human SIRPαV1 or V2 | AGTYY | 258 |
| Human SIRPαV1 | VEFKSGAGTE | 259 |
| Human SIRPαV2 | TEFKSGAGTE | 260 |

The present invention also provides an anti-SIRPα antibody or antigen-binding fragment thereof that competes for binding to SIRPα with an anti-SIRPα antibody according to the present invention. In one embodiment, the present invention provides an anti-SIRPα antibody or antigen-binding fragment thereof that competes for binding to SIRPα with any one of Antibody A-Antibody E. Competition assays may be conducted for example as described in PLoS One. 2014; 9(3): e92451 using a biosensor, or PLoS One 2020 Mar. 5; 15(3):e0229206, or by a method disclosed herein.

Therapeutic Uses

In one embodiment, the anti-SIRPα antibodies of the invention or antigen-binding fragments thereof are useful for treating and/or preventing SIRPα pathway disorders.

In another embodiment, the anti-SIRPα antibodies of the invention or antigen-binding fragments thereof are useful as a medicament.

Accordingly, in one embodiment, the invention provides a method of modulating the interaction between SIRPα and CD47 in a subject comprising administering to said subject a composition comprising an anti-SIRPα antibody or antigen-binding fragment thereof according to the invention in an amount sufficient to block CD47-mediated SIRPα signaling in said subject. In one embodiment, the present invention provides an anti-SIRPα antibody or antigen-binding fragment thereof according to the present invention for use in modulating the interaction between SIRPα and CD47 in a subject. In one embodiment, the invention provides the use of an anti-SIRPα antibody or antigen-binding fragment thereof according to the present invention in the manufacture of a medicament for modulating the interaction between SIRPα and CD47 in a subject.

In one embodiment, the invention provides a method of enhancing myeloid cell phagocytosis in a subject comprising administering to said subject a composition comprising an anti-SIRPα antibody or antigen-binding fragment thereof according to the invention in an amount sufficient to enhance an immune response in said subject. In one embodiment, the present invention provides an anti-SIRPα antibody or antigen-binding fragment thereof according to the invention for use in enhancing myeloid cell activity in a subject. In one embodiment, the present invention provides the use of an anti-SIRPα antibody or antigen-binding fragment thereof according to the present invention in the manufacture of a medicament for enhancing myleoid cell phagocytosis in a subject.

In one embodiment, a SIRPα pathway disease or disorder in a subject comprising administering to said subject a composition comprising an anti-SIRPα antibody or antigen-binding fragment thereof according to the present invention. In one embodiment, the present invention provides an anti-SIRPα antibody or antigen-binding fragment thereof according to the present invention for use in treating or preventing cancer, inflammatory disease, autoimmune disease, respiratory disease, infectious disease or fibrosis. in a subject. In one embodiment, the present invention provides the use of an anti-SIRPα antibody or antigen-binding fragment thereof according to the present invention in the manufacture of a medicament for treating or preventing cancer, inflammatory disease, autoimmune disease, respiratory disease, infectious disease or fibrosis in a subject.

Accordingly, in one embodiment, the invention provides a method of treating or preventing one of the above diseases or disorders in a subject comprising administering to said subject a composition comprising an anti-SIRPα antibody or antigen-binding fragment thereof according to the invention. In one embodiment, the present invention provides an anti-SIRPα antibody or antigen-binding fragment thereof according to the invention for use in treating or preventing one of the above diseases or disorders in a subject. In one embodiment, the present invention provides the use of an anti-SIRPα antibody or antigen-binding fragment thereof according to the present invention in the manufacture of a medicament for treating and/or preventing one of the above diseases or disorders in a subject.

Non-Therapeutic Uses

The antibodies described herein are useful as affinity purification agents. In this process, the antibodies are immobilized on a solid phase such a Protein A resin, using methods well known in the art. The immobilized antibody is contacted with a sample containing the SIRPα protein (or fragment thereof) to be purified, and thereafter the support is washed with a suitable solvent that will remove substantially all the material in the sample except the SIRPα protein, which is bound to the immobilized antibody. Finally, the support is washed with another suitable solvent that will release the SIRPα protein from the antibody.

The SIRPα antibodies and fragments thereof of the invention as disclosed herein are also useful in diagnostic assays to detect and/or quantify SIRPα protein, for example, detecting SIRPα expression in specific cells, tissues, or serum.

It will be advantageous in some embodiments, for example, for diagnostic purposes to label the antibody with a detectable moiety. Numerous detectable labels are available, including radioisotopes, fluorescent labels, enzyme substrate labels, quantum dots and the like. The label may be indirectly conjugated with the antibody using various known techniques. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody can be conjugated with a small hapten (such as digoxin) and one of the different types of labels mentioned above is conjugated with an anti-hapten antibody (e.g., anti-digoxin antibody). Thus, indirect conjugation of the label with the antibody can be achieved.

Diagnostic Kits

An anti-SIRPα antibody or fragment thereof can be used in a diagnostic kit, i.e., a packaged combination of reagents in predetermined amounts with instructions for performing the diagnostic assay. Where the antibody is labeled with an enzyme, the kit may include substrates and cofactors required by the enzyme such as a substrate precursor that provides the detectable chromophore or fluorophore. In addition, other additives may be included such as stabilizers, buffers (for example a block buffer or lysis buffer), and the like. The relative amounts of the various reagents may be varied widely to provide for concentrations in solution of the reagents that substantially optimize the sensitivity of the assay. The reagents may be provided as dry powders, usually lyophilized, including excipients that on dissolution will provide a reagent solution having the appropriate concentration.

Compositions, Combinations and Administration Thereof

A composition comprising an anti-SIRPα antibody or an antigen-binding fragment thereof according to the invention can be administered to a subject having or at risk of the SIRPα pathway diseases and/or disorders described herein. The invention further provides for the use of an anti-SIRPα antibody or an antigen-binding fragment thereof in the manufacture of a medicament for prevention or treatment of a SIRPα pathway disease or disorder. The term "subject" as used herein means any mammalian patient to which an anti-SIRPα antibody or an antigen-binding fragment thereof can be administered, including, e.g., humans and certain non-human mammals, such as primates, and dogs. Subjects specifically intended for treatment using the methods described herein include humans.

An anti-SIRPα antibody or an antigen-binding fragment thereof may be administered on their own or in combination with one or more additional therapeutic agents, such as state-of-the-art or standard-of-care compounds, such as e.g. cytostatic or cytotoxic substances, cell proliferation inhibitors, anti-angiogenic substances, steroids, immune modulators/checkpoint inhibitors, and the like.

In one aspect, the present invention also provides pharmaceutical compositions administered as pharmaceutical compositions comprising a therapeutically effective amount of the anti-SIRPα antibody or an antigen-binding fragment thereof and one or more pharmaceutically compatible ingredients, and optionally one or more additional therapeutic agents.

A further aspect of the invention provides a binding molecule of the invention for use in the therapy of cancer (e.g. an individual suffering from cancer or being at risk of developing cancer) wherein said therapy comprises one or more pharmacologically active substances.

A further aspect of the invention provides the use of one or more active ingredients in the manufacture of a medicament for the therapy of cancer and/or tumors (e.g. an individual suffering from cancer or being at risk of developing cancer) wherein said medicament comprises the binding molecule of the invention.

Cytostatic and/or cytotoxic active substances which may be administered in combination with an anti-SIRPα antibody or antigen-binding fragment thereof of the invention include, without being restricted thereto, hormones, hormone analogues and anti-hormones, aromatase inhibitors, LHRH agonists and antagonists, inhibitors of growth factors (e.g., platelet derived growth factor (PDGF), fibroblast growth factor (FGF), vascular endothelial growth factor (VEGF), epidermal growth factor (EGF), insulin-like growth factors (IGF), human epidermal growth factor (HER, e.g. HER2, HER3, HER4) and hepatocyte growth factor (HGF)), including, for example anti-growth factor antibodies or anti-growth factor receptor antibodies and tyrosine kinase inhibitors, such as, for example, cetuximab, gefitinib, afatinib, nintedanib, imatinib, lapatinib, bosutinib and trastuzumab; antimetabolites (e.g., antifolates such as methotrexate, raltitrexed, pyrimidine analogues such as 5-fluorouracil (5-FU), gemcitabine, irinotecan, doxorubicin, TAS-102, capecitabine and gemcitabine, purine and adenosine analogues such as mercaptopurine, thioguanine, cladribine and pentostatin, cytarabine (ara C), fludarabine); antitumor antibiotics (e.g., anthracyclins); platinum derivatives (e.g., cisplatin, oxaliplatin, carboplatin); alkylation agents (e.g., estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g., Vinca alkaloids such as for example vinblastine, vindesin, vinorelbin and vincristine; and taxanes such as paclitaxel, docetaxel); angiogenesis inhibitors, including bevacizumab, ramucirumab and aflibercept, tubuline inhibitors; DNA synthesis inhibitors, PARP inhibitors, topoisomerase inhibitors (e.g., epipodophyllotoxins such as for example etoposide and etopophos, teniposide, amsacrin, topotecan, irinotecan, mitoxantrone), serine/threonine kinase inhibitors (e.g., PDK1 inhibitors, Raf inhibitors, A-Raf inhibitors, B-Raf inhibitors, C-Raf inhibitors, mTOR inhibitors, mTORC1/2 inhibitors, PI3K inhibitors, PI3Kα inhibitors, dual mTOR/PI3K inhibitors, STK33 inhibitors, AKT inhibitors, PLK1 inhibitors (such as volasertib), inhibitors of CDKs, including CDK9 inhibitors, Aurora kinase inhibitors), tyrosine kinase inhibitors (e.g., PTK2/FAK inhibitors), protein interaction inhibitors, MEK inhibitors, ERK inhibitors, FLT3 inhibitors, BRD4 inhibitors, IGF-1R inhibitors, Bcl-xL inhibitors, Bcl-2 inhibitors, Bcl-2/Bcl-xL inhibitors, ErbB receptor inhibitors, BCR-ABL inhibitors, ABL inhibitors, Src inhibitors, rapamycin analogs (e.g., everolimus, temsirolimus, ridaforolimus, sirolimus), androgen synthesis inhibitors, androgen receptor inhibitors, DNMT inhibitors, HDAC inhibitors, ANG1/2 inhibitors, CYP17 inhibitors, radiopharmaceuticals, immunotherapeutic agents such as immune checkpoint inhibitors (e.g., CTLA4, PD1, PD-L1, LAG3, and TIM3 binding molecules/immunoglobulins, such as ipilimumab, nivolumab, pembrolizumab) and various chemotherapeutic agents such as amifostin, anagrelid, clodronat, filgrastin, interferon, interferon alpha, leucovorin, rituximab, procarbazine, levamisole, mesna, mitotane, pamidronate and porfimer; proteasome inhibitors (such as Bortezomib); Smac and BH3 mimetics; agents restoring p53 functionality including mdm2-p53 antagonist; inhibitors of the Wnt/beta-catenin signaling pathway; and/or cyclin-dependent kinase 9 inhibitors.

In one aspect of the invention, the anti-SIRPα antibody or antigen-binding fragment thereof is optionally administered in combination with an additional therapeutic agent. The additional therapeutic agent may be a chemotherapeutic agent, an anti-PD-1 or PD-L1 antibody, an anti-CTLA4 antibody, a T-cell engager, a CD137-agonist-anti-FAP bispecific antibody, a tumor-targeting antibody, a VEGF-ANG2 bispecific antibody, a STING agonist, a MDM2 antagonist, or radiation therapy.

In one aspect, the anti-SIRPα antibody or an antigen-binding fragment thereof is administered in combination with an anti-PD-1 antibody, for example, nivolumab, pembrolizumab, pidilizumab, ezabenlimab, or atezolizumab. In a further aspect, the anti-SIRPα antibody or an antigen-binding fragment thereof is administered in combination with an anti-PD-L1 antibody including, for example, avelumab or durvalumab.

In one aspect, the anti-SIRPα antibody or antigen-binding fragment thereof is administered in combination with a tumor targeting antibody targeting HER2 (e.g., trastuzumab), EGFR (e.g., cetuximab, panitumumab), CD20 (e.g., rituximab, ofatumumab), or CD52 (e.g., alemtuzumab).

In one aspect, the anti-SIRPα antibody or antigen-binding fragment thereof is administered in combination with two therapeutic agents. In a further aspect, the anti-SIRPα antibody or antigen-binding fragment thereof is administered in combination with an anti-PD-1 antibody (e.g., nivolumab, pembrolizumab, pidilizumab, ezabenlimab, or atezolizumab), or an anti-PD-L1 antibody (e.g., avelumab or durvalumab) and tumor targeting antibody targeting HER2 (e.g., trastuzumab), EGFR (e.g., tetuximab, panitumumab), CD20 (e.g., rituximab, ofatumumab), or CD52 (e.g., alemtuzumab).

Various delivery systems are known and can be used to administer the anti-SIRPα antibody or an antigen-binding fragment thereof. Methods of introduction include but are not limited to intravitreal, eye drops, intradermal, intramuscular, intraperitoneal, intravenous, subcutaneous, intranasal, epidural, and oral routes. The anti-SIRPα antibody or an antigen-binding fragment thereof can be administered, for example by infusion, bolus or injection, and can be administered together with other biologically active agents. Administration can be systemic or local. Formulations for such injections may be prepared in, for example, prefilled syringes. As such in an aspect of the invention, pre-filled syringes are provided that include an anti-SIRPα antibody or an antigen-binding fragment thereof.

To be used in therapy, the anti-SIRPα antibody of the invention is formulated into pharmaceutical compositions appropriate to facilitate administration to animals or humans. Typical formulations of the binding molecule or antibody molecule described herein can be prepared by mixing the binding molecule or antibody molecule with physiologically acceptable carriers, excipients or stabilizers, in the form of lyophilized or otherwise dried formulations or aqueous solutions or aqueous or non-aqueous suspensions. Carriers, excipients, modifiers or stabilizers are nontoxic at the dosages and concentrations employed.

In typical embodiments, the pharmaceutical composition is formulated in accordance with routine procedures as a pharmaceutical composition adapted for intravenous or subcutaneous administration to a subject. Typically, compositions for administration by injection are solutions in sterile isotonic aqueous buffer. Where necessary, the pharmaceutical composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing an anti-SIRPα antibody or an antigen-binding fragment thereof in lyophilized form and (b) a second container containing a pharmaceutically acceptable diluent (e.g., sterile water) for injection. The pharmaceutically acceptable diluent can be used for reconstitution or dilution of the lyophilized anti-SIRPα antibody or antigen-binding fragment thereof. Optionally associated with such container(s) can be a notice in the form prescribed by a governmental agency regulating the manufacture, use or sale of pharmaceuticals or biological products, which notice reflects approval by the agency of manufacture, use or sale for human administration.

In some embodiments, antibodies of the invention can be formulated to doses, which include for example a dose of 1 mg/kg to 200 mg/kg. including, for example, 1 mg/kg to 25 mg/kg, 25 mg/kg to 50 mg/kg, 50 mg/kg to 75 mg/kg, 75 mg/kg to 100 mg/kg, 100 mg/kg to 125 mg/kg, 125 mg/kg to 150 mg/kg, 150 mg/kg to 175 mg/kg, or 175 mg/kg to 200 mg/kg. With respect to therapeutic regimens for combinatorial administration, in a specific embodiment, an anti-SIRPα antibody or antigen-binding fragment thereof is administered concurrently with a second and/or third therapeutic agent. In another specific embodiment, the second and/or third therapeutic agent is administered prior or subsequent to administration of the anti-SIRPα antibody or antigen-binding fragment thereof.

Polynucleotides, Vectors, and Host Cells

The present invention relates to isolated polynucleotides that comprise a sequence encoding an anti-SIRPα antibody or antigen-binding fragment thereof, vectors, and host cells comprising the polynucleotides, and recombinant techniques for production of the antibody. The isolated polynucleotides can encode any desired form of the anti-SIRPα antibody including, for example, full length monoclonal antibodies, Fab, Fab', F(ab')$_2$, and Fv fragments, diabodies, linear antibodies, single-chain antibody molecules, and multispecific antibodies formed from antibody fragments.

The polynucleotide(s) that comprise a sequence encoding an anti-SIRPα antibody or a fragment or chain thereof can be fused to one or more regulatory or control sequence, as known in the art, and can be contained in suitable expression vectors or host cell as known in the art. Each of the polynucleotide molecules encoding the heavy or light chain variable domains can be independently fused to a polynucleotide sequence encoding a constant domain, such as a human constant domain, enabling the production of intact antibodies. Alternatively, polynucleotides, or portions thereof, can be fused together, providing a template for production of a single chain antibody.

For recombinant production, a polynucleotide encoding the antibody is inserted into a replicable vector for cloning (amplification of the DNA) or for expression. Many suitable vectors for expressing the recombinant antibody are available. The vector components generally include, but are not limited to, one or more of the following: a signal sequence, an origin of replication, one or more marker genes, an enhancer element, a promoter, and a transcription termination sequence.

The anti-SIRPα antibodies can also be produced as fusion polypeptides, in which the antibody is fused with a heterologous polypeptide, such as a signal sequence or other polypeptide having a specific cleavage site at the amino terminus of the mature protein or polypeptide. The heterologous signal sequence selected is typically one that is recognized and processed (e.g., cleaved by a signal peptidase) by the host cell. For prokaryotic host cells that do not recognize and process the anti-SIRPα antibody signal sequence, the signal sequence can be substituted by a prokaryotic signal sequence. The signal sequence can be, for example, alkaline phosphatase, penicillinase, lipoprotein, heat-stable enterotoxin II leaders, and the like. For yeast secretion, the native signal sequence can be substituted, for example, with a leader sequence obtained from yeast invertase alpha-factor (including *Saccharomyces* and *Kluyveromyces* α-factor leaders), acid phosphatase, *C. albicans* glucoamylase, or the signal described in WO 90/13646. In mammalian cells, mammalian signal sequences as well as viral secretory leaders, for example, the herpes simplex gD signal, can be used. The DNA for such precursor region is ligated in reading frame to DNA encoding the anti-SIRPα antibody.

Anti-SIRPα antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-SIRPα antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), K. wickeramii (ATCC 24,178), *K. waltii* (ATCC 56,500), *K. drosophilarum* (ATCC 36,906), *K. thermotolerans*, and *K. marxianus; yarrowia* (EP 402,226); *Pichia* pastors (EP 183,070); *Candida; Trichoderma* reesia (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated anti-SIRPα antibody are derived from multicellular organisms. Examples of invertebrate cells include plant and insect cells, including, e.g., numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silk worm). A variety of viral strains for transfection are publicly available, e.g., the L-1 variant of *Autographa californica* NPV and the Bm-5 strain of *Bombyx mori* NPV, and such viruses may be used, particularly for transfection of *Spodoptera frugiperda* cells.

Plant cell cultures of cotton, corn, potato, soybean, *petunia*, tomato, and tobacco can also be utilized as hosts.

The anti-SIRPα antibodies or antigen-binding fragments thereof can also be incorporated in viral vectors, e.g. the polynucleotide encoding for the anti-SIRPα antibody or antigen-binding fragment thereof is introduced into the viral vector and then expressed in the body of the subject after infection with the virus.

In another aspect, expression of the anti-SIRPα antibody or antigen-binding fragment thereof is carried out in vertebrate cells. The propagation of vertebrate cells in culture (tissue culture) has become routine procedure and techniques are widely available. Examples of useful mammalian host cell lines are monkey kidney CV1 line transformed by SV40 (COS-7, ATCC CRL 1651), human embryonic kidney line (293 or 293 cells subcloned for growth in suspension culture, (Graham et al., 1977, J. Gen Virol. 36: 59), baby hamster kidney cells (BHK, ATCC CCL 10), Chinese hamster ovary cells/-DHFR1 (CHO, Urlaub et al., 1980, Proc. Natl. Acad. Sci. USA 77: 4216; e.g., DG44), mouse sertoli cells (TM4, Mather, 1980, Biol. Reprod. 23:243-251), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TR1 cells (Mather et al., 1982, Annals N.Y. Acad. Sci. 383: 44-68), MRC 5 cells, FS4 cells, and human hepatoma line (Hep G2).

Also included are nucleic acids that hybridize under low, moderate, and high stringency conditions, in particular under high stringency conditions, as defined herein, to all or a portion (e.g., the portion encoding the variable region) of the nucleotide sequence represented by isolated polynucleotide sequence(s) that encode an anti-SIRPα antibody or antibody fragment. The hybridizing portion of the hybridizing nucleic acid is typically at least 15 (e.g., 20, 25, 30 or 50) nucleotides in length. The hybridizing portion of the hybridizing nucleic acid is at least 80%, e.g., at least 90%, at least 95%, at least 98%, or at least 99% identical to the sequence of a portion or all of a nucleic acid encoding an anti-SIRPα polypeptide (e.g., a heavy chain or light chain variable region), or its complement. Hybridizing nucleic acids of the type described herein can be used, for example, as a cloning probe, a primer, e.g., a PCR primer, or a diagnostic probe. In one aspect, "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

In one embodiment, the present invention relates to an isolated polynucleotide comprising a nucleotide sequence encoding a heavy chain variable region comprising the amino acid sequence of any one of SEQ ID NOs: 100, 101, 102, 103, 104, 105, 110, 111, 112, 113, 114, 115, 116, 117, 118, 119, 120, 121, 122, 123, 124, or 221.

In one embodiment, the present invention relates to an isolated polynucleotide comprising a nucleotide sequence encoding a light chain variable region comprising the amino acid sequence of any one of SEQ ID NOs: 105, 106, 107, 108, 109, 125, 126, 109, 127, 128, 129, 130, or 222.

In one embodiment, the present invention relates to an isolated polynucleotide comprising a nucleotide sequence encoding a heavy chain region comprising the amino acid sequence of any one of SEQ NO: 131,138,139, 140, 141, 142, 143, 144, 145, 146, 147, 148, 149, 150, 151, 152, 217, 135,153, 154, 156, 157, 158, 159, 160, 161, 162, 163, 164, 165, 166, 167, 168, 169, 170, 171, 172, 173, 219, 133, 134, 137, 132, or 136.

In one embodiment, the present invention relates to an isolated polynucleotide comprising the nucleotide sequence encoding of a light chain region comprising the amino acid sequence of any one any one of SEQ NO: 174, 181, 182, 183, 184, 185, 186, 187, 188, 189, 190, 191, 192, 193, 194, 195, 218, 178, 196, 197, 198, 199, 200, 201, 202, 203, 204, 205, 206, 207, 208, 209, 210, 211, 212, 213, 214, 215, 216, 220, 176, 177, 180, 175, or 179.

Articles of Manufacture

In another aspect, an article of manufacture containing materials useful for the treatment of the disorders described above is included. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port. For example, the container may be an intravenous solution bag or a vial having a stopper pierceable by a hypodermic injection needle. The active agent in the composition is the anti-SIRPα antibody or the antigen-binding fragment thereof. The label on or associated with the container indicates that the composition is used for treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

EXAMPLES

The present disclosure is now described with reference to the following Examples. These Examples are provided for the purpose of illustration only and the disclosure should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present disclosure and practice the claimed methods. The following working examples therefore, specifically point out the preferred embodiments of the present invention, and are not to be construed as limiting in any way the remainder of the disclosure.

Example 1: Generation of Anti-SIRPα Antibodies

Phage and Yeast Display.

Initial efforts to generate anti-SIRPα antibodies of desired selectivity, i.e., being able to block hSIRPαV1 and hSIRPαV2 and lacking binding to hSIRPγ, are conducted using phage display. Biotinylated extracellular domains of hSIRPαV1, hSIRPαV2, and cynomologus SIRPα proteins are used as the target proteins in three sequential screening rounds. Unlabeled hSIRPγ extracellular domain is included in each screening round as a deselecting agent in order to remove antibodies that could bind to hSIRPγ extracellular domain.

Phage display yielded thirteen candidate antibodies that were further characterized. Four of the candidate antibodies could block hSIRPαV1 and hSIRPαV2, but each of these antibodies was determined to also bind to hSIRPγ. Nine of the candidate antibodies did not bind to hSIRPγ, but also could only block hSIRPαV1 or hSIRPαV2 but not both. Thus, it was determined that none of the thirteen candidate antibodies possessed the desired selectivity.

A similar effort to generate anti-SIRPα antibodies of desired selectivity is conducted using yeast display. The majority of the candidate antibodies identified by yeast display (59 out of 66) could block hSIRPαV1 and hSIRPαV2 but also bound to hSIRPγ. The remaining seven antibodies did not bind to hSIRPγ, but could only block hSIRPαV1 but not hSIRPαV2. Thus, similarly to the phage display, it was determined that none of the candidate antibodies possessed the desired selectivity.

Immunization.

AlivaMab kappa mice are immunized subcutaneously with combinations of recombinantly produced extracellular domains of human and cynomologus SIRPα proteins [NP 542970, CAA71403 and NP 001271679] following standard laboratory immunization techniques. Briefly, mice are immunized subcutaneously once per week for four weeks with protein and adjuvant mixtures. An aqueous adjuvant is used and is expected to improve generation of antibodies with the desired selectivity by decreasing the exposure of sites that are internal to the native protein confirmation. After four immunizations, antibody titers are determined by ELISA methods. Animals that display a strong antibody response against all antigens are selected for antibody recovery.

B-Cell Recovery and Recombinant Antibody Production.

Antigen-specific memory B-cell recovery is performed via single B-cell flow cytometry and cell sorting. Recovered antibody sequences are synthesized and screened for various characteristics, including but not limited to, affinity to SIRPα, binding to huSIRPα-V1 and huSIRPα-V2 CHO cell lines, and blocking of SIRPα:CD47 interaction. Representative antibodies exhibiting the desired properties are shown in Table 26-27: Antibody A, Antibody B, Antibody C, Antibody D, and Antibody E.

Example 2. Removal of Sequence Liabilities for Antibody A and Antibody E

Fragment antibody (Fab) clones of the parent antibodies are prepared. Libraries are prepared with certain position variations so as to remove potential sequence liabilities (i.e. amino acid residues that may be immunogenic or that may create potential manufacturing problems). These mutated libraries usually have 5 to 10 binary positions per V-region. Separate saturation libraries are also made apart from single or double mutation libraries to address specific positions in more complex V-regions. Such libraries are prepared using standard methods known in the art and can be readily used by the skilled person.

The engineered Fabs are tested for desired properties, including affinity to huSIRPα-V1 and huSIRPα-V2. Representative variable regions for engineered antibodies for Antibody A and Antibody E are shown in Table 28-29.

Example 3. Binding Affinities (SPR $K_D$) of Antibodies to Purified Recombinant Human SIRPα, SIRPβ1, SIRPγ Proteins The binding affinity of anti-SIRPα antibodies to the various SIRPα analytes is determined by surface plasmon resonance (SPR) using a ProteOn XPR36 (Bio-Rad). The running buffer for this experiment and all dilutions (except where stated) are done in 1×HBS-EP+. The CM5 sensorchip is activated with equal mixture of EDC/NHS for 420 sec at a flow rate of 10 µl/min and immobilized with Protein A/G beads (50 µg/ml in 10 mM acetate pH 4.5) for 420 sec at a flowrate of 10 µl/min resulting in ~2600-2900 RU of Protein A/G on the surface. The sensorchip is deactivated with 1M ethanolamine HCl for 420 sec at a flowrate of 10 µl/min.

Each antibody is captured on the Protein A/G surface for 60 sec at a flowrate of 10 µl/min resulting in capture levels of ~280 RU. The analyte is injected over the captured antibody for 300 sec at a flowrate of 30 µl/min. The dissociation is done for 600 sec. Two-fold serial dilutions of each SIRP protein (Extracellular Domain+His-Tag) are injected as analyte with the highest concentrations indicated in table 36 below.

Table 36: List of various SIRP proteins and their highest concentration used for binding affinity analysis

| Analyte (Extracellular Domain + His-Tag) | Accession Number | Highest Concentration (nM) in experiment |
|---|---|---|
| hSIRPαV1 | NP_542970.1 | 100 |
| hSIRPαV2 | CAA71403.1 | 100 |
| hSIRPβ1 | NP_006056.2 | 1000 |
| hSIRPβ1v3 | NP_001129316.1 | 100 |
| hSIRPγ | NP_061026.2 | 1000 |
| cynoSIRPα | NP 001271679 | 1000 |
| cynoSIRPα | EGM_02252 | 1000 |
| cynoSIRPα | XP_015313155 | 1000 |
| cynoSIRPβ1 | XP_005568598 | 1000 |
| cynoSIRPβ1v3 | XP_005568593 | 1000 |
| cynoSIRPγ | XP_005568591 | 1000 |

Once each analyte injection is complete, the sensor surface is regenerated by injecting 0.85% phosphoric acid for 30 sec at a flowrate of 30 µl/min.

The analyte interaction with sensor surface (flow cell 1) and blank (HBS-EP+) are subtracted from the raw data. Sensorgrams are then fit globally to 1:1 Langmuir binding to provide on-rate ($k_a$), off-rate ($k_D$), and affinity ($K_D$) values as well as the steady state binding mode to provide the equilibrium affinity ($K_D$).

The above procedure is used to measure the binding affinity to the following analytes: human SIRPαV1, human SIRPαV2, human SIRPβ1, human SIRPβ1v3, human SIRPγ, cynomolgus (cyno) SIRPα, cyno SIRPβ1, cyno SIRPβ1v3, cyno SIRPγ, mouse SIRPα The results for binding affinities of SIRPα antibodies are shown in Tables 37-42 below.

TABLE 37

Binding affinity of SIRPa antibodies (Antibodies A-G) to human SIRP proteins.

| Antibodies | HuSIRPαV1 (M) | HuSIRPαV2 (M) | HuSIRPβ1 (M) | HuSIRPβ1v3 (M) | HuSIRPγ (M) |
|---|---|---|---|---|---|
| Antibody A | 8.81E−09 | 1.31E−08 | 7.82E−08 | NB | NB |
| Antibody B | 1.74E−08 | 7.15E−08 | NB | NB | NB |
| Antibody C | 6.27E−10 | 9.69E−11 | 2.14E−09 | NB | NB |
| Antibody D | 4.04E−09 | 4.05E−09 | 1.65E−08 | NB | NB |
| Antibody E | 4.56E−10 | 4.2E−10 | 1.23E−06 | 1.16E−09 | NB |
| Antibody F | 9.30E−09 | 1.41E−08 | 8.40E−08 | NB | NB |
| Antibody G | 4.97E−10 | 4.65E−10 | 1.27E−06 | 1.27E−09 | NB |

NB = No binding at highest concentration

TABLE 38

Binding affinity of SIRPα antibodies (Antibodies A-G) to cyno and mouse SIRP proteins.

| Antibodies | Mouse NP_031573 SIRPα (M) | CySIRPα NP_001271679 (M) | CySIRPα EGM_02252 (M) | CySIRPα XP_005568593 (M) |
|---|---|---|---|---|
| Antibody A | NB | 4.53E−07 | 2.01E−07 | 2.01E−07 |
| Antibody B | NB | NB | NA | NA |
| Antibody C | NB | 1.43E−08 | NA | NA |
| Antibody D | NB | NB | NA | NA |
| Antibody E | NB | 9.21E−09 | NB | 6.98E−09 |
| Antibody F | NB | 5.06E−07 | 2.30E−07 | 2.27E−07 |
| Antibody G | NB | 1.01E−08 | NB | 7.62E−09 |

NB = No binding at highest concentration
NA = Data Not Available

TABLE 39

Binding affinity of SIRPα antibodies (Antibodies A, A1-A16) to human SIRP proteins.

| Antibodies | HuSIRPαV1 (M) | HuSIRPαV2 (M) | HuSIRPβ1 (M) | HuSIRPβ1v3 (M) | HuSIRPγ (M) |
|---|---|---|---|---|---|
| Antibody A | 7.72E−09 | 9.03E−09 | 6.48E−08 | NB | NB |
| Antibody A15 | 7.06E−09 | 7.91E−09 | 5.88E−08 | NB | NB |
| Antibody A13 | 7.28E−09 | 8.36E−09 | 6.10E−08 | NB | NB |
| Antibody A9 | 7.34E−09 | 8.25E−09 | 5.88E−08 | NB | NB |
| Antibody A12 | 7.83E−09 | 8.96E−09 | 6.44E−08 | NB | NB |
| Antibody A10 | 7.95E−09 | 9.17E−09 | 6.90E−08 | NB | NB |
| Antibody A16 | 7.98E−09 | 8.22E−09 | 6.27E−08 | NB | NB |
| Antibody A14 | 8.13E−09 | 7.95E−09 | 5.83E−08 | NB | NB |
| Antibody A6 | 8.28E−09 | 1.81E−08 | 6.51E−08 | NB | NB |
| Antibody A4 | 8.46E−09 | 1.83E−08 | 6.72E−08 | NB | NB |
| Antibody A8 | 8.53E−09 | 1.88E−08 | 6.96E−08 | NB | NB |
| Antibody A1 | 8.60E−09 | 1.86E−08 | NB | NB | NB |
| Antibody A5 | 8.75E−09 | 1.78E−08 | 6.42E−08 | NB | NB |
| Antibody A3 | 9.06E−09 | 1.96E−08 | 7.03E−08 | NB | NB |
| Antibody A7 | 9.38E−09 | 2.04E−08 | 7.22E−08 | NB | NB |
| Antibody A2 | 9.39E−09 | 2.09E−08 | 7.75E−08 | NB | NB |

NB = No binding at highest concentration

TABLE 40

Binding affinity of SIRPα antibodies (Antibodies A, A1-A16) to cyno SIRP proteins.

| Antibodies | CySIRPα NP_001271679 (M) | CySIRPα EGM_02252 (M) | CySIRPα XP_015313155 (M) | Cyno SIRPβ1 XP_005568598 (M) | Cyno SIRPβ1v3 XP_005568593 (M) | Cyno SIRPγ XP_005568591 (M) |
|---|---|---|---|---|---|---|
| Antibody A | 3.36E−07 | 2.58E−07 | 1.65E−07 | NB | 2.46E−07 | NB |
| Antibody A15 | 3.17E−07 | 2.23E−07 | 1.54E−07 | NB | 2.32E−07 | NB |
| Antibody A13 | 3.30E−07 | 2.26E−07 | 1.60E−07 | NB | 2.38E−07 | NB |
| Antibody A9 | 3.46E−07 | 2.27E−07 | 1.56E−07 | NB | 2.57E−07 | NB |
| Antibody A12 | 3.84E−07 | 2.49E−07 | 1.82E−07 | NB | 2.79E−07 | NB |
| Antibody A10 | 3.78E−07 | 2.49E−07 | 1.80E−07 | NB | 2.71E−07 | NB |
| Antibody A16 | 3.06E−07 | 2.25E−07 | 1.51E−07 | NB | 2.25E−07 | NB |
| Antibody A14 | 3.16E−07 | 2.22E−07 | 1.53E−07 | NB | 2.35E−07 | NB |
| Antibody A6 | 6.84E−07 | 5.38E−07 | 3.66E−07 | NB | 4.69E−07 | NB |
| Antibody A4 | 6.69E−07 | 5.08E−07 | 3.74E−07 | NB | 4.60E−07 | NB |
| Antibody A8 | 6.39E−07 | 5.35E−07 | 3.50E−07 | NB | 4.49E−07 | NB |
| Antibody A1 | 7.80E−07 | 5.43E−07 | 3.69E−07 | NB | 5.57E−07 | NB |
| Antibody A5 | 6.65E−07 | 5.33E−07 | 3.47E−07 | NB | 4.65E−07 | NB |
| Antibody A3 | 8.57E−07 | 5.71E−07 | 4.38E−07 | NB | 5.64E−07 | NB |
| Antibody A7 | 7.41E−07 | 6.09E−07 | 3.89E−07 | NB | 4.94E−07 | NB |
| Antibody A2 | 8.87E−07 | 5.84E−07 | 4.24E−07 | NB | 5.52E−07 | NB |

NB = No binding at highest concentration
NA = Data Not Available

TABLE 41

Binding affinity of SIRPα antibodies (Antibodies E, E1-E22) to human SIRP proteins.

| Antibodies | HuSIRPα V1 (M) | huSIRPαV2 (M) | huSIRPβ1 (M) | huSIRPβ1v3 (M) | huSIRPγ (M) |
|---|---|---|---|---|---|
| Antibody E | 4.25E−10 | 3.30E−10 | 7.71E−07 | 8.10E−10 | NB |
| Antibody E1 | 7.23E−10 | 6.30E−10 | 1.48E−06 | 1.81E−09 | NB |
| Antibody E2 | 9.12E−10 | 6.87E−10 | NB | 1.93E−09 | NB |
| Antibody E3 | 9.64E−10 | 7.75E−10 | 2.14E−06 | 1.76E−09 | NB |
| Antibody E4 | 9.88E−10 | 8.24E−10 | 1.34E−06 | 1.95E−09 | NB |
| Antibody E5 | 1.02E−09 | 8.73E−10 | 1.38E−06 | 2.72E−09 | NB |
| Antibody E6 | 1.03E−09 | 8.75E−10 | NB | 2.72E−09 | NB |
| Antibody E7 | 1.20E−09 | 1.18E−09 | 8.74E−07 | 2.21E−09 | NB |
| Antibody E8 | 1.21E−09 | 5.42E−10 | 2.42E−06 | 2.58E−09 | NB |
| Antibody E9 | 1.22E−09 | 9.41E−10 | NB | 3.16E−09 | NB |
| Antibody E10 | 1.23E−09 | 1.20E−09 | 1.57E−06 | 2.37E−09 | NB |
| Antibody E11 | 1.41E−09 | 5.68E−10 | 3.28E−06 | 2.99E−09 | NB |
| Antibody E12 | 1.67E−09 | 1.26E−09 | 1.67E−06 | 3.43E−09 | NB |
| Antibody E13 | 1.70E−09 | 6.90E−10 | NB | 4.17E−09 | NB |
| Antibody E14 | 1.84E−09 | 1.36E−09 | NB | 4.80E−09 | NB |
| Antibody E15 | 1.91E−09 | 7.37E−10 | NB | 4.56E−09 | NB |
| Antibody E16 | 2.15E−09 | 1.93E−09 | 4.24E−06 | 4.02E−09 | NB |
| Antibody E17 | 2.36E−09 | 7.97E−10 | NB | 5.32E−09 | NB |
| Antibody E18 | 2.46E−09 | 8.98E−10 | NB | 4.80E−09 | NB |
| Antibody E19 | 2.52E−09 | 9.70E−10 | 1.66E−06 | 4.74E−09 | NB |
| Antibody E20 | 3.42E−09 | 1.11E−09 | 4.35E−07 | 8.48E−09 | NB |
| Antibody E21 | 4.46E−09 | 1.39E−09 | NB | 8.84E−09 | NB |
| Antibody E22 | 1.57E−09 | 1.47E−09 | NB | 3.19E−09 | NB |

NB = No binding at highest concentration

TABLE 42

Binding affinity of Antibody E, E1-E22 SIRPα antibodies to cyno SIRP proteins.

| Antibodies | CySIRPα NP_001271679 (M) | CySIRPα EGM_02252 (M) | CySIRPα XP_015313155 (M) | Cyno SIRPβ1 XP_005568598 (M) | Cyno SIRPβ1v3 XP_005568593 (M) | Cyno SIRPγ XP_005568591 (M) |
|---|---|---|---|---|---|---|
| Antibody E | 7.46E−09 | NB | 7.07E−09 | NB | 4.62E−09 | NB |
| Antibody E1 | 1.79E−08 | NB | 1.67E−08 | NB | 1.08E−08 | NB |
| Antibody E2 | 2.07E−08 | NB | 1.97E−08 | NB | 1.24E−08 | NB |
| Antibody E3 | 1.73E−08 | NB | 1.69E−08 | NB | 1.07E−08 | NB |
| Antibody E4 | 2.11E−08 | NB | 1.98E−08 | NB | 1.31E−08 | NB |
| Antibody E5 | 3.82E−08 | NB | 3.78E−08 | NB | 2.26E−08 | NB |
| Antibody E6 | 4.10E−08 | NB | 4.16E−08 | NB | 2.39E−08 | NB |
| Antibody E7 | 2.19E−08 | NB | 2.12E−08 | NB | 1.31E−08 | NB |
| Antibody E8 | 1.77E−08 | NB | 1.66E−08 | NB | 1.08E−08 | NB |
| Antibody E9 | 4.37E−08 | NB | 4.08E−08 | NB | 2.51E−08 | NB |
| Antibody E10 | 2.52E−08 | NB | 2.37E−08 | NB | 1.57E−08 | NB |
| Antibody E11 | 2.03E−08 | NB | 2.00E−08 | NB | 1.32E−08 | NB |
| Antibody E12 | 4.61E−08 | NB | 4.22E−08 | NB | 2.79E−08 | NB |
| Antibody E13 | 3.83E−08 | NB | 3.74E−08 | NB | 2.05E−08 | NB |
| Antibody E14 | 9.07E−08 | NB | 8.63E−08 | NB | 5.19E−08 | NB |
| Antibody E15 | 4.94E−08 | NB | 4.62E−08 | NB | 2.58E−08 | NB |
| Antibody E16 | 5.03E−08 | NB | 4.88E−08 | NB | 3.03E−08 | NB |
| Antibody E17 | 4.48 E−08 | NB | 4.32E−08 | NB | 2.70E−08 | NB |
| Antibody E18 | 5.25E−08 | NB | 5.00E−08 | NB | 2.78E−08 | NB |

TABLE 42-continued

Binding affinity of Antibody E, E1-E22 SIRPα antibodies to cyno SIRP proteins.

| Antibodies | CySIRPα NP_001271679 (M) | CySIRPα EGM_02252 (M) | CySIRPα XP_015313155 (M) | Cyno SIRPβ1 XP_005568598 (M) | Cyno SIRPβ1v3 XP_005568593 (M) | Cyno SIRPγ XP_005568591 (M) |
|---|---|---|---|---|---|---|
| Antibody E19 | 4.66E−08 | NB | 4.47E−08 | NB | 2.50E−08 | NB |
| Antibody E20 | 1.11E−07 | NB | 1.04E−07 | NB | 5.74E−08 | NB |
| Antibody E21 | 1.07E−07 | NB | 1.08E−07 | NB | 5.65E−08 | NB |
| Antibody E22 | 1.38E−08 | NB | 1.42E−08 | NB | 1.20E−08 | NB |

NB = No binding at highest concentration

Example 4. Binding of Antibodies to Full-Length Human V1-SIRPα or V2-SIRPα Expressed on CHO Cells Antibody binding to cells expressing SIRPα is evaluated by flow cytometry. CHO-K1 parental cells (negative control), CHO-K1 cells expressing full-length human SIRPαV1 (NP_542970.1) or CHO-K1 cells expressing full-length human SIRPαV2 (CAA71403.1) are blocked with donkey IgG and incubated on ice with increasing concentrations of antibodies for 60 minutes, washed and stained with AF647-conjugated donkey F(ab')$_2$ anti-human IgG secondary reagent. Cells are washed, fixed, and analyzed by flow cytometry. Median fluorescent intensity is determined and used as a measure of antibody binding.

Figure 1A:
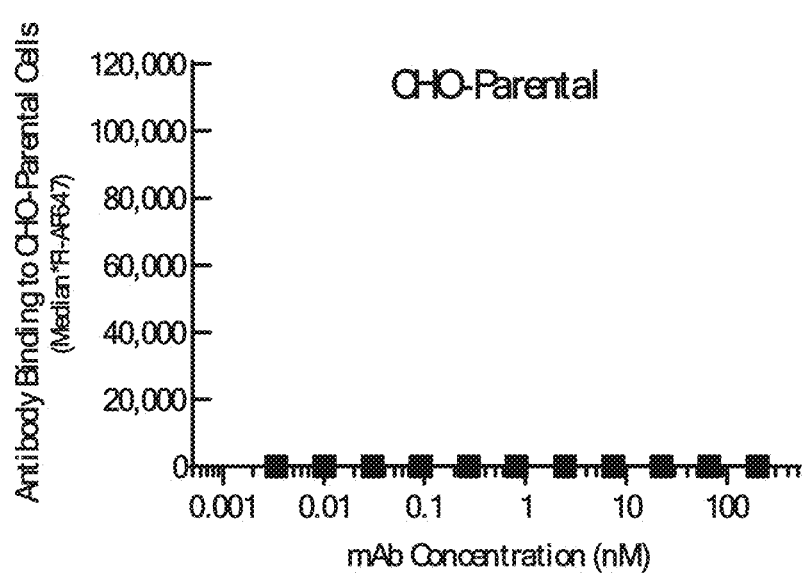
FIGS. 1A-1C are series of graphs depicting the binding of antibodies to full-length human V1-SIRPα or V2-SIRPα expressed on CHO cells.
Figure 1B:
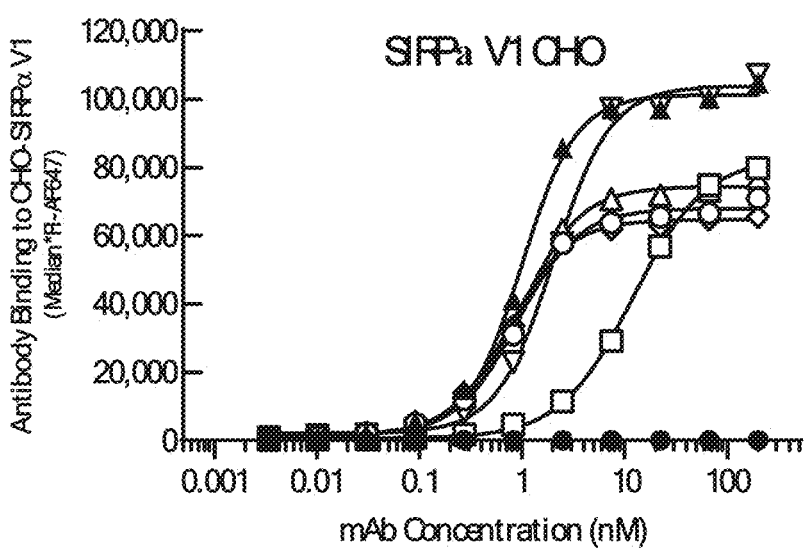
Figure 1C:
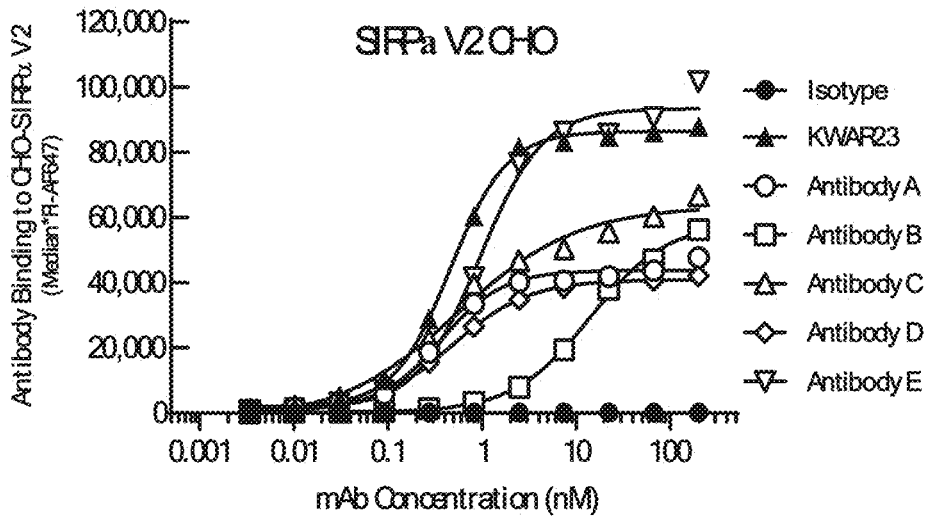

Anti-SIRPα antibody KWAR23 (WO2015138600) and antibodies A-E demonstrated dose-dependent binding to CHO cells expressing full-length human SIRPαV1 (FIG. 1B) or SIRPαV2 (FIG. 1C) with EC$_{50}$ values ranging between 0.4-14 nM (Table 43). None of the antibodies tested exhibited binding to parental CHO cells (FIG. 1A).

TABLE 43

EC$_{50}$ of Anti-SIRPα antibodies

| | Cell Binding EC$_{50}$ (nM) | | |
|---|---|---|---|
| Antibody | CHO-Parental | CHO-hSIRPαV1 | CHO-hSIRPαV2 |
| Isotype | NB | NB | NB |
| KWAR23 | NB | 1.0 | 0.5 |
| Antibody A | NB | 0.9 | 0.4 |
| Antibody B | NB | 12.0 | 14.2 |
| Antibody C | NB | 1.0 | 0.5 |
| Antibody D | NB | 0.7 | 0.5 |
| Antibody E | NB | 2.0 | 0.9 |

NB No binding

Example 5. Binding of Antibodies to Endogenous Human V1-SIRPα or V2-SIRPα Expressed on Human Monocytic Cell Lines Antibody binding to human monocytic cell lines homozygous for the V1-allele (U-937) or the V2-allele (THP-1) of SIRPα is assessed. U-937 or THP-1 cells are blocked with donkey IgG and incubated on ice with increasing concentrations of antibodies for 60 minutes, washed and stained with AF647-conjugated donkey F(ab')$_2$ anti-human IgG secondary reagent. Cells are washed, fixed, and analyzed by flow cytometry. Median fluorescent intensity is determined and used as a measure of antibody binding.

Figure 2A:
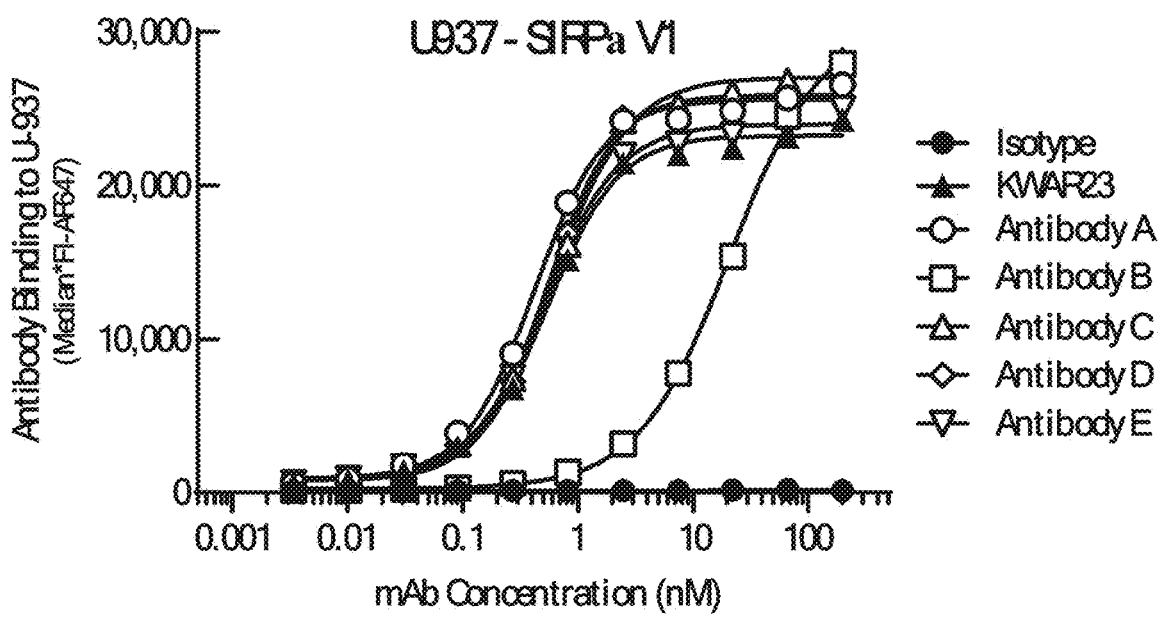
FIG. 2A and FIG. 2B are series of graphs depicting the binding of antibodies to endogenous human V1-SIRPα or V2-SIRPα expressed on human monocytic cell lines.
Figure 2B:
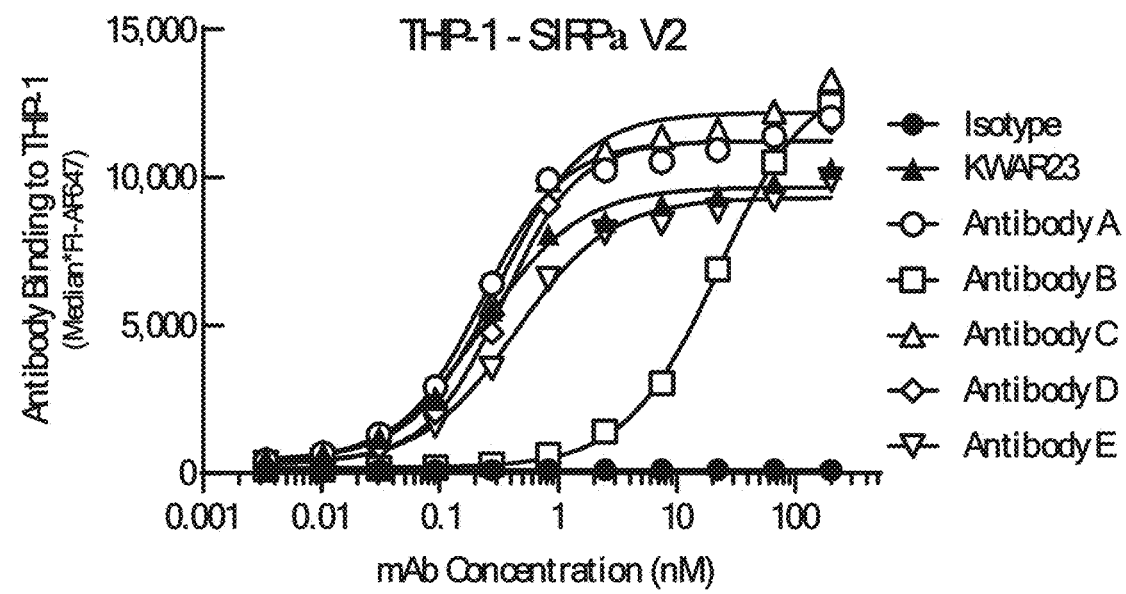
Figure 3A:
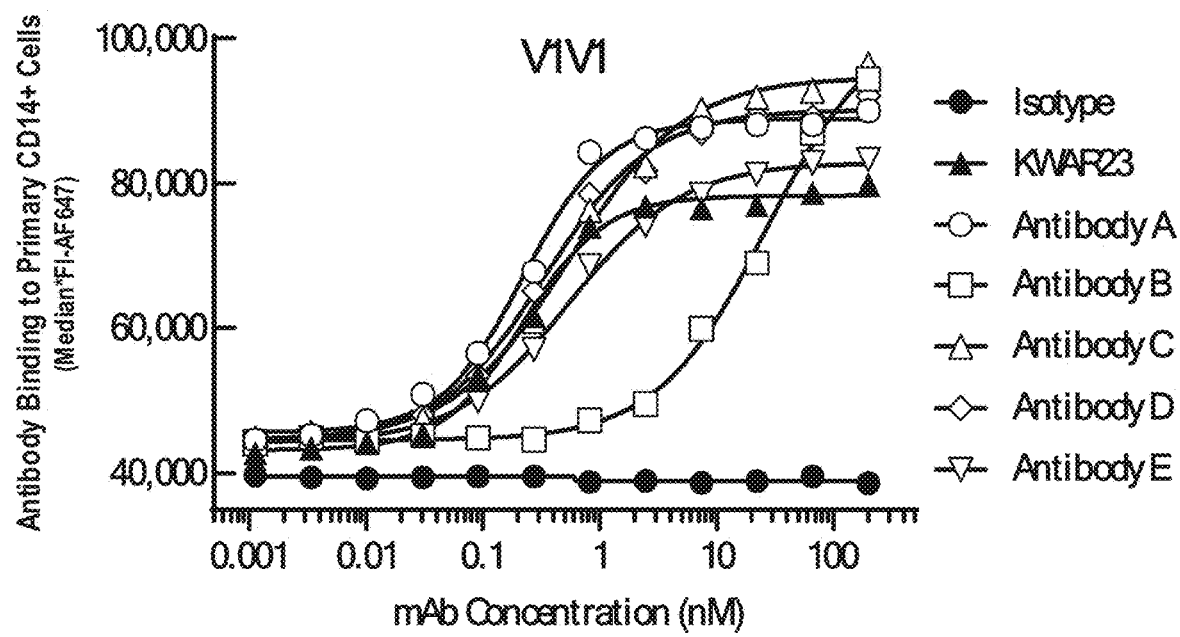
FIGS. 3A-3D are series of graphs depicting the binding of antibodies to endogenous human V1-SIRPα and/or V2-SIRPα expressed on primary human monocytes. Antibody binding to primary human CD14+ monocytes from donors homozygous for V1-SIRPα allele (FIGS. 3A-3D). Solid, dashed, and dotted lines indicate antibody molecules engineered on hIgG1 (LALA), hIgG4P, hIgG1 (K322A) backbones, respectively.
Figure 3B:
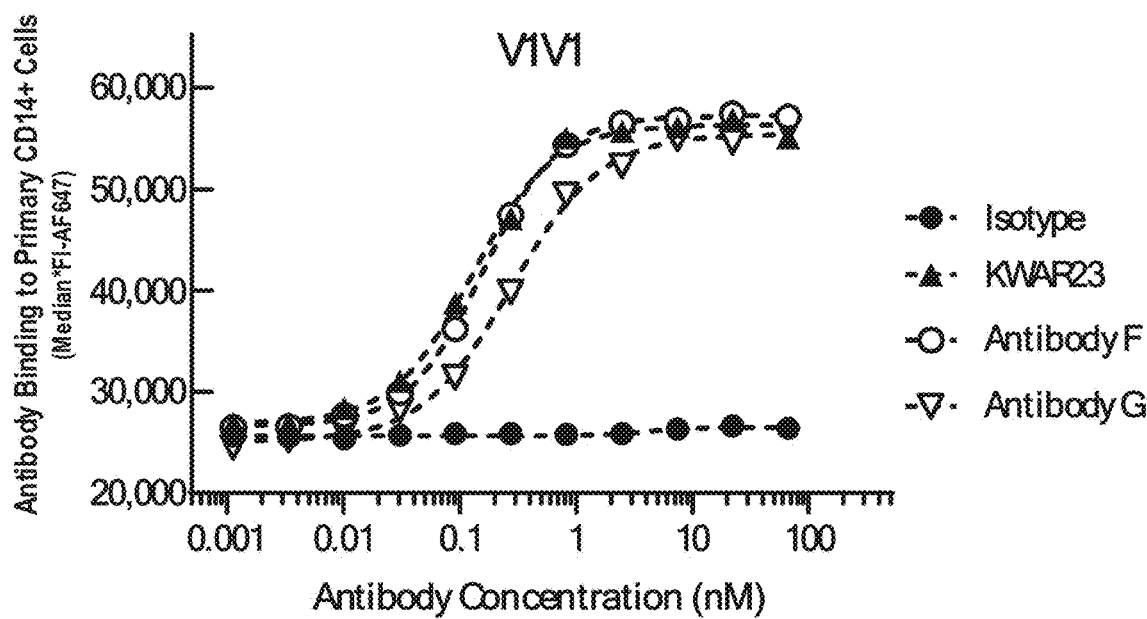
Figure 3C:
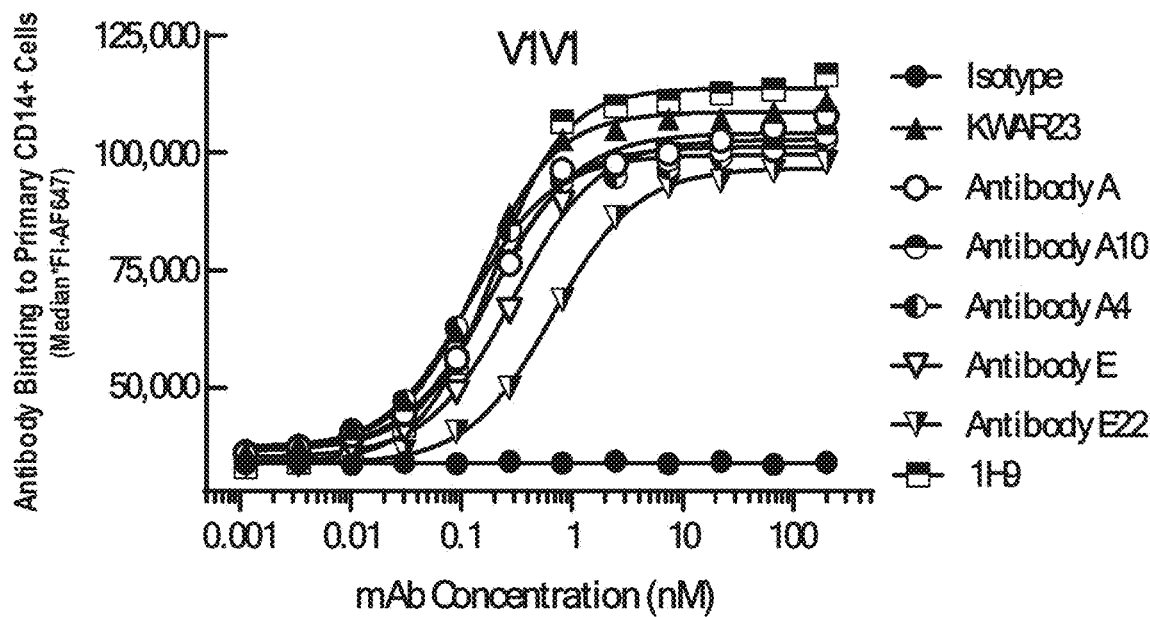
Figure 3D:
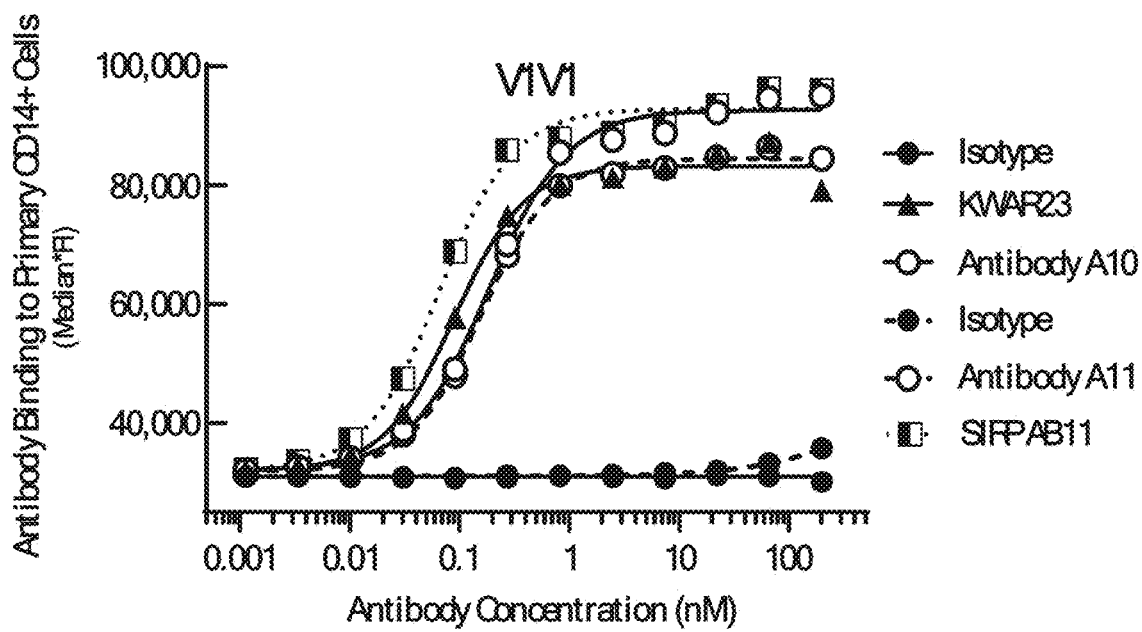
Figure 4A:
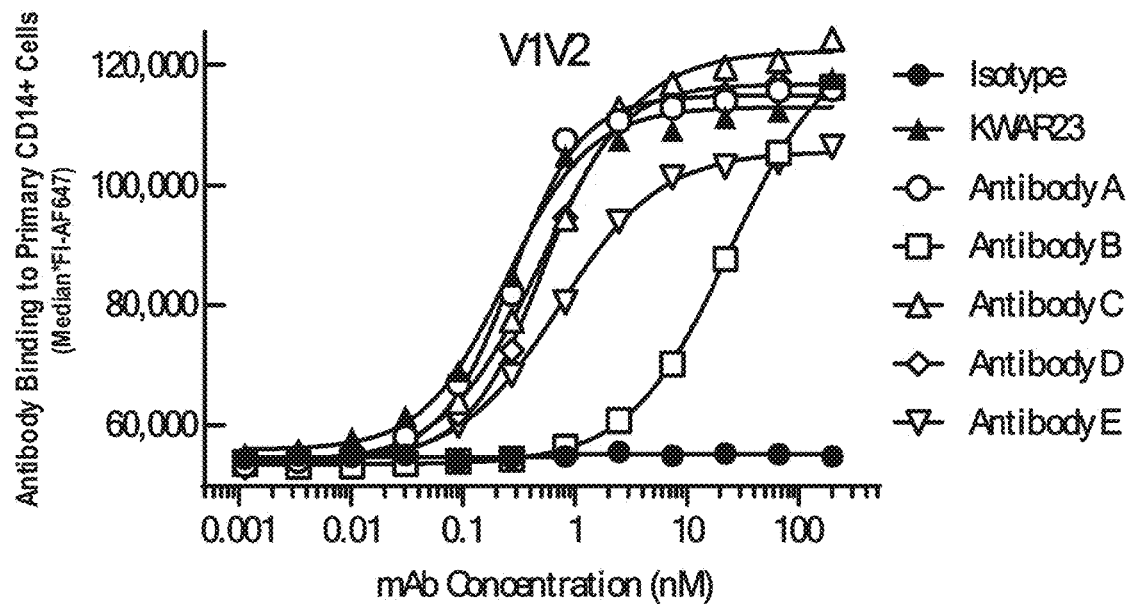
FIGS. 4A-4D are series of graphs depicting the binding of antibodies to endogenous human V1-SIRPα and/or V2-SIRPα expressed on primary human monocytes. Antibody binding to primary human CD14+ monocytes from donors heterozygous for V1- and V2-SIRPα alleles (FIGS. 4A-4D). Solid, dashed, and dotted lines indicate antibody molecules engineered on hIgG1 (LALA), hIgG4P, hIgG1 (K322A) backbones, respectively.
Figure 4B:
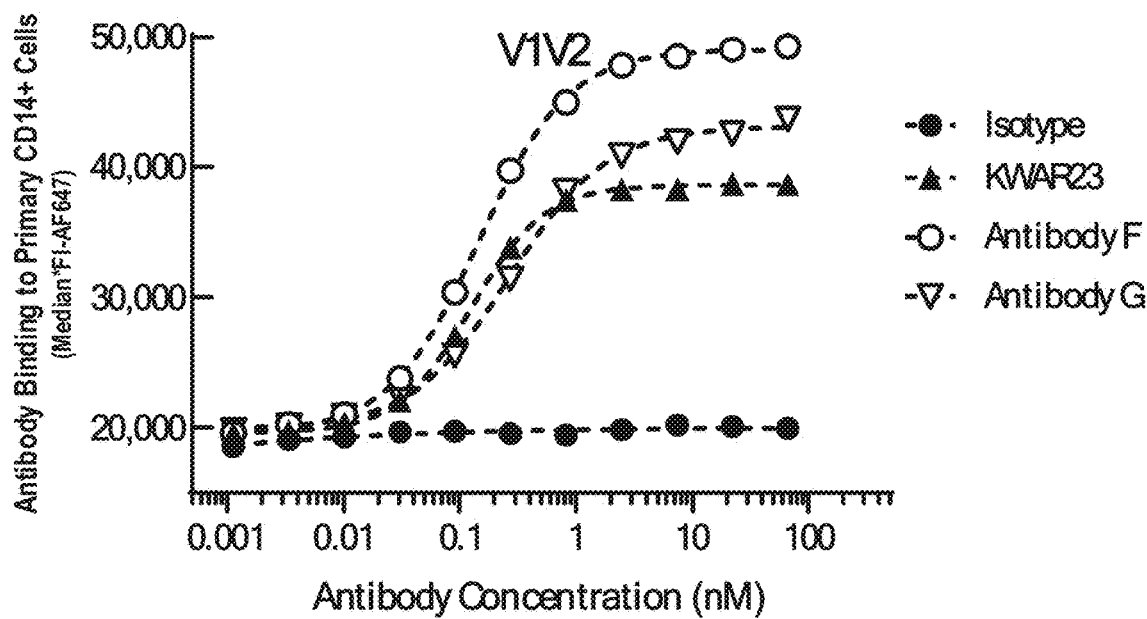
Figure 4C:
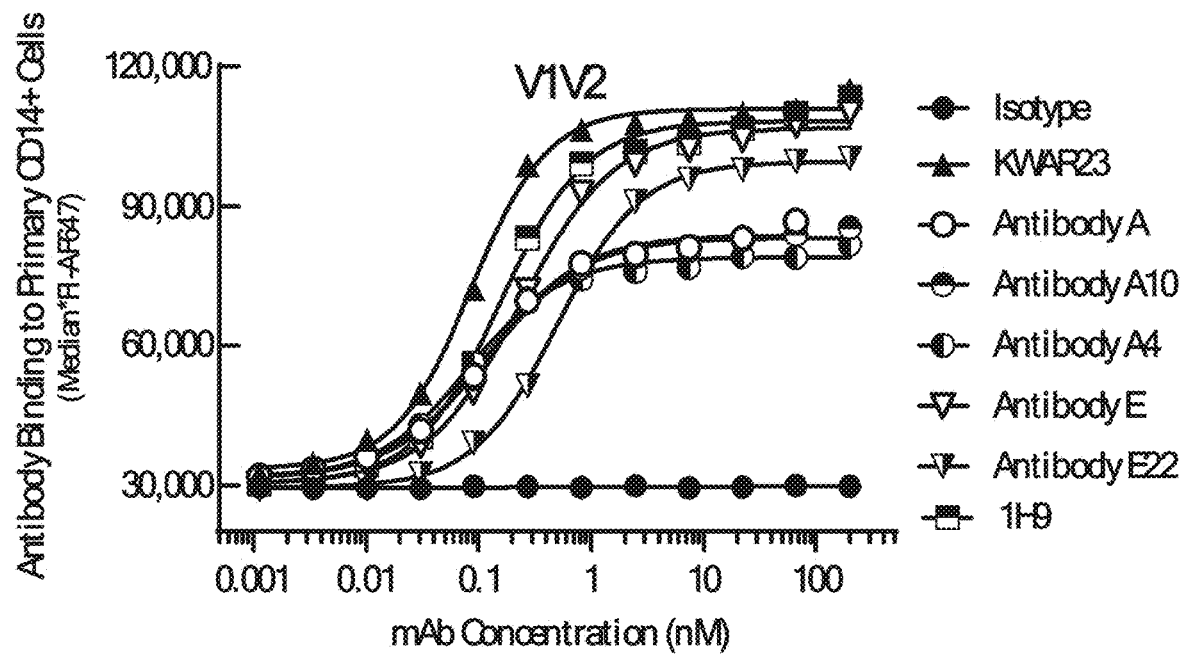
Figure 4D:
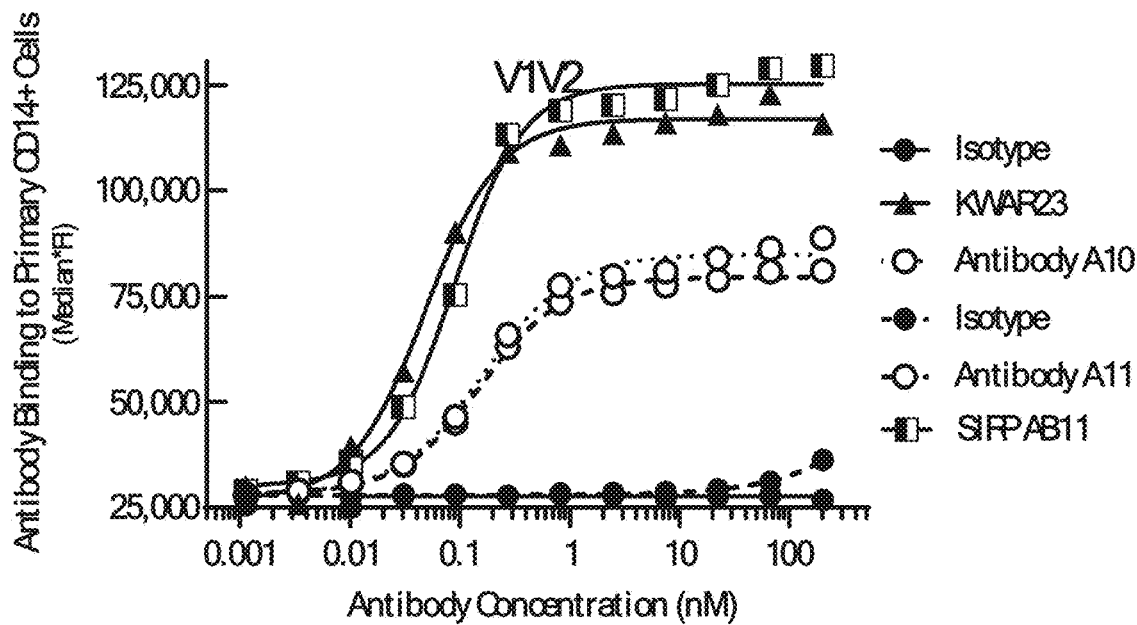
Figure 5A:
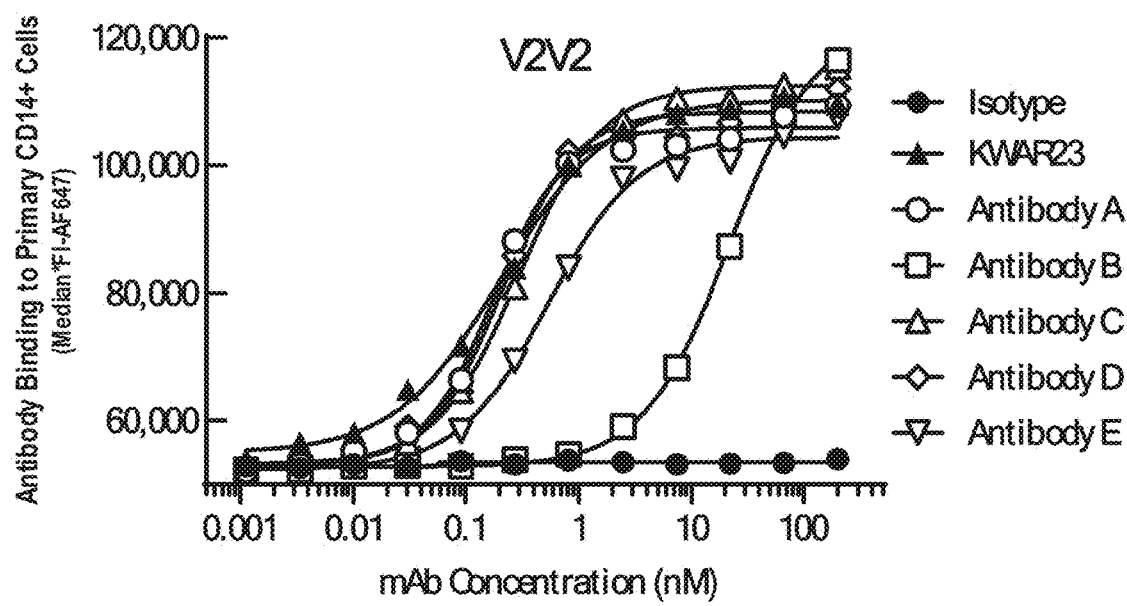
FIGS. 5A-5D are series of graphs depicting the binding of antibodies to endogenous human V1-SIRPα and/or V2-SIRPα expressed on primary human monocytes. Antibody binding to primary human CD14+ monocytes from donors homozygous for V2-SIRPα allele (FIGS. 5A-5D). Solid, dashed, and dotted lines indicate antibody molecules engineered on hIgG1 (LALA), hIgG4P, hIgG1 (K322A) backbones, respectively.
Figure 5B:
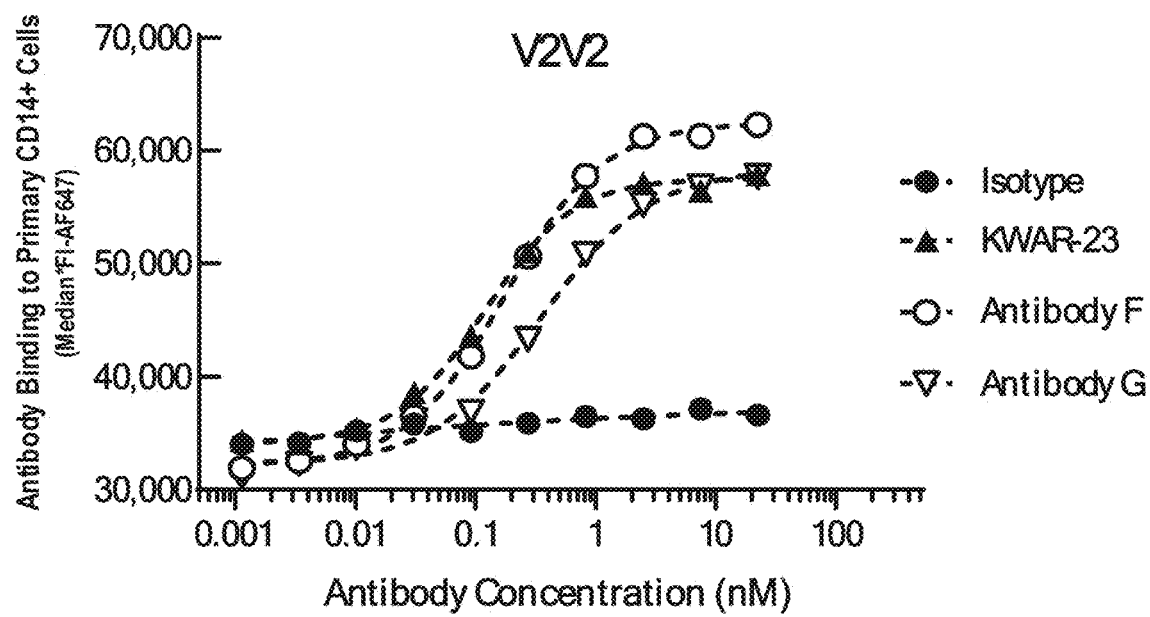
Figure 5C:
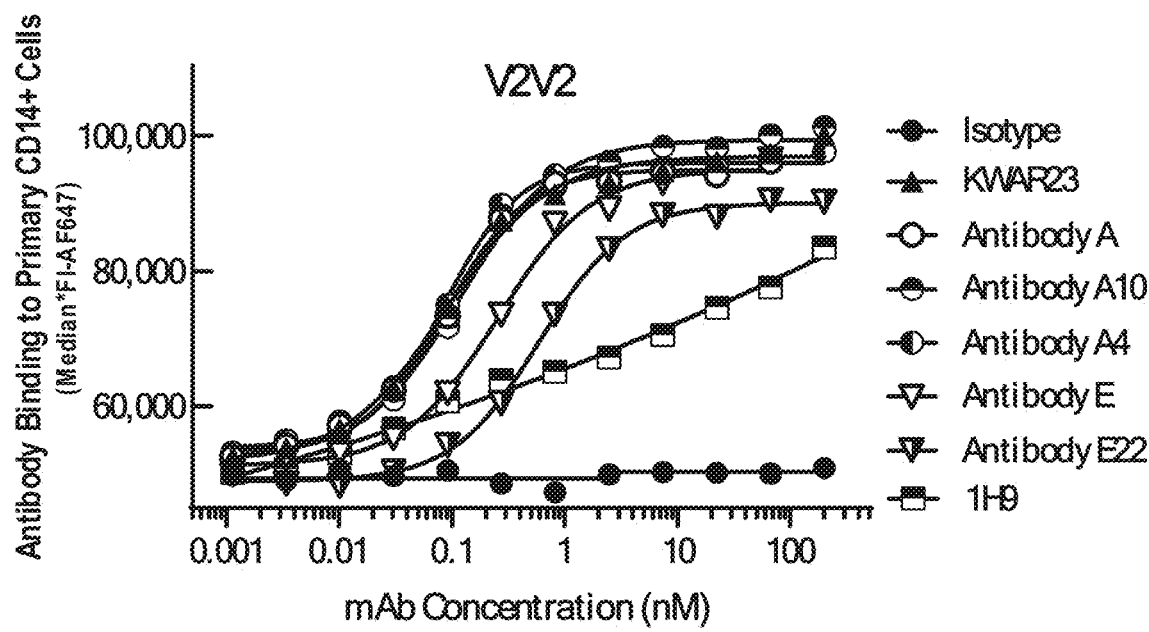
Figure 5D:
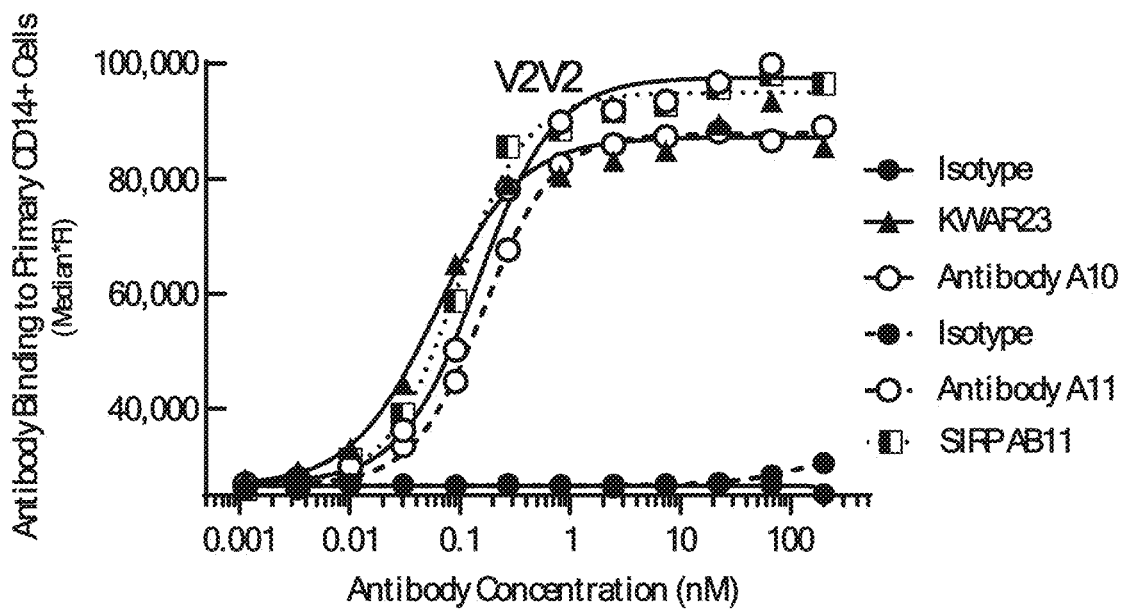
Figure 6A:
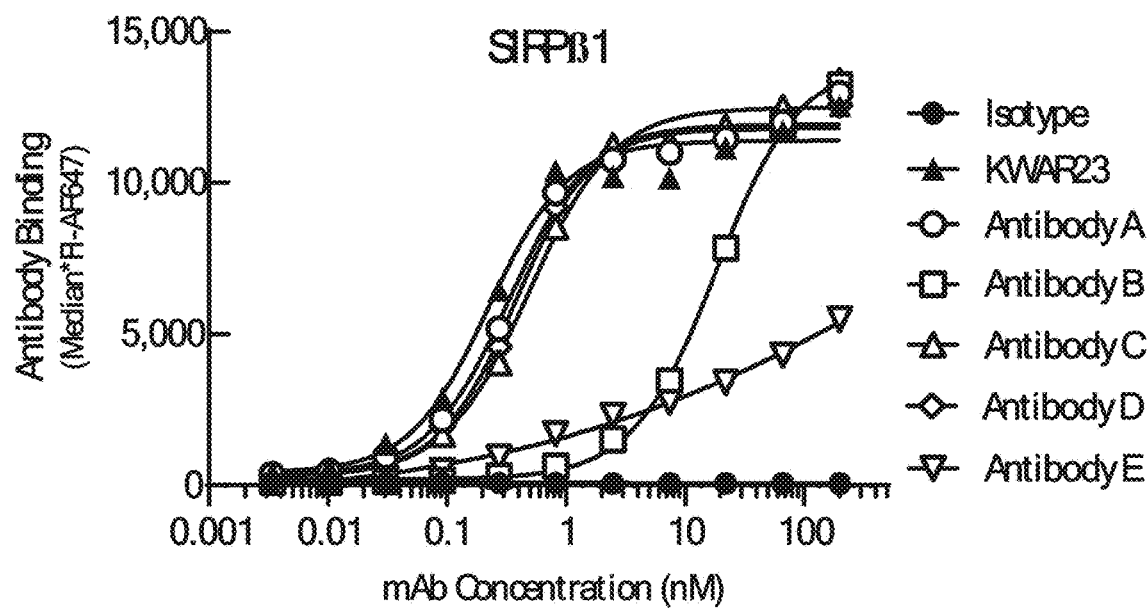
FIGS. 6A-6D are series of graphs depicting the binding of antibodies to full-length human SIRPβ1 expressed on $U973^{SIRP\alpha\ KO}$ cells. Antibody binding to $U937^{SIRP\alpha\ KO}$ cells expressing full-length human SIRPβ1 (NP_006056.2) (FIGS. 6A-6D). Solid, dashed, and dotted lines indicate antibody molecules engineered on hIgG1 (LALA), hIgG4P, hIgG1 (K322A) backbones, respectively.
Figure 6B:
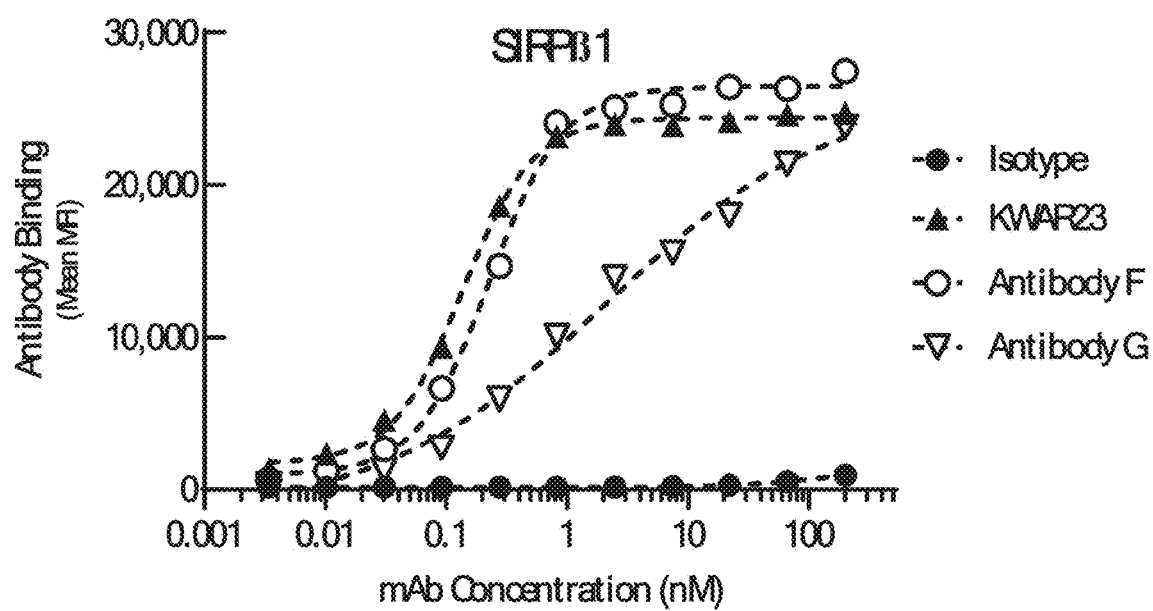
Figure 6C:
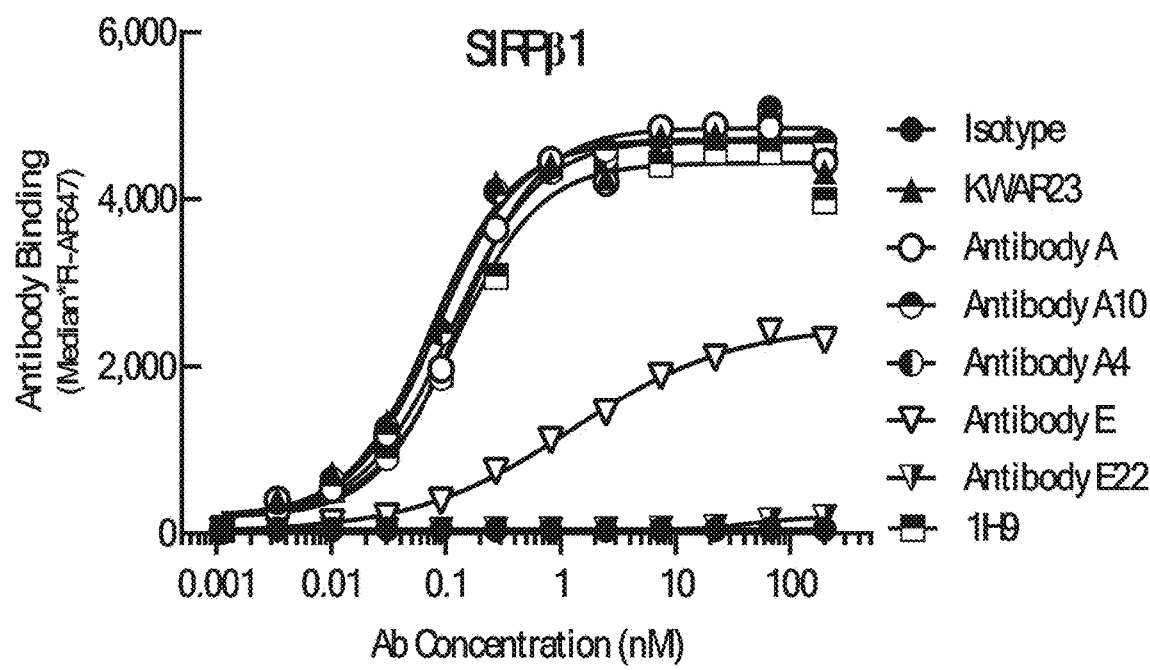
Figure 6D:
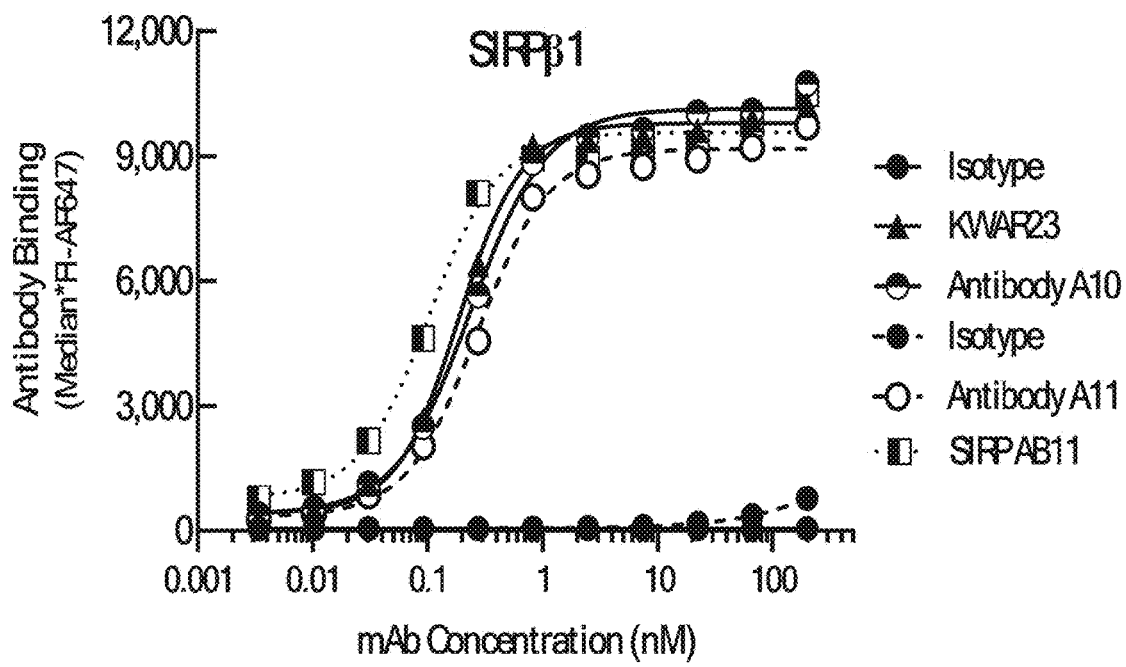
Figure 7A:
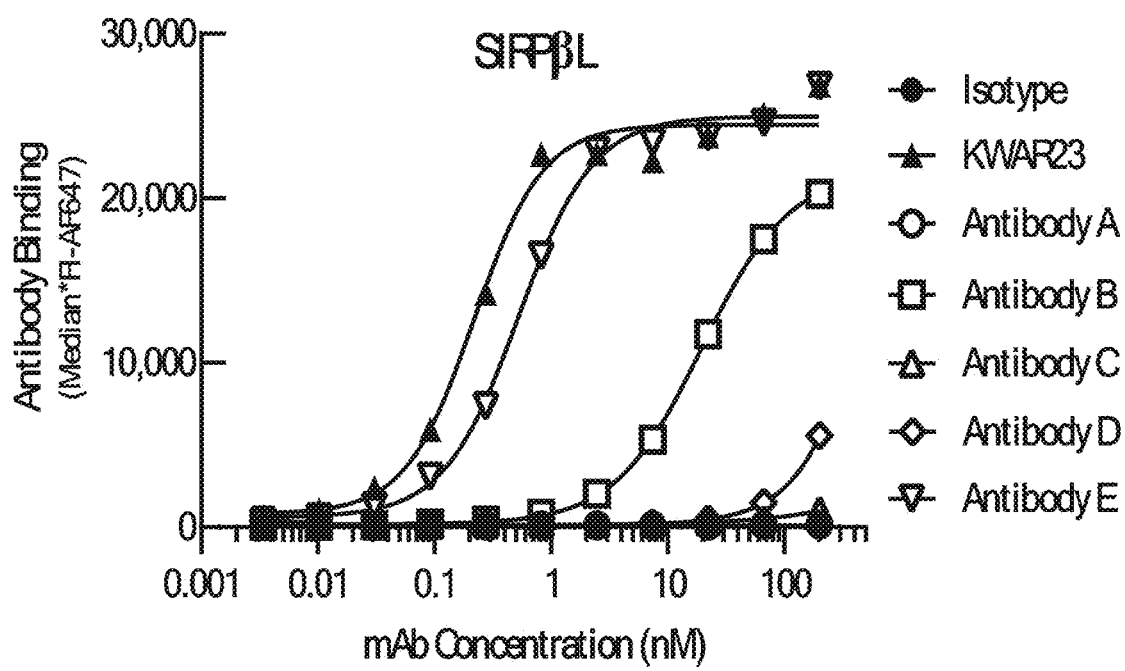
FIGS. 7A-7D are series of graphs depicting the binding of antibodies to full-length human SIRPβ1 expressed on $U973^{SIRP\alpha\ KO}$ cells. Antibody binding to $U937^{SIRP\alpha\ KO}$ cells expressing full-length human SIRPβL (NP_001129316.1) (FIGS. 7A-7D). Solid, dashed, and dotted lines indicate antibody molecules engineered on hIgG1 (LALA), hIgG4P, hIgG1 (K322A) backbones, respectively.
Figure 7B:
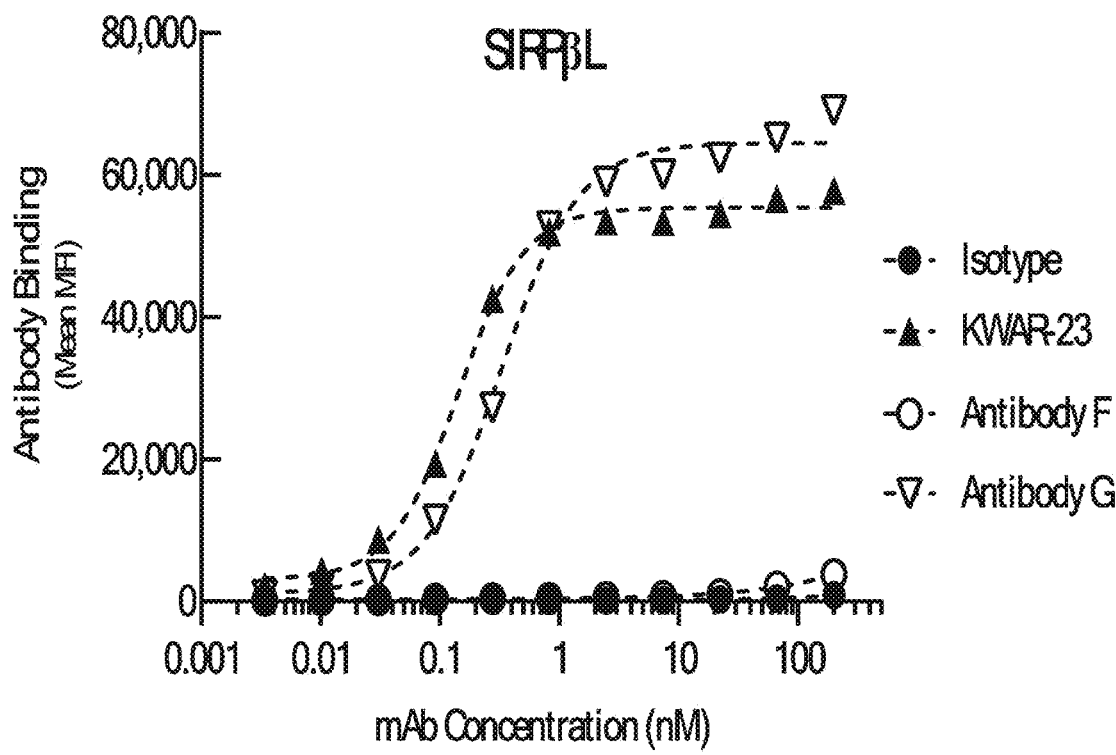
Figure 7C:
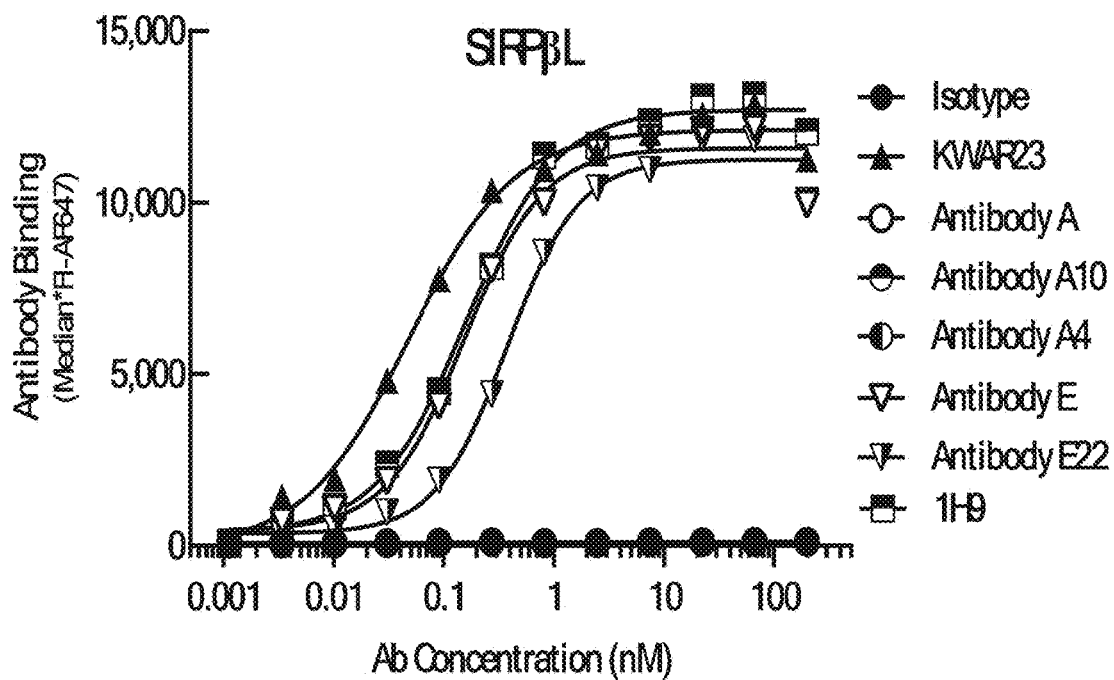
Figure 7D:
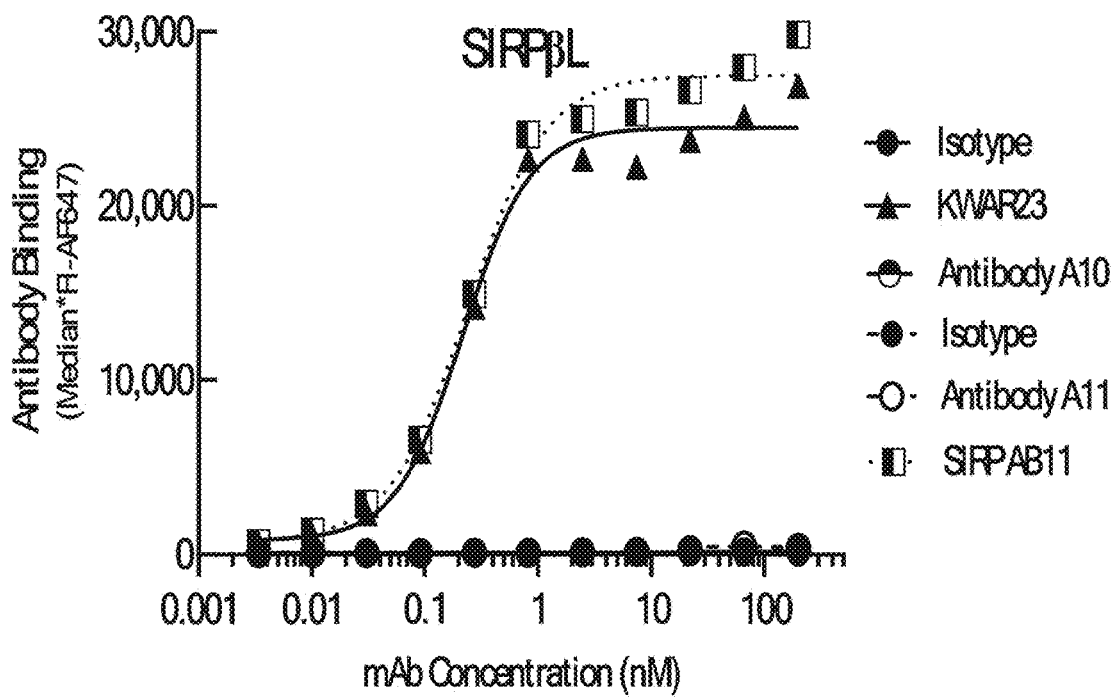

Anti-SIRPα antibody KWAR23 and antibodies A-E demonstrated dose-dependent binding to U-937 cells homozygous for human SIRPαV1 allele (FIG. 2A) and THP-1 cells homozygous for human SIRPαV2 allele (FIG. 2B) with EC$_{50}$ values ranging between 0.2-22 nM (Table 44).

TABLE 44

EC$_{50}$ of Anti-SIRPα antibodies

| | Cell Binding EC$_{50}$ (nM) | |
|---|---|---|
| Antibody | U937 | THP-1 |
| Isotype | NB | NB |
| KWAR23 | 0.5 | 0.2 |
| Antibody A | 0.4 | 0.2 |
| Antibody B | 21.1 | 22.3 |
| Antibody C | 0.6 | 0.3 |
| Antibody D | 0.5 | 0.3 |
| Antibody E | 0.5 | 0.4 |

NB No Binding

Example 6. Binding of Antibodies to Endogenous Human V1-SIRPα and/or V2-SIRPα Expressed on Primary Human Monocytes Antibody binding to primary human cells expressing SIRPα is evaluated by flow cytometry. Human peripheral blood mononuclear cells (PBMCs) from donors genotyped as homozygous for the SIRPα V1 allele, V2 allele, or heterozygous for both alleles are blocked with donkey IgG and incubated on ice with increasing concentrations of antibody for 60 minutes, washed and stained with AF647-conjugated donkey F(ab')$_2$ anti-human IgG secondary reagent. Washed cells are subsequently blocked with Human TruStain FcX™ (Biolegend) and stained with BV421-conjugated anti-human CD14 (Biolegend, clone M5E2). Cells are washed, fixed, and analyzed by flow cytometry. Median fluorescent intensity of the CD14+ population was determined and used as a measure of antibody binding.

All antibodies tested (Antibody A-G, A10, A4, A11, and E22) demonstrated dose-dependent binding to primary human monocytes from donors homozygous for V1 (FIGS. 3A-3D) or V2 (FIGS. 5A-5D) alleles or heterozygous for both alleles (FIGS. 4A-4D). Table 45 highlights the primary cell binding EC$_{50}$ calculated for each of the antibodies described above. Aside from Antibody B, all antibodies exhibited subnanomolar EC$_{50}$.

Binding of known anti-SIRPα antibodies, KWAR23, 1H9 (WO 2019/023347) and SIRP AB11 (WO 2020/068752), to primary human monocytes were also assessed as described above and $EC_{50}$ results are shown in Table 45. While 1H9 exhibited dose-dependent binding and subnanomolar binding $EC_{50}$ values for primary human monocytes from donors homozygous for V1 alleles or heterozygous for both alleles (FIGS. 3C and 4C), non-saturable antibody binding was detected on primary human monocytes from donors homozygous for V2 alleles. KWAR23 and SIRP AB11 antibodies exhibited subnanomolar binding $EC_{50}$ on primary human monocytes from donors of all genotypes (FIGS. 3A-3D, 4A-4D and 5A-5D; Table 45).

TABLE 45

$EC_{50}$ of Anti-SIRPα antibodies

Primary Human Monocyte Cell Binding $EC_{50}$, nM ± SD (n)

| Antibody | V1V1 | V1V2 | V2V2 |
|---|---|---|---|
| Isotype | NB | NB | NB |
| KWAR23 | 0.2 ± 0.04 (n = 7) | 0.1 ± 0.1 (n = 7) | 0.1 ± 0.05 (n = 7) |
| Antibody A | 0.2 ± 0.03 (n = 5) | 0.2 ± 0.1 (n = 5) | 0.1 ± 0.04 (n = 5) |
| Antibody B | 26.6 (n = 1) | 24.1 (n = 1) | 21.8 (n = 1) |
| Antibody C | 0.6 (n = 1) | 0.5 (n = 1) | 0.3 (n = 1) |
| Antibody D | 0.3 (n = 1) | 0.5 (n = 1) | 0.2 (n = 1) |
| Antibody E | 0.4 ± 0.1 (n = 5) | 0.4 ± 0.2 (n = 5) | 0.7 ± 0.3 (n = 5) |
| Antibody F | 0.2 (n = 1) | 0.1 (n = 1) | 0.2 (n = 1) |
| Antibody G | 0.3 (n = 1) | 0.3 (n = 1) | 0.4 (n = 1) |
| Antibody A10 | 0.2 ± 0.04 (n = 5) | 0.1 ± 0.05 (n = 5) | 0.1 ± 0.04 (n = 5) |
| Antibody A4 | 0.1 ± 0.01 (n = 3) | 0.1 ± 0.04 (n = 3) | 0.1 ± 0.03 (n = 3) |
| Antibody E22 | 0.8 ± 0.1 (n = 3) | 0.7 ± 0.2 (n = 3) | 0.4 ± 0.2 (n = 3) |
| Antibody A11 | 0.1 ± 0 .04 (n = 2) | 0.1 ± 0.06 (n = 2) | 0.1 ± 0.07 (n = 2) |
| 1H9 | 0.2 (n = 1) | 0.2 (n = 1) | NS (n = 1) |
| SIRP AB11 | 0.1 ± 0.01 (n = 2) | 0.1 ± 0.01 (n = 2) | 0.1 ± 0.001 (n = 2) |

NB No Binding
NS Non-saturable binding

Example 7. Binding of Antibodies to Full-Length Human SIRPβ1 or SIRPβL-Expressed on U937$^{SIRPα\ KO}$ Cells Antibody binding to cells expressing full-length human SIRPβ1 (NP_006056.2) and SIRPβL (NP_001129316.1) is evaluated by flow cytometry. SIRPβ1- or SIRPβL-expressing U937$^{SIRPα\ KO}$ cells are blocked with donkey IgG and incubated on ice with increasing concentrations of antibodies for 60 minutes, washed and stained with AF647-conjugated donkey F(ab')$_2$ anti-human IgG secondary reagent. Cells are washed, fixed, and analyzed by flow cytometry. Median fluorescent intensity is determined and used as a measure of antibody binding.

Antibodies A-G, A10, A4, and A11, but not isotype control or antibody E22, demonstrated dose-dependent binding to full length human SIRPβ1 expressed on U-937$^{SIRPα\ KO}$ cells (FIGS. 6A-6D). Table 44 highlights the binding $EC_{50}$ calculated for each of the antibodies described above. While antibodies A, C, D, F, A10, A4, and A11 exhibited subnanomolar $EC_{50}$ values to these cells, binding of antibodies B, E, and G were non-saturable at concentrations as high as 200 nM and no $EC_{50}$ values determined.

Antibodies E, G, and E22 demonstrated dose-dependent binding to full length human SIRPβL expressed on U-937$^{SIRPα\ KO}$ cells (FIGS. 7A-7D) with $EC_{50}$ less than 1 nM (Table 46). No binding of antibodies A, C, D, F, A10, A4 and A11 could be detected on SIRPβL-expressing U-937$^{SIRPα\ KO}$ cells (FIGS. 7A-7D). Binding of antibody B (FIG. 7A) was detected on SIRPβL-expressing U-937$^{SIRPα\ KO}$ cells; however, binding was non-saturable at concentrations as high as 200 nM Binding of known anti-SIRPα antibodies, KWAR23, 1H9 and SIRPAB11, to SIRPβ1- or SIRPβL-expressing U937$^{SIRPα\ KO}$ cells was also assessed as described above. All 3 molecules demonstrated dose-dependent binding to both cell types (FIGS. 6A-6D and 7A-7D) with sub-nanomolar binding $EC_{50}$ values (Table 46).

TABLE 46

$EC_{50}$ of Anti-SIRPα antibodies

Cell Binding $EC_{50}$, nM ± SD (n)

| Antibody | SIRPβ1 | SIRPβL |
|---|---|---|
| Isotype | NB (n = 6) | NB (n = 6) |
| KWAR23 | 0.2 ± 0.1 (n = 6) | 0.2 ± 0.1 (n = 6) |
| Antibody A | 0.2 ± 0.1 (n = 5) | NB (n = 5) |
| Antibody B | NS (n = 1) | NS (n = 1) |
| Antibody C | 0.5 (n = 1) | NB (n = 1) |
| Antibody D | 0.4 (n = 1) | NB (n = 1) |
| Antibody E | NS (n = 5) | 0.3 ± 0.1 (n = 5) |
| Antibody F | 0.2 (n = 1) | NB (n = 1) |
| Antibody G | NS (n = 1) | 0.3 (n = 1) |
| Antibody A10 | 0.2 ± 0.1 (n = 4) | NB (n = 4) |
| Antibody A4 | 0.2 ± 0.1 (n = 3) | NB (n = 3) |
| Antibody E22 | NB (n = 3) | 0.6 ± 0.2 (n = 3) |
| Antibody A11 | 0.3 (n = 1) | NB (n = 1) |
| 1H9 | 0.2 ± 1.0 (n = 2) | 0.3 ± 0.2 (n = 2) |
| SIRPAB11 | 0.1 (n = 1) | 0.2 (n = 1) |

NB No binding
NS Non-saturable binding as high a 200 nM

Example 8. Binding of Antibodies to Purified Recombinant Human SIRPγ Proteins by ELISA A biochemical ELISA-based assay is utilized to evaluate the binding of antibodies to SIRPγ. Black, 96-well flat-bottom immunoassay plates are coated with recombinant human SIRPγ extracellular domain (ECD)/His protein (NP_061026.2) diluted in DPBS and incubated overnight at 4° C. Plates are washed three times and subsequently blocked for about 1-2 h at room temperature (RT). Plates are washed and serially titrated antibodies are added to respective wells for an incubation of about 1-2 h at RT. After the incubation, the plates are washed and HRPO-conjugated mouse anti-human IgG secondary reagent (Jackson Immuno Research) is added to each well and incubated for about 1-2 hours. Following the final plate washing, Amplex™ red substrate is added and incubated at RT in the dark for 15-30 minutes. Fluorescence is detected ($\lambda_{Ex}/\lambda_{Em}$=530/590 nm) using EnVision Multilabel Plate Reader (Perkin Elmer). Average fluorescence is plotted for measuring the antibody binding.

Figure 8:
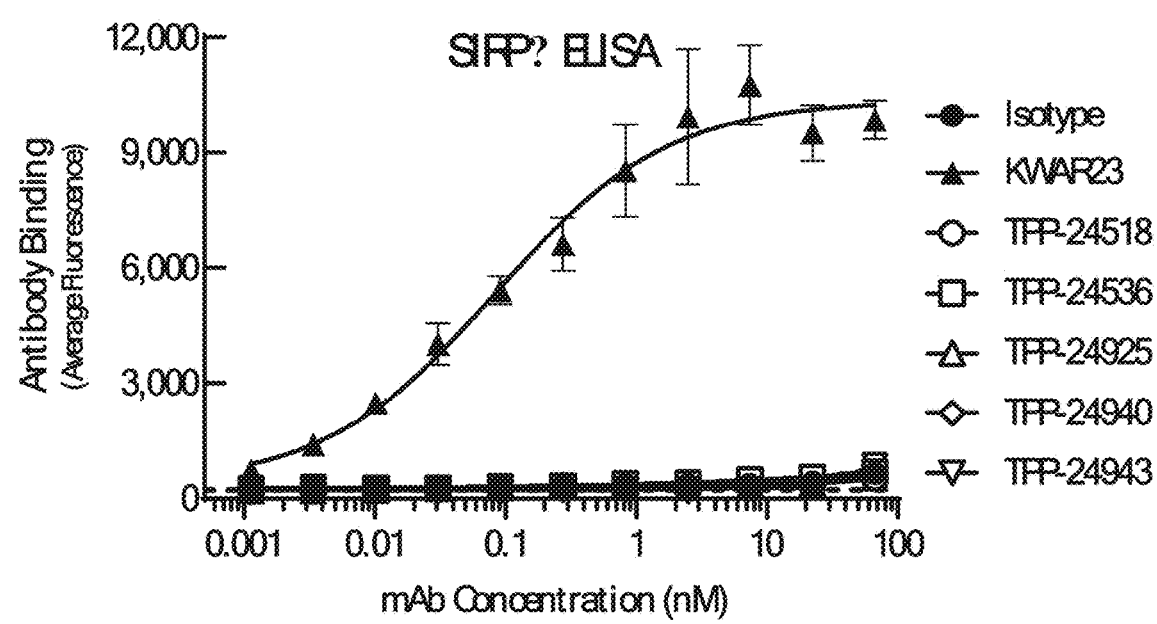
FIG. 8 is a graph depicting the binding of antibodies to recombinant SIRPγ protein. Antibody binding to immobilized recombinant His-tagged human SIRPγ extracellular domain (NP_061026.2).

Except SIRPγ-reactive mAb, KWAR23, none of the antibodies tested (Antibodies A-E) exhibited binding to immobilized recombinant human SIRPγ ECD/His protein (FIG. 8). The $EC_{50}$ value for KWAR23 was determined to be 0.1 nM (Table 47).

Example 9. Binding of Antibodies to Full-Length Human SIRPγ Expressed on CHO Cells Antibody binding to cells expressing human SIRPγ (NP_061026.2) is evaluated by flow cytometry. SIRPγ-expressing CHO cells are blocked with donkey IgG and incubated on ice with increasing concentrations of antibody for 60 minutes, washed and stained with AF647-conjugated donkey F(ab')$_2$ anti-human IgG secondary reagent. Cells are washed, fixed, and analyzed by flow cytometry. Median fluorescent intensity is determined and used as a measure of antibody binding.

Figure 9:
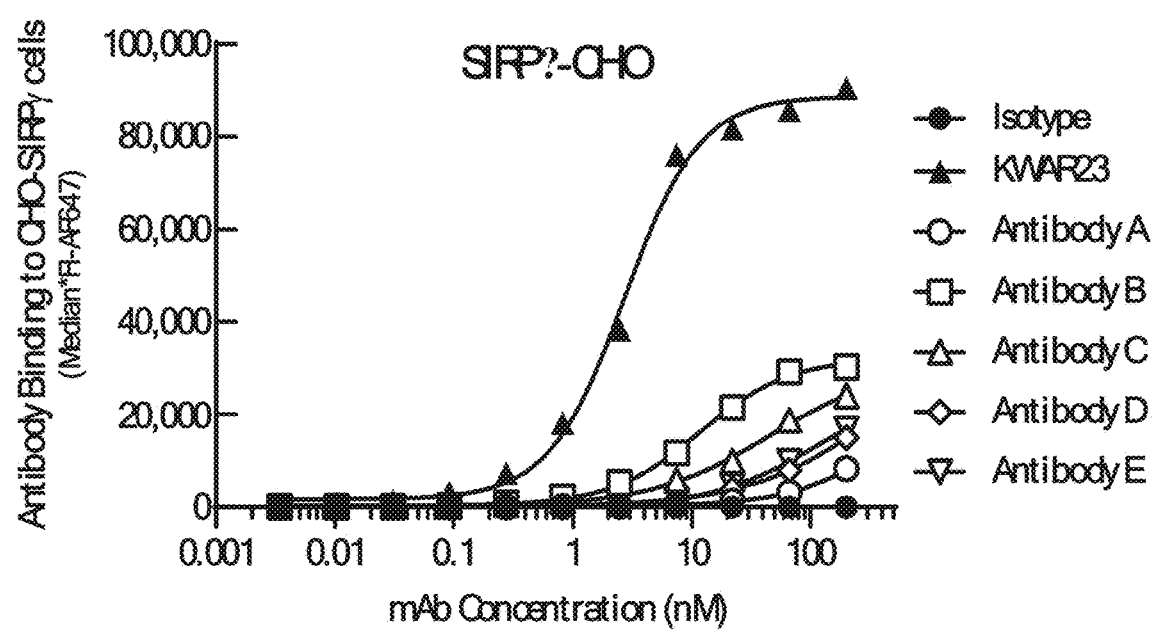
FIG. 9 is a graph depicting the binding of antibodies to full-length human SIRPγ expressed on CHO cells. Antibody binding to CHO cells expressing full-length human SIRPγ (NP_061026.2).
Figure 10A:
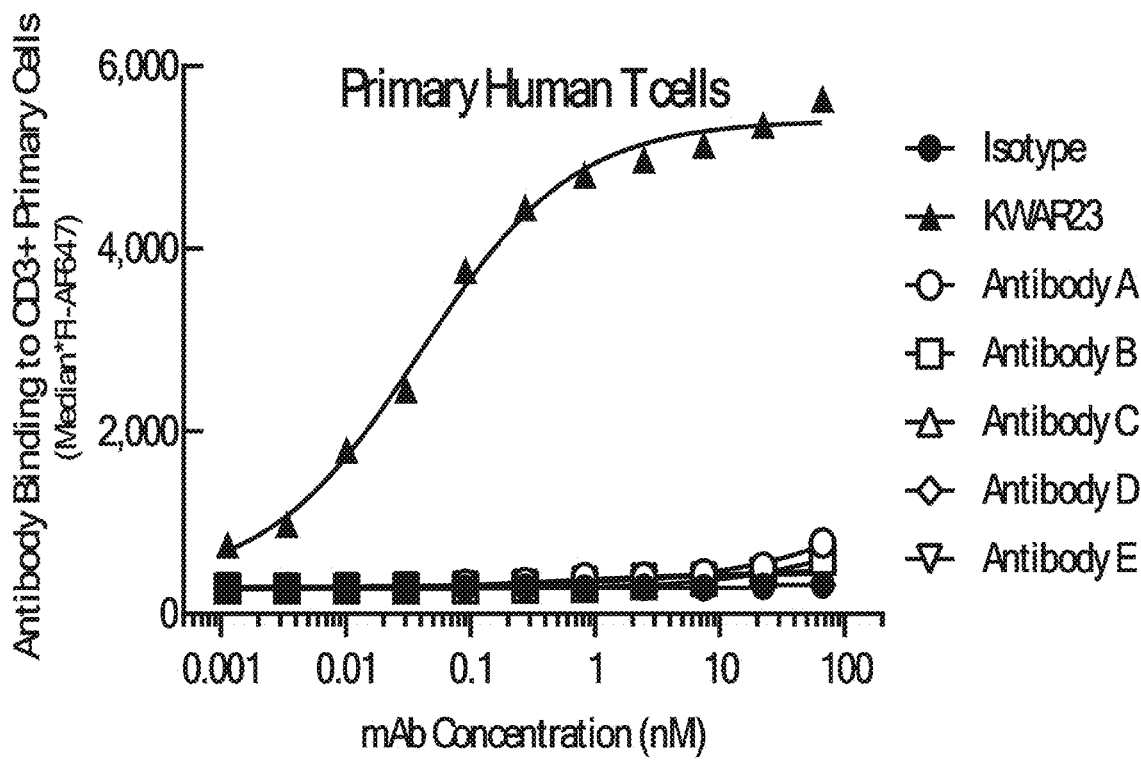
FIGS. 10A-10D are series of graphs depicting the binding of antibodies to primary human CD3+ T cells. Antibody binding to primary human CD3+ T cells (FIGS. 10A-10D). Solid, dashed, and dotted lines indicate antibody molecules engineered on hIgG1 (LALA), hIgG4P, hIgG1 (K322A) backbones, respectively.
Figure 10B:
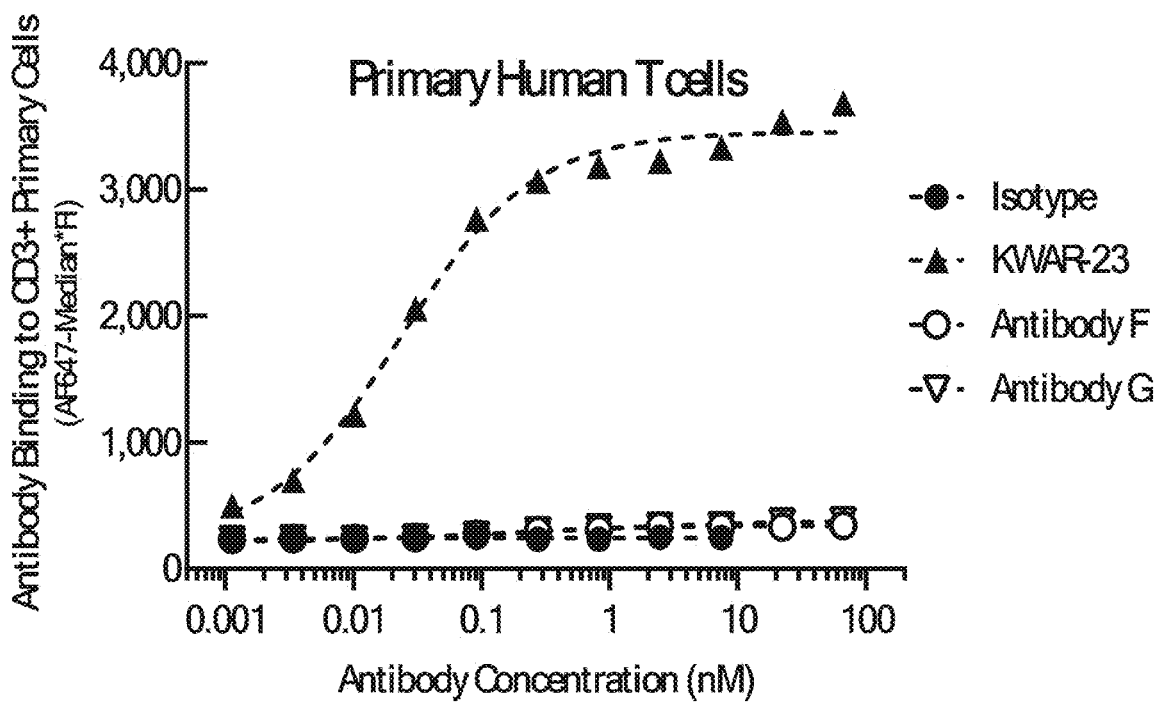
Figure 10C:
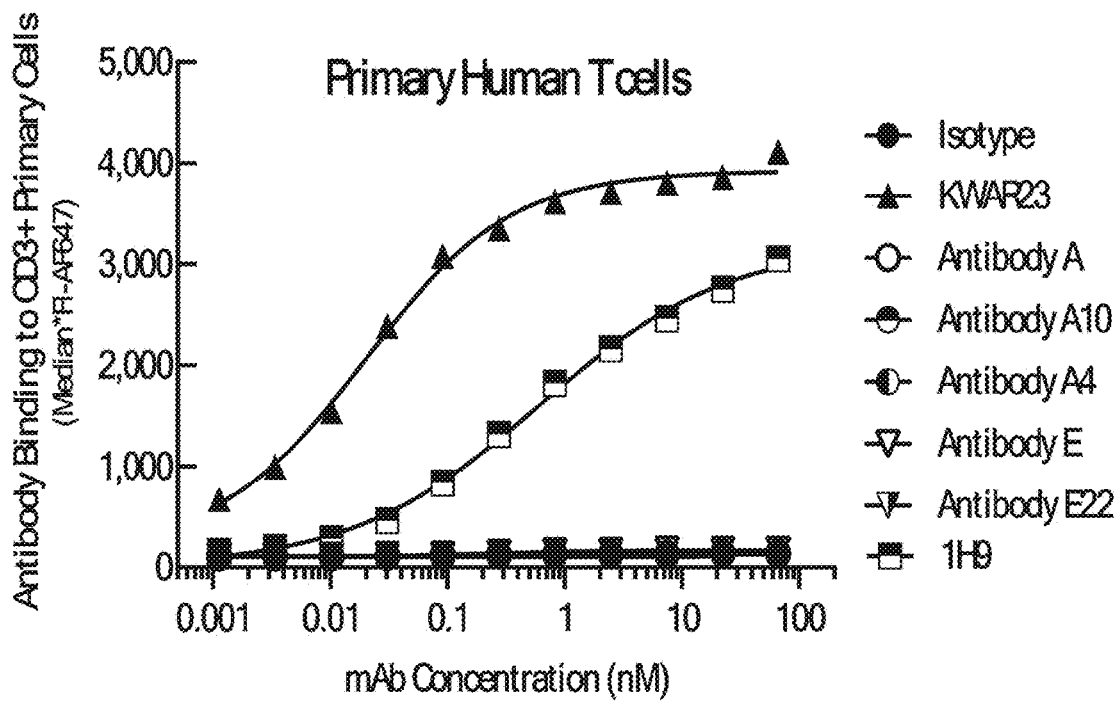
Figure 10D:
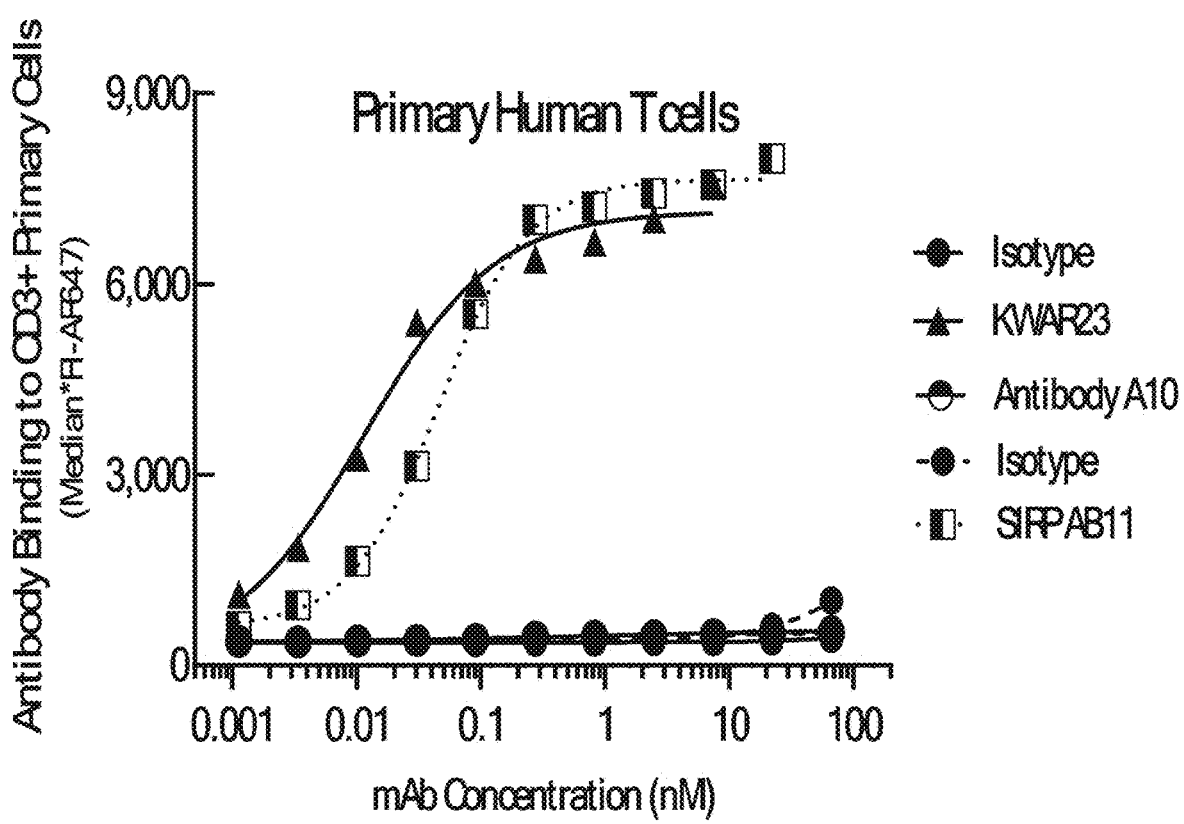

Binding for each of the antibodies on SIRPγ-expressing CHO cells was detected relative to isotype control (FIG. 9). Compared to SIRPγ-reactive mAb (KWAR23) that exhibited an $EC_{50}$ of 2.7 nM (Table 47), binding of antibodies A and C-E was non-saturable at concentrations as high as 200 nM and the magnitude of bound antibody detected was low.

Example 10. Binding of Antibodies to SIRPγ Expressed on Primary Human T Cells

Antibody binding to primary human T cells expressing endogenous SIRPγ is evaluated by flow cytometry. Human peripheral blood mononuclear cells (PBMCs) are blocked with donkey IgG and incubated on ice with increasing concentrations of antibody for 60 minutes, washed and stained with AF647-conjugated donkey F(ab')₂ anti-human IgG secondary reagent. Human PBMCs are subsequently blocked with Human TruStain FcX™ (Biolegend) and stained with BUV395-conjugated anti-human CD3 (BD Biosciences, clone SK7). Cells are washed, fixed, and analyzed by flow cytometry. Median fluorescent intensity of CD3+ gated population is determined and used as a measure of antibody binding.

Binding of known anti-SIRPα antibodies, KWAR23, 1H9 and SIRPAB11, to primary human T cells is also assessed as described above. KWAR23, 1H9 and SIRP AB11 demonstrated dose-dependent binding to primary human CD3+ cells (FIGS. 10A-10D) with $EC_{50}$ values less than 1 nM (Table 47), while no binding by antibodies A-G, A10, A4, A11, and E22 was detected.

TABLE 47

$EC_{50}$ of Anti-SIRPα antibodies

| | $EC_{50}$; nM ± SD (n) | | |
|---|---|---|---|
| Antibody | recombinant hSIRPγ | CHO-hSIRPγ | primary CD3 + cells |
| Isotype | NB (n = 1) | NB (n = 1) | NB (n = 18) |
| KWAR23 | 0.1 (n = 1) | 2.7 (n = 1) | 0.03 ± 0.01 (n = 15) |
| Antibody A | NB (n = 1) | NS (n = 1) | NB (n = 15) |
| Antibody B | NB (n = 1) | 11.8 (n = 1) | NB (n = 3) |
| Antibody C | NB (n = 1) | NS (n = 1) | NB (n = 3) |
| Antibody D | NB (n = 1) | NS (n = 1) | NB (n = 3) |
| Antibody E | NB (n = 1) | NS (n = 1) | NB (n = 15) |
| Antibody F | NT | NT | NB (n = 3) |
| Antibody G | NT | NT | NB (n = 3) |
| Antibody A10 | NT | NT | NB (n = 12) |
| Antibody A4 | NT | NT | NB (n = 9) |
| Antibody E22 | NT | NT | NB (n = 9) |
| Antibody A11 | NT | NT | NB (n = 3) |
| 1H9 | NT | NT | 0.2 ± 0.1 (n = 2) |
| SIRPAB11 | NT | NT | 0.02 ± 0.004 (n = 3) |

NB No binding
NT Not tested
NS Non-saturable binding

Example 11. Blocking of Human CD47 Binding to Full-Length Human V1-SIRPα or V2-SIRPα Expressed on CHO Cells Human CD47 tetramers are assembled using biotinylated human CD47 (NP_942088; AcroBiosystems) and AF647-conjugated streptavidin (Biolegend). To assess antibody ligand blocking potential, CHO-K1 cells expressing full-length human SIRPαV1 (NP_542970.1) or CHO-K1 cells expressing full-length human SIRPαV2 (CAA71403.1) are co-incubated with increasing concentrations of antibody and a fixed concentration of human CD47 tetramer on ice for 60 min. Cells are washed, fixed, and analyzed by flow cytometry. Median fluorescent intensity is determined and used as a measure of CD47 binding.

Figure 11A:
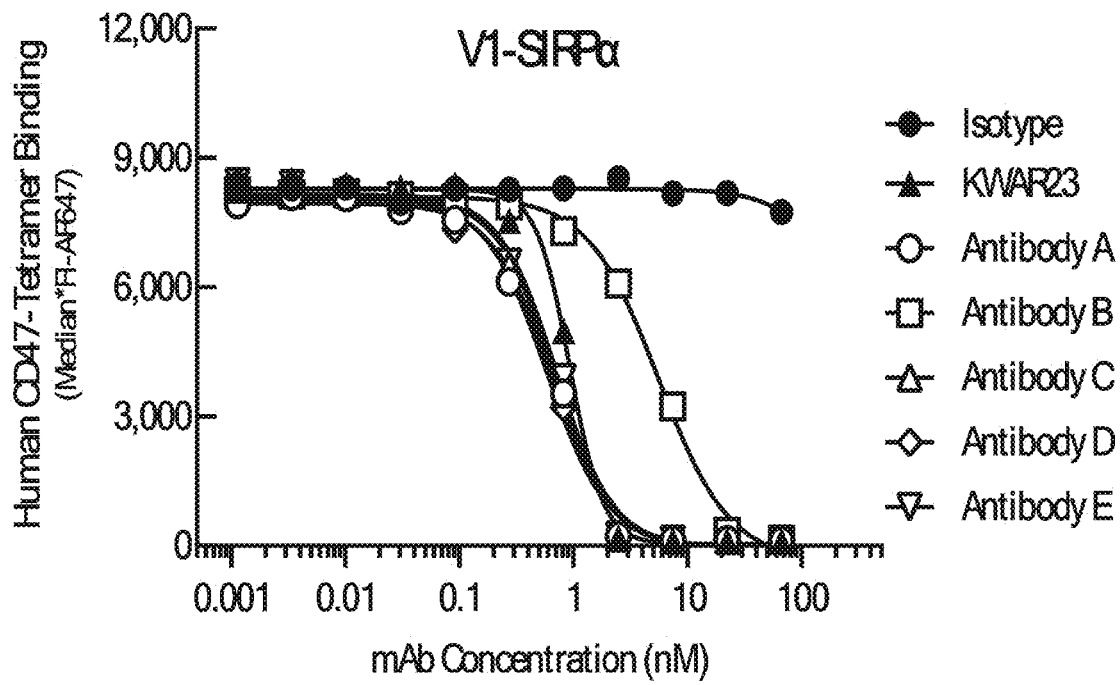
FIG. 11A and FIG. 11B are series of graphs depicting the blocking of human CD47 binding to human SIRPα. Figure A. Antibodies block human CD47 binding to CHO cells expressing full-length human SIRPαV1 (NP_542970.1). Figure B. Antibodies block human CD47 binding to CHO cells expressing full-length human SIRPαV2 (CAA71403.1).
Figure 11B:
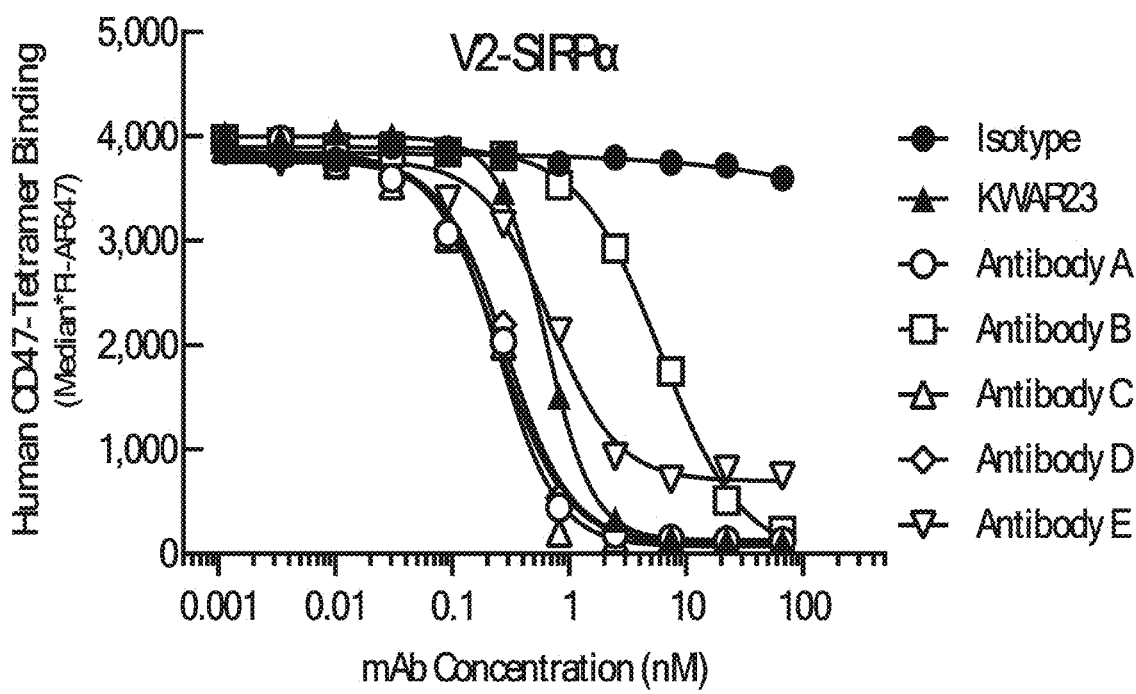
Figure 12A:
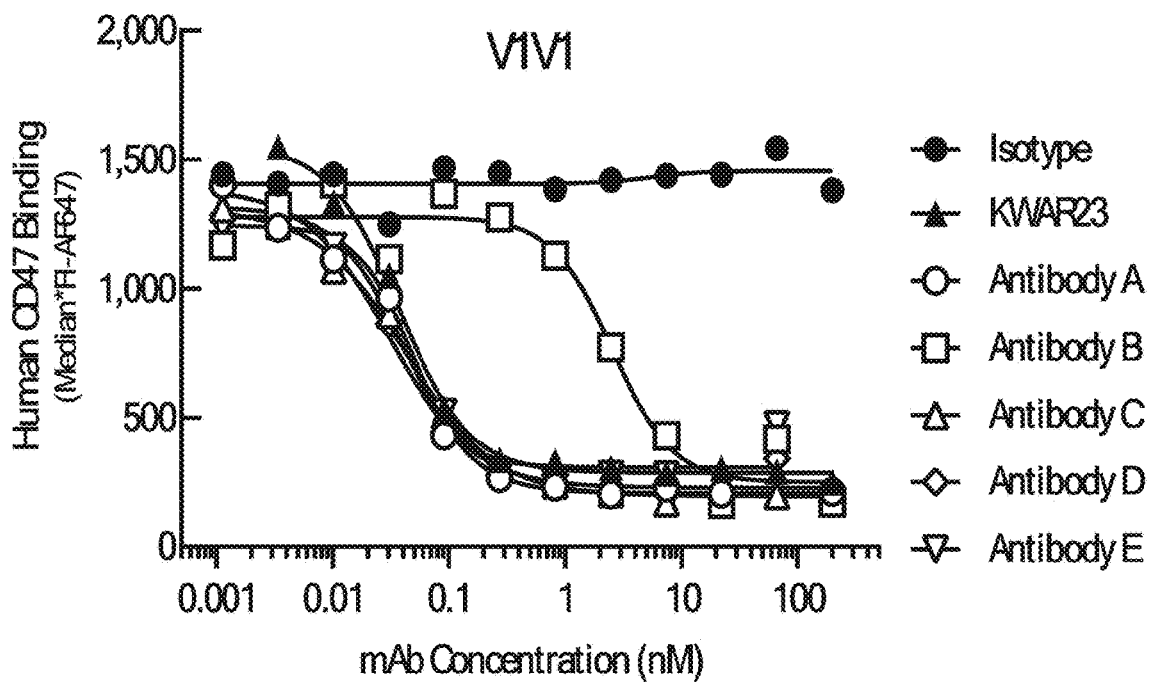
FIGS. 12A-12D are series of graphs depicting the blocking of human CD47 binding to SIRPα expressed on primary cells. Antibodies block human CD47 binding to primary human CD14+ monocytes from donors homozygous for V1 (FIGS. 12A-12D). Solid, dashed, and dotted lines indicate antibody molecules engineered on hIgG1 (LALA), hIgG4P, hIgG1 (K322A) backbones, respectively.
Figure 12B:
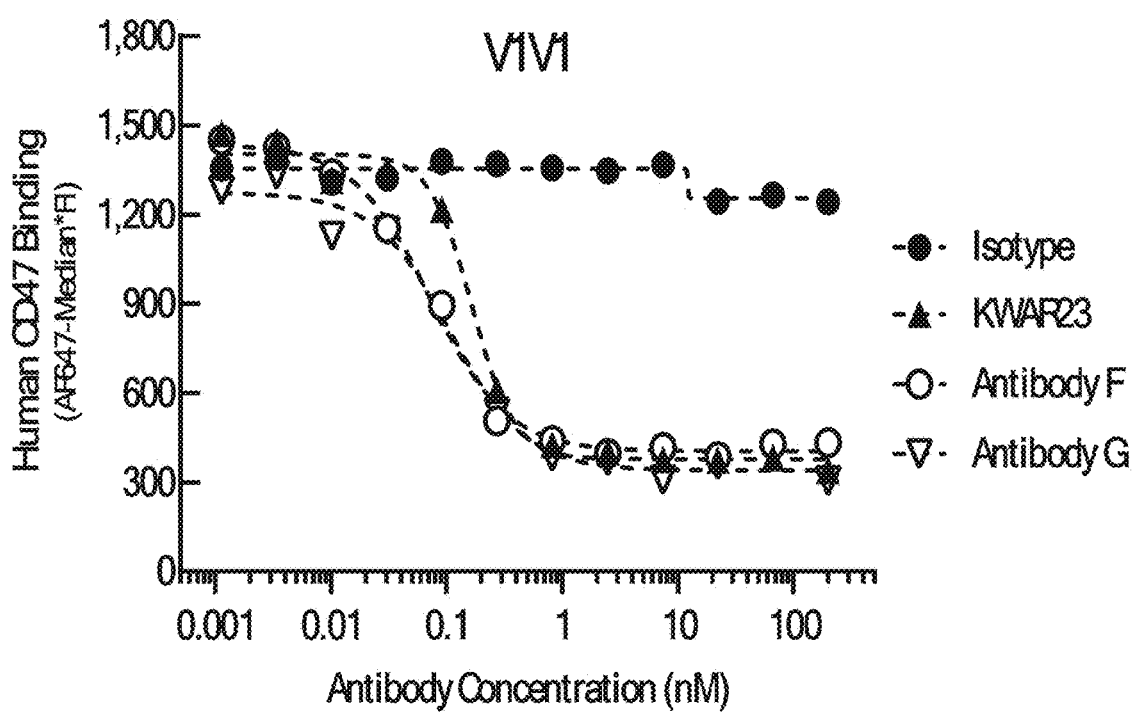
Figure 12C:
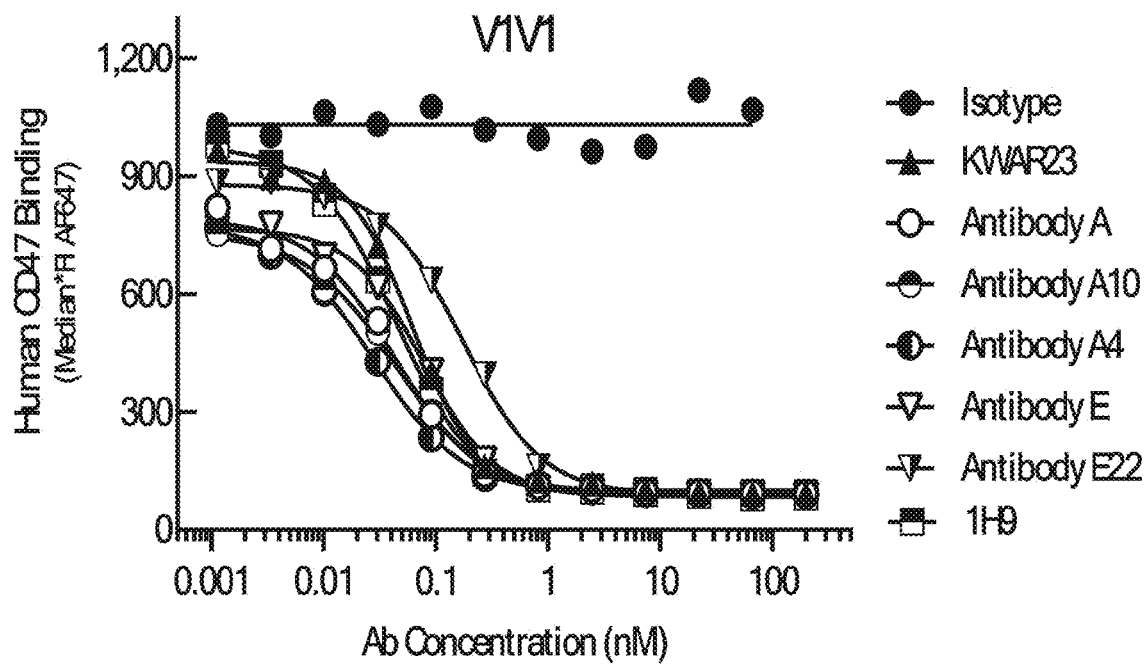
Figure 12D:
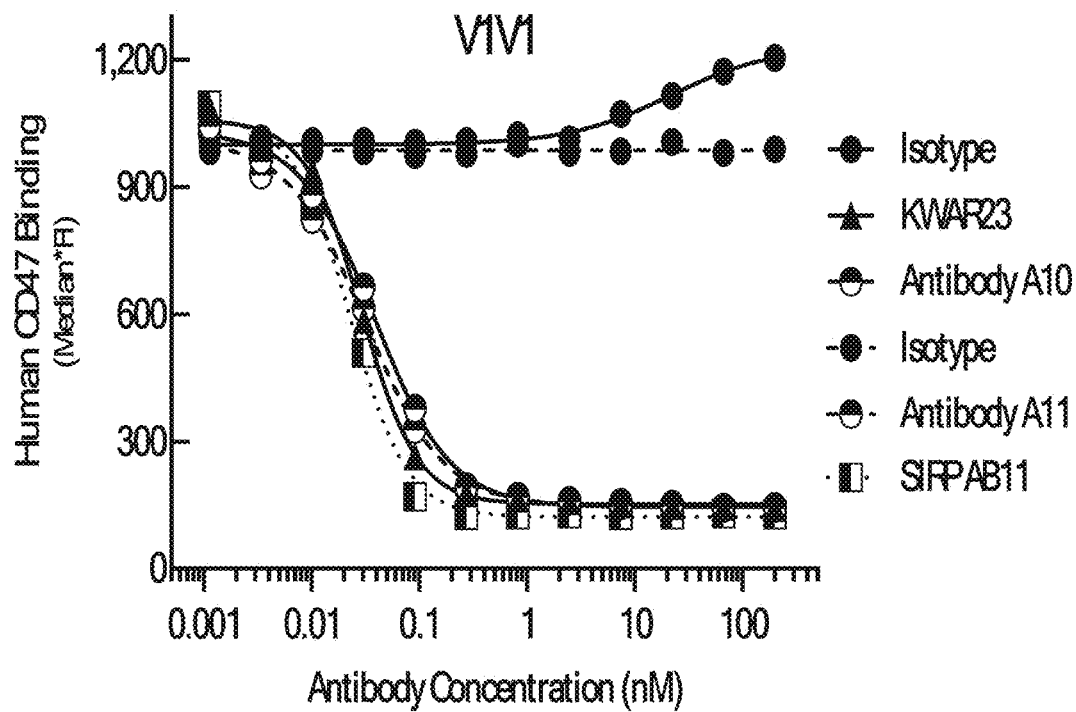
Figure 13A:
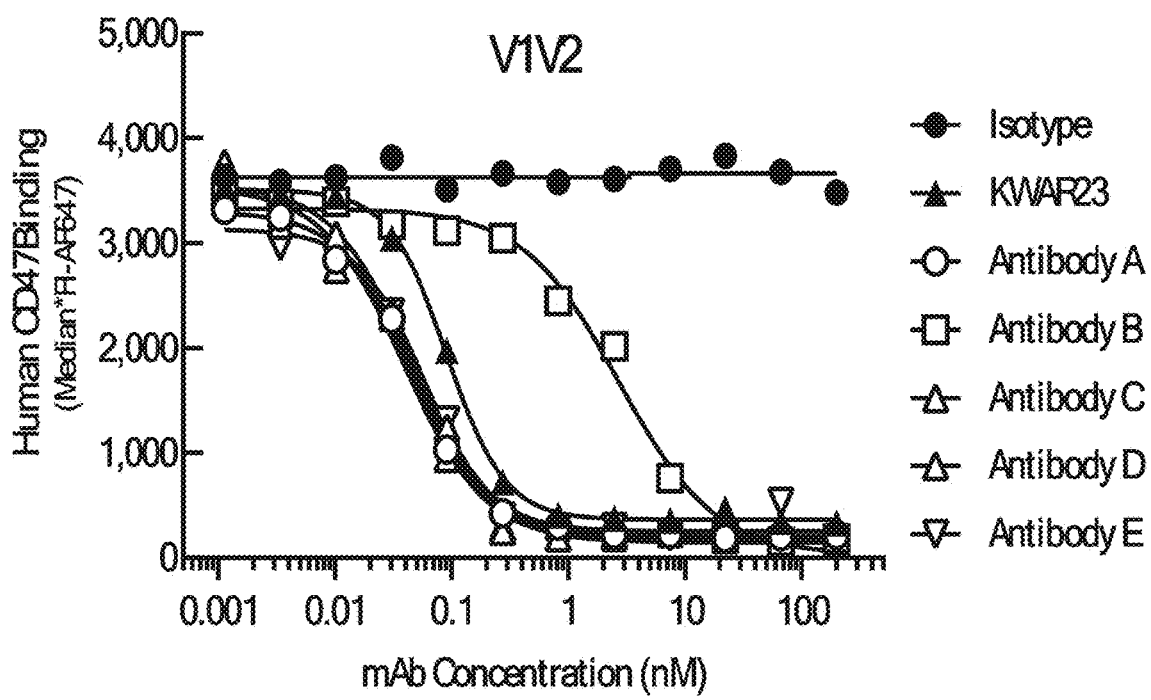
FIGS. 13A-13D are series of graphs depicting the blocking of human CD47 binding to SIRPα expressed on primary cells. Antibodies block human CD47 binding to primary human CD14+ monocytes from donors heterozygous for V1- and V2-SIRPα alleles. Solid, dashed, and dotted lines indicate antibody molecules engineered on hIgG1 (LALA), hIgG4P, hIgG1 (K322A) backbones, respectively.
Figure 13B:
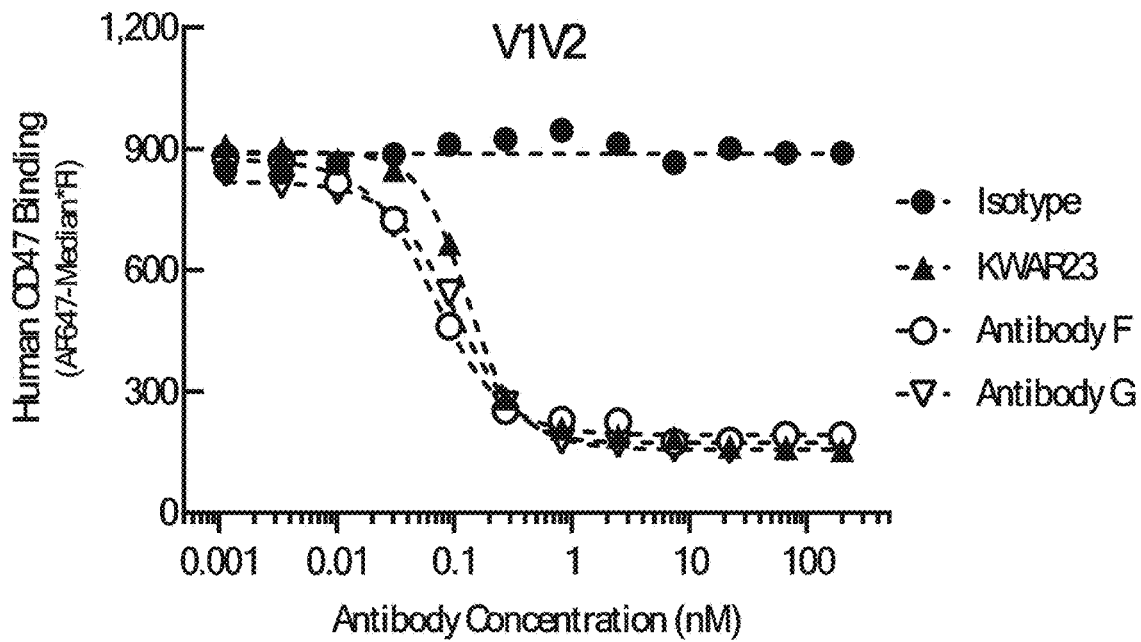
Figure 13C:
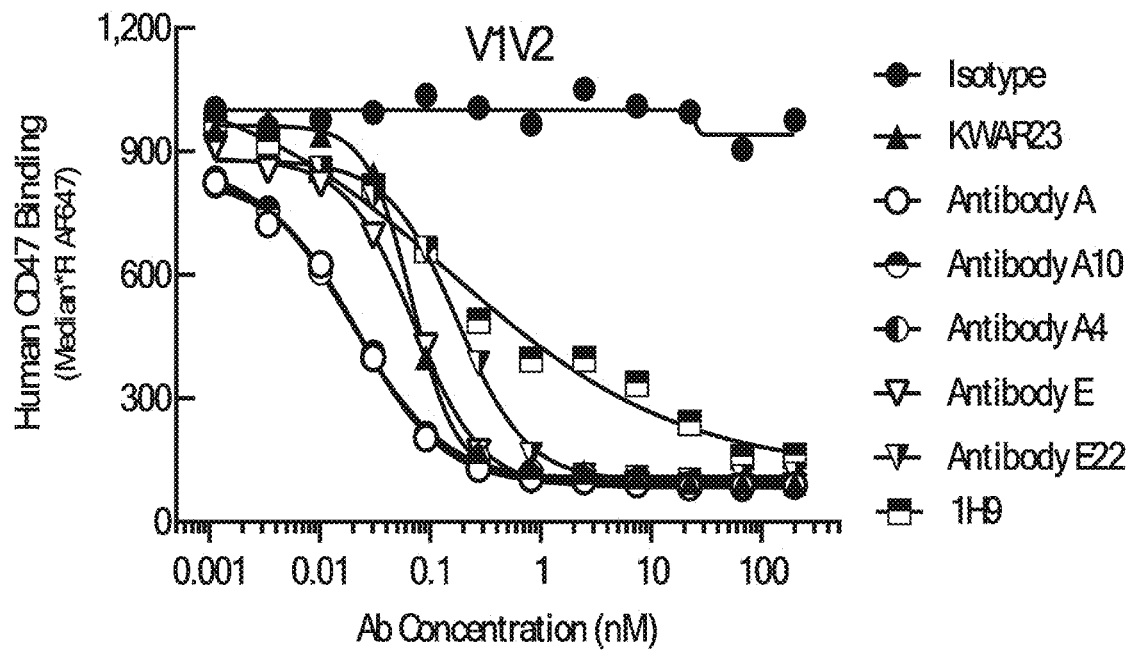
Figure 13D:
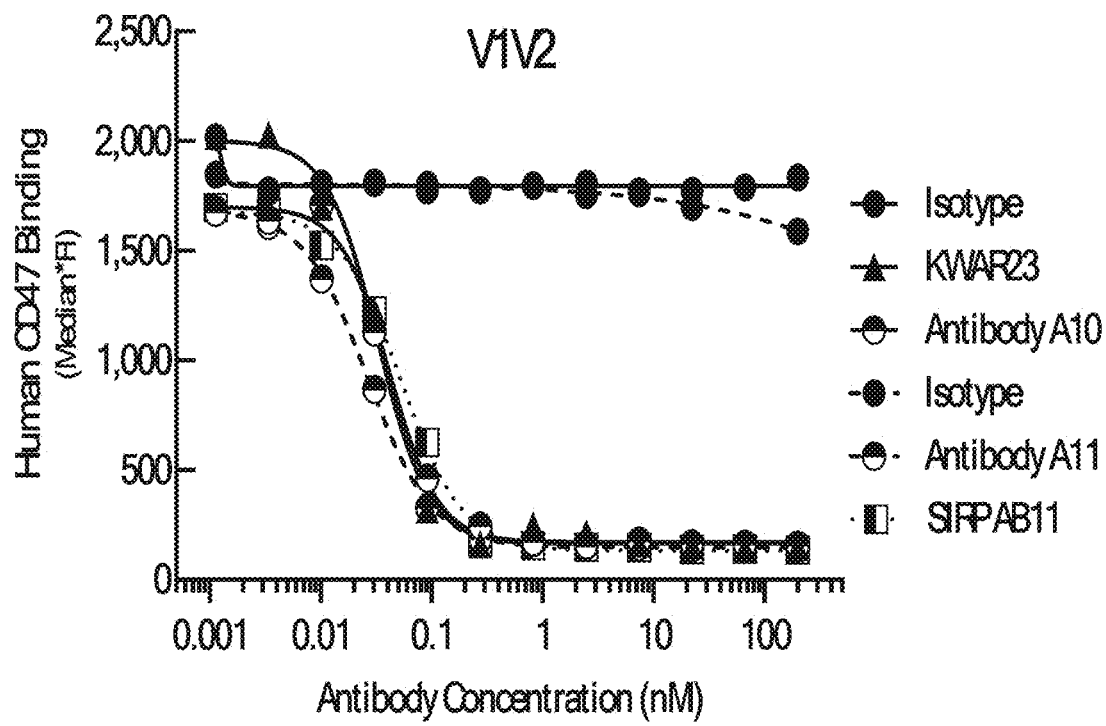

Known KWAR23 antibody and antibodies A-E dose-dependently blocked human CD47 binding to human SIRPαV1 and SIRPαV2-expressing CHO cells (FIGS. 11A and 11B) with half maximal inhibitory concentration ($IC_{50}$) values ranging between 0.3-6.0 nM (Table 48). Blockade of human CD47 binding to human SIRPαV2-expressing CHO cells by antibody E plateaued at about 80%.

TABLE 48

$IC_{50}$ of Anti-SIRPα antibodies

| | Blockade of Human CD47 Binding; $IC_{50}$ (nM) | |
|---|---|---|
| Antibody | CHO-hSIRPαV1 | CHO-hSIRPαV2 |
| Isotype | NB | NB |
| KWAR23 | 0.9 | 0.6 |
| Antibody A | 0.6 | 0.3 |
| Antibody B | 5.6 | 6.0 |
| Antibody C | 0.7 | 0.3 |
| Antibody D | 0.6 | 0.3 |
| Antibody E | 0.7 | 0.7* |

NB No blockade
*Inhibition plateaus at <100%

Example 12. Blocking of Human CD47 Binding to Endogenous Human V1-SIRPα and/or V2-SIRPα Expressed on Primary Human Monocytes Human CD47 tetramers are assembled using biotinylated human CD47 (NP_942088; AcroBiosystems) and AF647-conjugated streptavidin (Biolegend). Human peripheral blood mononuclear cells (PBMCs) from donors genotyped as homozygous for the SIRPα V1 allele, V2 allele, or heterozygous for both alleles are blocked with Human TruStain FcX™ (Biolegend) and co-incubated with increasing concentrations of antibody, a fixed concentration of human CD47 tetramer and BV421-conjugated anti-human CD14 on ice for 60 min. Cells are washed, fixed, and analyzed by flow cytometry. Median fluorescent intensity of CD14+ gated population is determined and used as a measure of CD47 binding.

Antibodies A-G, A10, A4, E22, and A11, but not isotype control, dose-dependently blocked human CD47 binding to primary human monocytes from donors homozygous for V1 (FIGS. 12A-12D) or V2 (FIGS. 14A-14D) alleles or heterozygous for both alleles (FIGS. 13A-13D). Aside from Antibody B, all antibodies exhibited $IC_{50}$ values less than 1 nM (Table 49).

Figure 14A:
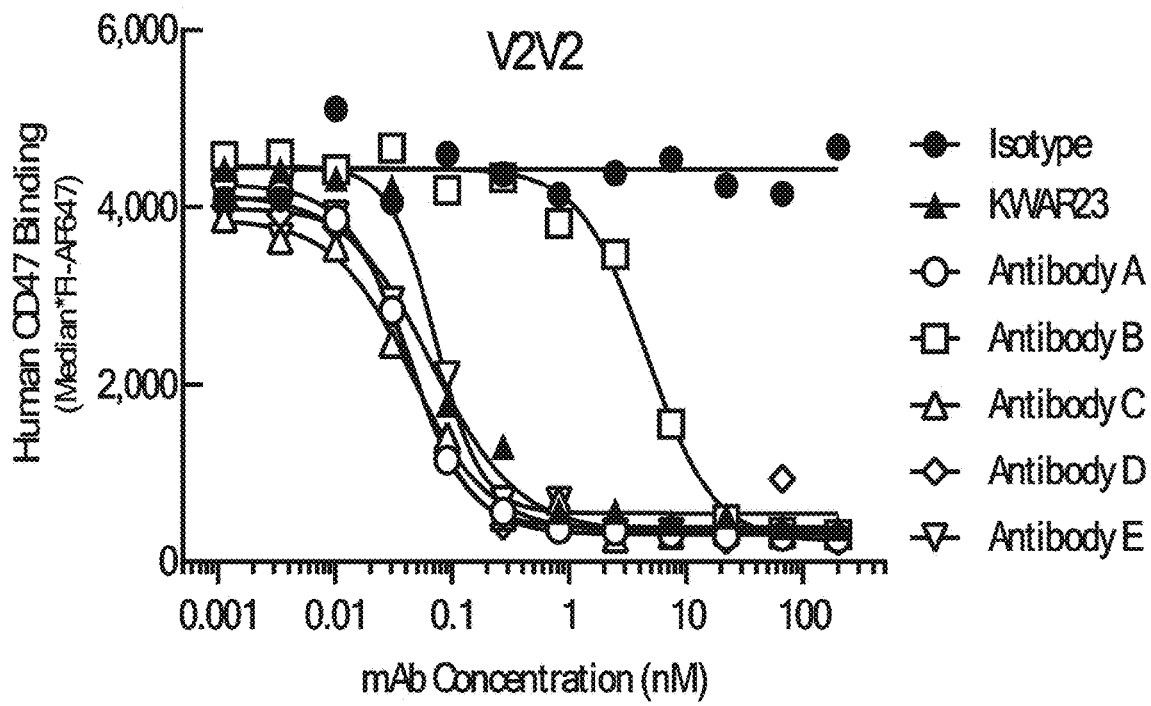
FIGS. 14A-14D are series of graphs depicting the blocking of human CD47 binding to SIRPα expressed on primary cells. Antibodies block human CD47 binding to primary human CD14+ monocytes from donors homozygous for V2 alleles. Solid, dashed, and dotted lines indicate antibody molecules engineered on hIgG1 (LALA), hIgG4P, hIgG1 (K322A) backbones, respectively.
Figure 14B:
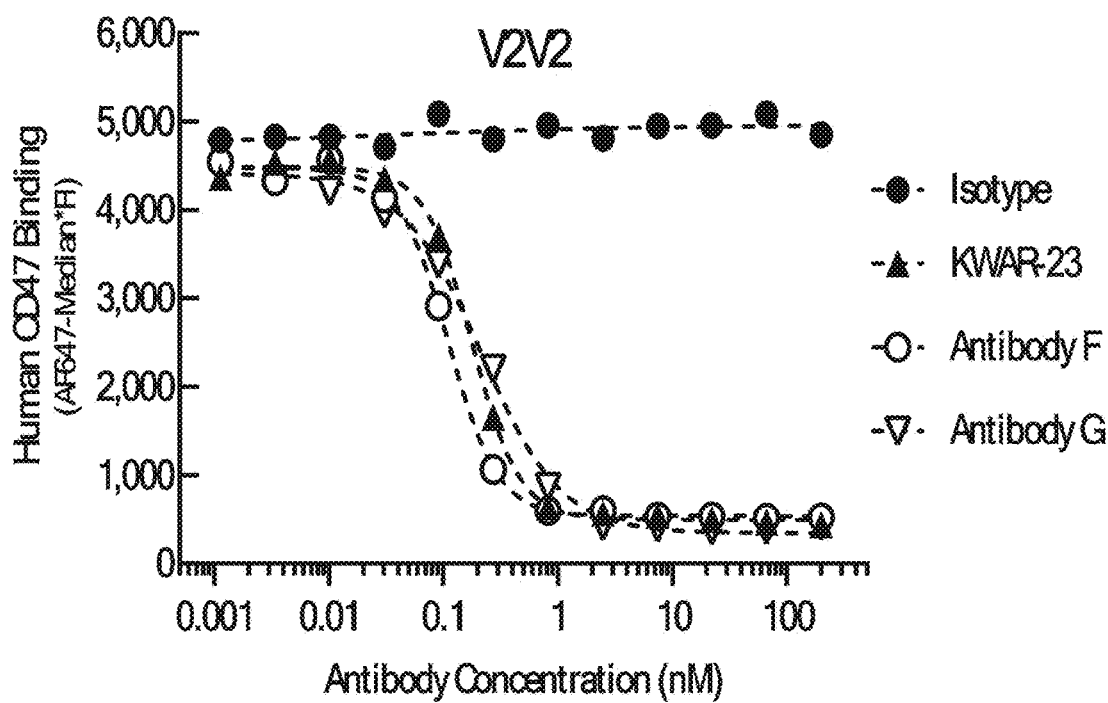
Figure 14C:
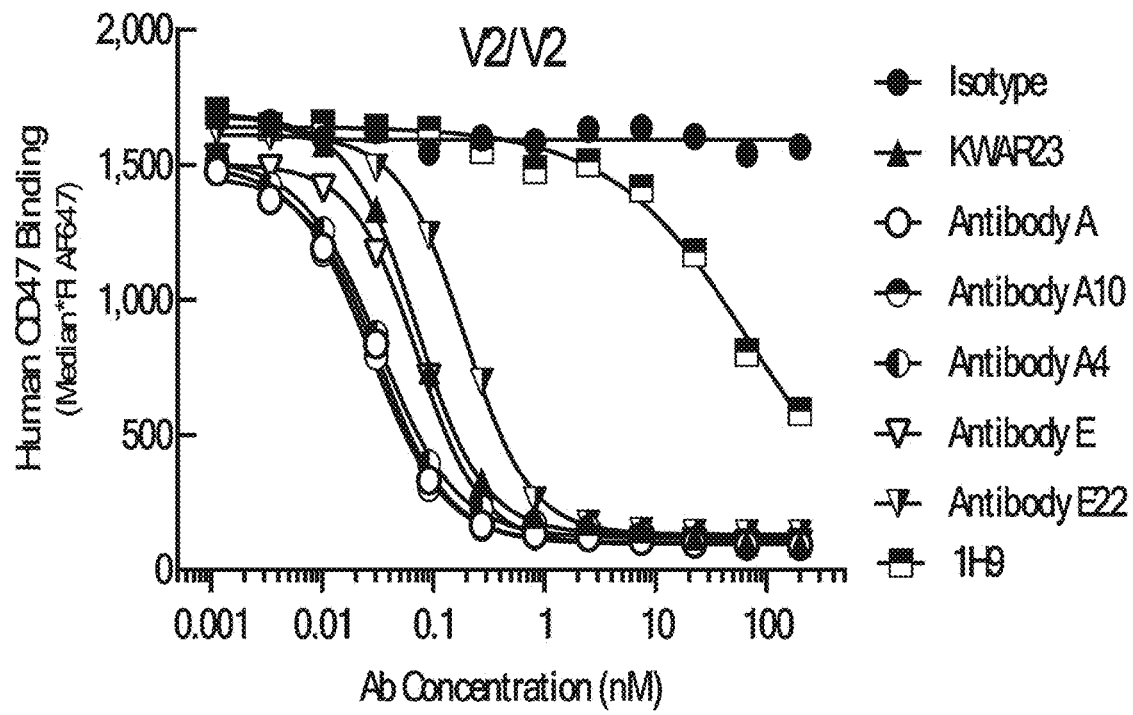
Figure 14D:
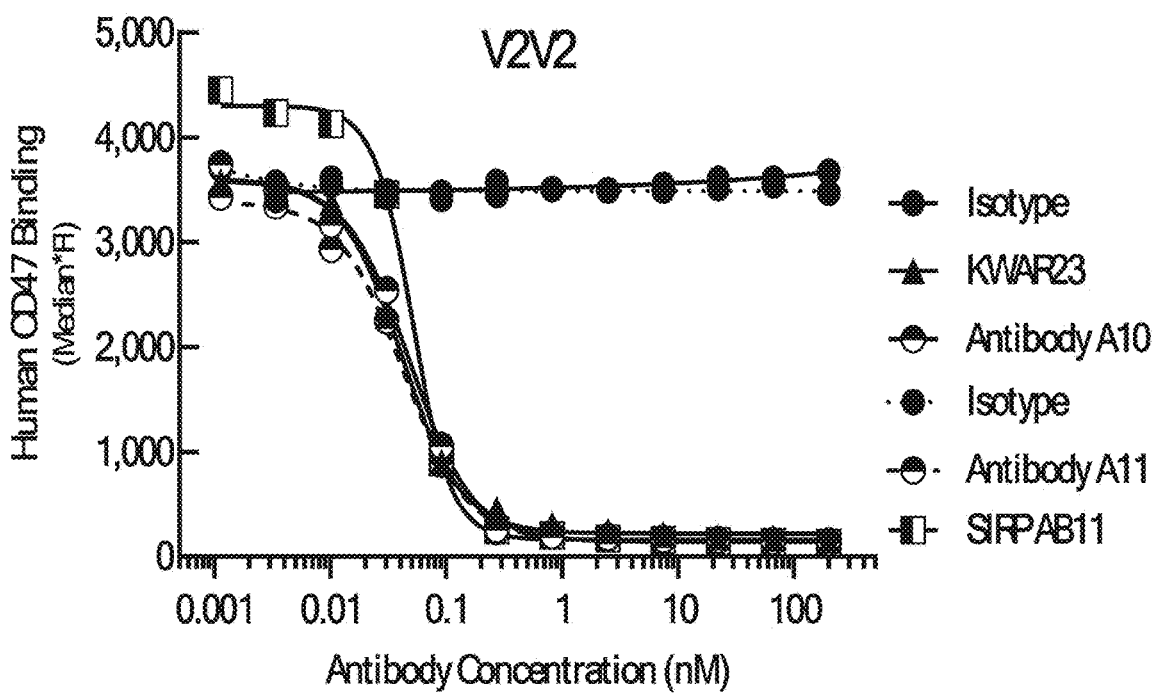
Figure 15A:
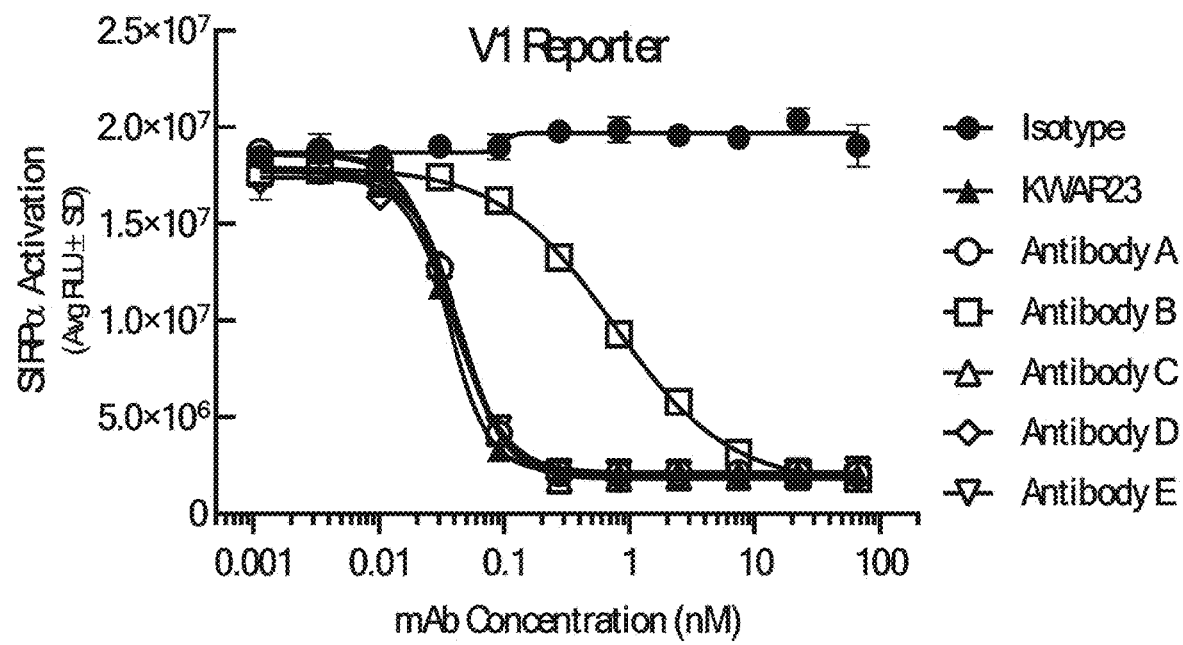
FIGS. 15A-15D are series of graphs showing that the cellular CD47-mediated SIRPα activation blocked by anti-SIRPα antibodies. Antibodies dose-dependently block cellular CD47-mediated V1-SIRPα signaling (FIGS. 15A-15D). Solid, dashed, and dotted lines indicate antibody molecules engineered on hIgG1 (LALA), hIgG4P, hIgG1 (K322A) backbones, respectively.
Figure 15B:
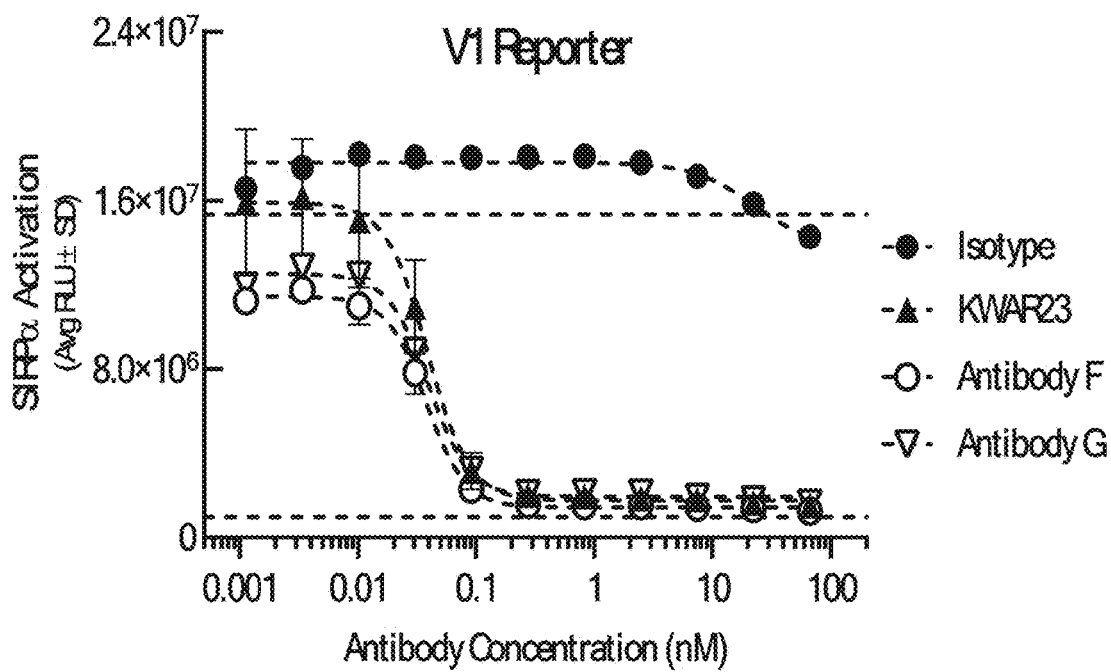
Figure 15C:
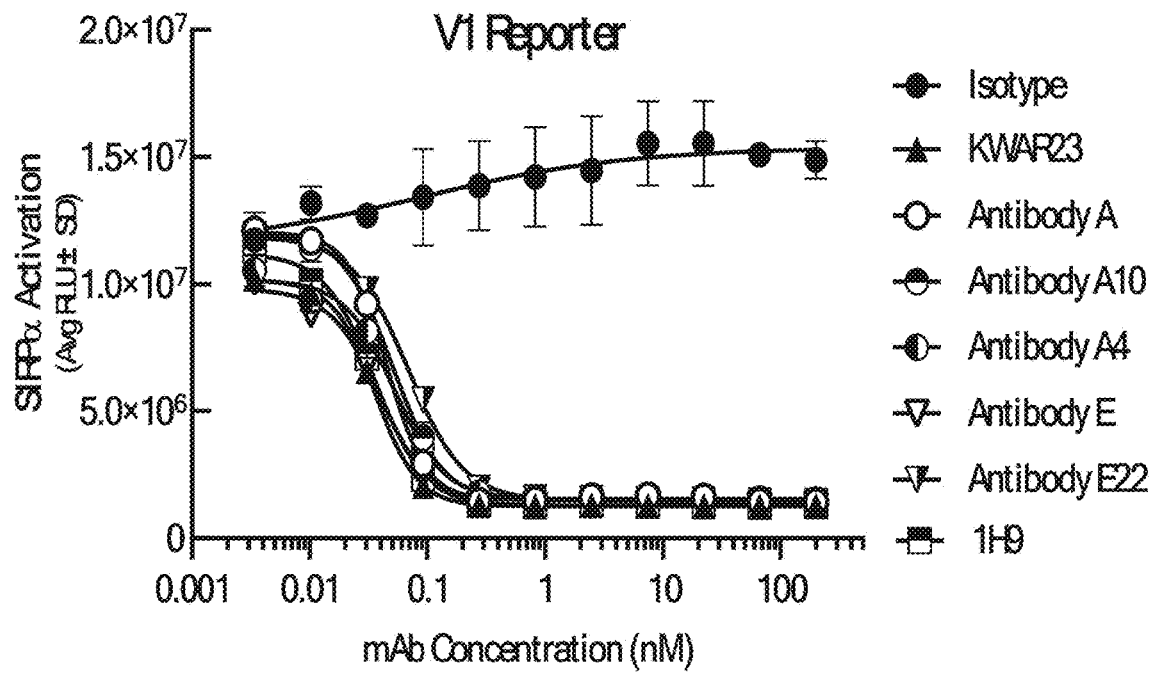
Figure 15D:
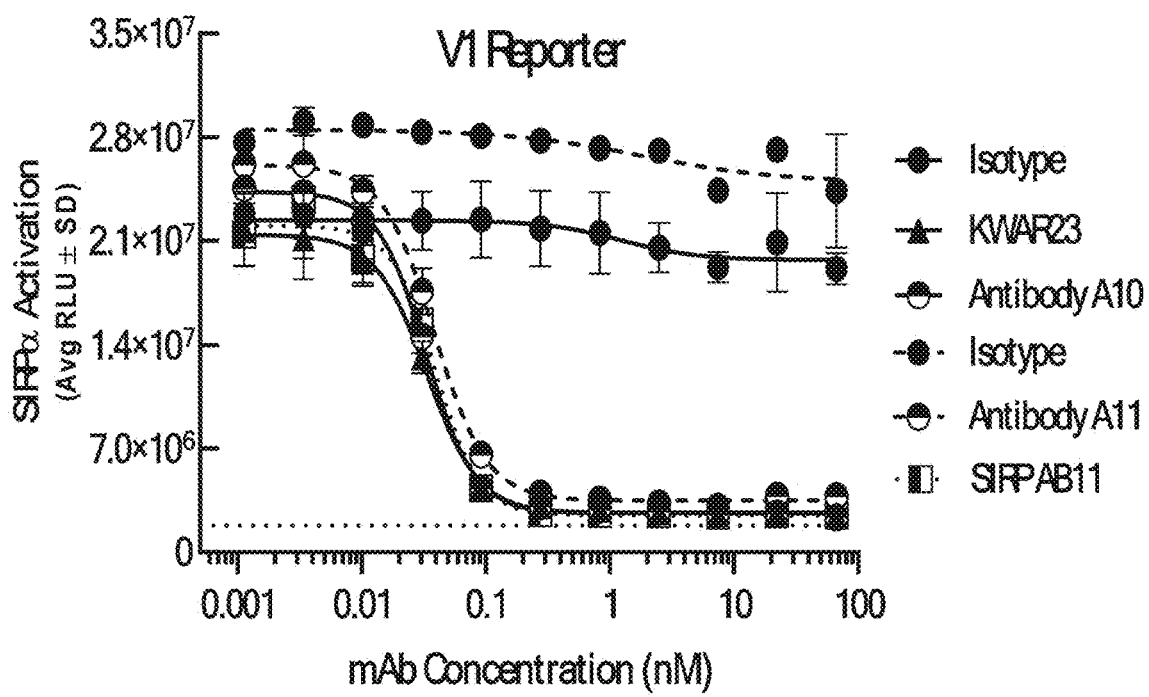
Figure 16A:
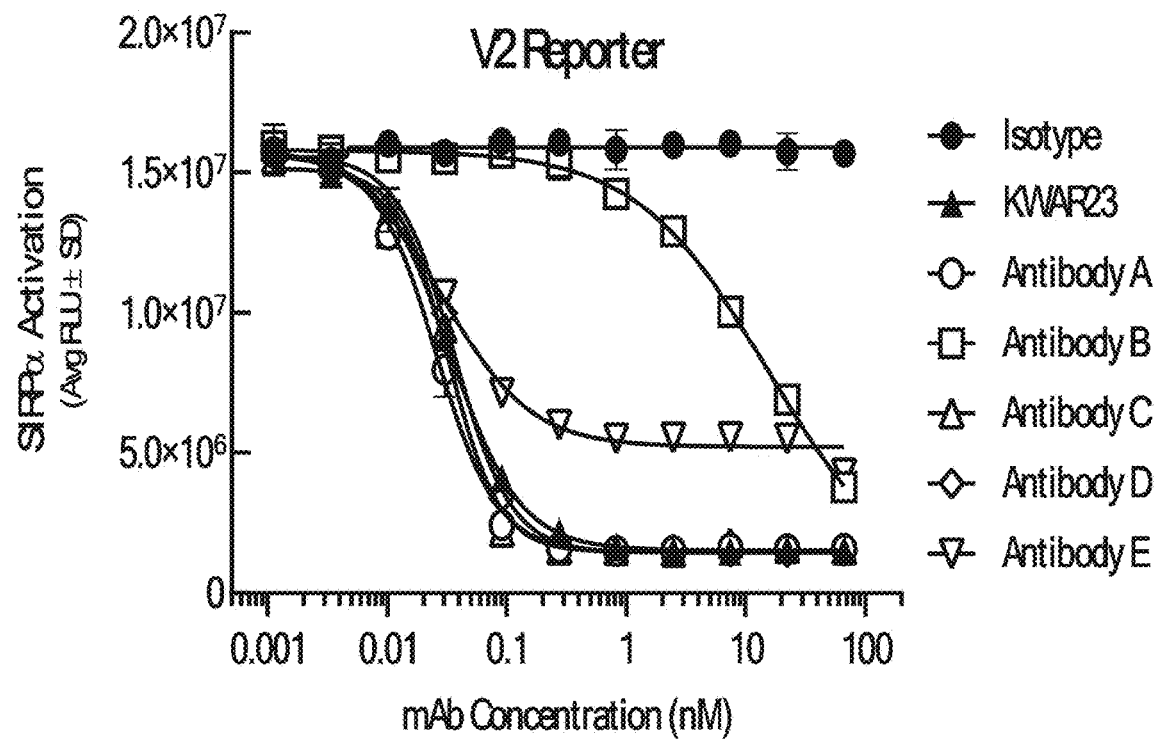
FIGS. 16A-16D are series of graphs showing that the cellular CD47-mediated SIRPα activation blocked by anti-SIRPα antibodies. Antibodies dose-dependently block cellular CD47-mediated V2-SIRPα signaling (FIGS. 16A-
Figure 16B:
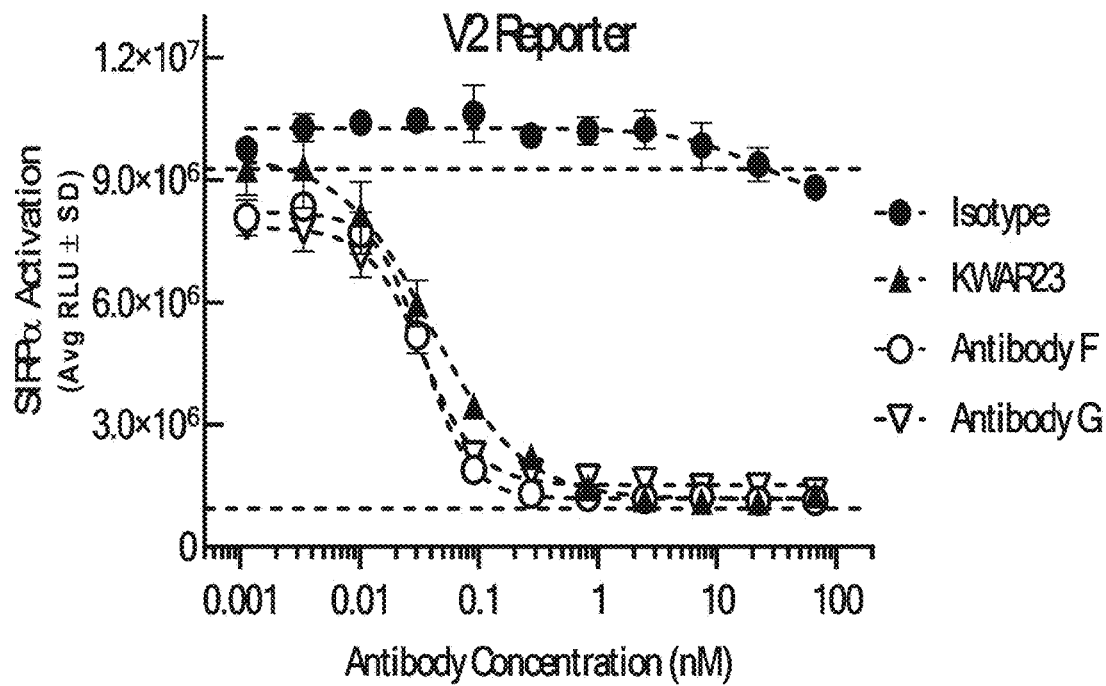
Figure 16C:
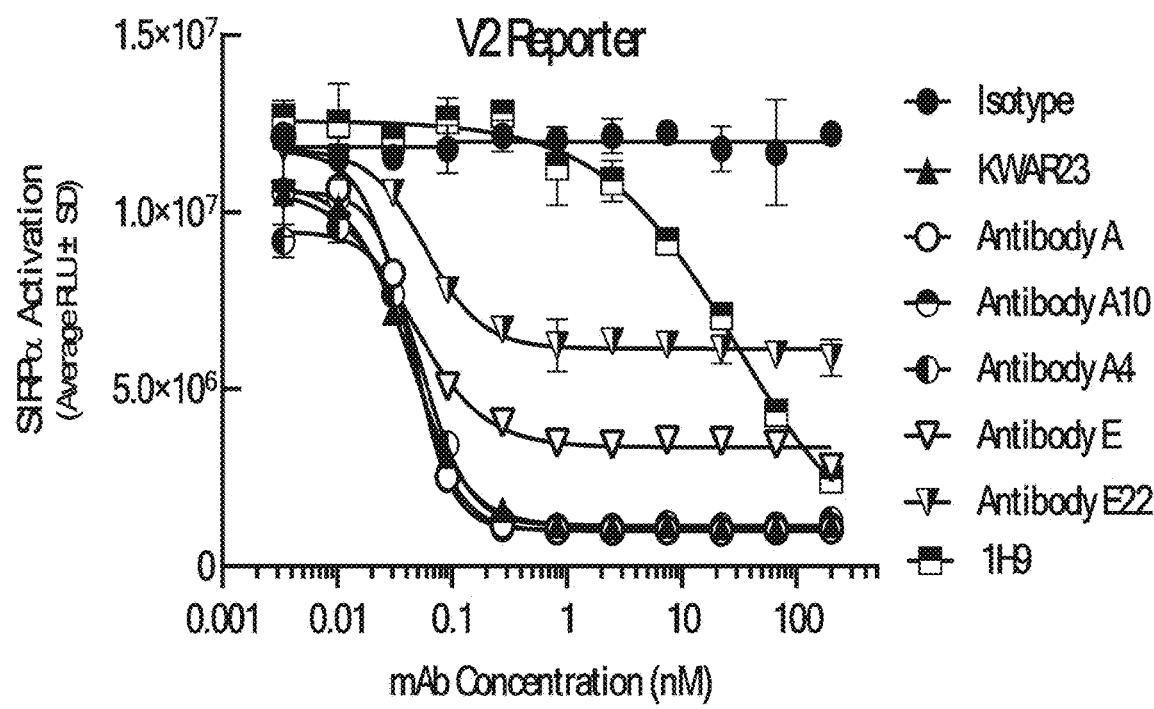
Figure 16D:
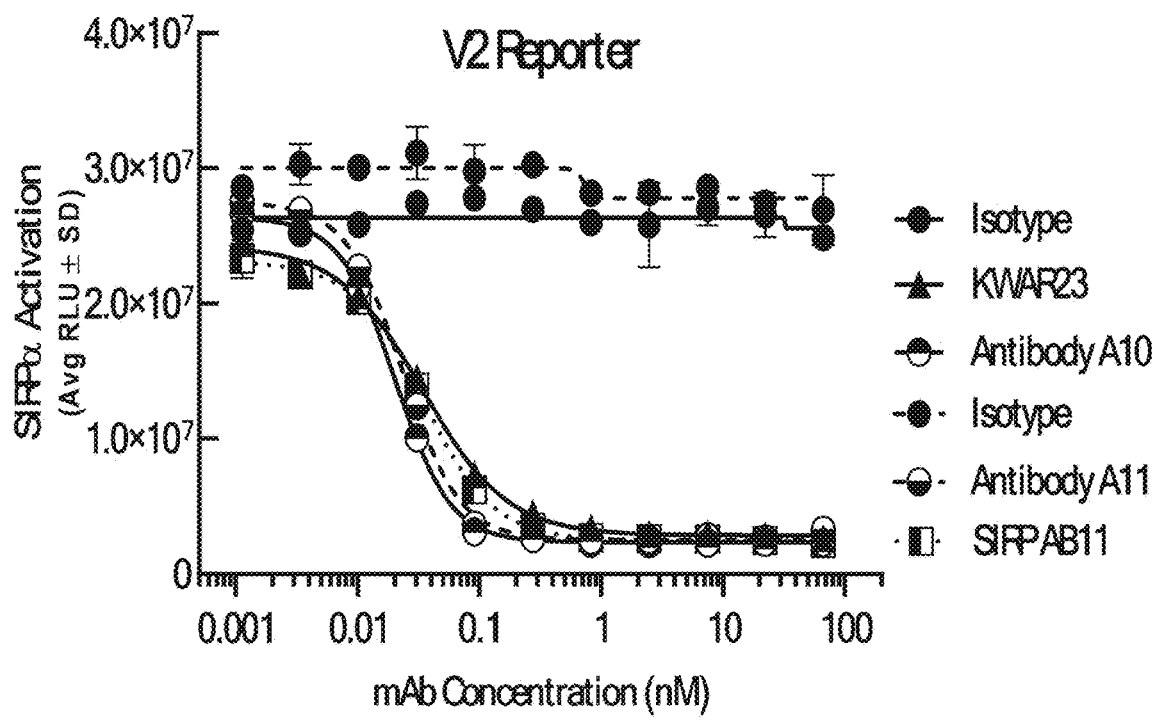

The ability of known anti-SIRPα antibodies, KWAR23, 1H9 and SIRPAB11, to block human CD47 binding to primary human monocytes is assessed as described above. While 1H9 blocked human CD47 from binding to primary human monocytes from donors homozygous for V1 alleles (FIG. 12C) or heterozygous for both alleles (FIG. 13C) with subnanomolar $IC_{50}$ values (Table 49), incomplete blockade to primary human monocytes from donors homozygous for V2 alleles was observed (FIG. 14C). KWAR23 and SIRPAB11 antibodies blocked human CD47 binding to primary human monocytes from donors of all genotypes (FIGS. 12A-12D, 13A-13D and 14A-14D; Table 49).

TABLE 49

IC$_{50}$ of Anti-SIRPα antibodies

| Antibody | Blockade of Human CD47 Binding; IC$_{50}$, nM ± SD (n) | | |
|---|---|---|---|
| | V1V1 | V1V2 | V2V2 |
| Isotype | NB (n = 6) | NB (n = 6) | NB (n = 6) |
| KWAR23 | 0.07 ± 0.04 (n = 6) | 0.10 ± 0.06 (n = 6) | 0.11 ± 0.06 (n = 6) |
| Antibody A | 0.06 ± 0.03 (n = 5) | 0.07 ± 0.05 (n = 5) | 0.06 ± 0.03 (n = 5) |
| Antibody B | 2.55 (n = 1) | 2.77 (n = 1) | 4.60 (n = 1) |
| Antibody C | 0.04 (n = 1) | 0.04 (n = 1) | 0.05 (n = 1) |
| Antibody D | 0.03 (n = 1) | 0.04 (n = 1) | 0.05 (n = 1) |
| Antibody E | 0.09 ± 0.03 (n = 5) | 0.10 ± 0.04 (n = 5) | 0.11 ± 0.04 (n = 5) |
| Antibody F | 0.07 (n = 1) | 0.07 (n = 1) | 0.11 (n = 1) |
| Antibody G | 0.11 (n = 1) | 0.11 (n = 1) | 0.22 (n = 1) |
| Antibody A10 | 0.05 ± 0.01 (n = 4) | 0.07 ± 0.08 (n = 4) | 0.05 ± 0.02 (n = 4) |
| Antibody A4 | 0.04 ± 0.01 (n = 3) | 0.05 ± 0.04 (n = 3) | 0.07 ± 0.04 (n = 3) |
| Antibody E22 | 0.25 ± 0.10 (n = 3) | 0.36 ± 0.21 (n = 3) | 0.30 ± 0.10 (n = 3) |
| Antibody A11 | 0.03 (n = 1) | 0.03 (n = 1) | 0.05 (n = 1) |
| 1H9 | 0.04 (n = 1) | 0.15 (n = 1) | NS (n = 1) |
| SIRPAB11 | 0.02 (n = 1) | 0.05 (n = 1) | 0.05 (n = 1) |

NB No Blockade
NS Non-saturable inhibition

Example 13. Blocking Human V1-SIRPα and V2-SIRPα Signaling Dependent on Cellular CD47 Expression A SIRPα signaling assay is used to measure SIRPα engagement induced by CD47 presented via cell-cell interaction. Detection of SIRPα signaling in this assay relies on enzyme fragment complementation (EFC). EFC uses a complementation system in β-galactosidase, which consists of the enzyme donor (ED) and the enzyme acceptor (EA) fragments. Independently, these fragments have no β-gal enzymatic activity; however, when brought into proximity they form an active β-gal enzyme. The reporter Jurkat cells are devoid of CD47 and stably co-express an ED-tagged SIRPα receptor and EA-tagged SH2 domain of the SHP-1 phosphatase. When the reporter cells are exposed to donor cells (Jurkat cells expressing endogenous levels of CD47), SIRPα is phosphorylated and recruits SHP-1 phosphatase. This interaction forces ED and EA fragments complementation and formation of active β-gal enzyme that is capable of hydrolyzing substrate to generate a chemiluminescent signal as a measure of receptor activation.

Jurkat SIRPα-V1 or -αV2 signaling cells (20,000) are incubated with serially titrated antibodies in 96-well white-bottom TC treated plates for 1 h at 37° C., 5% CO$_2$ prior to the addition of Jurkat$^{Parental}$ cells (30,000) in a total volume of 100 µl in PathHunter cell plating 0 reagent. Plates are incubated in a humidified incubator for 5 hours at 37° C., 5% CO$_2$. Following the addition of PathHunter BioAssay Detection Reagents and incubation at room temperature in the dark, the plates are read on an EnVision® luminometer. Average RLU units are plotted as a measure of receptor activation.

Antibodies A-G, A10, A4, E22, and A11, but not isotype control, completely blocked cellular CD47-mediated SIRPαV1 activation (FIGS. 15A-15D) with subnanomolar IC$_{50}$ values (Table 48). Similarly, all antibodies dose-dependently blocked cellular CD47-mediated SIRPαV2 activation (FIGS. 16A-16D; Table 50), though inhibition by antibodies E and E22 plateaued at about 80% and 55%, respectively and antibody B did not achieve saturable inhibition.

The ability of known SIRPα antibodies, KWAR23, 1H9 and SIRPAB11, to block cellular CD47-mediated SIRPα signaling is assessed as described above. While 1H9 completely blocked cellular CD47-mediated SIRPαV1 activation with an IC$_{50}$ of 0.04 nM (FIG. 15C; Table 50), blockade of cellular CD47-mediated SIRPαV2 activation did not achieve saturable inhibition (FIG. 16C; Table 50). KWAR23 and SIRP AB11 antibodies were capable of blocking cellular CD47-mediated SIRPα signaling of by cells expressing either SIRPα allele.

TABLE 50

IC$_{50}$ of Anti-SIRPα antibodies

| Antibody | Blockade of Cellular CD47-Mediated SIRPα Signaling; IC$_{50}$, nM ± SD (n) | |
|---|---|---|
| | V1V1 | V2V2 |
| Isotype | NB (n = 6) | NB (n = 6) |
| KWAR23 | 0.04 ± 0.01 (n = 6) | 0.04 ± 0.01 (n = 6) |
| Antibody A | 0.04 ± 0.01 (n = 5) | 0.04 ± 0.01 (n = 5) |
| Antibody B | 0.76 (n = 1) | NS (n = 6) |
| Antibody C | 0.04 (n = 1) | 0.03 (n = 1) |
| Antibody D | 0.04 (n = 1) | 0.04 (n = 1) |
| Antibody E | 0.04 ± 0.01 (n = 5) | 0.04 ± 0.01 (n = 5)* |
| Antibody F | 0.04 (n = 1) | 0.03 (n = 1) |
| Antibody G | 0.04 (n = 1) | 0.03 (n = 1) |
| Antibody A10 | 0.04 ± 0.01 (n = 4) | 0.04 ± 0.01 (n = 4) |
| Antibody A4 | 0.04 ± 0.01 (n = 3) | 0.05 ± 0.01 (n = 3) |
| Antibody E22 | 0.07 ± 0.01 (n = 3) | 0.07 ± 0.01 (n = 3)* |
| Antibody A11 | 0.04 (n = 1) | 0.02 (n = 1) |
| 1H9 | 0.04 (n = 1) | NS (n = 1) |
| SIRPAB11 | 0.04 (n = 1) | 0.03 (n = 1) |

NB No Blockade
NS Non-saturable inhibition
*Inhibition plateaus at <100%

Example 14. SIRPα Antagonist Revert Inhibition of Phagocytosis Caused by CD47 in Human Monocytic Cell Lines A flow-based phagocytosis assay was developed to quantify the SIRPα-mediated regulation of phagocytosis induced by CD47. U-937 cells devoid of endogenous SIRPα are transduced with lentivirus containing full-length V1- or V2-SIRPα alleles. These cells are preincubated with anti-SIRPα antibodies at the indicated concentrations in 96-well V-bottom tissue culture (TC)-treated plates for 30 minutes prior to the addition of fluorescently conjugated microbeads (Spherotech) coated with or without human CD47 (NP_942088; AcroBiosystems) and opsonized with human IgG1 antibodies to induce Fc-receptor mediated phagocytosis. Following a 2 h incubation at 37° C., 5% CO$_2$, samples are washed, blocked with Human TruStain FcX™ (Biolegend) and stained with fluorescently-conjugated antibody that recognize the external surface of the beads to enable differentiation between beads stuck on the outside of the cells and those that were inside. Cells are washed, fixed, and analyzed by flow cytometry. Phagocytosis is represented as the percentage of cells with internalized beads.

Internalization of opsonized beads by U-937 cells expressing SIRPα for either V1 or V2 alleles dropped when cells were incubated with CD47-coated beads (white bars); an effect not observed when cells were incubated with beads lacking CD47 (black bars). Pre-treatment of cells with 67 nM of the indicated antibodies restored both V1—(FIG. 17A) and V2-(FIG. 17B) SIRPα-expressing U-937 cell's ability to phagocytize CD47-coated beads (white bars) indicating that the antibodies can block CD47-mediated SIRPα signaling.

Example 15. SIRPα Antagonist Revert Inhibition of Phagocytosis Caused by CD47 in Primary Human Monocyte-Derived Macrophages of any Combination of SIRPα Alleles A flow-based phagocytosis assay was developed to quantify the SIRPα-mediated regulation of phagocytosis induced by CD47. Monocytes enriched from human PBMCs (Easy-Sep Monocyte Enrichment Kit, StemCell Technologies) from donors genotyped as homozygous for the SIRPα V1 allele, V2 allele, or heterozygous for both alleles are differentiated into macrophages following 6-7 days of culture in ImmunoCult™-SF macrophage differentiation medium spiked with 50 ng/ml human recombinant M-CSF (Peprotech). Monocyte-derived macrophages (MDMs) are preincubated with anti-SIRPα antibodies at the indicated concentrations in 96-well ultra-low attachment TC plates for 30 minutes prior to the addition of fluorescently conjugated microbeads (Spherotech) coated with or without human CD47 (NP_942088; AcroBiosystems) and with or without human IgG1 opsonization to induce Fc-receptor mediated phagocytosis. Following a 1 h incubation at 37° C., 5% $CO_2$, samples are washed, blocked with Human TruStain FcX™ (Biolegend) and stained with fluorescently-conjugated antibody that recognize the external surface of the beads to enable differentiation between beads stuck on the outside of the cells and those that were inside. Cells are washed, fixed, and analyzed by flow cytometry. Phagocytosis is represented as the percentage of cells with internalized beads.

Internalization of beads (with or without opsonization) by MDMs from donors homozygous for V1 or V2 alleles (FIGS. 18A-18B and 20A-20B, respectively) or heterozygous for both alleles (FIGS. 19A-19B) dropped when cells were incubated with CD47-coated beads (white bars); an effect not observed when cells were incubated with beads lacking CD47 (black bars). Pre-treatment of cells with 67 nM of the indicated antibodies restored the cells' ability to phagocytize CD47-coated beads (white bars) with (FIGS. 18A, 19A, and 20A) and without (FIGS. 18B, 19B, and 20B) opsonization indicating that the antibodies can block CD47-mediated SIRPα signaling. Further experiments showed that anti-SIRPα antibodies could restore CD47-mediated inhibition of phagocytosis by primary MDMs derived from donors of all genotypes in a dose-dependent manner (FIGS. 18C, 19C, and 20C).

Example 16. SIRPα Antagonist Revert Inhibition of Phagocytosis Caused by CD47 in Primary Human Monocyte-Derived Dendritic Cells of any Combination of SIRPα Alleles A flow-based phagocytosis assay was developed to quantify the SIRPα-mediated regulation of phagocytosis induced by CD47. Monocytes enriched from human PBMCs (Easy-Sep™ Monocyte Enrichment Kit, StemCell Technologies) from donors genotyped as homozygous for the SIRPα V1 allele, V2 allele, or heterozygous for both alleles are differentiated into dendritic cells following 5-6 day of culture in ImmunoCult™-ACF Dendritic Cell Medium spiked with ImmunoCult™-ACF Dendritic Cell Differentiation Supplement. Monocyte-derived dendritic cells (MDDCs) are pre-incubated with anti-SIRPα antibodies at the indicated concentrations in 96-well ultra-low attachment TC plates for 30 minutes prior to the addition of fluorescently conjugated microbeads (Spherotech) coated with or without human CD47 (NP_942088; AcroBiosystems) and with or without human IgG1 opsonization to induce Fc-receptor mediated phagocytosis. Following a 1 h incubation at 37° C., 5% $CO_2$, samples are washed, blocked with Human TruStain FcX™ (Biolegend) and stained with fluorescently-conjugated antibody that recognize the beads to enable differentiation between beads stuck on the outside of the cells and those that were inside. Cells are washed, fixed, and analyzed by flow cytometry. Phagocytosis is represented as the percentage of cells with internalized beads.

Internalization of beads (with or without opsonization) by MDDCs from donors homozygous for V1 or V2 alleles (FIGS. 21A-21B and 23A-23B, respectively) or heterozygous for both alleles (FIGS. 22A-22B) dropped when cells were incubated with CD47-coated beads (white bars); an effect not observed when cells were incubated with beads lacking CD47 (black bars). Pre-treatment of cells with 67 nM of the indicated antibodies restored the cells' ability to phagocytize CD47-coated beads (white bars) with (FIGS. 21A, 22A, and 23A) and without (FIGS. 21B, 22B, and 23B) opsonization indicating that the antibodies can block CD47-mediated SIRPα signaling.

Example 17. Anti-SIRPα Antibodies Potentiate U-937 Phagocytosis of Human Tumor Cells The functional activity of select molecules were evaluated in an antibody-dependent cellular phagocytosis assay. Raji cells (Burkitt's lymphoma cell line; ATCC), are labeled with PKH26 Red (Sigma) according to manufacturer's instructions and subsequently opsonized with Rituximab. Raji cells are washed to remove unbound Rituximab. V1- or V2-SIRPα-expressing U-937 cells (50,000) are treated with serially titrated anti-SIRPα mAb in 96-well ultra-low attachment TC plates for 30 minutes prior to the addition of 50,000 Raji target cells (±Rituximab opsonization). Following a 2 h incubation in a humidified incubator at 37° C., 5% $CO_2$, samples are washed, blocked with Human TruStain FcX™ (Biolegend) and stained with PB-conjugated anti-human CD13 (U-937 marker; clone WM15; BD Biosciences) and AF647-conjugated anti-human CD19 (Raji marker; clone HIB19; Biolegend) cocktail. Cells are washed, fixed, and analyzed by flow cytometry. Phagocytosis is represented as the percentage of CD13+ cells that stained negative for CD19 and positive for PKH26.

The results showed that V1- and V2-SIRPα-expressing U-937 cells were incapable of phagocytizing Raji cells devoid of Rituximab opsonization. Opsonization of Raji cells induced an increase in cellular phagocytosis (about 0.2% to about 6%), which was further enhanced, in a dose-dependent manner, by treatment with anti-SIRPα antibodies.

Example 18. Anti-SIRPα Antibodies Potentiate Monocyte-Derived Macrophage Phagocytosis of Human Tumor Cells The functional activity of select molecules were evaluated in an antibody-dependent cellular phagocytosis assay. Raji cells (Burkitt's lymphoma cell line; ATCC), are labeled with PKH26 Red (Sigma) according to manufacturer's instructions and subsequently opsonized with Rituximab. Raji cells are washed to remove unbound Rituximab. Monocytes enriched from human PBMCs (EasySep™ Monocyte Enrichment Kit, StemCell Technologies) from donors genotyped as homozygous for the SIRPα V1 allele, are differentiated into macrophages following 6-7 days in culture in ImmunoCult™-SF macrophage differentiation medium spiked with 50 ng/ml human recombinant M-CSF (Peprotech). Monocyte-derived macrophages (MDMs) are treated with serially titrated anti-SIRPα mAb in 96-well ultra-low attachment U-bottom plates for 30 minutes prior to the addition of 50,000 Raji target cells (±Rituximab opsonization). Following a 2 h incubation at 37° C., 5% $CO_2$, samples are washed, blocked with Human TruStain FcX™ (Biolegend) and stained with BV421-conjugated anti-human CD14 (MDM marker; clone M5E2; Biolegend) and AF647-conjugated anti-human CD19 (Raji marker; clone HIB19; Biolegend) cocktail. Cells are washed, fixed, and analyzed by flow cytometry. Phagocytosis is represented as the percentage of CD13+ cells that stained negative for CD19 and positive for PKH26.

The results showed that MDMs were incapable of phagocytizing Raji cells devoid of opsonization regardless of cell treatment. Opsonization of Raji cells induced an increase in cellular phagocytosis (about 1.3 to about 17%), which was further enhanced by anti-SIRPα antibody treatment.

Example 19. Mixed Lymphocyte Reaction

Selected molecules are evaluated in a mixed lymphocyte reaction. 96-well round bottom tissue culture treated plates were coated with recombinant human CD47 extracellular domain (ECD)/hFc protein diluted in DPBS and incubated overnight at 4° C. Plates are washed 3× in DPBS/CF. Cryopreserved human monocyte-derived dendritic cells (Astarte Biologics) are thawed, washed and resuspended at 0.1 million/ml in X-VIVO 15 media. MDDCs are then pre-incubated with various anti-SIRPα mAb together with or without anti-PD1 antagonist at a 1:1 volume ratio for 60 minutes prior to transferring MDDC±mAb treatment to respective wells of a 96-well round bottom TC plate previously coated with or without human CD47 fusion protein. Human CD4+ T cells (about 100,000), enriched from allogeneic human PBMC donors (EasySep™ Human CD4+ T Cell Isolation Kit) are added to respective wells and plates are incubated in a humidified incubator at 37° C., 5% $CO_2$ for 5 days. Sixteen to eighteen hours prior to harvest, culture wells are pulsed with 1 μCi (10 μl at 100 μCi/ml) of $^3$[H]thymidine (Moravek Biochemicals Inc.). Cells are subsequently harvested onto filter mats (Wallac) using the Molecular Devices Micro96 Harvester, dried, and then sealed in sample bags (Perkin Elmer) with 10 ml of Beta-Plate Scintillation (Perkin-Elmer, cat #1205-440). $^3$[H]Thymidine incorporation is measured using a MicroBeta2 2450 Microplate Counter (Perkin Elmer).

FIGS. 24A-24B show that platebound human CD47 fusion protein inhibited CD4 T cell proliferation mediated by dendritic cells in Mixed Lymphocyte Reaction, demonstrating that CD47-mediated signaling can be highly immune-suppressive. CD47-Fc mediated immunosuppression in these assays can be reverted to various degrees by anti-SIRPα antibodies (KWAR23, antibody A and E) alone or in combination with anti-PD1 antagonist.

Example 20. Crystallization of Anti-SIRPα Fab:SIRPα Complexes

To understand the mechanistic bases for antibody binding to SIRPα, an analysis was performed on the structure of the antibody-SIRPα complexes for Antibody E and Antibody A in complex with domain 1 of human SIRPα-V2 (FIGS. 25A-25F and FIGS. 26A-26B).

In order to obtain complex structures we generated a construct for expression of SIRPαV2 (Amino acids 31-148, comprising an N-terminal GST tag) using the Gateway cloning system. Protein was expressed in Origami B(DE3) cells and purified using standard protocols for GST-tagged proteins. Fractions were analyzed by SDS-PAGE and fractions containing the desired protein were pooled and concentrated to 24 mg/ml in 25 mM HEPES; 100 mM NaCl; 5% Glycerin; pH 7.0. SIRPαV2 protein was mixed with Fab fragments of Antibody A or E and purified by size-exclusion chromatography in 10 mM Tris; 150 mM NaCl; 1 mM TCEP; pH 7.5. Crystals of SIRPαV2 Fab complexes were obtained by vapor diffusion sitting drop method at a complex concentration of 5 mg/ml (reservoir solution: Antibody A: 20% PEG3350 and 180 mM tri-Ammonium citrate and Antibody E: 15% PEG 4000 and 100 mM HEPES, pH 7.0). Data was collected at the Swiss Light Source (SLS) and the structures were solved and modelled at resolutions of 1.4 Å (Antibody A) and 1.6 Å (Antibody E).

The crystal structure analysis demonstrated that the two antibodies can contact SIRPα on different areas and in different orientations. While both antibodies obstruct the CD47-binding site on SIRPα, Antibody A can contact most of the SIRPα residues that are engaged by CD47 indicating how this antibody can achieve complete CD47 antagonism. The SIRPα residues contacted by these antibodies explained how both alleles of SIRPα can be bound equally without detrimental effects by the variant residues between the alleles. The contact points also explain the selectivity against SIRPγ (FIGS. 25A-25F and FIGS. 26A-26B and Tables 51-52).

TABLE 51

Epitope, contact points on SIRPα-V2 and Antibody A

| Residues on SIRPα V2 that contact Antibody A | Residues on the Heavy Chain that contact SIRPα V2 | Residues on the Light Chain that contact SIRPα V2 |
| --- | --- | --- |
| LEU 60 | H-SER 31 | L-ASP 28 |
| ILE 61 | H-TYR 32 | L-ASN 30 |
| VAL 63 | H-ASP 33 | L-ASN 31 |
| GLY 64 | H-THR 53 | L-TYR 32 |
| PRO 65 | H-ARG 97 | L-TYR 49 |
| GLN 82 | H-GLY 98 | L-THR 50 |
| LYS 83 | H-GLY 99 | L-TYR 91 |
| GLU 84 | H-VAL 100 | L-VAL 92 |
| THR 97 | H-TRP 101 | L-TYR 96 |
| LYS 98 | H-ASP 102 | |
| ARG 99 | H-ASP 103 | |
| GLU 100 | | |
| (ASN 100 in V1) | | |
| LYS 126 | | |
| GLY 127 | | |
| SER 128 | | |
| PRO 129 | | |
| ASP 130 | | |

TABLE 52

Epitope, contact points on SIRPα-V2 and Antibody E

| Residues on SIRPα V2 that contact Antibody E | Residues on the Heavy Chain that contact SIRPα V2 | Residues on the Light Chain that contact SIRPα V2 |
| --- | --- | --- |
| ARG 70 | H-ARG 30 | L-TYR 31 |
| GLY 71 | H-ASN 31 | L-SER 32 |
| ALA 72 | H-TYR 33 | L-ASN 33 |
| GLY 73 | H-TYR 52 | L-THR 99 |
| PRO 74 | H-TYR 53 | |
| ALA 75 | H-ASN 54 | |
| (GLY 75 on V1) | | |
| ARG 76 | H-ARG 56 | |
| GLU 77 | H-PHE 58 | |
| ALA 114 | H-ALA 100 | |

TABLE 52-continued

Epitope, contact points on SIRPα-V2 and Antibody E

| Residues on SIRPα V2 that contact Antibody E | Residues on the Heavy Chain that contact SIRPα V2 | Residues on the Light Chain that contact SIRPα V2 |
|---|---|---|
| ALA 116 | H-TYR 101 | |
| GLY 117 | H-SER 102 | |
| THR 118 | H-GLY 103 | |
| TYR 120 | H-ILE 104 | |
| THR 131 | H-GLY 105 | |
| (VAL 132 on V1) | | |
| GLU 132 (133 on V1) | H-LEU 106 | |
| PHE 133 (134 on V1) | | |
| SER 135 (136 on V1 | | |
| GLU 140 (141 on V1) | | |

See FIG. 26 for SIRPαV1 and SIRPαV2 alignment and numbering.

Example 21. Competition Assay with Commercial Anti-SIRP mAb, Clone SE5A5

Antibodies were assessed for their ability to compete with commercial anti-SIRP mAb, clone SE5A5, binding to V1- and V2-SIRPα-expressing U-937 cells. Cells blocked with Human TruStain FcX™ (Biolegend) are incubated with anti-SIRPα antibodies on ice for 30 minutes prior to the addition of fluorescently conjugated SE5A5 (Biolegend). Cells are washed, fixed, and analyzed by flow cytometry. Median fluorescent intensity is plotted.

FIGS. 27A-27B show that KWAR23 and antibody A blocked the binding of fluorescently conjugated SE5A5 to both V1- and V2-SIRPα expressing U-937 cells. Antibody E blocked SE5A5 binding to V1-SIRPα-expressing U-937 cells, but not V2-SIRPα-expressing cells.

Example 22. Binding of Antibodies to Full-Length Cynomologus SIRPα Expressed on CHO Cells Antibody binding to cells expressing cynomolgus (cyno) SIRPα was evaluated by flow cytometry. CHO-K1 cells expressing full-length cyno SIRPα; derived from protein sequence accession numbers (A) EGM-02252; (B) XP_015313155; or (C) NP_001271679, are blocked with donkey IgG and incubated on ice with increasing concentrations of antibodies for 60 minutes, washed and stained with AF647-conjugated donkey F(ab')$_2$ anti-human IgG secondary reagent. Cells are washed, fixed, and analyzed by flow cytometry. Median fluorescent intensity is determined and used as a measure of antibody binding.

KWAR23 demonstrated dose-dependent binding to all cyno SIRPα-expressing CHO cells lines (H3A9, P3HD10, and HC6) encoding various cynomolgus SIRPα sequences (FIGS. 28A-28C) with EC$_{50}$ values ranging between 0.5-2.0 nM (Table 53). Antibodies E and E22 exhibited diverse binding profiles achieving saturable binding curves and EC$_{50}$ values between 1.1 and 2.5 for clones P3HD10 and HC6 and little to no binding to clone H3A9. While antibodies A and A10 exhibited binding to all 3 clones, binding was strongest to clone H3A9 and up to 5-fold weaker EC$_{50}$ values for clones P3HD10 and HC6. Titratable binding of antibody A4 was detected on each of the three cell lines but did not achieve saturation at concentrations as high as 200 nM.

TABLE 53

EC$_{50}$ of Anti-SIRPα antibodies

| | Cynomolgus SIRPα; EC$_{50}$, nM | | |
|---|---|---|---|
| Antibody | EGM-02252 Clone H3A9 | XP_015313155 Clone P3HD10 | NP_001271679 Clone HC6 |
| Isotype | NB | NB | NB |
| KWAR23 | 0.9 | 0.5 | 2 |
| Antibody A | 1.9 | 5 | 4.5 |
| Antibody E | NS | 1.1 | 2.5 |
| Antibody A10 | 1.5 | 7.2 | 3.7 |
| Antibody A4 | NS | NS | NS |
| Antibody E22 | NS | 1.3 | 1.4 |

NB No binding
NS Non-saturable binding

Example 23. Binding of Antibodies to Full-Length Cynomologus SIRPβ1- and SIRPβ1v3 Expressed on CHO Cells Antibody binding to cells expressing full-length cynomolgus SIRPβ1 (XP_005568598) and SIRPβ1v3 (XP_005568593) is evaluated by flow cytometry. SIRPβ1- or SIRPβ1V3-expressing CHO cells are blocked with donkey IgG and incubated on ice with increasing concentrations of antibodies for 60 minutes, washed and stained with AF647-conjugated donkey F(ab')$_2$ anti-human IgG secondary reagent. Cells are washed, fixed, and analyzed by flow cytometry. Median fluorescent intensity is determined and used as a measure of antibody binding.

KWAR23 demonstrated dose-dependent binding to cyno SIRPβ1- and SIRPβ1v3-expressing CHO cells (FIGS. 29A and 29B, respectively) with subnanomolar EC$_{50}$ values (Table 54). Antibodies E and E22 exhibited diverse binding profiles achieving saturable binding curves and subnanomolar EC$_{50}$ values for SIRPβ1v3-expressing CHO cells (FIG. 29B, Table 54), but little to no detectable binding to SIRPβ1-expressing CHO cells (FIG. 29A). In contrast, antibodies A and A10 showed dose-dependent binding to SIRPβ1-expressing CHO cells (FIG. 29A) with subnanomolar EC$_{50}$ values (Table 54) and non-saturable binding to SIRPβ1v3-expressing cells (FIG. 29B). Dose-dependent binding of antibody A4 was detected on each of two cell lines but did not achieve saturation at concentrations as high as 67 nM.

TABLE 54

EC$_{50}$ of Anti-SIRPα antibodies

| | Cynomolgus SIRPβ1; EC$_{50}$, nM | |
|---|---|---|
| Antibody | SIRPβ1 XP_005568598 Clone PA2 | SIRPβ1v3 XP-005568593 Clone 1HC6 |
| Isotype | NB | NB |
| KWAR23 | 0.2 | 0.4 |
| Antibody A | 0.7 | NS |
| Antibody E | NB | 0.8 |
| Antibody A10 | 0.6 | NS |
| Antibody A4 | NS | NS |
| Antibody E22 | NB | 1 |

NB No binding
NS Non-saturable binding

The disclosures of each and every patent, patent application, and publication cited herein are hereby incorporated herein by reference in their entirety. While this disclosure has been disclosed with reference to specific embodiments,

Example 24. Pharmacokinetics (PK) in Cynomolgus Monkeys

A pharmacokinetic study is conducted in naïve male cynomolgus monkeys (*Macaca fascicularis*) 2-5 years of age with a body weight range between 2.1-6.0 kg. The monkeys are divided into two treatment groups that are administered Antibody A10. Group 1 (n=3) receives 1 mg/kg and Group 2 (n=3) receives 5 mg/kg of the antibody. The antibody is administered intravenously (i.v.) as a 2 mg/ml solution in citrate buffer (50 mM sodium citrate/115 mM sodium chloride, pH 5.0). Blood samples are collected over 6 weeks from a peripheral vein and serum is recovered for analysis.

Serum samples are analyzed using an ELISA format. Briefly, HuSIRPα-V1 is bound to a NUNC™ ELISA plate (Thermo Fisher Scientific). The plates are washed with 0.05% TWEEN™ 20 in phosphate buffered saline and blocked with 5% BSA Buffer (Sera Care cat #AP-4510-01), in PBS (Gibco ref 10010-023) prior to incubation with serum samples. The antibody is detected utilizing Novus, pAb anti-goat anti-human IgG HRP, Cat #NB7489 at 1:8000 dilution. PK parameters are determined by non-compartmental analysis using Phoenix WINNONLIN™ software (Version 8.2, Certara USA, Inc. Princeton, N.J.).

The PK study results are shown FIG. 30 and the PK paramters are summarized in Table 55 below. The antibody demonstrated dose dependent CL between 1 and 5 mg/kg, suggestive of target-mediated drug distribution (TMDD) contributions to overall clearance.

TABLE 55

| Dose (mg/kg) | $AUC_{0-inf}$ (hr * ng/mL) | CL (mL/d/kg) | $t_{1/2z}$ (d) | $V_{ss}$ (mL/kg) | MRT (d) |
|---|---|---|---|---|---|
| 1.0 IV | 101000 (15800) | 24.2 (3.54) | 1.79 (0.79) | 34.7 (6.50) | 1.43 (0.157) |
| 5.0 IV | 11800000 (4260000) | 11.0 (3.79) | 3.4 (0.906) | 47.4 (4.04) | 4.58 (1.24) |

Abbreviations:
$AUC_{0-inf}$: area under the curve from dosing to the last measurement and extrapolated to infinity;
CL: Clearance;
$t_{1/2z}$: Terminal Half-life;
$V_{ss}$: volume distribution at steady state;
MRT: Mean Residence Time

Example 25. Toxicology in Cynomolgus Monkeys

A repeat dose toxicity study is conducted in cynomolgus monkeys with Antibody A10. Parameters evaluated in this study include bioanalysis, toxicokinetic, clinical observation, body weight, food consumption, hematology, blood chemistry, coagulation, urinalysis, immunophenotyping, neurobehavioral examination, electrocardiogram examination, and ophthalmic examination.

Groups of male and female cynomolgus monkeys (n=3/sex/group) receive the antibody at dose levels of 100 and 250 mg/kg/dose q1w for 4 weeks (5 dose administrations).

There were no antibody-related changes in body weight, clinical observations, food consumption, ophthalmic examination, neurobehavioral examination, electrocardiogram, immunophenotyping, hematology, coagulation, clinical chemistry, or urinalysis.

In conclusion, intravenous administration of the antibody at 100 and 250 mg/kg/dose q1w for 4 weeks (5 doses total) was tolerated in monkeys with no antibody-related adverse findings. Under the condition of this study, the no-observed-adverse-effect-level (NOAEL) at steady state (Day 22) was considered to be 250 mg/kg/dose q1w.

Example 26. Binding of Antibodies to Full-Length Human V1-SIRPα with Various Amino Acid Point Mutations Expressed on Expi-CHO Cells To study the structural basis of the observed antibody selectivity, antibody binding to cells engineered to express modified V1-SIRPα protein sequences is tested by flow cytometry. Expi-CHO parental cells are transduced with lentiviruses containing either full-length wild-type human SIRPαV1 allele (NP_542970.1) or full-length human SIRPαV1 with amino acid point mutations (Table 56) and sorted to achieve matching expression levels. These cells are blocked with donkey IgG and incubated on ice with increasing concentrations of antibodies for 60 minutes, washed and stained with AF647-conjugated donkey F(ab')$_2$ anti-human IgG antibodies. Stained cells are washed, fixed, and analyzed by flow cytometry. Median fluorescent intensity is determined and used as a measure of antibody binding.

Antibodies A-E, A4, A10, E22 and KWAR23, but not isotype control, showed dose-dependent binding to Expi-CHO cells expressing full-length wild-type human SIRPαV1 (FIG. 31A) with $EC_{50}$ values ranging between 0.3 to 3.8 nM (Table 57). Antibody binding to cells expressing SIRPαV1 N→E and D→E variants were comparable to binding to SIRPαV1 WT-expressing cells (FIGS. 31B-31C; Table 57). In contrast, binding of antibodies A-D, A4, and A10 to Expi-CHO cells expressing SIRPαV1 D→N and DD→EN variants was affected, showing abolished, weaker (>$EC_{50}$), or non-saturable binding (FIGS. 31D-31E; Table 57). None of the antibodies tested exhibited binding to parental CHO cells (FIG. 31F).

TABLE 56

| Target | Sequence | SEQ ID NO: |
|---|---|---|
| αV1 WT | EEELQVIQPDKSVLVAAGETATLRCTATSLIPVGPIQWFRGAGP GRELIYNQKEGHFPRVTTVSDLTKRNNMDFSIRIGNITPADAGT YYCVKFRKGSPDDVEFKSGAGTELSVRAKPSAPVVSGPAARATP QHTVSFTCESHGFSPRDITLKWFKNGNELSDFQTNVDPVGESVS YSIHSTAKVVLTREDVHSQVICEVAHVTLQGDPLRGTANLSETI RVPPTLEVTQQPVRAENQVNVTCQVRKFYPQRLQLTWLENGNVS RTETASTVTENKDGTYNWMSWLLVNVSAHRDDVKLTCQVEHDGQ PAVSKSHDLKVSAHPKEQGSNTAAENTGSNERNIYIVVGVVCTL LVALLMAALYLVRIRQKKAQGSTSSTRLHEPEKNAREITQDTND ITYADLNLPKGKKPAPQAAEPNNHTEYASIQTSPQPASEDTLTY ADLDMVHLNRTPKQPAPKPEPSFSEYASVQVPRK | 268 |

TABLE 56-continued

| Target | Sequence | SEQ ID NO: |
|---|---|---|
| αV1 N→E | EEELQVIQPDKSVLVAAGETATLRCTATSLIPVGPIQWFRGAGP<br>GRELIYNQKEGHFPRVTTVSDLTKRENMDFSIRIGNITPADAGT<br>YYCVKFRKGSPDDVEFKSGAGTELSVRAKPSAPVVSGPAARATP<br>QHTVSFTCESHGFSPRDITLKWFKNGNELSDFQTNVDPVGESVS<br>YSIHSTAKVVLTREDVHSQVICEVAHVTLQGDPLRGTANLSETI<br>RVPPTLEVTQQPVRAENQVNVTCQVRKFYPQRLQLTWLENGNVS<br>RTETASTVTENKDGTYNWMSWLLVNVSAHRDDVKLTCQVEHDGQ<br>PAVSKSHDLKVSAHPKEQGSNTAAENTGSNERNIYIVVGVVCTL<br>LVALLMAALYLVRIRQKKAQGSTSSTRLHEPEKNAREITQDTND<br>ITYADLNLPKGKKPAPQAAEPNNHTEYASIQTSPQPASEDTLTY<br>ADLDMVHLNRTPKQPAPKPEPSFSEYASVQVPRK | 269 |
| αV1 D→E | EEELQVIQPDKSVLVAAGETATLRCTATSLIPVGPIQWFRGAGP<br>GRELIYNQKEGHFPRVTTVSDLTKRNNMDFSIRIGNITPADAGT<br>YYCVKFRKGSPEDVEFKSGAGTELSVRAKPSAPVVSGPAARATP<br>QHTVSFTCESHGFSPRDITLKWFKNGNELSDFQTNVDPVGESVS<br>YSIHSTAKVVLTREDVHSQVICEVAHVTLQGDPLRGTANLSETI<br>RVPPTLEVTQQPVRAENQVNVTCQVRKFYPQRLQLTWLENGNVS<br>RTETASTVTENKDGTYNWMSWLLVNVSAHRDDVKLTCQVEHDGQ<br>PAVSKSHDLKVSAHPKEQGSNTAAENTGSNERNIYIVVGVVCTL<br>LVALLMAALYLVRIRQKKAQGSTSSTRLHEPEKNAREITQDTND<br>ITYADLNLPKGKKPAPQAAEPNNHTEYASIQTSPQPASEDTLTY<br>ADLDMVHLNRTPKQPAPKPEPSFSEYASVQVPRK | 270 |
| αV1 D→N | EEELQVIQPDKSVLVAAGETATLRCTATSLIPVGPIQWFRGAGP<br>GRELIYNQKEGHFPRVTTVSDLTKRNNMDFSIRIGNITPADAGT<br>YYCVKFRKGSPDNVEFKSGAGTELSVRAKPSAPVVSGPAARATP<br>QHTVSFTCESHGFSPRDITLKWFKNGNELSDFQTNVDPVGESVS<br>YSIHSTAKVVLTREDVHSQVICEVAHVTLQGDPLRGTANLSETI<br>RVPPTLEVTQQPVRAENQVNVTCQVRKFYPQRLQLTWLENGNVS<br>RTETASTVTENKDGTYNWMSWLLVNVSAHRDDVKLTCQVEHDGQ<br>PAVSKSHDLKVSAHPKEQGSNTAAENTGSNERNIYIVVGVVCTL<br>LVALLMAALYLVRIRQKKAQGSTSSTRLHEPEKNAREITQDTND<br>ITYADLNLPKGKKPAPQAAEPNNHTEYASIQTSPQPASEDTLTY<br>ADLDMVHLNRTPKQPAPKPEPSFSEYASVQVPRK | 271 |
| αV1 DD→EN | EEELQVIQPDKSVLVAAGETATLRCTATSLIPVGPIQWFRGAGP<br>GRELIYNQKEGHFPRVTTVSDLTKRNNMDFSIRIGNITPADAGT<br>YYCVKFRKGSPENVEFKSGAGTELSVRAKPSAPVVSGPAARATP<br>QHTVSFTCESHGFSPRDITLKWFKNGNELSDFQTNVDPVGESVS<br>YSIHSTAKVVLTREDVHSQVICEVAHVTLQGDPLRGTANLSETI<br>RVPPTLEVTQQPVRAENQVNVTCQVRKFYPQRLQLTWLENGNVS<br>RTETASTVTENKDGTYNWMSWLLVNVSAHRDDVKLTCQVEHDGQ<br>PAVSKSHDLKVSAHPKEQGSNTAAENTGSNERNIYIVVGVVCTL<br>LVALLMAALYLVRIRQKKAQGSTSSTRLHEPEKNAREITQDTND<br>ITYADLNLPKGKKPAPQAAEPNNHTEYASIQTSPQPASEDTLTY<br>ADLDMVHLNRTPKQPAPKPEPSFSEYASVQVPRK | 272 |

TABLE 57

| | Cell Binding $EC_{50}$ (nM) | | | | |
|---|---|---|---|---|---|
| Antibody | αV1 WT | αV1 N→E | αV1 D→E | αV1 D→N | αV1 DD→EN |
| Isotype | NB | NB | NB | NB | NB |
| KWAR23 | 0.3 | 0.5 | 0.2 | 0.2 | 0.2 |
| Antibody A | 0.4 | 0.4 | 0.3 | NS | NS |
| Antibody B | 3.8 | 4.5 | 3.7 | NS | NS |
| Antibody C | 0.3 | 0.3 | 0.2 | 2.7 | 1.1 |
| Antibody D | 0.3 | 0.3 | 0.2 | 9.6 | 6.6 |
| Antibody E | 0.5 | 0.5 | 0.4 | 0.4 | 0.4 |
| Antibody A4 | 0.4 | 0.4 | 0.3 | NS | NS |
| Antibody A10 | 0.4 | 0.4 | 0.3 | NS | NS |
| Antibody E22 | 0.8 | 0.9 | 0.7 | 0.8 | 0.6 |

NB: No binding
NS: Non-saturable binding at 67 nM

Example 27. Binding of Antibodies to Full-Length Human V2-SIRPα with Various Amino Acid Point Mutations Expressed on Expi-CHO Cells To study the structural basis of the observed antibody selectivity, antibody binding to cells engineered to express modified V2-SIRPα protein sequences is tested by flow cytometry. Expi-CHO parental cells are transduced with lentiviruses containing either full-length wild-type human SIRPαV2 allele (CAA71403.1) or full-length human SIRPαV2 with amino acid point mutations (Table 58) and sorted to achieve matching expression levels. These cells are blocked with donkey IgG and incubated on ice with increasing concentrations of antibodies for 60 minutes, washed and stained with AF647-conjugated donkey F(ab')$_2$ anti-human IgG antibodies. Stained cells are washed, fixed, and analyzed by flow cytometry. Median fluorescent intensity is determined and used as a measure of antibody binding.

Antibodies A-E, A4, A10, E22 and KWAR23, but not isotype control, showed dose-dependent binding to Expi-CHO cells expressing full-length wild-type human SIRPαV2 (FIG. 32A) with $EC_{50}$ values ranging between 0.2 to 3.6 nM (Table 59). Antibody binding to cells expressing SIRPαV2 E→N were comparable to binding to SIRPαV2 WT-expressing cells (FIG. 32B; Table 59). In contrast, binding of antibodies A, D, A4 and A10, but not B, C, E, E22, and KWAR23, to Expi-CHO cells expressing SIRPαV2 D→E was affected, showing 3.1 to 7.7 fold greater $EC_{50}$'s than $EC_{50}$ values observed for SIRPαV2 WT-expressing cells (FIG. 32C; Table 59).

TABLE 58

| Target | Sequence | SEQ ID NO: |
|---|---|---|
| αV2 WT | EEELQVIQPDKSVSVAAGESAILHCTVTSLIPVGPIQWFRGAGPA<br>RELIYNQKEGHFPRVTTVSESTKRENMDFSISISNITPADAGTYY<br>CVKFRKGSPDTEFKSGAGTELSVRAKPSAPVVSGPAARATPQHTV<br>SFTCESHGFSPRDITLKWFKNGNELSDFQTNVDPVGESVSYSIHS<br>TAKVVLTREDVHSQVICEVAHVTLQGDPLRGTANLSETIRVPPTL<br>EVTQQPVRAENQVNVTCQVRKFYPQRLQLTWLENGNVSRTETAST<br>VTENKDGTYNWMSWLLVNVSAHRDDVKLTCQVEHDGQPAVSKSHD<br>LKVSAHPKEQGSNTAAENTGSNERNIYIVVGVVCTLLVALLMAAL<br>YLVRIRQKKAQGSTSSTRLHEPEKNAREITQDTNDITYADLNLPK<br>GKKPAPQAAEPNNHTEYASIQTSPQPASEDTLTYADLDMVHLNRT<br>PKQPAPKPEPSFSEYASVQVPRK | 273 |
| αV2 E→N | EEELQVIQPDKSVSVAAGESAILHCTVTSLIPVGPIQWFRGAGPA<br>RELIYNQKEGHFPRVTTVSESTKRNNMDFSISISNITPADAGTYY<br>CVKFRKGSPDTEFKSGAGTELSVRAKPSAPVVSGPAARATPQHTV<br>SFTCESHGFSPRDITLKWFKNGNELSDFQTNVDPVGESVSYSIHS<br>TAKVVLTREDVHSQVICEVAHVTLQGDPLRGTANLSETIRVPPTL<br>EVTQQPVRAENQVNVTCQVRKFYPQRLQLTWLENGNVSRTETAST<br>VTENKDGTYNWMSWLLVNVSAHRDDVKLTCQVEHDGQPAVSKSHD<br>LKVSAHPKEQGSNTAAENTGSNERNIYIVVGVVCTLLVALLMAAL<br>YLVRIRQKKAQGSTSSTRLHEPEKNAREITQDTNDITYADLNLPK<br>GKKPAPQAAEPNNHTEYASIQTSPQPASEDTLTYADLDMVHLNRT<br>PKQPAPKPEPSFSEYASVQVPRK | 274 |
| αV2 D→E | EEELQVIQPDKSVSVAAGESAILHCTVTSLIPVGPIQWFRGAGPA<br>RELIYNQKEGHFPRVTTVSESTKRENMDFSISISNITPADAGTYY<br>CVKFRKGSPETEFKSGAGTELSVRAKPSAPVVSGPAARATPQHTV<br>SFTCESHGFSPRDITLKWFKNGNELSDFQTNVDPVGESVSYSIHS<br>TAKVVLTREDVHSQVICEVAHVTLQGDPLRGTANLSETIRVPPTL<br>EVTQQPVRAENQVNVTCQVRKFYPQRLQLTWLENGNVSRTETAST<br>VTENKDGTYNWMSWLLVNVSAHRDDVKLTCQVEHDGQPAVSKSHD<br>LKVSAHPKEQGSNTAAENTGSNERNIYIVVGVVCTLLVALLMAAL<br>YLVRIRQKKAQGSTSSTRLHEPEKNAREITQDTNDITYADLNLPK<br>GKKPAPQAAEPNNHTEYASIQTSPQPASEDTLTYADLDMVHLNRT<br>PKQPAPKPEPSFSEYASVQVPRK | 275 |

TABLE 59

| | Cell Binding $EC_{50}$ (nM) | | |
|---|---|---|---|
| Antibody | αV2 WT | αV2 E→N | αV2 D→E |
| Isotype | NB | NB | NB |
| KWAR23 | 0.2 | 0.2 | 0.2 |
| Antibody A | 0.3 | 0.3 | 1.0 |
| Antibody B | 3.6 | 4.1 | 3.7 |
| Antibody C | 0.2 | 0.2 | 0.2 |
| Antibody D | 0.2 | 0.2 | 0.6 |
| Antibody E | 0.3 | 0.3 | 0.3 |
| Antibody A4 | 0.2 | 0.2 | 1.8 |
| Antibody A10 | 0.2 | 0.3 | 0.7 |
| Antibody E22 | 0.4 | 0.4 | 0.4 |

NB: No binding
NS: Non-saturable binding at 67 nM

Example 28. Binding of Antibodies to Full-Length Human SIRPβ1 with Various Amino Acid Point Mutations Expressed on Expi-CHO Cells To study the structural basis of the observed antibody selectivity, antibody binding to cells engineered to express modified SIRPβ1 protein sequences is tested by flow cytometry. Expi-CHO parental cells are transduced with lentiviruses containing either full-length wild-type human SIRPβ1 (000241) or full-length human SIRPβ1 with a single amino acid point mutation (Table 60) and sorted to achieve matching expression levels. These cells are blocked with donkey IgG and incubated on ice with increasing concentrations of antibodies for 60 minutes, washed and stained with AF647-conjugated donkey $F(ab')_2$ anti-human IgG antibodies. Stained cells are washed, fixed, and analyzed by flow cytometry. Median fluorescent intensity is determined and used as a measure of antibody binding.

Antibodies A-E, A4, A10 and KWAR23, but not isotype control or antibody E22, showed dose-dependent binding to full length wild-type human SIRPβ1 expressed on Expi-CHO cells (FIG. 33A). Table 61 highlights the binding $EC_{50}$ calculated for each of the antibodies. While antibodies A, C, D, A4, and A10 exhibited $EC_{50}$ values ranging between 0.2 to 1.6 nM on wild-type human SIRPβ1-expressing cells, binding of antibodies B and E were non-saturable and no $EC_{50}$ values were determined. Except for KWAR23, antibody binding was completely lost when a single amino acid substitution (DH) was introduced within the loop region (FIG. 33B).

TABLE 60

| Target | Sequence | SEQ ID NO: |
|---|---|---|
| β1 WT | EDELQVIQPEKSVSVAAGESATLRCAMTSLIPVGPIMWFRGAGA<br>GRELIYNQKEGHFPRVTTVSELTKRNNLDFSISISNITPADAGT<br>YYCVKFRKGSPDDVEFKSGAGTELSVRAKPSAPVVSGPAVRATP<br>EHTVSFTCESHGFSPRDITLKWFKNGNELSDFQTNVDPAGDSVS<br>YSIHSTARVVLTRGDVHSQVICEIAHITLQGDPLRGTANLSEAI | 276 |

TABLE 60-continued

| Target | Sequence | SEQ ID NO: |
|---|---|---|
| | RVPPTLEVTQQPMRAENQANVTCQVSNFYPRGLQLTWLENGNVS<br>RTETASTLIENKDGTYNWMSWLLVNTCAHRDDVVLTCQVEHDGQ<br>QAVSKSYALEISAHQKEHGSDITHEAALAPTAPLLVALLLGPKL<br>LLVVGVSAIYICWKQKA | |
| β1 D→H | EDELQVIQPEKSVSVAAGESATLRCAMTSLIPVGPIMWFRGAGA<br>GRELIYNQKEGHFPRVTTVSELTKRNNLDFSISISNITPADAGT<br>YYCVKFRKGSPD<u>H</u>VEFKSGAGTELSVRAKPSAPVVSGPAVRATP<br>EHTVSFTCESHGFSPRDITLKWFKNGNELSDFQTNVDPAGDSVS<br>YSIHSTARVVLTRGDVHSQVICEIAHITLQGDPLRGTANLSEAI<br>RVPPTLEVTQQPMRAENQANVTCQVSNFYPRGLQLTWLENGNVS<br>RTETASTLIENKDGTYNWMSWLLVNTCAHRDDVVLTCQVEHDGQ<br>QAVSKSYALEISAHQKEHGSDITHEAALAPTAPLLVALLLGPKL<br>LLVVGVSAIYICWKQKA | 277 |

TABLE 61

| | Cell Binding EC$_{50}$ (nM) | |
|---|---|---|
| Antibody | β1 WT | β1 D→H |
| Isotype | NB | NB |
| KWAR23 | 0.2 | 0.01 |
| Antibody A | 1.6 | NB |
| Antibody B | NS | NB |
| Antibody C | 0.2 | NB |
| Antibody D | 0.2 | NB |
| Antibody E | NS | NB |
| Antibody A4 | 1.5 | NB |
| Antibody A10 | 1.6 | NB |
| Antibody E22 | NB | NB |

NB: No binding
NS: Non-saturable binding at 67 nM

Example 29. Binding of Antibodies to Full-Length Human SIRPβL with Various Amino Acid Point Mutations Expressed on Expi-CHO Cells To study the structural basis of the observed antibody selectivity, antibody binding to cells engineered to express modified SIRPβL protein sequences is tested by flow cytometry. Expi-CHO parental cells are transduced with lentiviruses containing either full-length wild-type human SIRPβL (Q5TFQ8) or full-length human SIRPβL with a single amino acid point mutation (Table 62) and sorted to achieve matching expression levels. These cells are blocked with donkey IgG and incubated on ice with increasing concentrations of antibodies for 60 minutes, washed and stained with AF647-conjugated donkey F(ab')$_2$ anti-human IgG antibodies. Stained cells are washed, fixed, and analyzed by flow cytometry. Median fluorescent intensity is determined and used as a measure of antibody binding.

Antibodies E, E22 and KWAR23 showed dose-dependent binding to full length human SIRPβL expressed on Expi-CHO cells (FIG. 34A) with EC$_{50}$ values less than 1.2 nM (Table 63). No binding of antibodies A, A4, and A10 could be detected on SIRPβL-expressing cells, while antibodies B, C, and D exhibited non-saturable binding (FIG. 34A, Table 63). A single amino acid substitution (HD) introduced within the loop region maintained, strengthened, or facilitated antibody binding to these cells (FIG. 34B, Table 63).

TABLE 62

| Target | Sequence | SEQ ID NO: |
|---|---|---|
| βL WT | EEELQVIQPDKSISVAAGESATLHCTVTSLIPVGPIQWFRGAGP<br>GRELIYNQKEGHFPRVTTVSDLTKRNNMDFSIRISNITPADAGT<br>YYCVKFRKGSPDHVEFKSGAGTELSVRAKPSAPVVSGPAARATP<br>QHTVSFTCESHGFSPRDITLKWFKNGNELSDFQTNVDPAGDSVS<br>YSIHSTAKVVLTREDVHSQVICEVAHVTLQGDPLRGTANLSETI<br>RVPPTLEVTQQPVRAENQVNVTCQVRKFYPQRLQLTWLENGNVS<br>RTETASTLTENKDGTYNWMSWLLVNVSAHRDDVKLTCQVEHDGQ<br>PAVSKSHDLKVSAHPKEQGSNTAPGPALASAAPLLIAFLLGPKV<br>LLVVGVSVIYVYWKQKA | 278 |
| βL H→D | EEELQVIQPDKSISVAAGESATLHCTVTSLIPVGPIQWFRGAGP<br>GRELIYNQKEGHFPRVTTVSDLTKRNNMDFSIRISNITPADAGT<br>YYCVKFRKGSPD<u>D</u>VEFKSGAGTELSVRAKPSAPVVSGPAARATP<br>QHTVSFTCESHGFSPRDITLKWFKNGNELSDFQTNVDPAGDSVS<br>YSIHSTAKVVLTREDVHSQVICEVAHVTLQGDPLRGTANLSETI<br>RVPPTLEVTQQPVRAENQVNVTCQVRKFYPQRLQLTWLENGNVS<br>RTETASTLTENKDGTYNWMSWLLVNVSAHRDDVKLTCQVEHDGQ<br>PAVSKSHDLKVSAHPKEQGSNTAPGPALASAAPLLIAFLLGPKV<br>LLVVGVSVIYVYWKQKA | 279 |

TABLE 63

| Antibody | Cell Binding EC$_{50}$ (nM) | |
| --- | --- | --- |
|  | βL WT | βL WT H→D |
| Isotype | NB | NB |
| KWAR23 | 1.0 | 0.5 |
| Antibody A | NB | 0.5 |
| Antibody B | NS | 6.7 |
| Antibody C | NS | 0.3 |
| Antibody D | NS | 0.2 |
| Antibody E | 1.0 | 0.5 |
| Antibody A4 | NB | 0.5 |
| Antibody A10 | NB | 0.6 |
| Antibody E22 | 1.2 | 0.7 |

NB: No binding
NS: Non-saturable binding at 67 nM

Example 30. Binding of Antibodies to Full-Length Human SIRPγ with Various Amino Acid Point Mutations Expressed on Expi-CHO Cells To study the structural basis of the observed antibody selectivity, antibody binding to cells engineered to express modified SIRPγ protein sequences is tested by flow cytometry. Expi-CHO parental cells are transduced with lentiviruses containing either full-length wild-type human SIRPγ (NP_542970.1) or full-length human SIRPγ with amino acid point mutations (Table 64) and sorted to achieve matching expression levels. These cells are blocked with donkey IgG and incubated on ice with increasing concentrations of antibodies for 60 minutes, washed and stained with AF647-conjugated donkey F(ab')$_2$ anti-human IgG antibodies. Stained cells are washed, fixed, and analyzed by flow cytometry. Median fluorescent intensity is determined and used as a measure of antibody binding.

Except KWAR23, none the antibodies tested (Antibodies A-E, A4, A10, E22) showed saturable binding to Expi-CHO cells expressing full-length wild-type human SIRPγ or SIRPγ E→D expressing cells (FIGS. 35A and 35B, respectively). In contrast, antibodies A-D, A4, and A10 showed saturable antibody binding to Expi-CHO cells expressing SIRPγ N→D and EN→DD variants with all but antibody B with sub nanomolar EC$_{50}$ values (FIGS. 35C and 35D, respectively, and Table 65).

TABLE 64

| Target | Sequence | SEQ ID NO: |
| --- | --- | --- |
| γWT | EEELQMIQPEKLLLVTVGKTATLHCTVTSLLPVGPVLWFRGVGP GRELIYNQKEGHFPRVTTVSDLTKRNNMDFSIRISSITPADVGT YYCVKFRKGSPENVEFKSGPGTEMALGAKPSAPVVLGPAARTTP EHTVSFTCESHGFSPRDITLKWFKNGNELSDFQTNVDPTGQSVA YSIRSTARVVLDPWDVRSQVICEVAHVTLQGDPLRGTANLSEAI RVPPTLEVTQQPMRVGNQVNVTCQVRKFYPQSLQLTWSENGNVC QRETASTLTENKDGTYNWTSWFLVNISDQRDDVVLTCQVKHDGQ LAVSKRLALEVTVHQKDQSSDATPGPASSLTALLLIAVLLGPIY VPWKQKT | 280 |
| γE→D | EEELQMIQPEKLLLVTVGKTATLHCTVTSLLPVGPVLWFRGVGP GRELIYNQKEGHFPRVTTVSDLTKRNNMDFSIRISSITPADVGT YYCVKFRKGSP<u>D</u>NVEFKSGPGTEMALGAKPSAPVVLGPAARTTP EHTVSFTCESHGFSPRDITLKWFKNGNELSDFQTNVDPTGQSVA YSIRSTARVVLDPWDVRSQVICEVAHVTLQGDPLRGTANLSEAI RVPPTLEVTQQPMRVGNQVNVTCQVRKFYPQSLQLTWSENGNVC QRETASTLTENKDGTYNWTSWFLVNISDQRDDVVLTCQVKHDGQ LAVSKRLALEVTVHQKDQSSDATPGPASSLTALLLIAVLLGPIY VPWKQKT | 281 |
| γN→D | EEELQMIQPEKLLLVTVGKTATLHCTVTSLLPVGPVLWFRGVGP GRELIYNQKEGHFPRVTTVSDLTKRNNMDFSIRISSITPADVGT YYCVKFRKGSPE<u>D</u>VEFKSGPGTEMALGAKPSAPVVLGPAARTTP EHTVSFTCESHGFSPRDITLKWFKNGNELSDFQTNVDPTGQSVA YSIRSTARVVLDPWDVRSQVICEVAHVTLQGDPLRGTANLSEAI RVPPTLEVTQQPMRVGNQVNVTCQVRKFYPQSLQLTWSENGNVC QRETASTLTENKDGTYNWTSWFLVNISDQRDDVVLTCQVKHDGQ LAVSKRLALEVTVHQKDQSSDATPGPASSLTALLLIAVLLGPIY VPWKQKT | 282 |
| γEN→DD | EEELQMIQPEKLLLVTVGKTATLHCTVTSLLPVGPVLWFRGVGP GRELIYNQKEGHFPRVTTVSDLTKRNNMDFSIRISSITPADVGT YYCVKFRKGSP<u>DD</u>VEFKSGPGTEMALGAKPSAPVVLGPAARTTP EHTVSFTCESHGFSPRDITLKWFKNGNELSDFQTNVDPTGQSVA YSIRSTARVVLDPWDVRSQVICEVAHVTLQGDPLRGTANLSEAI RVPPTLEVTQQPMRVGNQVNVTCQVRKFYPQSLQLTWSENGNVC QRETASTLTENKDGTYNWTSWFLVNISDQRDDVVLTCQVKHDGQ LAVSKRLALEVTVHQKDQSSDATPGPASSLTALLLIAVLLGPIY VPWKQKT | 283 |

TABLE 65

| Antibody | Cell Binding EC$_{50}$ (nM) | | | |
|---|---|---|---|---|
| | γ WT | γ E→D | γ N→D | γ EN→DD |
| Isotype | NB | NB | NB | NB |
| KWAR23 | 0.113 | 0.3 | 0.3 | 0.3 |
| Antibody A | NB | NB | 0.4 | 0.6 |
| Antibody B | NS | NS | 4.8 | 5.3 |
| Antibody C | NS | NS | 0.2 | 0.2 |
| Antibody D | NS | NS | 0.3 | 0.3 |
| Antibody E | NB | NB | NB | NB |
| Antibody A4 | NB | NB | 0.5 | 0.7 |
| Antibody A10 | NB | NB | 0.5 | 0.7 |
| Antibody E22 | NB | NB | NB | NB |

NB: No binding
NS: Non-saturable binding at 67 nM

Example 31. Amino Acids 125-132 of SIRPαV1 and 125-131 of SIRPαV2 are Determinants for Antibody Selectivity A particular area of the SIRPα epitope bound by Antibody A was identified within the loop region located at amino acids 125-131 of SIRPαV2 (sequence RKGSPDT), corresponding to amino acids 125-132 of SIRPαV1 (sequence RKGSPDDV). We identified this loop as a determinant for the observed binding properties of Antibody A, including selective binding to SIRPαV1 and SIRPαV2, with no detectable binding to human SIRPγ and human SIRPβL (Table 37). The potential role of this loop in conferring binding selectivity was identified by determination of the crystal structure of Antibody A in complex SIRPαV2 (Example 20), and from the sequence comparison of epitope amino acids in related SIRP isoforms, and was confirmed by binding studies described above (Examples 26-30). Notably, this loop differs in length between SIRPαV1 and SIRPαV2, i.e., 8 amino acids in SIRPαV1 and 7 amino acids in SIRPαV2. Despite this difference in loop length, Antibody A shows similar binding affinity for both SIRPαV1 and SIRPαV2 (see, e.g., Table 37). FIG. 36A illustrates how Antibody A binds to this loop from the side, which is believed to allow for specific recognition of the loops with different length in SIRPαV1 and SIRPαV2. We observed that the general configuration of the SIRPα interaction with Antibody A is like the SIRPα interaction with the natural binding partner, CD47, where the loops of SIRPαV1 and SIRPαV2 are approached in a similar orientation (FIG. 36B). However, unlike Antibody A, CD47 also binds to SIRPγ, indicating that Antibody A can confer binding selectivity despite this general similarity.

Even though loops of different length can be recognized by Antibody A, this part of the epitope is nonetheless able to confer the selectivity observed for the SIRP proteins. We identified the sequence motif PDDV in SIRPαV1 as an important difference from SIRPγ and SIRPβL, where the corresponding sequences are PENV and PDHV respectively (FIGS. 37A-37F).

To further study the structural basis of the observed selectivity of Antibody A, we tested its ability to bind to cells engineered to expressed modified SIRP protein sequences (see Examples 26-30). The results of these experiments confirmed the importance of the variant residues in this loop to conferring binding selectivity. We observed that exchanging the respective sequence motif in SIRPαV1 (PDDV) to either PDNV or PENV sequence of SIRPγ strongly impaired binding to Antibody A (FIGS. 31D-31E). Similarly, binding of Antibody A to SIRPβ1 with its PDDV motif was completely abrogated by the exchange to PDHV motif of SIRPβL (FIG. 33B). Reciprocally, binding can be restored when exchanging the PENV motif of SIRPγ to either PEDV or PDDV of SIRPαV1 (FIGS. 35C-35D) or exchanging the PDHV motif of SIRPβL to PDDV of SIRPβ1 (FIG. 34B). These results highlight the properties of the epitope, allowing on the one hand for tolerance of two different loop length in the SIRPα proteins, but on the other hand providing high sensitivity to amino acid changes in the binding interface. Together, these properties result in the selectivity pattern described for Antibody A and its variants (e.g., A4 and A10), namely, strong binding to SIRPαV1, SIRPαV2 and SIRPβ1, complemented by pronounced absence of binding to SIRPγ and SIRPβL.

Example 32. Antibody Titer and Purity

Methods

Transfection. For transfection, combine heavy chain DNA, light chain DNA, Filler DNA and XBP-1 DNA with Opti-Pro SFM (Thermo Fisher) and sterilize by filtering through 0.2 μm filter. Prepare cells at 2×10$^6$ cells/mL or 4×10$^6$ cells/mL (in BalanCD Transfectory CHO (Irvine Scientific)+4 mM L-Glutamine) for required scale of transfection. Add the calculated volume of TransIT Pro (Mirus) transfection reagent to the prepared Opti-Pro SFM+DNA mix and immediately transfer to the prepared cells. Place the shake flask in incubator at 37° C., 5% CO$_2$, and 140 rpm or 200 rpm shake speed. 24 hours post-transfection, temperature is shifted to 30° C., and Transfectory Supplement and Anti-Clumping Supplement (both Irvine Scientific) are added to the transfected cells. CHO CD Efficient Feed B (Gibco) is added between day 5 or day 7, depending on when glucose levels drop between 2 g/L-1 g/L. The transfected culture is maintained for 7-10 days.

Harvest by centrifugation and sterile filtration. The clarified cell culture supernatant is sampled for titer by ForteBio/Pall Octet Red 96 instrument with Protein A biosensors. The measured antibody concentration is reported as the expression titer (mg/L).

Protein A (ProA) Purification: The purification is performed at room temperature (RT) using a GE AKTA Pure system. Each sample is captured from the harvested cell culture fluid (HCCF) by recombinant Protein-A affinity chromatography using MabSelect SuRe resin (GE Healthcare). Chromatography steps and buffer details can be found in Tables 66 and 67, respectively. Protein binds to Protein A at neutral pH at room temperature and is washed with high salt (1M NaCl). Each sample is eluted in an isocratic mode using 30 mM sodium acetate, pH 3.5. Eluted sample is neutralized to pH 5.0 using 1% solution of 3M sodium acetate, pH 9.0. Neutralized protein is sterile filtered with 0.22 μm filtration system. The concentration is calculated based on the absorbance measurement at 280 nm using a NanoDrop 8000 Spectrophotometer (Thermo Fisher).

TABLE 66

| Buffer | Composition |
|---|---|
| Equilibration/Wash 1 | DPBS: 8.05 mM sodium phosphate, 137 mM NaCl, 1.47 mM potassium phosphate, 2.6 mM potassium chloride, pH 7.4 |
| Wash 2 | 1M NaCl in DPBS |
| Wash 3 | DPBS: 8.05 mM sodium phosphate, 137 mM NaCl, 1.47 mM potassium phosphate, 2.6 mM potassium chloride, pH 7.2 |

TABLE 66-continued

| Buffer | Composition |
| --- | --- |
| Elution | 30 mM Sodium Acetate, pH 3.5 |
| Neutralization | 3M Sodium Acetate, pH~9 |
| Regeneration | 0.25N NaOH |
| Storage | 20% Ethanol |

TABLE 67

| Step | Buffer/Solution | Volume |
| --- | --- | --- |
| Equilibration | DPBS, pH 7.4 | ≥5 CV |
| Load | Media | varies |
| Wash 1 | DPBS, pH 7.4 | ≥5 CV |
| Wash 2 | DPBS + 1M NaCl | ≥5 CV |
| Wash 3 | DPBS, pH 7.4 | ≥5 CV |
| Elution | 30 mM sodium acetate, pH 3.5 | ≥5 CV<br>Remark:<br>OD wavelength 280 nm<br>Start pool collection when OD ≥100 mAU<br>End pool collection when OD ≥100 mAU |
| Neutralization | 3M sodium acetate, pH9 | 1% volume of pool post elution |
| Pre-regeneration wash | DPBS, pH 7.4 | ≥5 CV<br>Remark:<br>Ensure the column is equilibrated in DPBS, pH 7.2 by checking pH of the column wash |
| Regeneration | 0.25N NaOH | ≥5 CV<br>Remark:<br>Ensure the column is washed enough in 0.25N NaOH to clean from sticky contaminants<br>Don't leave the column in regeneration buffer for ≥30 min |
| Post-regeneration wash | DPBS, pH 7.4 | ≥4 CV<br>Remark:<br>Ensure the column is equilibrated in DPBS, pH 7.2 by checking pH of the column wash |
| Storage | 20% Ethanol | ≥4 CV |

Cation exchange chromatography (CEX). Cation exchange chromatography is performed at room temperature. The buffers and process conditions are summarized in Tables 68 and 69. The Protein A affinity chromatography purified sample is polished using a Poros 50 XS column (Thermo Fisher) using an AKTA Avant chromatography system (Cytiva). The antibody is bound to the column which is pre-equilibrated with 5CV (column volumes) of 50 mM sodium acetate, pH5.0, washed with 5CV of the same buffer. The antibody is then eluted using gradient of 0 to 0.5M NaCl in 20 CV. Eluted sample is adjusted to the final ionic strength of ~100 mM NaCl. Protein is sterile filtered into a 50 mL falcon tube by 0.22 µm Steriflip (Millipore) using vacuum filtration system. The antibody concentration is calculated based on the absorbance measured as 280 nm using the NanoDrop 8000 (Thermo Fisher). Purified antibody is stored at 4° C.

TABLE 68

| Buffer | Composition |
| --- | --- |
| Equilibration/Wash | 50 mM Sodium Acetate, pH 5.0 |
| Elution | 50 mM Sodium Acetate, 1M NaCl, pH 5.0<br>Gradient elution in 20 CV of 50% B |
| Regeneration | 0.25N NaOH |
| Storage | 20% Ethanol |

TABLE 69

| Step | Buffer | Volume |
| --- | --- | --- |
| Equilibration | 50 mM sodium acetate, pH 5.0 | 5 CV |
| Load | 50 mM sodium acetate, pH 5.0 | varies |
| Wash | 50 mM sodiumm acetate, pH 5.0 | 5 CV |
| Elutions | 50 mM Sodium Acetate and 1M NaCl, pH 5.0 | 20 CV<br>Remark:<br>OD wavelength 280 nm<br>Start pool collection when OD ≥100 mAU<br>End pool collection when OD ≤100 mAU |
| Regeneration | 0.25N NaOH | ≥5 CV |
| Post-regeneration wash | DPBS, pH 7.4 | ≥5 CV |
| Storage | 20% Ethanol | ≥5 CV |

Analytical Size Exclusion Chromatography. Analytical Size Exclusion Chromatography (aSEC) is performed using a Acquity UPLC (Waters, Milford, Mass.) system using a Protein BEH SEC column 200 Å, 1.7 µm, 4.6×150 mm (Waters part #186005225). Running conditions are as follows: Mobile phase: 50 mM Sodium Phosphate, 200 mM Arginine and 0.05% Sodium Azide; Flow rate: 0.5 ml/min; Runtime: 5 minutes; Sample loading amount: 10 µg; Peak detection: A280 nm. The results are analyzed to determine the percentage of the antibody present as a monomer, low molecular weight (LMVV), and high molecular weight (HMW).

Low pH hold is performed by adjusting the pH to 3.5 with 1M acetic acid, pH 2.45. After 90 minutes incubation at room temperature, the sample is neutralized to pH 5.0 by 1M Tris HCl, pH 9.0. Final concentration is determined using a NanoDrop 8000 (Thermo Fisher) by measuring absorbance at 280 nm. Size purity of the samples is characterized by analytical size exclusion chromatography.

Results

The above procedures are used to express and purify antibodies of the present disclosure. Tables 70 and 71 show the titer and size purity results from two different trials for the antibodies as indicated. Table 70 shows the expression titer and results of Protein A purification and cation exchange chromatography. Repeated rows for a given antibody indicate multiple replicates. Table 71 shows the expression titer and results of Protein A purification. Table 72 shows size purity results for the indicated antibodies following pH 3.5 treatment (2 replicates) compared to the same antibody held at pH 5.0.

TABLE 70

| Name | Titer (mg/L) | Pro A load amount (mg) | Recovery from ProA (%) | Monomer following ProA (%) | CEX Load Amount | Recovery from CEX (%) | Monomer following CEX (%) |
|---|---|---|---|---|---|---|---|
| A | 334 | 334 | 82.20% | 97.03 | 264.54 | 78.40% | 100 |
| B | 206 | 206 | 70.78% | 95.66 | 145.81 | 60.69% | 99.2 |
| C | 277 | 277 | 82.46% | 97.76 | 228.41 | 76.18% | 99.89 |
| D | 227 | 227 | 80.61% | 98.26 | 182.98 | 81.26% | 99.95 |
| E | 136 | 136 | 68.71% | 98.05 | 93.45 | 74.31% | 99.98 |
| A10 | 231 | 462 | 101% | 97.32 | 453 | 84.41% | 99.88 |
| A10 | 287 | 287 | 102% | 97.15 | 292 | 80.61% | 99.91 |
| A10 | 246.5 | 247 | 101.00% | 96.02 | 235 | 79.40% | 99.64 |
| A4 | 137 | 274 | 105.60% | 99.44 | 274 | 85.19% | 99.9 |
| E22 | 77 | 385 | 189.10% | 95.99 | 694 | 79.24% | 99.49 |

TABLE 71

| Antibody | Expression Titer (mg/L) | Purified Concentration (mg/mL) following Protein A purification | % Monomer (main peak) following Protein A purification |
|---|---|---|---|
| A | 286 | 3.68 | 98.57 |
| A1 | 215.1 | 3.61 | 98.62 |
| A2 | 199.4 | 3.57 | 99.11 |
| A3 | 222.6 | 3.64 | 98.78 |
| A4 | 230.5 | 3.67 | 98.69 |
| A5 | 254.7 | 3.72 | 98.13 |
| A6 | 226.5 | 3.62 | 98.59 |
| A7 | 256.2 | 3.58 | 98.37 |
| A8 | 249.8 | 3.59 | 98.58 |
| A9 | 251.1 | 3.68 | 98.03 |
| A10 | 256.3 | 3.67 | 97.54 |
| A12 | 271.6 | 3.68 | 98.57 |
| A13 | 259.2 | 3.67 | 98.39 |
| A14 | 261.4 | 3.72 | 98.48 |
| A15 | 249.2 | 3.63 | 97.56 |
| A16 | 281.3 | 3.7 | 98.64 |
| E | 146 | 3.19 | 99.09 |
| E1 | 216.1 | 3.24 | 87.86 |
| E2 | 157.6 | 3.37 | 97.12 |
| E3 | 237.7 | 3.27 | 88.32 |
| E4 | 169.8 | 3.31 | 97.58 |
| E5 | 240.6 | 3.26 | 88.92 |
| E6 | 193.4 | 3.37 | 98.51 |
| E7 | 209.2 | 3.44 | 86.42 |
| E8 | 92.8 | 3.12 | 98.9 |
| E9 | 209.7 | 3.39 | 88.79 |
| E10 | 162.9 | 3.28 | 100 |
| E11 | 58.6 | 1.95 | 100 |
| E12 | 235 | 3.43 | 88.83 |
| E13 | 204.6 | 3.3 | 89.09 |
| E14 | 227.5 | 3.41 | 92.98 |
| E15 | 118 | 3.21 | 99.14 |
| E16 | 245.2 | 3.35 | 88.1 |
| E17 | 84.9 | 2.93 | 92.69 |
| E18 | 183.8 | 3.35 | 97.63 |
| E19 | 230.3 | 3.39 | 87.89 |
| E20 | 208 | 3.49 | 89.2 |
| E21 | 237.5 | 3.46 | 91.24 |
| E22 | 78.5 | 2.89 | 97.27 |

TABLE 72

| | Monomer % | | | Avg. | HMW % | | |
|---|---|---|---|---|---|---|---|
| Antibody | pH 5.0 | pH 3.5 (trial #1) | pH 3.5 (trial #2) | Change in Monomer % | pH 5.0 | pH 3.5 (trial #1) | pH 3.5 (trial #2) |
| A10 | 97.49 | 97.37 | 97.40 | 0.10 | 2.52 | 2.62 | 2.60 |
| A4 | 99.29 | 99.13 | 98.40 | 0.53 | 0.71 | 0.87 | 1.60 |
| E22 | 96.64 | 96.33 | 96.98 | −0.02 | 3.36 | 3.66 | 3.03 |

Example 33. Antibody Binding Kinetics

Methods

The binding kinetics of anti-SIRPα antibodies to various SIRPα analytes are determined by surface plasmon resonance (SPR) using a Biacore 8K+ (Cytiva). 1×HBS-EP+ (Cytiva) is used as running buffer and for all the dilutions unless stated otherwise. The Series S CM5 sensorchip is activated with a 1:1 mixture of 0.1 M NHS (N-hydroxysuccinimide) and 0.4 M EDC (1-Ethyl-3-(3-dimethylaminopropyl) carbodiimide hydrochloride) for 420 seconds at a flow rate of 10 μl/min and immobilized with Protein A/G (Thermo Scientific, 10 μg/ml in 10 mM acetate pH 4.5) for 420 seconds at a flowrate of 10 μl/min resulting in approximately 3000 RU of Protein A/G on the surface. The sensorchip is then deactivated with 1 M ethanolamine HCl pH 8.5 for 420 seconds at a flowrate of 10 μl/min.

Antibodies (approximately 1 ug/ml) are captured on the Protein A/G surface for 60 seconds at a flowrate of 10 μl/min resulting in capture levels of approximately 240 RU. Dilutions of each SIRP protein (Extracellular Domain+His-Tag, with the concentrations as indicated) are injected as analytes over the captured antibody for 300 seconds of association at a flowrate of 30 μl/min, followed by a dissociation for 600 seconds. The surfaces are regenerated with a 30 second injection of 0.85% phosphoric acid at 30 μl/min. SPR sensorgrams are fit globally to 1:1 Langmuir binding to provide on-rate ($k_a$), off-rate ($k_d$), and dissociation constant ($K_D$) values or fit globally to a steady state affinity to provide $K_D$ in the Biacore Insight Evaluation software.

Results

The above procedures are used to measure binding properties of antibodies of the present disclosure. For each analyte used, the highest concentration was as indicated in Example 3 (see Table 36). On-rate, off-rate, and dissociation constant of each indicated antibody for each analyte measured are shown in Tables 73-74.

TABLE 73

| Antibody | huSIRPαV1 | | | huSIRPαV2 | | |
|---|---|---|---|---|---|---|
| | $k_a$ (1/Ms) | $k_d$ (1/s) | $K_D$ (nM) | $k_a$ (1/Ms) | $k_d$ (1/s) | $K_D$ (nM) |
| A | 4.97E+05 | 3.84E-03 | 7.72 | 8.07E+05 | 7.28E-03 | 9.03 |
| E | 4.79E+05 | 2.03E-04 | 0.43 | 5.47E+05 | 1.81E-04 | 0.33 |
| A1 | 7.27E+05 | 6.25E-03 | 8.60 | 8.69E+05 | 1.62E-02 | 18.6 |
| A2 | 7.29E+05 | 6.85E-03 | 9.39 | 8.83E+05 | 1.84E-02 | 20.9 |
| A3 | 7.30E+05 | 6.61E-03 | 9.06 | 9.07E+05 | 1.78E-02 | 19.6 |
| A4 | 7.29E+05 | 6.17E-03 | 8.46 | 8.92E+05 | 1.63E-02 | 18.3 |
| A5 | 6.84E+05 | 5.98E-03 | 8.75 | 9.09E+05 | 1.62E-02 | 17.8 |
| A6 | 7.66E+05 | 6.34E-03 | 8.28 | 9.47E+05 | 1.71E-02 | 18.1 |
| A7 | 7.16E+05 | 6.72E-03 | 9.38 | 9.33E+05 | 1.90E-02 | 20.4 |
| A8 | 7.08E+05 | 6.04E-03 | 8.53 | 8.59E+05 | 1.62E-02 | 18.8 |
| A9 | 4.95E+05 | 3.63E-03 | 7.34 | 7.91E+05 | 6.52E-03 | 8.25 |
| A10 | 5.98E+05 | 4.02E-03 | 6.75 | 6.93E+05 | 6.98E-03 | 10.6 |
| A11 | 5.86E+05 | 4.00E-03 | 6.87 | 6.80E+05 | 7.09E-03 | 10.9 |
| A12 | 4.82E+05 | 3.78E-03 | 7.83 | 7.69E+05 | 6.89E-03 | 8.96 |
| A13 | 4.84E+05 | 3.52E-03 | 7.28 | 7.60E+05 | 6.35E-03 | 8.36 |
| A14 | 4.88E+05 | 3.97E-03 | 8.13 | 8.16E+05 | 6.48E-03 | 7.95 |
| A15 | 5.26E+05 | 3.71E-03 | 7.06 | 8.48E+05 | 6.71E-03 | 7.91 |
| A16 | 4.72E+05 | 3.77E-03 | 7.98 | 7.66E+05 | 6.30E-03 | 8.22 |
| E1 | 4.14E+05 | 2.99E-04 | 0.72 | 5.23E+05 | 3.30E-04 | 0.63 |
| E2 | 4.59E+05 | 4.19E-04 | 0.91 | 5.35E+05 | 3.67E-04 | 0.69 |
| E3 | 3.85E+05 | 3.71E-04 | 0.96 | 4.72E+05 | 3.66E-04 | 0.78 |
| E4 | 4.38E+05 | 4.33E-04 | 0.99 | 5.11E+05 | 4.21E-04 | 0.82 |
| E5 | 3.31E+05 | 3.36E-04 | 1.02 | 4.06E+05 | 3.55E-04 | 0.87 |
| E6 | 3.74E+05 | 3.86E-04 | 1.03 | 4.29E+05 | 3.75E-04 | 0.88 |
| E7 | 3.78E+05 | 4.53E-04 | 1.20 | 4.68E+05 | 5.52E-04 | 1.18 |
| E8 | 3.22E+05 | 3.90E-04 | 1.21 | 4.35E+05 | 2.36E-04 | 0.54 |
| E9 | 5.18E+05 | 6.31E-04 | 1.22 | 5.83E+05 | 5.48E-04 | 0.94 |
| E10 | 4.22E+05 | 5.18E-04 | 1.23 | 4.98E+05 | 5.96E-04 | 1.20 |
| E11 | 3.52E+05 | 4.98E-04 | 1.41 | 4.53E+05 | 2.58E-04 | 0.57 |
| E12 | 4.90E+05 | 8.19E-04 | 1.67 | 5.62E+05 | 7.09E-04 | 1.26 |
| E13 | 3.94E+05 | 6.71E-04 | 1.70 | 4.90E+05 | 3.38E-04 | 0.69 |
| E14 | 4.03E+05 | 7.43E-04 | 1.84 | 4.53E+05 | 6.15E-04 | 1.36 |
| E15 | 4.21E+05 | 8.02E-04 | 1.91 | 5.01E+05 | 3.69E-04 | 0.74 |
| E16 | 4.90E+05 | 1.06E-03 | 2.15 | 5.47E+05 | 1.05E-03 | 1.93 |
| E17 | 4.05E+05 | 9.55E-04 | 2.36 | 5.08E+05 | 4.05E-04 | 0.80 |
| E18 | 4.10E+05 | 1.01E-03 | 2.46 | 4.93E+05 | 4.43E-04 | 0.90 |
| E19 | 3.34E+05 | 8.43E-04 | 2.52 | 4.11E+05 | 3.99E-04 | 0.97 |
| E20 | 4.80E+05 | 1.64E-03 | 3.42 | 5.63E+05 | 6.27E-04 | 1.11 |
| E21 | 4.76E+05 | 2.12E-03 | 4.46 | 5.49E+05 | 7.61E-04 | 1.39 |

TABLE 74

| Antibody | cynoSIRPα (NP_001271679) | | | cynoSIRPα (EGM_02252) | | | cynoSIRPα (XP_015313155) | | |
|---|---|---|---|---|---|---|---|---|---|
| | $k_a$ (1/Ms) | $k_d$ (1/s) | $K_D$ (nM) | $k_a$ (1/Ms) | $k_d$ (1/s) | $K_D$ (nM) | $k_a$ (1/Ms) | $k_d$ (1/s) | $K_D$ (nM) |
| A | 8.73E+05 | 1.38E-01 | 158 | n/a | n/a | 258* | n/a | n/a | 165* |
| E | 2.35E+05 | 1.91E-03 | 8.14 | | NB | | 2.41E+05 | 1.70E-03 | 7.07 |

TABLE 74-continued

| Antibody | cynoSIRPα (NP_001271679) | | | cynoSIRPα (EGM_02252) | | | cynoSIRPα (XP_015313155) | | |
| --- | --- | --- | --- | --- | --- | --- | --- | --- | --- |
| | $k_a$ (1/Ms) | $k_d$ (1/s) | $K_D$ (nM) | $k_a$ (1/Ms) | $k_d$ (1/s) | $K_D$ (nM) | $k_a$ (1/Ms) | $k_d$ (1/s) | $K_D$ (nM) |
| A1 | n/a | n/a | 780* | n/a | n/a | 523* | n/a | n/a | 427* |
| A2 | n/a | n/a | 887* | n/a | n/a | 556* | n/a | n/a | 469* |
| A3 | n/a | n/a | 857* | n/a | n/a | 560* | n/a | n/a | 480* |
| A4 | n/a | n/a | 669* | n/a | n/a | 488* | n/a | n/a | 420* |
| A5 | n/a | n/a | 665* | n/a | n/a | 517* | n/a | n/a | 415* |
| A6 | n/a | n/a | 684* | n/a | n/a | 521* | n/a | n/a | 420* |
| A7 | n/a | n/a | 741* | n/a | n/a | 588* | n/a | n/a | 466* |
| A8 | n/a | n/a | 639* | n/a | n/a | 520* | n/a | n/a | 415* |
| A9 | n/a | n/a | 346* | n/a | n/a | 230* | n/a | n/a | 174* |
| A10 | n/a | n/a | 388* | n/a | n/a | 282* | n/a | n/a | 203* |
| A11 | n/a | n/a | 410* | n/a | n/a | 298* | n/a | n/a | 204* |
| A12 | n/a | n/a | 384* | n/a | n/a | 247* | n/a | n/a | 195* |
| A13 | n/a | n/a | 330* | n/a | n/a | 223* | n/a | n/a | 177* |
| A14 | n/a | n/a | 316* | n/a | n/a | 222* | n/a | n/a | 176* |
| A15 | n/a | n/a | 317* | n/a | n/a | 224* | n/a | n/a | 174* |
| A16 | n/a | n/a | 306* | n/a | n/a | 224* | n/a | n/a | 174* |
| E1 | 1.83E+05 | 3.27E−03 | 17.9 | NB | | | 1.90E+05 | 3.17E−03 | 16.7 |
| E2 | 2.54E+05 | 5.26E−03 | 20.7 | NB | | | 2.60E+05 | 5.12E−03 | 19.7 |
| E3 | 1.68E+05 | 2.91E−03 | 17.3 | NB | | | 1.70E+05 | 2.88E−03 | 16.9 |
| E4 | 2.22E+05 | 4.68E−03 | 21.1 | NB | | | 2.28E+05 | 4.51E−03 | 19.8 |
| E5 | 1.23E+05 | 4.71E−03 | 38.2 | NB | | | 1.21E+05 | 4.59E−03 | 37.8 |
| E6 | 1.89E+05 | 7.74E−03 | 41.0 | NB | | | 1.75E+05 | 7.29E−03 | 41.6 |
| E7 | 1.58E+05 | 3.46E−03 | 21.9 | NB | | | 1.59E+05 | 3.37E−03 | 21.2 |
| E8 | 2.04E+05 | 3.60E−03 | 17.7 | NB | | | 2.07E+05 | 3.44E−03 | 16.6 |
| E9 | 3.21E+05 | 1.40E−02 | 43.7 | NB | | | 3.24E+05 | 1.32E−02 | 40.8 |
| E10 | 2.16E+05 | 5.45E−03 | 25.2 | NB | | | 2.22E+05 | 5.26E−03 | 23.7 |
| E11 | 2.67E+05 | 5.42E−03 | 20.3 | NB | | | 2.75E+05 | 5.49E−03 | 20.0 |
| E12 | 2.79E+05 | 1.29E−02 | 46.1 | NB | | | 2.97E+05 | 1.25E−02 | 42.2 |
| E13 | 1.97E+05 | 7.55E−03 | 38.3 | NB | | | 1.90E+05 | 7.11E−03 | 37.4 |
| E14 | 1.90E+05 | 1.73E−02 | 90.7 | NB | | | 2.00E+05 | 1.73E−02 | 86.3 |
| E15 | 2.43E+05 | 1.20E−02 | 49.4 | NB | | | 2.45E+05 | 1.13E−02 | 46.2 |
| E16 | 3.13E+05 | 1.58E−02 | 50.0 | NB | | | 3.00E+05 | 1.47E−02 | 48.8 |
| E17 | 2.82E+05 | 1.26E−02 | 44.8 | NB | | | 2.92E+05 | 1.26E−02 | 43.2 |
| E18 | 2.24E+05 | 1.18E−02 | 52.5 | NB | | | 2.26E+05 | 1.13E−02 | 50.0 |
| E19 | 1.56E+05 | 7.25E−03 | 46.6 | NB | | | 1.54E+05 | 6.87E−03 | 44.7 |
| E20 | 2.51E+05 | 2.78E−02 | 111.0 | NB | | | 2.51E+05 | 2.61E−02 | 104.0 |
| E21 | 2.25E+05 | 2.42E−02 | 107.0 | NB | | | 2.28E+05 | 2.45E−02 | 108.0 |

Abbreviations for Tables 73-74.
NB: No binding.
*indicates steady-state affinity ($k_a$ and $k_d$ values unavailable).

Example 34. Antibody Concentration Effects on Stability

Antibody A10 is prepared at varying concentrations in 10 mM histidine (pH 6.0). Each prepared sample is assessed for turbidity, viscosity, and for high molecular weight (HMW), antibody monomer, and low molecular weight (LMW) levels by size exclusion chromatography (SEC). SEC is performed initially and after one week at 25° C. Results are shown in Table 75 below.

Intrinsic fluorescence measurements are used to assess domain unfolding and aggregation formation as a function of temperature. Results are shown in Table 76 below.

TABLE 75

Antibody properties with varying concentration

| Nominal Conc [mg/mL] | Measured Conc [mg/mL] n = 2 | Turbidity [FNU] n = 2 | Viscosity @ 20°C [mPa * s] n = 2 | Initial | | | 1 wk @ 25° C. | | |
| --- | --- | --- | --- | --- | --- | --- | --- | --- | --- |
| | | | | HMW [%] | Mono [%] | LMW [%] | HMW [%] | Mono [%] | LMW [%] |
| 50 | 50.12 | 7.98 | 1.86 | 0.2 | 99.38 | 0.41 | 0.3 | 99.27 | 0.43 |
| 62.5 | 66.24 | 7.69 | 2.6 | 0.22 | 99.37 | 0.41 | 0.36 | 99.21 | 0.43 |
| 100 | 94.35 | 8.39 | 4.16 | 0.27 | 99.25 | 0.48 | 0.46 | 99.11 | 0.43 |
| 150 | 144.28 | 8.37 | 14.73 | 0.34 | 99.22 | 0.44 | 0.72 | 98.81 | 0.46 |
| 200 | 201.50 | 9.72 | 75.66** | 0.45 | 99.09 | 0.45 | 1 | 98.53 | 0.47 |
| 250 | 229.50 | 8.79 | 206.0** | 0.5 | 99.04 | 0.46 | 1.13 | 98.4 | 0.47 |

**viscosity measurement n = 1.
Abbreviations:
Conc: Concentration;
FNU: Formazin Nephelometric Unit;
HMW: High Molecular Weight;
Mono.: Monomer;
LMW: Low Molecular Weight.

TABLE 76

Intrinsic fluorescence measurement of antibody aggregation with varying concentration.

| Nominal Concentration [mg/mL] | Measured Concentration [mg/mL] n = 2 | IF $T_{off}$ [° C.] (n = 3) | IF $T_{m1}$ [° C.] (n = 3) | IF $T_{m2}$ [° C.] (n = 3) | IF $T_{agg}$ [° C.] (n = 3) |
|---|---|---|---|---|---|
| 50 | 50.12 | 63.4 | 69.3 | 80.0 | 76.5 |
| 62.5 | 66.24 | 63.4 | 69.3 | 80.3 | 76.4 |
| 100 | 94.35 | 63.4 | 69.2 | 80.5 | 75.7 |
| 150 | 144.28 | 63.6 | 68.8 | 80.7 | 75.4 |
| 200 | 201.50 | 63.6 | 68.3 | 81.0 | 76.0 |
| 250 | 229.50 | 63.4 | 68.1 | 81.2 | 74.5 |

Abbreviations:
$T_{off}$: transition onset point;
$T_{m1}$: first transition mid point;
$T_{m2}$: second transition mid point;
$T_{agg}$: transition onset of aggregation.

Methods

Turbidity. Turbidity is measured using a turbidity photometer. For each measurement, 130 μL of sample is placed in a single-use borosilicate glass round-bottom cuvette. The irradiation wavelength is 633 nm, and turbidity is measured by right angle light scattering. At least two replicates of each measurement are taken with a permitted deviation of ≤2%.

Viscosity. Viscosity is measured using the Haake MARS III Rheometer, Thermo Scientific. The measurement parameters are as follows: Cone: C35/1 (Ø 35 mm and 1° angle), titanium. Volume=210 μL, undiluted. Data analysis: 100 data points at shear rate 1000 s$^{-1}$. Temperature: 20° C.

Size exclusion chromatography. Size exclusion chromatography is conducted on UPLC-System e.g. Agilent 1290 Infinity II using the pre-column KrudKatcher Ultra HPLC In-Line Filter 0.5 μm×0.004 μm ID (Phenomenex, Torrance, Calif.) and the column Acquity UPLC BEH200SEC 300×4.6 mm, (Waters Corp., Milford, Mass.). The mobile phase is 40 mM NaH2PO4×H2O, 0.4 M NaClO4, pH 6.8 and the flow rate is 0.3 mL/min. The autosampler is maintained at 5° C. and the column is at room temperature. The detection is done by UV detector at wavelength of 280 nm. Peakwidth is >0.05 min (1 s) (for EmPower) or approx. 10 Hz (other software). The slit is 4 nm. Samples are diluted to 5 mg/mL in the mobile phase. The load amount is 30 μg per injection. The run time is 15 min. Integration is performed automatically with the algorithm Apex Track as default, peak area is approximately within a retention time of 4.5-11.5 min, with activation of the "detect shoulders" setting. The peak width is 20 sec and the detection threshold is 14.

Intrinsic fluorescence. Intrinsic fluorescence is measured using the Prometheus NT. 48 nano DSF (NanoTemper Technologies GmbH, Munich, Germany) using a standardized method. The sample volume is 10 μL per capillary, and the sample concentration and formulation is as indicated. Prometheus NT.48 Series nanoDSF Grade Standard Capillaries is used for protein concentrations >0.2 mg/mL, and Prometheus NT.48 Series nanoDSF Grade High Sensitivity Capillaries for concentrations 0.2 mg/mL. The temperature ramp is 20° C.-95° C. at 1° C./min. The excitation wavelength for intrinsic fluorescence is set to 285 nm and intensity is between 10%-30% (adapted depending on the optimal measuring range). The value of the detection ratio at 350/330 nm is plotted as a function against the temperature. The first derivation of this function is used for determination of Tonset and melting temperature, and Tonset is determined by light backscattering.

Example 35. Antibody Stability Testing

Antibody A10 is formulated at a concentration of 50 mg antibody/mL in 25 mM histidine and pH 6.0, with varying NaCl concentration. Properties of each formulation were assessed by SPR (Table 77) and SEC (Tables 78 and 79) initially and after 4 and 8 weeks held at 40° C.

TABLE 77

Change in binding activity (by SPR).

| | Activity [% change from baseline] | |
|---|---|---|
| NaCl [mM] | 4 weeks@40° C. | 8 weeks@40° C. |
| 25 | 84.92 | 73.35 |
| 50 | 85.63 | 74.13 |
| 75 | 86.01 | 74.86 |
| 100 | 86.58 | 76.08 |
| 150 | 87.64 | 77.52 |
| 200 | 88.37 | 78.79 |
| 250 | 89.02 | 79.95 |
| 500 | 90.71 | 82.68 |

TABLE 78

High molecular weight species levels.

| | High Molecular Weight [%] | |
|---|---|---|
| NaCl [mM] | 4 weeks@40° C. | 8 weeks@40° C. |
| 25 | 2.57 | 3.73 |
| 50 | 2.56 | 3.67 |
| 75 | 2.56 | 3.57 |
| 100 | 2.36 | 3.30 |
| 150 | 2.08 | 2.94 |
| 200 | 2.08 | 2.79 |
| 250 | 2.37 | 2.76 |
| 500 | 2.16 | 2.61 |

TABLE 79

Monomer levels.

| | Monomer [%] | |
|---|---|---|
| NaCl [mM] | 4 weeks@40° C. | 8 weeks@40° C. |
| 25 | 95.26 | 92.87 |
| 50 | 95.24 | 92.87 |
| 75 | 95.22 | 92.94 |
| 100 | 95.39 | 93.16 |
| 150 | 95.68 | 93.50 |
| 200 | 95.64 | 93.61 |
| 250 | 95.35 | 93.64 |
| 500 | 95.50 | 93.63 |

Methods

Surface plasmon resonance. Surface plasmon resonance spectroscopy is performed using the Biacore T200 (Cytiva, Marlborough, Mass.). Running- and dilution buffer are HBS-EP+ (Cytiva, Marlborough, Mass.). The analysis temperature was 25° C. and the data collection rate is 1 Hz using one flow cell. The Sensor Chip CM5 is used with high density Protein A/G immobilization. A predefined standard amine coupling method of the software is applied. The immobilization buffer is acetate at pH 4.5, 30 μg/ml, 420 s, 10μl/min. Analysis is performed by preparing a calibration curve from 2000-62.5 ng/ml with factor 1:2 and additional blank injections. Antibody samples are diluted to 1 μg/ml.

Human SIRPα V1 & V2 antigens are diluted to 10 µg/ml. For the build method, one cycle includes: capture of the antibody for 180 s, 10 µl/min; injecting antigen for 180 s, 10 µl/min; and regeneration with 50 mM HCl for 12 s, 50p/min. Evaluation of the received sensorgram was performed using the calibration curve to calculate Biacore concentration of samples for Protein A/G and antigen and calculate the binding activity for the antigen binding site.

Size exclusion chromatography. Size exclusion chromatography is performed as described in Example 34, above.

Example 36. Intrinsic Biophysical Profile Analysis

Methods

Physicochemical descriptors for the variable regions of selected antibodies are computed according to the methods described in Ahmed et al., *Proc Natl Acad Sci USA*. 2021. Sep. 14; 118(37):e2020577118 with a pH value of 7.4 and 137 mM salt. The five descriptors are: surface area buried between VL and VH domains (BSA_VL:VH), ratio of charged to hydrophobic surface patches (RP), ratio of dipole and hydrophobic moments (RM), hydrophobic anisotropy (Avg_HI), and structure-based isoelectric point (pIFv_3D). Each of these five descriptor values was used to compute Z-scores by comparing them with the average and standard deviation (SD) values of the corresponding descriptors for the 79 Fv regions contained in 77 approved antibody-based biotherapeutics (two of the approved biotherapeutics each contain two Fv regions). Each descriptor with a Z-score >1.96 or <−1.96 contributes a flag for an Fv region. The number of flags was summed for each selected antibody, such that an Fv region can collect up to five flags. The individual Z-scores for each Fv region are also combined to obtain its Z-distance as described (id.).

Results

The above procedures are used to evaluate intrinsic biophysical properties of selected antibodies. The variable region sequences of antibodies A-E, A1-A16, and E1-E22 are as disclosed above, and the sequence of antibodies L14, P11, S4, SB6, S7, S10, and S14 are as shown in Tables 80-81. Table 82 shows the values of each of the five descriptors. Table 83 shows the Z-score corresponding to each descriptor value, as well as the Z-distance computed from the five descriptors. Table 84 shows the flag values for each descriptor (0 indicate no flag and 1 indicates a flag, i.e., Z-score >1.96 or <−1.96) and the total number of flags for each antibody. For a given antibody, higher absolute Z-score values, higher numbers of flags, and higher Z-distance values each indicate greater deviation from the average properties of the 79 Fv regions contained in the 77 approved biotherapeutics used in the analysis.

TABLE 80

Sequences of Antibody Heavy Chain Variable Regions

| Antibody | Heavy Chain Variable Region Sequence | SEQ ID NO: |
|---|---|---|
| L14 | QVQLVQSGAEVKKPGASVKVSCKASGYNFNIYWINWVRQAPGQGL EWIGNIYPSSISTNYNEKFKTRATLTVDKSTSTVYMELSSLRSED TAVYYCARSEGTYYGGRYEGDWFGYWGQGTLVTVSS | 284 |
| P11 | EVQLVESGGGLVKPGGSLRLSCAASGFTFSSYVMSWVRQTPGKGL EWVATISSGGTYTYYPDSVKGRFTLSRDNAKNSLYLQMNSLRAED TAVYYCASQLTGSEFDYWGQGTTVTVSS | 286 |
| S4 | QSVEESGGRLGTPGTPLTLTCTVSGFSLSSYVMGWFRQAPGKGLE YIGIISSSGSPYYASWVNGRFTISKTSTTMDLKMNSPTTEDTATY FCARVGPLGVDYFNIWGPGTLVTVSL | 288 |
| SB6 | RQLVESGGGLVQPGGSLRLSCTASGFSLSSHGISWVRQAPGKGLE YIGTIGTGVITYFASWAKGRFTGSKTSSTAYMELSSLRSEDTAVY FCARGSAWNDPFDPWGQGTLVTVSS | 290 |
| S7 | RSVEESGGRLVTPGTPLTLTCTVSGFSLSSHGISWVRQAPGKGLE YIGTIGTGVITYFASWAKGRFTGSKTSTTVDLKITSPTTEDTATY FCARGSAWNDPFDPWGPGTLVTVSS | 292 |
| S10 | KVEESGGGLVQPGGSLRLSCAASGFSLSSYVMGWVRQAPGKGLEW VSIISSSGSPYYASWVNGRFTISKDNSEGMVYLQMNSLRAEDTAV YYCARVGPLGVDYFNIWGQGTTVTVSS | 294 |
| S14 | RQLVESGGGLVQPGGSLRLSCTASGFSLSSHGISWVRQAPGKGLE YIGTIGTGVITYFASWAKGRFTGSKTSSTAYMELSSLRSEDTAVY FCARGSAWNDPFDPWGQGTLVTVSS | 296 |

TABLE 81

Sequences of Antibody Light Chain Variable Regions

| Antibody | Light Chain Variable Region Sequence | SEQ ID NO: |
|---|---|---|
| L14 | DIQMTQSPSSLSASVGDRVTITCRASQDIRNYLNWYQQKPGKAPK LLIYFTSTLHSGVPSRFSGSGSGTDFTLTISSLQPEDFATYYCQQ GNTLPWTFGGGTKVEIK | 285 |
| P11 | DIVITQSPASLAVSLGERATISCRASESVDSYGNSFMHWYQQKPG QPPKLLIYRASNLESGVPDRFSGSGSRTDFTLTINPLQAEDVATY YCHQSGDLPWTFGGGTKVEIK | 287 |

TABLE 81-continued

Sequences of Antibody Light Chain Variable Regions

| Antibody | Light Chain Variable Region Sequence | SEQ ID NO: |
|---|---|---|
| S4 | DIVMTQTPSSVEAAVGGTVTIKCQAGQSINSYLAWYQQKPGQRPK LLIYYASTLESGVPSRFKGSGSGTDYTLTISDLESADAATYYCQS WHYISRSYAFGGGTEVVVK | 289 |
| SB6 | DIVMTQSPSSLSASVGDRVTITCQASQSVYGNNDLAWYQQKPGQA PKLLIYLASTLATGVPSRFSGSGSGTDFTLTISSLQPEDFATYYC LGGGDDEADNTFGQGTKVEIK | 291 |
| S7 | ALVMTQTPASVSAAVGGTVTTKCQASQSVYGNNDLAWYQHKPGQP PKLLIYLASTLATGVPSRFSGSGSGTQFTLTITGVQSDDAATYYC LGGGDDEADNVFGGGTEVVV | 293 |
| S10 | DIVMTQSPDSLAVSLGERATINCQAGQSINSYLAWYQQKPGQPPK LLIYYASTLESGVPDRFSGSGSGTDFTLTISSLQAEDVAVYYCQS WHYISRSYAFGGGTKLEIK | 295 |
| S14 | DIEMTQSPSSVSASVGDRVTLTCQASQSVYGNNDLAWYQQKPGQA PKLLIYLASTLATGVPSRFSGSGSGTDFTLTISSLQPEDFATYYC LGGGDDEADNVFGGGTKVEIK | 297 |

TABLE 82

Intrinsic Biophysical Properties of Antibodies

| Antibody | BSA_LC:HC | RP | RM | Avg_HI | pIFv_3D |
|---|---|---|---|---|---|
| A | 757.565 | 2.182 | 1.052 | 1.147 | 7.401 |
| B | 880.962 | 1.78 | 1.174 | 1.897 | 8.426 |
| C | 746.141 | 3.2 | 1.097 | 0.822 | 7.342 |
| D | 724.277 | 2.028 | 0.794 | 0.884 | 7.357 |
| E | 814.084 | 1.605 | 1.135 | 0.576 | 8.001 |
| A1 | 772.203 | 1.236 | 0.567 | 0.645 | 7.313 |
| A2 | 754.856 | 2.407 | 0.941 | 1.007 | 7.84 |
| A3 | 749.195 | 1.6 | 0.981 | 0.956 | 7.65 |
| A4 | 774.46 | 1.54 | 1.03 | 0.614 | 7.445 |
| A5 | 779.811 | 1.913 | 1.157 | 0.578 | 7.474 |
| A6 | 811.151 | 1.946 | 0.961 | 0.641 | 6.771 |
| A7 | 754.862 | 2.094 | 0.949 | 0.956 | 7.826 |
| A8 | 758.408 | 1.415 | 1.145 | 0.571 | 7.474 |
| A9 | 722.586 | 1.472 | 1.131 | 0.781 | 5.415 |
| A10 | 740.85 | 1.5 | 1.048 | 1.182 | 7.401 |
| A11 | 771.402 | 2.031 | 1.088 | 1.083 | 7.372 |
| A12 | 763.62 | 1.882 | 1.071 | 1.117 | 7.386 |
| A13 | 716.196 | 1.592 | 1.303 | 0.659 | 6.581 |
| A14 | 752.533 | 1.771 | 1.283 | 0.629 | 6.405 |
| A15 | 731.64 | 1.228 | 1.096 | 0.758 | 5.783 |
| A16 | 730.942 | 1.604 | 1.298 | 0.741 | 6.443 |
| E1 | 897.824 | 2 | 0.972 | 0.818 | 7.84 |
| E2 | 862.05 | 1.5 | 1.327 | 0.624 | 8.031 |
| E3 | 880.578 | 1.786 | 1.121 | 0.915 | 8.397 |
| E4 | 865.757 | 1.969 | 1.241 | 0.953 | 8.119 |
| E5 | 806.757 | 3 | 1.123 | 1.295 | 8.646 |
| E6 | 871.934 | 3.333 | 1.292 | 1.147 | 8.529 |
| E7 | 858.2 | 2.152 | 0.991 | 0.996 | 8.368 |
| E8 | 892.703 | 2.086 | 0.745 | 0.553 | 7.518 |
| E9 | 848.808 | 1.426 | 1.155 | 0.659 | 8.001 |
| E10 | 849.995 | 2.194 | 1.133 | 1.144 | 8.397 |
| E11 | 842.435 | 1.789 | 0.796 | 0.685 | 7.401 |
| E12 | 910.73 | 1.478 | 1.219 | 0.883 | 8.353 |
| E13 | 827.903 | 1.744 | 0.928 | 0.567 | 8.148 |
| E14 | 835.996 | 2.3 | 1.314 | 1.12 | 8.646 |
| E15 | 817.36 | 1.639 | 1.007 | 1.031 | 8.031 |
| E16 | 874.806 | 1.795 | 1.236 | 0.971 | 8.397 |
| E17 | 847.622 | 1.65 | 0.94 | 0.514 | 7.606 |
| E18 | 840.334 | 1.933 | 1.234 | 1.14 | 8.236 |
| E19 | 871.606 | 1.634 | 1.124 | 0.756 | 8.294 |
| E20 | 821.97 | 1.465 | 0.903 | 0.447 | 7.928 |
| E21 | 842.136 | 1.477 | 1.447 | 0.956 | 8.382 |
| E22 | 886.351 | 2.793 | 1.236 | 0.985 | 7.987 |
| L14 | 992.129 | 1.929 | 0.654 | 1.426 | 8.617 |
| P11 | 759.501 | 1.795 | 1.69 | 0.685 | 6.481 |
| S4 | 893.191 | 1.829 | 1.359 | 1.002 | 6.756 |
| SB6 | 895.402 | 1.784 | 1.251 | 1.265 | 5.846 |
| S7 | 819.933 | 2.129 | 0.765 | 0.353 | 5.757 |
| S10 | 841.792 | 1.523 | 0.882 | 1.133 | 5.415 |
| S14 | 871.617 | 1.822 | 1.511 | 1.403 | 5.313 |

TABLE 83

Z-scores and Z-distances Computed from Intrinsic Biophysical Properties of Antibodies

| Antibody | Z score | | | | | Z-distance |
|---|---|---|---|---|---|---|
| | BSA_LC:HC | RP | RM | Avg_HI | pIFv_3D | |
| A | −0.813 | −0.003 | −0.098 | 0.551 | −0.306 | 1.034 |
| B | 0.678 | −0.315 | 0.068 | 2.503 | 0.515 | 2.664 |
| C | −0.952 | 0.787 | −0.038 | −0.293 | −0.353 | 1.318 |
| D | −1.216 | −0.123 | −0.454 | −0.131 | −0.342 | 1.354 |
| E | −0.13 | −0.451 | 0.015 | −0.933 | 0.175 | 1.059 |
| A1 | −0.636 | −0.737 | −0.766 | −0.753 | −0.377 | 1.498 |
| A2 | −0.846 | 0.172 | −0.252 | 0.188 | 0.046 | 0.92 |
| A3 | −0.915 | −0.455 | −0.197 | 0.055 | −0.107 | 1.047 |

TABLE 83-continued

Z-scores and Z-distances Computed from Intrinsic Biophysical Properties of Antibodies

| Antibody | Z score | | | | | Z-distance |
|---|---|---|---|---|---|---|
| | BSA_LC:HC | RP | RM | Avg_HI | pIFv_3D | |
| A4 | −0.609 | −0.501 | −0.129 | −0.833 | −0.271 | 1.186 |
| A5 | −0.544 | −0.212 | 0.045 | −0.927 | −0.248 | 1.124 |
| A6 | −0.166 | −0.186 | −0.223 | −0.764 | −0.811 | 1.164 |
| A7 | −0.846 | −0.071 | −0.241 | 0.056 | 0.034 | 0.885 |
| A8 | −0.803 | −0.598 | 0.029 | −0.947 | −0.248 | 1.401 |
| A9 | −1.236 | −0.554 | 0.01 | −0.401 | −1.898 | 2.366 |
| A10 | −1.015 | −0.532 | −0.105 | 0.643 | −0.306 | 1.354 |
| A11 | −0.646 | −0.12 | −0.05 | 0.385 | −0.33 | 0.831 |
| A12 | −0.74 | −0.236 | −0.072 | 0.473 | −0.318 | 0.966 |
| A13 | −1.314 | −0.461 | 0.247 | −0.718 | −0.964 | 1.855 |
| A14 | −0.874 | −0.322 | 0.219 | −0.797 | −1.104 | 1.664 |
| A15 | −1.127 | −0.743 | −0.038 | −0.46 | −1.603 | 2.146 |
| A16 | −1.135 | −0.452 | 0.239 | −0.505 | −1.074 | 1.72 |
| E1 | 0.882 | −0.144 | −0.209 | −0.305 | 0.046 | 0.968 |
| E2 | 0.45 | −0.532 | 0.28 | −0.808 | 0.198 | 1.121 |
| E3 | 0.674 | −0.311 | −0.004 | −0.051 | 0.492 | 0.891 |
| E4 | 0.495 | −0.168 | 0.161 | 0.048 | 0.269 | 0.611 |
| E5 | −0.219 | 0.632 | −0.001 | 0.938 | 0.691 | 1.343 |
| E6 | 0.569 | 0.891 | 0.232 | 0.553 | 0.597 | 1.354 |
| E7 | 0.403 | −0.027 | −0.183 | 0.159 | 0.468 | 0.664 |
| E8 | 0.82 | −0.078 | −0.521 | −0.994 | −0.213 | 1.409 |
| E9 | 0.29 | −0.59 | 0.043 | −0.716 | 0.175 | 0.989 |
| E10 | 0.304 | 0.006 | 0.013 | 0.544 | 0.492 | 0.794 |
| E11 | 0.213 | −0.308 | −0.451 | −0.649 | −0.306 | 0.927 |
| E12 | 1.038 | −0.549 | 0.13 | −0.134 | 0.456 | 1.274 |
| E13 | 0.037 | −0.343 | −0.27 | −0.958 | 0.292 | 1.093 |
| E14 | 0.135 | 0.089 | 0.262 | 0.483 | 0.691 | 0.897 |
| E15 | −0.091 | −0.425 | −0.161 | 0.25 | 0.198 | 0.562 |
| E16 | 0.604 | −0.303 | 0.155 | 0.093 | 0.492 | 0.855 |
| E17 | 0.275 | −0.416 | −0.252 | −1.094 | −0.142 | 1.237 |
| E18 | 0.187 | −0.196 | 0.152 | 0.534 | 0.362 | 0.716 |
| E19 | 0.565 | −0.428 | 0.001 | −0.464 | 0.409 | 0.941 |
| E20 | −0.035 | −0.559 | −0.303 | −1.268 | 0.116 | 1.424 |
| E21 | 0.209 | −0.55 | 0.444 | 0.054 | 0.48 | 0.881 |
| E22 | 0.744 | 0.471 | 0.154 | 0.13 | 0.163 | 0.918 |
| L14 | 2.022 | −0.2 | −0.646 | 1.278 | 0.668 | 2.574 |
| P11 | −0.79 | −0.303 | 0.779 | −0.649 | −1.043 | 1.683 |
| S4 | 0.826 | −0.277 | 0.323 | 0.174 | −0.823 | 1.254 |
| SB6 | 0.853 | −0.312 | 0.176 | 0.858 | −1.552 | 2 |
| S7 | −0.059 | −0.044 | −0.494 | −1.513 | −1.623 | 2.275 |
| S10 | 0.205 | −0.515 | −0.333 | 0.515 | −1.898 | 2.07 |
| S14 | 0.565 | −0.282 | 0.533 | 1.218 | −1.979 | 2.467 |

TABLE 84

Flag Values Computed from Intrinsic Biophysical Properties of Antibodies

| Antibody | Flag | | | | | Total |
|---|---|---|---|---|---|---|
| | BSA_LC:HC | RP | RM | Avg_HI | pIFv_3D | |
| A | 0 | 0 | 0 | 0 | 0 | 0 |
| B | 0 | 0 | 0 | 1 | 0 | 1 |
| C | 0 | 0 | 0 | 0 | 0 | 0 |
| D | 0 | 0 | 0 | 0 | 0 | 0 |
| E | 0 | 0 | 0 | 0 | 0 | 0 |
| A1 | 0 | 0 | 0 | 0 | 0 | 0 |
| A2 | 0 | 0 | 0 | 0 | 0 | 0 |
| A3 | 0 | 0 | 0 | 0 | 0 | 0 |
| A4 | 0 | 0 | 0 | 0 | 0 | 0 |
| A5 | 0 | 0 | 0 | 0 | 0 | 0 |
| A6 | 0 | 0 | 0 | 0 | 0 | 0 |
| A7 | 0 | 0 | 0 | 0 | 0 | 0 |
| A8 | 0 | 0 | 0 | 0 | 0 | 0 |
| A9 | 0 | 0 | 0 | 0 | 0 | 0 |
| A10 | 0 | 0 | 0 | 0 | 0 | 0 |
| A11 | 0 | 0 | 0 | 0 | 0 | 0 |
| A12 | 0 | 0 | 0 | 0 | 0 | 0 |
| A13 | 0 | 0 | 0 | 0 | 0 | 0 |
| A14 | 0 | 0 | 0 | 0 | 0 | 0 |
| A15 | 0 | 0 | 0 | 0 | 0 | 0 |
| A16 | 0 | 0 | 0 | 0 | 0 | 0 |
| E1 | 0 | 0 | 0 | 0 | 0 | 0 |
| E2 | 0 | 0 | 0 | 0 | 0 | 0 |
| E3 | 0 | 0 | 0 | 0 | 0 | 0 |
| E4 | 0 | 0 | 0 | 0 | 0 | 0 |
| E5 | 0 | 0 | 0 | 0 | 0 | 0 |
| E6 | 0 | 0 | 0 | 0 | 0 | 0 |
| E7 | 0 | 0 | 0 | 0 | 0 | 0 |
| E8 | 0 | 0 | 0 | 0 | 0 | 0 |
| E9 | 0 | 0 | 0 | 0 | 0 | 0 |
| E10 | 0 | 0 | 0 | 0 | 0 | 0 |
| E11 | 0 | 0 | 0 | 0 | 0 | 0 |
| E12 | 0 | 0 | 0 | 0 | 0 | 0 |
| E13 | 0 | 0 | 0 | 0 | 0 | 0 |
| E14 | 0 | 0 | 0 | 0 | 0 | 0 |
| E15 | 0 | 0 | 0 | 0 | 0 | 0 |

TABLE 84-continued

Flag Values Computed from Intrinsic Biophysical Properties of Antibodies

| Antibody | BSA_LC:HC | RP | RM | Avg_HI | pIFv_3D | Total |
|---|---|---|---|---|---|---|
| E16 | 0 | 0 | 0 | 0 | 0 | 0 |
| E17 | 0 | 0 | 0 | 0 | 0 | 0 |
| E18 | 0 | 0 | 0 | 0 | 0 | 0 |
| E19 | 0 | 0 | 0 | 0 | 0 | 0 |
| E20 | 0 | 0 | 0 | 0 | 0 | 0 |
| E21 | 0 | 0 | 0 | 0 | 0 | 0 |
| E22 | 0 | 0 | 0 | 0 | 0 | 0 |
| L14 | 1 | 0 | 0 | 0 | 0 | 1 |
| P11 | 0 | 0 | 0 | 0 | 0 | 0 |
| S4 | 0 | 0 | 0 | 0 | 0 | 0 |
| SB6 | 0 | 0 | 0 | 0 | 0 | 0 |
| S7 | 0 | 0 | 0 | 0 | 0 | 0 |
| S10 | 0 | 0 | 0 | 0 | 0 | 0 |
| S14 | 0 | 0 | 0 | 0 | 1 | 1 |

Example 37. Analysis of Humanness of Antibody Sequences

Methods

Percentage human identity ("humanness") values are computed for the variable light and variable heavy sequences of selected antibodies using the methods described in Jones et al. MAbs. 2016; 8(1):1-9. doi: 10.1080/19420862.2015.1114320. In brief, the humanized sequences are compared to their closest human germline counterparts, and percentage identity is determined for each.

Results

The above procedures are used to measure the percentage humanness of the light- and heavy-chain variable regions of selected antibodies. Results are shown in Table 85. Higher % Humanness values indicate greater similarity to human germline antibody sequences.

TABLE 85

Percentage Humanness Values of Antibodies

| Antibody | VH Germ line | VH % Humanness | VL Germ line | VL % Humanness |
|---|---|---|---|---|
| A | IGHV3-13*01 | 96.907 | IGKV1-16*02 | 94.737 |
| B | IGHV1-2*02 | 98.958 | IGKV1-12*01 | 98.947 |
| C | IGHV3-13*01 | 96.907 | IGKV1-16*02 | 93.684 |
| D | IGHV3-13*01 | 94.845 | IGKV1-16*02 | 95.789 |
| E | IGHV4-59*01 | 86.598 | IGKV2-28*01 | 96 |
| A1 | IGHV3-13*01 | 94.845 | IGKV1-16*02 | 94.737 |
| A2 | IGHV3-13*01 | 95.876 | IGKV1-16*02 | 94.737 |
| A3 | IGHV3-13*01 | 95.876 | IGKV1-16*02 | 94.737 |
| A4 | IGHV3-13*01 | 94.845 | IGKV1-16*02 | 94.737 |
| A5 | IGHV3-13*01 | 94.845 | IGKV1-16*02 | 94.737 |
| A6 | IGHV3-13*01 | 94.845 | IGKV1-16*02 | 94.737 |
| A7 | IGHV3-13*01 | 96.907 | IGKV1-16*02 | 94.737 |
| A8 | IGHV3-13*01 | 95.876 | IGKV1-16*02 | 94.737 |
| A9 | IGHV3-13*01 | 94.845 | IGKV1-16*02 | 94.737 |
| A10 | IGHV3-13*01 | 95.876 | IGKV1-16*02 | 94.737 |
| A11 | IGHV3-13*01 | 95.876 | IGKV1-16*02 | 94.737 |
| A12 | IGHV3-13*01 | 95.876 | IGKV1-16*02 | 94.737 |
| A13 | IGHV3-13*01 | 94.845 | IGKV1-16*02 | 94.737 |
| A14 | IGHV3-13*01 | 94.845 | IGKV1-16*02 | 94.737 |
| A15 | IGHV3-13*01 | 94.845 | IGKV1-16*02 | 94.737 |
| A16 | IGHV3-13*01 | 95.876 | IGKV1-16*02 | 94.737 |
| E1 | IGHV4-59*01 | 87.629 | IGKV2-28*01 | 94 |
| E2 | IGHV4-59*01 | 87.629 | IGKV2-28*01 | 96 |
| E3 | IGHV4-59*01 | 88.66 | IGKV2-28*01 | 94 |
| E4 | IGHV4-59*01 | 88.66 | IGKV2-28*01 | 96 |
| E5 | IGHV4-59*01 | 88.66 | IGKV2-28*01 | 94 |
| E6 | IGHV4-59*01 | 88.66 | IGKV2-28*01 | 96 |
| E7 | IGHV4-59*01 | 89.691 | IGKV2-28*01 | 94 |
| E8 | IGHV4-4*08 | 85.567 | IGKV2-28*01 | 94 |
| E9 | IGHV4-59*01 | 87.629 | IGKV2-28*01 | 96 |
| E10 | IGHV4-59*01 | 89.691 | IGKV2-28*01 | 96 |
| E11 | IGHV4-4*08 | 85.567 | IGKV2-28*01 | 96 |
| E12 | IGHV4-59*01 | 88.66 | IGKV2-28*01 | 96 |
| E13 | IGHV4-59*01 | 87.629 | IGKV2-28*01 | 94 |
| E14 | IGHV4-59*01 | 88.66 | IGKV2-28*01 | 96 |
| E15 | IGHV4-59*01 | 87.629 | IGKV2-28*01 | 96 |
| E16 | IGHV4-59*01 | 89.691 | IGKV2-28*01 | 96 |
| E17 | IGHV4-4*08 | 85.567 | IGKV2-28*01 | 96 |
| E18 | IGHV4-59*01 | 88.66 | IGKV2-28*01 | 96 |
| E19 | IGHV4-59*01 | 88.66 | IGKV2-28*01 | 94 |
| E20 | IGHV4-59*01 | 87.629 | IGKV2-28*01 | 96 |
| E21 | IGHV4-59*01 | 88.66 | IGKV2-28*01 | 96 |
| E22 | IGHV4-59*01 | 88.66 | IGKV2-28*01 | 92 |
| L14 | IGHV1-46*02 | 80.612 | IGKV1-39*01 | 88.421 |
| P11 | IGHV3-2V01 | 88.66 | IGKV7-3*01 | 73.737 |
| S4 | IGHV3-64*04 | 60.215 | IGKV1-27*01 | 70.652 |
| SB6 | IGHV3-66*01 | 67.368 | IGKV1-6*01 | 85.556 |
| S7 | IGHV3-53*04 | 54.348 | IGKV1-6*01 | 65.934 |
| S10 | IGHV3-66*01 | 81.522 | IGKV4-1*01 | 82.653 |
| S14 | IGHV3-66*01 | 67.368 | IGKV1-6*01 | 83.333 |

What is claimed is:

1. An anti-SIRPα antibody or an antigen-binding fragment thereof comprising:
   a heavy chain variable region comprising the amino acid sequence of SEQ ID NO: 33 (H-CDR1); the amino acid sequence of SEQ ID NO: 34 (H-CDR2); and the amino acid sequence of SEQ ID NO: 35 (H-CDR3); and
   a light chain variable region comprising the amino acid sequence of SEQ ID NO: 36 or SEQ ID NO: 37 (L-CDR1); the amino acid sequence of SEQ ID NO: 38 (L-CDR2); and the amino acid sequence of SEQ ID NO: 39 (L-CDR3).

2. The anti-SIRPα antibody or antigen-binding fragment thereof according to claim 1, wherein the antibody or antigen-binding fragment thereof comprises:
   a heavy chain variable region comprising the amino acid sequence of SEQ ID NO: 33 (H-CDR1); the amino acid sequence of SEQ ID NO: 34 (H-CDR2); and the amino acid sequence of SEQ ID NO: 35 (H-CDR3); and
   a light chain variable region comprising the amino acid sequence of SEQ ID NO: 37 (L-CDR1); the amino acid sequence of SEQ ID NO: 38 (L-CDR2); and the amino acid sequence of SEQ ID NO: 39 (L-CDR3).

3. The anti-SIRPα antibody or antigen-binding fragment thereof according to claim 1, wherein the antibody or antigen-binding fragment thereof comprises:
   a heavy chain variable region comprising the amino acid sequence of SEQ ID NO: 33 (H-CDR1); the amino acid sequence of SEQ ID NO: 34 (H-CDR2); and the amino acid sequence of SEQ ID NO: 35 (H-CDR3); and
   a light chain variable region comprising the amino acid sequence of SEQ ID NO: 36 (L-CDR1); the amino acid sequence of SEQ ID NO: 38 (L-CDR2); and the amino acid sequence of SEQ ID NO: 39 (L-CDR3).

4. The anti-SIRPα antibody or antigen-binding fragment thereof according to claim 1, wherein the antibody or antigen-binding fragment thereof comprises:
- a) a heavy chain variable region comprising the amino acid sequence of SEQ ID NO: 100; and a light chain variable region comprising the amino acid sequence of SEQ ID NO: 105; or
- b) a heavy chain variable region comprising the amino acid sequence of SEQ ID NO: 110; and a light chain variable region comprising the amino acid sequence of SEQ ID NO: 125; or
- c) a heavy chain variable region comprising the amino acid sequence of SEQ ID NO: 111; and a light chain variable region comprising the amino acid sequence of SEQ ID NO: 125; or
- d) a heavy chain variable region comprising the amino acid sequence of SEQ ID NO: 112; and a light chain variable region comprising the amino acid sequence of SEQ ID NO: 125; or
- e) a heavy chain variable region comprising the amino acid sequence of SEQ ID NO: 113; and a light chain variable region comprising the amino acid sequence of SEQ ID NO: 125; or
- f) a heavy chain variable region comprising the amino acid sequence of SEQ ID NO: 114; and a light chain variable region comprising the amino acid sequence of SEQ ID NO: 125; or
- g) a heavy chain variable region comprising the amino acid sequence of SEQ ID NO: 115; and a light chain variable region comprising the amino acid sequence of SEQ ID NO: 125; or
- h) a heavy chain variable region comprising the amino acid sequence of SEQ ID NO: 116; and a light chain variable region comprising the amino acid sequence of SEQ ID NO: 125; or
- i) a heavy chain variable region comprising the amino acid sequence of SEQ ID NO: 117; and a light chain variable region comprising the amino acid sequence of SEQ ID NO: 125; or
- j) a heavy chain variable region comprising the amino acid sequence of SEQ ID NO: 110; and a light chain variable region comprising the amino acid sequence of SEQ ID NO: 126; or
- k) a heavy chain variable region comprising the amino acid sequence of SEQ ID NO: 111; and a light chain variable region comprising the amino acid sequence of SEQ ID NO: 126; or
- l) a heavy chain variable region comprising the amino acid sequence of SEQ ID NO: 112; and a light chain variable region comprising the amino acid sequence of SEQ ID NO: 126; or
- m) a heavy chain variable region comprising the amino acid sequence of SEQ ID NO: 113; and a light chain variable region comprising the amino acid sequence of SEQ ID NO: 126; or
- n) a heavy chain variable region comprising the amino acid sequence of SEQ ID NO: 114; and a light chain variable region comprising the amino acid sequence of SEQ ID NO: 126; or
- o) a heavy chain variable region comprising the amino acid sequence of SEQ ID NO: 115; and a light chain variable region comprising the amino acid sequence of SEQ ID NO: 126; or
- p) a heavy chain variable region comprising the amino acid sequence of SEQ ID NO: 117; and a light chain variable region comprising the amino acid sequence of SEQ ID NO: 126.

5. The anti-SIRPα antibody or antigen-binding fragment thereof according to claim 1, wherein the antibody or antigen-binding fragment thereof comprises:
- a heavy chain variable region comprising the amino acid sequence of SEQ ID NO: 100; and a light chain variable region comprising the amino acid sequence of SEQ ID NO: 105.

6. The anti-SIRPα antibody according to claim 1, wherein the antibody comprises:
- a) a heavy chain comprising the amino acid sequence of SEQ ID NO: 131; and a light chain comprising the amino acid sequence of SEQ ID NO: 174; or
- b) a heavy chain comprising the amino acid sequence of SEQ ID NO: 138; and a light chain comprising the amino acid sequence of SEQ ID NO: 181; or
- c) a heavy chain comprising the amino acid sequence of SEQ ID NO: 139; and a light chain comprising the amino acid sequence of SEQ ID NO: 182; or
- d) a heavy chain comprising the amino acid sequence of SEQ ID NO: 140; and a light chain comprising the amino acid sequence of SEQ ID NO: 183; or
- e) a heavy chain comprising the amino acid sequence of SEQ ID NO: 141; and a light chain comprising the amino acid sequence of SEQ ID NO: 184; or
- f) a heavy chain comprising the amino acid sequence of SEQ ID NO: 142; and a light chain comprising the amino acid sequence of SEQ ID NO: 185; or
- g) a heavy chain comprising the amino acid sequence of SEQ ID NO: 143; and a light chain comprising the amino acid sequence of SEQ ID NO: 186; or
- h) a heavy chain comprising the amino acid sequence of SEQ ID NO: 144; and a light chain comprising the amino acid sequence of SEQ ID NO: 187; or
- i) a heavy chain comprising the amino acid sequence of SEQ ID NO: 145; and a light chain comprising the amino acid sequence of SEQ ID NO: 188; or
- j) a heavy chain comprising the amino acid sequence of SEQ ID NO: 146; and a light chain comprising the amino acid sequence of SEQ ID NO: 189; or
- k) a heavy chain comprising the amino acid sequence of SEQ ID NO: 147; and a light chain comprising the amino acid sequence of SEQ ID NO: 190; or
- l) a heavy chain comprising the amino acid sequence of SEQ ID NO: 148; and a light chain comprising the amino acid sequence of SEQ ID NO: 191; or
- m) a heavy chain comprising the amino acid sequence of SEQ ID NO: 149; and a light chain comprising the amino acid sequence of SEQ ID NO: 192; or
- n) a heavy chain comprising the amino acid sequence of SEQ ID NO: 150; and a light chain comprising the amino acid sequence of SEQ ID NO: 193; or
- o) a heavy chain comprising the amino acid sequence of SEQ ID NO: 151; and a light chain comprising the amino acid sequence of SEQ ID NO: 194; or
- p) a heavy chain comprising the amino acid sequence of SEQ ID NO: 152; and a light chain comprising the amino acid sequence of SEQ ID NO: 195; or
- q) a heavy chain comprising the amino acid sequence of SEQ ID NO: 217; and a light chain comprising the amino acid sequence of SEQ ID NO: 218.

7. The anti-SIRPα antibody according to claim 1, wherein the antibody comprises:
- a) a heavy chain comprising the amino acid sequence of SEQ ID NO: 131; and a light chain comprising the amino acid sequence of SEQ ID NO: 174; or b) a heavy chain comprising the amino acid sequence of SEQ ID NO: 132; and a light chain comprising the amino acid sequence of SEQ ID NO: 175.

8. The anti-SIRPα antibody or antigen-binding fragment thereof according to claim 1, wherein the anti-SIRPα antibody is a monoclonal antibody.

9. The anti-SIRPα antibody or antigen-binding fragment thereof according to claim 1, wherein the anti-SIRPα antibody is a human antibody.

10. The anti-SIRPα antibody or antigen-binding fragment thereof according to claim 1, wherein the anti-SIRPα antibody or antigen-binding fragment thereof binds to human SIRPα at a $K_D \leq 10$ nM.

11. The anti-SIRPα antibody or antigen-binding fragment thereof according to claim 10, wherein the anti-SIRPα antibody or antigen-binding fragment thereof binds to cynomolgus SIRPα at a $K_D \leq 400$ nM.

12. A pharmaceutical composition comprising the anti-SIRPα antibody or antigen-binding fragment thereof according to claim 1 and a pharmaceutically acceptable carrier.

13. A method of treating a cancer in a subject in need thereof, the method comprising administering a therapeutically effective amount of the anti-SIRPα antibody or antigen-binding fragment thereof according to claim 1 to the subject in need thereof.

14. An isolated polynucleotide composition, the isolated polynucleotide composition comprising:
   a) a first isolated polynucleotide encoding the heavy chain variable region according to claim 1; and/or
   b) a second isolated polynucleotide encoding the light chain variable region according to claim 1.

15. An expression vector composition, the expression vector composition comprising:
   a) a first expression vector comprising the first isolated polynucleotide of claim 14; and/or
   b) a second expression vector comprising the second isolated polynucleotide of claim 14.

16. A host cell comprising the isolated polynucleotide composition according to claim 14.

17. A method for the production of an anti-SIRPα antibody or antigen-binding fragment thereof, comprising the steps:
   a) cultivating the host cell of claim 16 under conditions for expression of the anti-SIRPα antibody or antigen-binding fragment thereof; and
   b) recovering the anti-SIRPα antibody or antigen-binding fragment thereof.

18. An anti-SIRPα antibody or antigen-binding fragment thereof, wherein the anti-SIRPα antibody or antigen-binding fragment thereof comprises:
   a heavy chain variable region comprising the amino acid sequence of SEQ ID NO: 113; and a light chain variable region comprising the amino acid sequence of SEQ ID NO: 125.

19. An anti-SIRPα antibody, wherein the anti-SIRPα antibody comprises:
   a heavy chain variable region comprising the amino acid sequence of SEQ ID NO: 113; and a light chain variable region comprising the amino acid sequence of SEQ ID NO: 125.

20. An anti-SIRPα antibody or antigen-binding fragment thereof, wherein the anti-SIRPα antibody or antigen-binding fragment thereof comprises:
   a heavy chain variable region comprising the amino acid sequence of SEQ ID NO: 111; and a light chain variable region comprising the amino acid sequence of SEQ ID NO: 126.

21. An anti-SIRPα antibody, wherein the anti-SIRPα antibody comprises:
   a heavy chain variable region comprising the amino acid sequence of SEQ ID NO: 111; and a light chain variable region comprising the amino acid sequence of SEQ ID NO: 126.

22. An anti-SIRPα antibody, wherein the anti-SIRPα antibody comprises:
   a heavy chain comprising the amino acid sequence of SEQ ID NO: 141; and a light chain comprising the amino acid sequence of SEQ ID NO: 184.

23. An anti-SIRPα antibody, wherein the anti-SIRPα antibody comprises:
   a heavy chain comprising the amino acid sequence of SEQ ID NO: 147; and a light chain comprising the amino acid sequence of SEQ ID NO: 190.

24. An anti-SIRPα antibody, wherein the anti-SIRPα antibody comprises:
   a heavy chain comprising the amino acid sequence of SEQ ID NO: 217; and a light chain comprising the amino acid sequence of SEQ ID NO: 218.

25. The anti-SIRPα antibody according to claim 4, wherein the anti-SIRPα antibody is a monoclonal antibody.

26. The anti-SIRPα antibody according to claim 4, wherein the anti-SIRPα antibody is a human antibody.

27. The anti-SIRPα antibody or antigen-binding fragment thereof according to claim 4, wherein the anti-SIRPα antibody or antigen-binding fragment thereof binds to human SIRPα at a $K_D \leq 10$ nM.

28. The anti-SIRPα antibody or antigen-binding fragment thereof according to claim 27, wherein the anti-SIRPα antibody or antigen-binding fragment thereof binds to cynomolgus SIRPα at a $K_D \leq 400$ nM.

29. A pharmaceutical composition comprising the anti-SIRPα antibody or antigen-binding fragment thereof according to claim 4 and a pharmaceutically acceptable carrier.

30. A method of treating a cancer in a subject in need thereof, the method comprising administering a therapeutically effective amount of the anti-SIRPα antibody or antigen-binding fragment thereof according to claim 4 to the subject in need thereof.

31. An isolated polynucleotide composition, the isolated polynucleotide composition comprising:
   a) a first isolated polynucleotide encoding the heavy chain variable region according to claim 4; and/or
   b) a second isolated polynucleotide encoding the light chain variable region according to claim 4.

32. An expression vector composition, the expression vector composition comprising:
   a) a first expression vector comprising the first isolated polynucleotide of claim 31; and/or
   b) a second expression vector comprising the second isolated polynucleotide of claim 31.

33. A host cell comprising the isolated polynucleotide composition according to claim 31.

34. A method for the production of an anti-SIRPα antibody or antigen-binding fragment thereof, comprising the steps:
   a) cultivating the host cell of claim 33 under conditions for expression of the anti-SIRPα antibody or antigen-binding fragment thereof; and b) recovering the anti-SIRPα antibody or antigen-binding fragment thereof.

35. The anti-SIRPα antibody according to claim 6, wherein the anti-SIRPα antibody is a monoclonal antibody.

36. The anti-SIRPα antibody according to claim 6, wherein the anti-SIRPα antibody binds to human SIRPα at a $K_D \leq 10$ nM.

37. The anti-SIRPα antibody according to claim 36, wherein the anti-SIRPα antibody binds to cynomolgus SIRPα at a $K_D \leq 400$ nM.

38. A pharmaceutical composition comprising the anti-SIRPα antibody according to claim 6 and a pharmaceutically acceptable carrier.

39. A method of treating a cancer in a subject in need thereof, the method comprising administering a therapeutically effective amount of the anti-SIRPα antibody according to claim 6 to the subject in need thereof.

40. An isolated polynucleotide composition, the isolated polynucleotide composition comprising:
    a) a first isolated polynucleotide encoding the heavy chain according to claim 6; and/or
    b) a second isolated polynucleotide encoding the light chain according to claim 6.

41. An expression vector composition, the expression vector composition comprising:
    a) a first expression vector comprising the first isolated polynucleotide of claim 40; and/or
    b) a second expression vector comprising the second isolated polynucleotide of claim 40.

42. A host cell comprising the isolated polynucleotide composition according to claim 40.

43. A method for the production of an anti-SIRPα antibody, comprising the steps:
    a) cultivating the host cell of claim 42 under conditions for expression of the anti-SIRPα antibody; and
    b) recovering the anti-SIRPα antibody.

44. A pharmaceutical composition comprising the anti-SIRPα antibody according to claim 22 and a pharmaceutically acceptable carrier.

45. A method of treating a cancer in a subject in need thereof, the method comprising administering a therapeutically effective amount of the anti-SIRPα antibody according to claim 22 to the subject in need thereof.

46. An isolated polynucleotide composition, the isolated polynucleotide composition comprising:
    a) a first isolated polynucleotide encoding the heavy chain according to claim 22; and/or
    b) a second isolated polynucleotide encoding the light chain according to claim 22.

47. An expression vector composition, the composition comprising:
    a) a first expression vector comprising the first isolated polynucleotide of claim 46; and/or
    b) a second expression vector comprising the second isolated polynucleotide of claim 46.

48. A host cell comprising the isolated polynucleotide composition according to claim 46.

49. A method for the production of an anti-SIRPα antibody, comprising the steps:
    a) cultivating the host cell of claim 48 under conditions for expression of the anti-SIRPα antibody; and
    b) recovering the anti-SIRPα antibody.

50. A pharmaceutical composition comprising the anti-SIRPα antibody according to claim 23 and a pharmaceutically acceptable carrier.

51. A method of treating a cancer in a subject in need thereof, the method comprising administering a therapeutically effective amount of the anti-SIRPα antibody according to claim 23 to the subject in need thereof.

52. An isolated polynucleotide composition, the isolated polynucleotide composition comprising:
    a) a first isolated polynucleotide encoding the heavy chain according to claim 23; and/or
    b) a second isolated polynucleotide encoding the light chain according to claim 23.

53. An expression vector composition, the expression vector composition comprising:
    a) a first expression vector comprising the first isolated polynucleotide of claim 52; and/or
    b) a second expression vector comprising the second isolated polynucleotide of claim 52.

54. A host cell comprising the isolated polynucleotide composition according to claim 52.

55. A method for the production of an anti-SIRPα antibody, comprising the steps:
    a) cultivating a host cell of claim 54 under conditions for expression of the anti-SIRPα antibody; and
    b) recovering the anti-SIRPα antibody.

56. A pharmaceutical composition comprising the anti-SIRPα antibody according to claim 24 and a pharmaceutically acceptable carrier.

57. A method of treating a cancer in a subject in need thereof, the method comprising administering a therapeutically effective amount of the anti-SIRPα antibody according to claim 24 to the subject in need thereof.

58. An isolated polynucleotide composition, the isolated polynucleotide composition comprising:
    a) a first isolated polynucleotide encoding the heavy chain according to claim 24; and/or
    b) a second isolated polynucleotide encoding the light chain according to claim 24.

59. An expression vector composition, the expression vector composition comprising:
    a) a first expression vector comprising the first isolated polynucleotide of claim 58; and/or
    b) a second expression vector comprising the second isolated polynucleotide of claim 58.

60. A host cell comprising the isolated polynucleotide composition according to claim 58.

61. A method for the production of an anti-SIRPα antibody, comprising the steps:
    a) cultivating the host cell of claim 60 under conditions for expression of the anti-SIRPα antibody; and
    b) recovering the anti-SIRPα antibody.

* * * * *

SEQUENCE LISTING

<160> NUMBER OF SEQ ID NOS: 297

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Tyr Tyr Trp Ser
1               5

```
<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Ile Tyr Tyr Asn Gly Arg Thr Phe Tyr Asn Ser Ser Leu Lys Ser
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Phe Ile Tyr Tyr Asn Gly Arg Thr Phe Tyr Asn Pro Ser Leu Lys Ser
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Phe Ile Tyr Asp Asn Gly Arg Thr Phe Tyr Asn Pro Ser Leu Lys Ser
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Ile Tyr Tyr Thr Gly Arg Thr Phe Tyr Asn Pro Ser Leu Lys Ser
1               5                   10                  15

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Arg Ala Tyr Ser Gly Ile Gly Leu Asp Gly Thr Asp Val
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7
```

```
Lys Ser Ser Gln Ser Leu Leu Tyr Ser Asn Gly Tyr Asn Tyr Leu Asp
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Ser Ser Gln Ser Leu Leu Tyr Ser Asn Gly Tyr Ala Tyr Leu Asp
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Ser Ser Gln Ser Leu Leu Tyr Ser Asn Ala Tyr Asn Tyr Leu Asp
1               5                   10                  15

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Gly Ser Asn Arg Ala Ser
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Gly Ser Asn Arg Ala Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Gln Ala Leu Gln Thr Pro Leu Thr
1               5

<210> SEQ ID NO 13
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 13

Gly Gly Ser Ile Arg Asn Tyr Tyr
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Tyr Tyr Asn Gly Arg Thr
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ile Tyr Asp Asn Gly Arg Thr
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ile Tyr Tyr Thr Gly Arg Thr
1               5

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Arg Val Arg Ala Tyr Ser Gly Ile Gly Leu Asp Gly Thr Asp Val
1               5                   10                  15

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ser Leu Leu Tyr Ser Asn Gly Tyr Asn Tyr
1               5                   10
```

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ser Leu Leu Tyr Ser Asn Gly Tyr Ala Tyr
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Ser Leu Leu Tyr Ser Asn Ala Tyr Asn Tyr
1               5                   10

<210> SEQ ID NO 21
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Gly Ser
1

<210> SEQ ID NO 22
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Gly Ser
1

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Ser Ile Arg Asn Tyr Tyr Trp Ser
1               5                   10

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 24

Tyr Tyr Asn Gly Arg
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr Asp Asn Gly Arg
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Tyr Tyr Thr Gly Arg
1               5

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Val Ser Gly Gly Ser Ile Arg Asn Tyr Tyr Trp Ser
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Phe Ile Tyr Tyr Asn Gly Arg Thr Phe
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Phe Ile Tyr Asp Asn Gly Arg Thr Phe
1               5

<210> SEQ ID NO 30
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 30

Phe Ile Tyr Tyr Thr Gly Arg Thr Phe
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr Leu Gly Ser Asn Arg Ala Ser
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Gln Gly Ser Asn Arg Ala Ser
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Tyr Asp Met His
1               5

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Ile Gly Thr Ala Gly Asp Thr Tyr Tyr Thr Gly Ser Val Lys Gly
1               5                   10                  15

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly Val Trp Asp Asp Ala Phe Asp Ile
1               5                   10
```

```
<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ala Ser Gln Asp Ile Asn Asn Tyr Leu Ala
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Ala Ser Gln Gly Ile Asn Asn Tyr Ala Ala
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Ala Ser Ser Leu His Ser
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Gln Tyr Val Ser Tyr Pro Tyr Thr
1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Phe Thr Leu Ser Ser Tyr Asp
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 41

Ile Gly Thr Ala Gly Asp Thr
1               5

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Val Arg Gly Gly Val Trp Asp Asp Ala Phe Asp Ile
1               5                   10

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Asp Ile Asn Asn Tyr
1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Gly Ile Asn Asn Tyr
1               5

<210> SEQ ID NO 45
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Ala Ser
1

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Phe Thr Leu Ser Ser Tyr Asp Met His
1               5                   10

<210> SEQ ID NO 47
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Phe Thr Leu Ser Ser Tyr
1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Thr Ala Gly Asp
1               5

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Ala Ser Gly Phe Thr Leu Ser Ser Tyr Asp Met His
1               5                   10

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Ile Gly Thr Ala Gly Asp Thr Tyr
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Tyr Thr Ala Ser Ser Leu His Ser
1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Asn Tyr Met His
```

```
<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Trp Ile Asn Pro Asn Ser Gly Gly Thr Asn Tyr Ala Gln Lys Phe Gln
1               5                   10                  15
Gly

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Ser Gly Trp Tyr Glu Asn Tyr Tyr Tyr Tyr Gly Met Asp Val
1               5                   10                  15

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Ala Ser Gln Gly Ile Ser Ser Trp Leu Ala
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Glu Ser Ser Leu Gln Ser
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Gln Ala Asn Ser Phe Pro Leu Thr
1               5

<210> SEQ ID NO 58
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 58

Gly Tyr Thr Phe Thr Gly Asn Tyr
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ile Asn Pro Asn Ser Gly Gly Thr
1               5

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Val Ser Gly Ser Gly Trp Tyr Glu Asn Tyr Tyr Tyr Gly Met Asp
1               5                   10                  15
Val

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Gly Ile Ser Ser Trp
1               5

<210> SEQ ID NO 62
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Glu Ser
1

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Phe Thr Phe Ser Ser Tyr Asp Met His
```

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Tyr Thr Phe Thr Gly Asn
1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asn Pro Asn Ser Gly Gly
1               5

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Lys Ala Ser Gly Tyr Thr Phe Thr Gly Asn Tyr Met His
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Trp Ile Asn Pro Asn Ser Gly Gly Thr Asn
1               5                   10

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Val Ser Gly Ser Gly Trp Tyr Glu Asn Tyr Tyr Tyr Tyr Gly Met Asp
1               5                   10                  15

Val

<210> SEQ ID NO 69
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 69

Tyr Ala Glu Ser Ser Leu Gln Ser
1               5

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Val Ile Gly Ile Ala Gly Asp Thr Tyr Tyr Pro Gly Ser Val Lys Gly
1               5                   10                  15

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Gly Ser Trp Asp Asp Ala Phe Asp Ile
1               5                   10

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Ala Ser Ser Leu Gln Ser
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Phe Thr Phe Ser Ser Tyr Asp
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Gly Ile Ala Gly Asp Thr
1               5
```

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Arg Gly Gly Ser Trp Asp Asp Ala Phe Asp Ile
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Phe Thr Phe Ser Ser Tyr Asp Met His
1               5                   10

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Val Ile Gly Ile Ala Gly Asp Thr Tyr Tyr Pro Gly Ser Val Lys Gly
1               5                   10                  15

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Gly Ser Trp Asp Asp Ala Phe Asp Ile
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Ala Ser Ser Leu Gln Ser
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 80

Gly Phe Thr Phe Ser Ser Tyr
1               5

<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Ile Ala Gly Asp
1               5

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Gly Ser Trp Asp Asp Ala Phe Asp Ile
1               5                   10

<210> SEQ ID NO 83
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Ala Ser Gly Phe Thr Phe Ser Ser Tyr Asp Met His
1               5                   10

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Val Ile Gly Ile Ala Gly Asp Thr Tyr
1               5

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Arg Gly Gly Ser Trp Asp Asp Ala Phe Asp Ile
1               5                   10

<210> SEQ ID NO 86
<211> LENGTH: 8
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 86

Tyr Thr Ala Ser Ser Leu Gln Ser
1               5

<210> SEQ ID NO 87
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Thr Ile Gly Ile Ala Gly Asp Thr Tyr Phe Pro Gly Ser Val Lys Gly
1               5                   10                  15

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Gly Asn Trp Asp Asp Ala Leu Asp Ile
1               5                   10

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Gln Tyr Asn Thr Tyr Pro Tyr Thr
1               5

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Arg Gly Gly Asn Trp Asp Asp Ala Leu Asp Ile
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Phe Thr Phe Ser Ser Phe Asp Met His
1               5                   10

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Thr Ile Gly Ile Ala Gly Asp Thr Tyr Phe Pro Gly Ser Val Lys Gly
1               5                   10                  15

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Gly Asn Trp Asp Asp Ala Leu Asp Ile
1               5                   10

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Phe Thr Phe Ser Ser Phe
1               5

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Gly Asn Trp Asp Asp Ala Leu Asp Ile
1               5                   10

<210> SEQ ID NO 96
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ala Ala Ser Gly Phe Thr Phe Ser Ser Phe Asp Met His
1               5                   10

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Thr Ile Gly Ile Ala Gly Asp Thr Tyr
1               5

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Arg Gly Gly Asn Trp Asp Asp Ala Leu Asp Ile
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Ala Ser Gln Asp Ile Asn Asn Tyr Leu Ala
1               5                   10

<210> SEQ ID NO 100
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Val
                85                  90                  95

Arg Gly Gly Val Trp Asp Asp Ala Phe Asp Ile Trp Gly Gln Gly Thr
            100                 105                 110

Met Val Thr Val Ser Ser
        115

<210> SEQ ID NO 101
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Gly Asn
            20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Val Ser Gly Ser Gly Trp Tyr Glu Asn Tyr Tyr Tyr Gly Met Asp
            100                 105                 110

Val Trp Gly Gln Gly Thr Thr Val Thr Val Ser Ser
        115                 120

<210> SEQ ID NO 102
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
            35                  40                  45

Ser Val Ile Gly Ile Ala Gly Asp Thr Tyr Tyr Pro Gly Ser Val Lys
        50                  55                  60

Gly Arg Phe Thr Ile Ser Arg Glu Asn Ala Lys Asn Ser Leu Tyr Leu
65                  70                  75                  80

Gln Met Asn Ser Leu Arg Val Gly Asp Thr Ala Val Tyr Tyr Cys Ala
                85                  90                  95

Arg Gly Gly Ser Trp Asp Asp Ala Phe Asp Ile Trp Gly Gln Gly Thr
            100                 105                 110

Met Val Thr Val Ser Ser
        115

<210> SEQ ID NO 103
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Asp Met His Trp Val Arg Gln Pro Thr Gly Lys Gly Leu Glu Trp Val
            35                  40                  45

```
Ser Thr Ile Gly Ile Ala Gly Asp Thr Tyr Phe Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Gly Asn Trp Asp Asp Ala Leu Asp Ile Trp Gly Gln Gly Thr
                100                 105                 110

Met Val Thr Val Ser Ser
            115
```

<210> SEQ ID NO 104
<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
                20                  25                  30

Tyr Trp Ser Trp Ile Arg Gln Pro Pro Gly Lys Gly Leu Glu Trp Ile
                35                  40                  45

Gly Phe Ile Tyr Tyr Asn Gly Arg Thr Phe Tyr Asn Ser Ser Leu Lys
    50                  55                  60

Ser Arg Val Thr Ile Ser Leu Asp Met Ser Met Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
                100                 105                 110

Gly Gln Gly Thr Thr Val Thr Val Ser Ser Ala Arg Phe Thr Val Asp
                115                 120                 125

Lys Ser Ser Thr Ala Tyr Met Gln Phe Ser Ser Leu Thr Ser Glu
130                 135                 140

Asp Thr Ala Val Tyr Phe Cys Ala Arg Ser Gly Pro Tyr Ser Tyr Tyr
145                 150                 155                 160

Ala Gly Gly Tyr Ala Leu Asp Tyr Trp Gly Gln Gly Thr Ser Val Thr
                165                 170                 175

Val Ser Ser
```

<210> SEQ ID NO 105
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
                20                  25                  30
```

```
Leu Ala Trp Phe Gln Gln Lys Pro Gly Lys Ala Pro Lys Ser Leu Ile
            35                  40                  45

Tyr Thr Ala Ser Ser Leu His Ser Gly Val Pro Ser Lys Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Val Ser Tyr Pro Tyr
                 85                  90                  95

Thr Phe Gly Gln Gly Thr Lys Leu Glu Ile Lys
            100                 105
```

<210> SEQ ID NO 106
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
            35                  40                  45

Tyr Ala Glu Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Leu
                 85                  90                  95

Thr Phe Gly Gly Gly Thr Lys Val Glu Ile Lys
            100                 105
```

<210> SEQ ID NO 107
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

```
Asp Ile Gln Met Thr Gln Ser Pro Ser Ser Leu Ser Ala Ser Ile Gly
 1               5                  10                  15

Asp Lys Val Thr Ile Thr Cys Arg Ala Ser Gln Asp Ile Asn Asn Tyr
            20                  25                  30

Leu Ala Trp Phe Gln Gln Lys Pro Gly Lys Ala Pro Lys Ser Leu Ile
            35                  40                  45

Tyr Thr Ala Ser Ser Leu Gln Ser Gly Val Pro Ser Lys Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Val Ser Tyr Pro Tyr
                 85                  90                  95

Thr Phe Gly Gln Gly Thr Lys Leu Glu Ile Lys
            100                 105
```

<210> SEQ ID NO 108
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Phe Gln Gln Lys Pro Gly Lys Ala Pro Lys Ser Leu Ile
        35                  40                  45

Tyr Thr Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Tyr
                85                  90                  95

Thr Phe Gly Gln Gly Thr Lys Leu Glu Ile Lys
            100                 105

<210> SEQ ID NO 109
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Gly Tyr Asn Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 110
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr

```
            20                  25                  30

Asp Met His Trp Val Arg Gln Ala Pro Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Asp Asp Thr Ala Val Tyr Tyr Cys Val
                85                  90                  95

Arg Gly Gly Val Trp Asp Asp Ala Phe Asp Ile Trp Gly Gln Gly Thr
            100                 105                 110

Met Val Thr Val Ser Ser
        115

<210> SEQ ID NO 111
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Ala Asp Thr Ala Val Tyr Tyr Cys Val
                85                  90                  95

Arg Gly Gly Val Trp Asp Asp Ala Phe Asp Ile Trp Gly Gln Gly Thr
            100                 105                 110

Met Val Thr Val Ser Ser
        115

<210> SEQ ID NO 112
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
```

```
                65                  70                  75                  80
Gln Met Asn Ser Leu Arg Ala Ser Asp Thr Ala Val Tyr Tyr Cys Val
                    85                  90                  95

Arg Gly Gly Val Trp Asp Asp Ala Phe Asp Ile Trp Gly Gln Gly Thr
                100                 105                 110

Met Val Thr Val Ser Ser
        115

<210> SEQ ID NO 113
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Pro Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Ala Asp Thr Ala Val Tyr Tyr Cys Val
                85                  90                  95

Arg Gly Gly Val Trp Asp Asp Ala Phe Asp Ile Trp Gly Gln Gly Thr
            100                 105                 110

Met Val Thr Val Ser Ser
        115

<210> SEQ ID NO 114
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Pro Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Ser Asp Thr Ala Val Tyr Tyr Cys Val
                85                  90                  95

Arg Gly Gly Val Trp Asp Asp Ala Phe Asp Ile Trp Gly Gln Gly Thr
            100                 105                 110

Met Val Thr Val Ser Ser
```

<210> SEQ ID NO 115
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Pro Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Glu Asp Thr Ala Val Tyr Tyr Cys Val
                85                  90                  95

Arg Gly Gly Val Trp Asp Asp Ala Phe Asp Ile Trp Gly Gln Gly Thr
            100                 105                 110

Met Val Thr Val Ser Ser
        115
```

<210> SEQ ID NO 116
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Val
                85                  90                  95

Arg Gly Gly Val Trp Asp Asp Ala Phe Asp Ile Trp Gly Gln Gly Thr
            100                 105                 110

Met Val Thr Val Ser Ser
        115
```

<210> SEQ ID NO 117
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 117

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Leu Ser Ser Tyr
            20                  25                  30

Asp Met His Trp Val Arg Gln Ala Pro Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Val
                85                  90                  95

Arg Gly Gly Val Trp Asp Asp Ala Phe Asp Ile Trp Gly Gln Gly Thr
            100                 105                 110

Met Val Thr Val Ser Ser
        115
```

<210> SEQ ID NO 118
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Gln Val Gln Leu Gln Glu Ser Gly Pro Gly Leu Val Arg Pro Ser Glu
 1               5                  10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Asn Gly Arg Thr Phe Tyr Asn Pro Ser Leu Lys
    50                  55                  60

Ser Arg Val Thr Ile Ser Leu Asp Met Ser Ile Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Asp Val Trp
            100                 105                 110

Gly Gln Gly Thr Thr Val Thr Val Ser Ser
        115                 120
```

<210> SEQ ID NO 119
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Gln Val Gln Leu Gln Glu Ser Gly Pro Gly Leu Val Arg Pro Ser Glu
 1               5                  10                  15

Thr Leu Ser Leu Thr Cys Thr Val Ser Gly Gly Ser Ile Arg Asn Tyr
            20                  25                  30
```

Tyr Trp Ser Trp Ile Arg Gln Pro Pro Gly Lys Gly Leu Glu Trp Ile
            35                  40                  45

Gly Phe Ile Tyr Tyr Asn Gly Arg Thr Phe Tyr Asn Pro Ser Leu Lys
        50                  55                  60

Ser Arg Val Thr Ile Ser Leu Asp Met Ser Lys Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser
            115                 120

<210> SEQ ID NO 120
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
            35                  40                  45

Gly Phe Ile Tyr Tyr Asn Gly Arg Thr Phe Tyr Asn Pro Ser Leu Lys
        50                  55                  60

Ser Arg Val Thr Ile Ser Leu Asp Lys Ser Lys Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser
            115                 120

<210> SEQ ID NO 121
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
            35                  40                  45

Gly Phe Ile Tyr Tyr Asn Gly Arg Thr Phe Tyr Asn Pro Ser Leu Lys
        50                  55                  60

Ser Arg Val Thr Ile Ser Leu Asp Thr Ser Lys Asn Gln Phe Ser Leu
65                  70                  75                  80

```
Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser
        115                 120

<210> SEQ ID NO 122
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Met
        35                  40                  45

Gly Phe Ile Tyr Asp Asn Gly Arg Thr Phe Tyr Asn Pro Ser Leu Lys
    50                  55                  60

Ser Arg Val Thr Ile Ser Leu Asp Met Ser Met Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser
        115                 120

<210> SEQ ID NO 123
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Thr Gly Arg Thr Phe Tyr Asn Pro Ser Leu Lys
    50                  55                  60

Ser Arg Val Thr Ile Ser Leu Asp Met Ser Ile Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser
        115                 120
```

```
<210> SEQ ID NO 124
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Thr Gly Arg Thr Phe Tyr Asn Pro Ser Leu Lys
    50                  55                  60

Ser Arg Val Thr Ile Ser Leu Asp Met Ser Lys Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser
        115                 120

<210> SEQ ID NO 125
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Ala Ala Trp Phe Gln Gln Lys Pro Gly Lys Ala Pro Lys Ser Leu Ile
        35                  40                  45

Tyr Thr Ala Ser Ser Leu His Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Tyr Pro Tyr
                85                  90                  95

Thr Phe Gly Gln Gly Thr Lys Leu Glu Ile Lys
            100                 105

<210> SEQ ID NO 126
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Phe Gln Gln Lys Pro Gly Lys Ala Pro Lys Ser Leu Ile
        35                  40                  45

Tyr Thr Ala Ser Ser Leu His Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Tyr Pro Tyr
                85                  90                  95

Thr Phe Gly Gln Gly Thr Lys Leu Glu Ile Lys
            100                 105
```

<210> SEQ ID NO 127
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

```
Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Gly Tyr Ala Tyr Leu Asp Trp Tyr Leu Gln Arg Pro Gly Gln Ser
        35                  40                  45

Pro Gln Leu Leu Ile Tyr Gln Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Tyr Cys Met Gln Ala
                85                  90                  95

Leu Gln Thr Pro Leu Thr Phe Gly Gly Gly Thr Lys Val Glu Ile Lys
            100                 105                 110
```

<210> SEQ ID NO 128
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

```
Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Gly Tyr Ala Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110
```

<210> SEQ ID NO 129
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

```
Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Gly Tyr Ala Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110
```

<210> SEQ ID NO 130
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

```
Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Ala Tyr Asn Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110
```

<210> SEQ ID NO 131
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 131

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Val
            85                  90                  95

Arg Gly Gly Val Trp Asp Asp Ala Phe Asp Ile Trp Gly Gln Gly Thr
        100                 105                 110

Met Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415
```

-continued

```
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly
            435                 440                 445

<210> SEQ ID NO 132
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Leu Ser Ser Tyr
            20                  25                  30
Asp Met His Trp Val Arg Gln Ala Thr Gly Lys Gly Leu Glu Trp Val
        35                  40                  45
Ser Ala Ile Gly Thr Ala Gly Asp Thr Tyr Tyr Thr Gly Ser Val Lys
    50                  55                  60
Gly Arg Phe Thr Ile Ser Arg Glu Asn Ala Lys Asn Ser Leu Tyr Leu
65                  70                  75                  80
Gln Met Asn Ser Leu Arg Ala Gly Asp Thr Ala Val Tyr Tyr Cys Val
                85                  90                  95
Arg Gly Gly Val Trp Asp Asp Ala Phe Asp Ile Trp Gly Gln Gly Thr
            100                 105                 110
Met Val Thr Val Ser Ser Ala Ser Thr Lys Gly Pro Ser Val Phe Pro
        115                 120                 125
Leu Ala Pro Cys Ser Arg Ser Thr Ser Glu Ser Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Lys Thr Tyr Thr Cys Asn Val Asp His Lys Pro Ser
        195                 200                 205
Asn Thr Lys Val Asp Lys Arg Val Glu Ser Lys Tyr Gly Pro Pro Cys
    210                 215                 220
Pro Pro Cys Pro Ala Pro Glu Phe Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser Gln Glu Asp Pro Glu Val Gln
            260                 265                 270
Phe Asn Trp Tyr Val Asp Gly Val Glu Val His Asn Ala Lys Thr Lys
        275                 280                 285
Pro Arg Glu Glu Gln Phe Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Gly Leu Pro Ser Ser Ile Glu Lys Thr Ile Ser Lys
```

```
            325                 330                 335
Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
            435                 440

<210> SEQ ID NO 133
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Asn
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Val Ser Gly Ser Gly Trp Tyr Glu Asn Tyr Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240
```

Ala Ala Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
        260                 265                 270

Val Ser His Glu Asp Pro Glu Val Lys Phe Asn Trp Tyr Val Asp Gly
    275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 134
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Val Ile Gly Ile Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Val Gly Asp Thr Ala Val Tyr Tyr Cys Ala
                85                  90                  95

Arg Gly Gly Ser Trp Asp Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 135
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Asn Gly Arg Thr Phe Tyr Asn Ser Ser Leu Lys

```
            50                  55                  60
Ser Arg Val Thr Ile Ser Leu Asp Met Ser Met Asn Gln Phe Ser Leu
 65                  70                  75                  80

Lys Met Thr Ser Val Thr Ala Ala Asp Thr Ala Val Tyr Tyr Cys Ala
                 85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Arg Val Glu Pro Lys Ser
        210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 136
```

```
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136
```

| | | | | | | | | | | | | | | | |
|---|---|---|---|---|---|---|---|---|---|---|---|---|---|---|---|
| Gln | Val | Gln | Leu | Gln | Glu | Ser | Gly | Pro | Gly | Leu | Val | Arg | Pro | Ser | Glu |
| 1 | | | | 5 | | | | | 10 | | | | | 15 | |
| Thr | Leu | Ser | Leu | Thr | Cys | Thr | Val | Ser | Gly | Gly | Ser | Ile | Arg | Asn | Tyr |
| | | | 20 | | | | | 25 | | | | | 30 | | |
| Tyr | Trp | Ser | Trp | Ile | Arg | Gln | Pro | Pro | Gly | Lys | Gly | Leu | Glu | Trp | Ile |
| | | 35 | | | | | 40 | | | | | 45 | | | |
| Gly | Phe | Ile | Tyr | Tyr | Asn | Gly | Arg | Thr | Phe | Tyr | Asn | Ser | Ser | Leu | Lys |
| 50 | | | | | 55 | | | | | 60 | | | | | |
| Ser | Arg | Val | Thr | Ile | Ser | Leu | Asp | Met | Ser | Met | Asn | Gln | Phe | Ser | Leu |
| 65 | | | | | 70 | | | | | 75 | | | | | 80 |
| Lys | Met | Thr | Ser | Val | Thr | Ala | Ala | Asp | Thr | Ala | Val | Tyr | Tyr | Cys | Ala |
| | | | | 85 | | | | | 90 | | | | | 95 | |
| Arg | Val | Arg | Ala | Tyr | Ser | Gly | Ile | Gly | Leu | Asp | Gly | Thr | Asp | Val | Trp |
| | | | 100 | | | | | 105 | | | | | 110 | | |
| Gly | Gln | Gly | Thr | Thr | Val | Thr | Val | Ser | Ser | Ala | Ser | Thr | Lys | Gly | Pro |
| | | | 115 | | | | | 120 | | | | | 125 | | |
| Ser | Val | Phe | Pro | Leu | Ala | Pro | Cys | Ser | Arg | Ser | Thr | Ser | Glu | Ser | Thr |
| | | 130 | | | | | 135 | | | | | 140 | | | |
| Ala | Ala | Leu | Gly | Cys | Leu | Val | Lys | Asp | Tyr | Phe | Pro | Glu | Pro | Val | Thr |
| 145 | | | | | 150 | | | | | 155 | | | | | 160 |
| Val | Ser | Trp | Asn | Ser | Gly | Ala | Leu | Thr | Ser | Gly | Val | His | Thr | Phe | Pro |
| | | | | 165 | | | | | 170 | | | | | 175 | |
| Ala | Val | Leu | Gln | Ser | Ser | Gly | Leu | Tyr | Ser | Leu | Ser | Ser | Val | Val | Thr |
| | | | 180 | | | | | 185 | | | | | 190 | | |
| Val | Pro | Ser | Ser | Ser | Leu | Gly | Thr | Lys | Thr | Tyr | Thr | Cys | Asn | Val | Asp |
| | | | 195 | | | | | 200 | | | | | 205 | | |
| His | Lys | Pro | Ser | Asn | Thr | Lys | Val | Asp | Lys | Arg | Val | Glu | Ser | Lys | Tyr |
| | 210 | | | | | 215 | | | | | 220 | | | | |
| Gly | Pro | Pro | Cys | Pro | Pro | Cys | Pro | Ala | Pro | Glu | Phe | Leu | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | Gln | Glu | Asp |
| | | | 260 | | | | | 265 | | | | | 270 | | |
| Pro | Glu | Val | Gln | Phe | Asn | Trp | Tyr | Val | Asp | Gly | Val | Glu | Val | His | Asn |
| | | | 275 | | | | | 280 | | | | | 285 | | |
| Ala | Lys | Thr | Lys | Pro | Arg | Glu | Glu | Gln | Phe | Asn | Ser | Thr | Tyr | Arg | Val |
| | 290 | | | | | 295 | | | | | 300 | | | | |
| Val | Ser | Val | Leu | Thr | Val | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Gly | Leu | Pro | Ser | Ser | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Tyr | Thr |
| | | | 340 | | | | | 345 | | | | | 350 | | |
| Leu | Pro | Pro | Ser | Gln | Glu | Glu | Met | Thr | Lys | Asn | Gln | Val | Ser | Leu | Thr |
| | | | 355 | | | | | 360 | | | | | 365 | | |
| Cys | Leu | Val | Lys | Gly | Phe | Tyr | Pro | Ser | Asp | Ile | Ala | Val | Glu | Trp | Glu |

```
                 370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

<210> SEQ ID NO 137
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Asp Met His Trp Val Arg Gln Pro Thr Gly Lys Gly Leu Glu Trp Val
        35                  40                  45

Ser Thr Ile Gly Ile Ala Gly Asp Thr Tyr Phe Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Gly Asn Trp Asp Asp Ala Leu Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 138
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Pro Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Asp Asp Thr Ala Val Tyr Tyr Cys Val
                85                  90                  95

Arg Gly Gly Val Trp Asp Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
            210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 139
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Ala Asp Thr Ala Val Tyr Tyr Cys Val
                85                  90                  95

Arg Gly Gly Val Trp Asp Asp Ala Phe Asp Ile Trp Gly Gln Gly Thr
            100                 105                 110

Met Val Thr Val Ser Ser Ala Ser Thr Lys Gly Pro Ser Val Phe Pro

```
            115                 120                 125
Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 140
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30
```

-continued

```
Asp Met His Trp Val Arg Gln Ala Thr Gly Lys Gly Leu Glu Trp Val
         35                  40                  45
Ser Ala Ile Gly Thr Ala Gly Asp Thr Tyr Tyr Thr Gly Ser Val Lys
 50                  55                  60
Gly Arg Phe Thr Ile Ser Arg Glu Asn Ala Lys Asn Ser Leu Tyr Leu
 65                  70                  75                  80
Gln Met Asn Ser Leu Arg Ala Ser Asp Thr Ala Val Tyr Tyr Cys Val
                 85                  90                  95
Arg Gly Gly Val Trp Asp Asp Ala Phe Asp Ile Trp Gly Gln Gly Thr
                100                 105                 110
Met Val Thr Val Ser Ser Ala Ser Thr Lys Gly Pro Ser Val Phe Pro
                115                 120                 125
Leu Ala Pro Ser Ser Lys Ser Thr Ser Gly Gly Thr Ala Ala Leu Gly
130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
                180                 185                 190
Ser Leu Gly Thr Gln Thr Tyr Ile Cys Asn Val Asn His Lys Pro Ser
                195                 200                 205
Asn Thr Lys Val Asp Lys Arg Val Glu Pro Lys Ser Cys Asp Lys Thr
                210                 215                 220
His Thr Cys Pro Pro Cys Pro Ala Pro Glu Ala Ala Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Asp Val Ser His Glu Asp Pro
                260                 265                 270
Glu Val Lys Phe Asn Trp Tyr Val Asp Gly Val Glu Val His Asn Ala
                275                 280                 285
Lys Thr Lys Pro Arg Glu Glu Gln Tyr Asn Ser Thr Tyr Arg Val Val
                290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Glu Glu Met Thr Lys Asn Gln Val Ser Leu Thr Cys
                355                 360                 365
Leu Val Lys Gly Phe Tyr Pro Ser Asp Ile Ala Val Glu Trp Glu Ser
                370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly
                435                 440                 445
```

```
<210> SEQ ID NO 141
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Pro Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Ala Asp Thr Ala Val Tyr Tyr Cys Val
                85                  90                  95

Arg Gly Gly Val Trp Asp Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365
```

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 142
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
                20                  25                  30

Asp Met His Trp Val Arg Gln Ala Pro Gly Lys Gly Leu Glu Trp Val
                35                  40                  45

Ser Ala Ile Gly Thr Ala Gly Asp Thr Tyr Tyr Thr Gly Ser Val Lys
                50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Ser Asp Thr Ala Val Tyr Tyr Cys Val
                85                  90                  95

Arg Gly Gly Val Trp Asp Asp Ala Phe Asp Ile Trp Gly Gln Gly Thr
                100                 105                 110

Met Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Arg Val Glu Pro Lys Ser Cys Asp Lys Thr
                210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

```
Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 143
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Pro Gly Lys Gly Leu Glu Trp Val
        35                  40                  45

Ser Ala Ile Gly Thr Ala Gly Asp Thr Tyr Tyr Thr Gly Ser Val Lys
50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Glu Asp Thr Ala Val Tyr Tyr Cys Val
            85                  90                  95

Arg Gly Gly Val Trp Asp Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
```

```
            195                 200                 205
Asn Thr Lys Val Asp Lys Arg Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 144
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Val
                85                  90                  95

Arg Gly Gly Val Trp Asp Asp Ala Phe Asp Ile Trp Gly Gln Gly Thr
            100                 105                 110
```

```
Met Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 145
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30
```

```
Asp Met His Trp Val Arg Gln Ala Pro Gly Lys Gly Leu Glu Trp Val
        35                  40                  45

Ser Ala Ile Gly Thr Ala Gly Asp Thr Tyr Tyr Thr Gly Ser Val Lys
 50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Val
                 85                  90                  95

Arg Gly Gly Val Trp Asp Asp Ala Phe Asp Ile Trp Gly Gln Gly Thr
                100                 105                 110

Met Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445
```

<210> SEQ ID NO 146
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Pro Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Asp Asp Thr Ala Val Tyr Tyr Cys Val
                85                  90                  95

Arg Gly Gly Val Trp Asp Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

```
Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
        435                 440                 445

<210> SEQ ID NO 147
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Ala Asp Thr Ala Val Tyr Tyr Cys Val
            85                  90                  95

Arg Gly Gly Val Trp Asp Asp Ala Phe Asp Ile Trp Gly Gln Gly Thr
        100                 105                 110

Met Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
```

```
                275                 280                 285
Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
                435                 440                 445
```

<210> SEQ ID NO 148
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
65              70                  75                  80

Gln Met Asn Ser Leu Arg Ala Ser Asp Thr Ala Val Tyr Tyr Cys Val
            85                  90                  95

Arg Gly Gly Val Trp Asp Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly
    435                 440                 445

<210> SEQ ID NO 149
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Pro Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Ala Asp Thr Ala Val Tyr Tyr Cys Val
            85                  90                  95

Arg Gly Gly Val Trp Asp Asp Ala Phe Asp Ile Trp Gly Gln Gly Thr
        100                 105                 110

Met Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 150
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr

```
                20                  25                  30
Asp Met His Trp Val Arg Gln Ala Pro Gly Lys Gly Leu Glu Trp Val
            35                  40                  45
Ser Ala Ile Gly Thr Ala Gly Asp Thr Tyr Tyr Thr Gly Ser Val Lys
            50                  55                  60
Gly Arg Phe Thr Ile Ser Arg Glu Asn Ala Lys Asn Ser Leu Tyr Leu
65                  70                  75                  80
Gln Met Asn Ser Leu Arg Ala Ser Asp Thr Ala Val Tyr Tyr Cys Val
                85                  90                  95
Arg Gly Gly Val Trp Asp Asp Ala Phe Asp Ile Trp Gly Gln Gly Thr
            100                 105                 110
Met Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
            130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
            195                 200                 205
Asn Thr Lys Val Asp Lys Arg Val Glu Pro Lys Ser Cys Asp Lys Thr
            210                 215                 220
His Thr Cys Pro Pro Cys Pro Ala Pro Glu Ala Ala Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
            290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly
            435                 440                 445
```

<210> SEQ ID NO 151
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 151

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Pro Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Glu Asp Thr Ala Val Tyr Tyr Cys Val
                85                  90                  95

Arg Gly Gly Val Trp Asp Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
```

```
                    355                 360                 365
Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
                435                 440                 445

<210> SEQ ID NO 152
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Pro Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Val
                85                  90                  95

Arg Gly Gly Val Trp Asp Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

-continued

```
Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 153
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Asn Gly Arg Thr Phe Tyr Asn Pro Ser Leu Lys
    50                  55                  60

Ser Arg Val Thr Ile Ser Leu Asp Met Ser Ile Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190
```

Val Pro Ser Ser Leu Gly Thr Gln Thr Tyr Ile Cys Asn Val Asn
            195                 200                 205

His Lys Pro Ser Asn Thr Lys Val Asp Lys Arg Val Glu Pro Lys Ser
        210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 154
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Asn Gly Arg Thr Phe Tyr Asn Pro Ser Leu Lys
    50                  55                  60

Ser Arg Val Thr Ile Ser Leu Asp Met Ser Ile Asn Gln Phe Ser Leu
65                  70                  75                  80

Lys Met Thr Ser Val Thr Ala Ala Asp Thr Ala Val Tyr Tyr Cys Ala

```
            85                  90                  95
Arg Val Arg Ala Tyr Ser Gly Ile Gly Leu Asp Gly Thr Asp Val Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Arg Val Glu Pro Lys Ser
            210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly
    450

<210> SEQ ID NO 155
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 155

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Asn Gly Arg Thr Phe Tyr Asn Pro Ser Leu Lys
    50                  55                  60

Ser Arg Val Thr Ile Ser Leu Asp Met Ser Lys Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
```

Val Asp Lys Ser Arg Trp Gln Gln Gly Asn Val Phe Ser Cys Ser Val
            405                 410                 415
420                 425                 430

Met His Glu Ala Leu His Asn His Tyr Thr Gln Lys Ser Leu Ser Leu
            435                 440                 445

Ser Pro Gly
    450

<210> SEQ ID NO 156
<211> LENGTH: 451
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 156

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Asn Gly Arg Thr Phe Tyr Asn Pro Ser Leu Lys
    50                  55                  60

Ser Arg Val Thr Ile Ser Leu Asp Met Ser Lys Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

```
Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 157
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Asn Gly Arg Thr Phe Tyr Asn Pro Ser Leu Lys
    50                  55                  60

Ser Arg Val Thr Ile Ser Leu Asp Lys Ser Lys Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205
```

```
His Lys Pro Ser Asn Thr Lys Val Asp Lys Arg Val Glu Pro Lys Ser
        210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 158
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Asn Gly Arg Thr Phe Tyr Asn Pro Ser Leu Lys
    50                  55                  60

Ser Arg Val Thr Ile Ser Leu Asp Lys Ser Lys Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
```

```
                100             105             110
Gly Gln Gly Thr Thr Val Thr Val Ser Ser Ala Ser Thr Lys Gly Pro
            115                 120             125

Ser Val Phe Pro Leu Ala Pro Ser Ser Lys Ser Thr Ser Gly Gly Thr
    130                 135             140

Ala Ala Leu Gly Cys Leu Val Lys Asp Tyr Phe Pro Glu Pro Val Thr
145                 150             155                 160

Val Ser Trp Asn Ser Gly Ala Leu Thr Ser Gly Val His Thr Phe Pro
                165             170             175

Ala Val Leu Gln Ser Ser Gly Leu Tyr Ser Leu Ser Ser Val Val Thr
            180             185                 190

Val Pro Ser Ser Ser Leu Gly Thr Gln Thr Tyr Ile Cys Asn Val Asn
                195             200             205

His Lys Pro Ser Asn Thr Lys Val Asp Lys Arg Val Glu Pro Lys Ser
    210                 215             220

Cys Asp Lys Thr His Thr Cys Pro Pro Cys Pro Ala Pro Glu Ala Ala
225                 230             235                 240

Gly Gly Pro Ser Val Phe Leu Phe Pro Pro Lys Pro Lys Asp Thr Leu
                245             250             255

Met Ile Ser Arg Thr Pro Glu Val Thr Cys Val Val Val Asp Val Ser
            260             265                 270

His Glu Asp Pro Glu Val Lys Phe Asn Trp Tyr Val Asp Gly Val Glu
            275                 280             285

Val His Asn Ala Lys Thr Lys Pro Arg Glu Glu Gln Tyr Asn Ser Thr
            290             295             300

Tyr Arg Val Val Ser Val Leu Thr Val Leu His Gln Asp Trp Leu Asn
305                 310             315                 320

Gly Lys Glu Tyr Lys Cys Lys Val Ser Asn Lys Ala Leu Pro Ala Pro
                325             330             335

Ile Glu Lys Thr Ile Ser Lys Ala Lys Gly Gln Pro Arg Glu Pro Gln
            340             345             350

Val Tyr Thr Leu Pro Pro Ser Arg Glu Glu Met Thr Lys Asn Gln Val
            355             360             365

Ser Leu Thr Cys Leu Val Lys Gly Phe Tyr Pro Ser Asp Ile Ala Val
    370                 375             380

Glu Trp Glu Ser Asn Gly Gln Pro Glu Asn Asn Tyr Lys Thr Thr Pro
385                 390             395                 400

Pro Val Leu Asp Ser Asp Gly Ser Phe Phe Leu Tyr Ser Lys Leu Thr
                405             410             415

Val Asp Lys Ser Arg Trp Gln Gln Gly Asn Val Phe Ser Cys Ser Val
            420             425             430

Met His Glu Ala Leu His Asn His Tyr Thr Gln Lys Ser Leu Ser Leu
            435             440             445

Ser Pro Gly
    450

<210> SEQ ID NO 159
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159
```

-continued

```
Gln Val Gln Leu Gln Glu Ser Gly Pro Gly Leu Val Arg Pro Ser Glu
  1               5                  10                  15
Thr Leu Ser Leu Thr Cys Thr Val Ser Gly Gly Ser Ile Arg Asn Tyr
             20                  25                  30
Tyr Trp Ser Trp Ile Arg Gln Pro Pro Gly Lys Gly Leu Glu Trp Ile
         35                  40                  45
Gly Phe Ile Tyr Tyr Asn Gly Arg Thr Phe Tyr Asn Pro Ser Leu Lys
     50                  55                  60
Ser Arg Val Thr Ile Ser Leu Asp Thr Ser Lys Asn Gln Phe Ser Leu
 65                  70                  75                  80
Lys Met Thr Ser Val Thr Ala Ala Asp Thr Ala Val Tyr Tyr Cys Ala
                 85                  90                  95
Arg Val Arg Ala Tyr Ser Gly Ile Gly Leu Asp Gly Thr Asp Val Trp
             100                 105                 110
Gly Gln Gly Thr Thr Val Thr Val Ser Ser Ala Ser Thr Lys Gly Pro
         115                 120                 125
Ser Val Phe Pro Leu Ala Pro Ser Ser Lys Ser Thr Ser Gly Gly Thr
     130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                 165                 170                 175
Ala Val Leu Gln Ser Ser Gly Leu Tyr Ser Leu Ser Ser Val Val Thr
             180                 185                 190
Val Pro Ser Ser Ser Leu Gly Thr Gln Thr Tyr Ile Cys Asn Val Asn
         195                 200                 205
His Lys Pro Ser Asn Thr Lys Val Asp Lys Arg Val Glu Pro Lys Ser
     210                 215                 220
Cys Asp Lys Thr His Thr Cys Pro Pro Cys Pro Ala Pro Glu Ala Ala
225                 230                 235                 240
Gly Gly Pro Ser Val Phe Leu Phe Pro Pro Lys Pro Lys Asp Thr Leu
                 245                 250                 255
Met Ile Ser Arg Thr Pro Glu Val Thr Cys Val Val Val Asp Val Ser
             260                 265                 270
His Glu Asp Pro Glu Val Lys Phe Asn Trp Tyr Val Asp Gly Val Glu
         275                 280                 285
Val His Asn Ala Lys Thr Lys Pro Arg Glu Glu Gln Tyr Asn Ser Thr
     290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                 325                 330                 335
Ile Glu Lys Thr Ile Ser Lys Ala Lys Gly Gln Pro Arg Glu Pro Gln
             340                 345                 350
Val Tyr Thr Leu Pro Pro Ser Arg Glu Glu Met Thr Lys Asn Gln Val
         355                 360                 365
Ser Leu Thr Cys Leu Val Lys Gly Phe Tyr Pro Ser Asp Ile Ala Val
     370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                 405                 410                 415
Val Asp Lys Ser Arg Trp Gln Gln Gly Asn Val Phe Ser Cys Ser Val
```

```
                    420             425             430
Met His Glu Ala Leu His Asn His Tyr Thr Gln Lys Ser Leu Ser Leu
                435             440             445

Ser Pro Gly
    450

<210> SEQ ID NO 160
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
                20                  25                  30

Tyr Trp Ser Trp Ile Arg Gln Pro Pro Gly Lys Gly Leu Glu Trp Met
            35                  40                  45

Gly Phe Ile Tyr Asp Asn Gly Arg Thr Phe Tyr Asn Pro Ser Leu Lys
    50                  55                  60

Ser Arg Val Thr Ile Ser Leu Asp Met Ser Met Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320
```

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 161
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Asn Gly Arg Thr Phe Tyr Asn Pro Ser Leu Lys
    50                  55                  60

Ser Arg Val Thr Ile Ser Leu Asp Met Ser Ile Asn Gln Phe Ser Leu
65              70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

-continued

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 162
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Asn Gly Arg Thr Phe Tyr Asn Pro Ser Leu Lys
    50                  55                  60

Ser Arg Val Thr Ile Ser Leu Asp Thr Ser Lys Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser Ala Ser Thr Lys Gly Pro 115                 120                 125
Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Arg Val Glu Pro Lys Ser
            210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 163
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Gln Val Gln Leu Gln Glu Ser Gly Pro Gly Leu Val Arg Pro Ser Glu
1               5                   10                  15

```
Thr Leu Ser Leu Thr Cys Thr Val Ser Gly Gly Ser Ile Arg Asn Tyr
             20                  25                  30

Tyr Trp Ser Trp Ile Arg Gln Pro Pro Gly Lys Gly Leu Glu Trp Met
         35                  40                  45

Gly Phe Ile Tyr Asp Asn Gly Arg Thr Phe Tyr Asn Pro Ser Leu Lys
     50                  55                  60

Ser Arg Val Thr Ile Ser Leu Asp Met Ser Met Asn Gln Phe Ser Leu
 65                  70                  75                  80

Lys Met Thr Ser Val Thr Ala Ala Asp Thr Ala Val Tyr Tyr Cys Ala
                 85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
```

Ser Pro Gly
    450

<210> SEQ ID NO 164
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Asn Gly Arg Thr Phe Tyr Asn Pro Ser Leu Lys
    50                  55                  60

Ser Arg Val Thr Ile Ser Leu Asp Met Ser Lys Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

```
Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 165
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Thr Gly Arg Thr Phe Tyr Asn Pro Ser Leu Lys
    50                  55                  60

Ser Arg Val Thr Ile Ser Leu Asp Met Ser Ile Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240
```

```
Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 166
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Asn Gly Arg Thr Phe Tyr Asn Pro Ser Leu Lys
    50                  55                  60

Ser Arg Val Thr Ile Ser Leu Asp Lys Ser Lys Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
```

```
                130                 135                 140
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Arg Val Glu Pro Lys Ser
            210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 167
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30
```

Tyr Trp Ser Trp Ile Arg Gln Pro Pro Gly Lys Gly Leu Glu Trp Ile
                35                  40                  45

Gly Phe Ile Tyr Tyr Thr Gly Arg Thr Phe Tyr Asn Pro Ser Leu Lys
 50                  55                  60

Ser Arg Val Thr Ile Ser Leu Asp Met Ser Ile Asn Gln Phe Ser Leu
 65                  70                  75                  80

Lys Met Thr Ser Val Thr Ala Ala Asp Thr Ala Val Tyr Tyr Cys Ala
                 85                  90                  95

Arg Val Arg Ala Tyr Ser Gly Ile Gly Leu Asp Gly Thr Asp Val Trp
                100                 105                 110

Gly Gln Gly Thr Thr Val Thr Val Ser Ser Ala Ser Thr Lys Gly Pro
                115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
                355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly

<210> SEQ ID NO 168
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 168

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Asn Gly Arg Thr Phe Tyr Asn Pro Ser Leu Lys
    50                  55                  60

Ser Arg Val Thr Ile Ser Leu Asp Thr Ser Lys Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

```
Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 169
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Met
        35                  40                  45

Gly Phe Ile Tyr Asp Asn Gly Arg Thr Phe Tyr Asn Pro Ser Leu Lys
    50                  55                  60

Ser Arg Val Thr Ile Ser Leu Asp Met Ser Met Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255
```

```
Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 170
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Thr Gly Arg Thr Phe Tyr Asn Pro Ser Leu Lys
    50                  55                  60

Ser Arg Val Thr Ile Ser Leu Asp Met Ser Lys Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
```

Val Ser Trp Asn Ser Gly Ala Leu Thr Ser Gly Val His Thr Phe Pro
145                 150                 155                 160

Ala Val Leu Gln Ser Ser Gly Leu Tyr Ser Leu Ser Ser Val Val Thr
            165                 170                 175

Val Pro Ser Ser Ser Leu Gly Thr Gln Thr Tyr Ile Cys Asn Val Asn
        180                 185                 190

His Lys Pro Ser Asn Thr Lys Val Asp Lys Arg Val Glu Pro Lys Ser
    195                 200                 205

Cys Asp Lys Thr His Thr Cys Pro Pro Cys Pro Ala Pro Glu Ala Ala
210                 215                 220

Gly Gly Pro Ser Val Phe Leu Phe Pro Pro Lys Pro Lys Asp Thr Leu
225                 230                 235                 240

Met Ile Ser Arg Thr Pro Glu Val Thr Cys Val Val Val Asp Val Ser
            245                 250                 255

His Glu Asp Pro Glu Val Lys Phe Asn Trp Tyr Val Asp Gly Val Glu
        260                 265                 270

Val His Asn Ala Lys Thr Lys Pro Arg Glu Glu Gln Tyr Asn Ser Thr
    275                 280                 285

Tyr Arg Val Val Ser Val Leu Thr Val Leu His Gln Asp Trp Leu Asn
290                 295                 300

Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
            325                 330                 335

Val Tyr Thr Leu Pro Pro Ser Arg Glu Glu Met Thr Lys Asn Gln Val
        340                 345                 350

Ser Leu Thr Cys Leu Val Lys Gly Phe Tyr Pro Ser Asp Ile Ala Val
    355                 360                 365

Glu Trp Glu Ser Asn Gly Gln Pro Glu Asn Asn Tyr Lys Thr Thr Pro
370                 375                 380

Pro Val Leu Asp Ser Asp Gly Ser Phe Phe Leu Tyr Ser Lys Leu Thr
385                 390                 395                 400

Val Asp Lys Ser Arg Trp Gln Gln Gly Asn Val Phe Ser Cys Ser Val
            405                 410                 415

Met His Glu Ala Leu His Asn His Tyr Thr Gln Lys Ser Leu Ser Leu
        420                 425                 430

Ser Pro Gly
    435                 440                 445

450

<210> SEQ ID NO 171
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

```
Gly Phe Ile Tyr Tyr Thr Gly Arg Thr Phe Tyr Asn Pro Ser Leu Lys
 50                  55                  60

Ser Arg Val Thr Ile Ser Leu Asp Met Ser Lys Asn Gln Phe Ser Leu
 65                  70                  75                  80

Lys Met Thr Ser Val Thr Ala Ala Asp Thr Ala Val Tyr Tyr Cys Ala
                 85                  90                  95

Arg Val Arg Ala Tyr Ser Gly Ile Gly Leu Asp Gly Thr Asp Val Trp
                100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
450
```

<210> SEQ ID NO 172
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 172

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Thr Gly Arg Thr Phe Tyr Asn Pro Ser Leu Lys
    50                  55                  60

Ser Arg Val Thr Ile Ser Leu Asp Met Ser Ile Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

```
Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
                435                 440                 445

Ser Pro Gly
    450
```

<210> SEQ ID NO 173
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

```
Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Thr Gly Arg Thr Phe Tyr Asn Pro Ser Leu Lys
    50                  55                  60

Ser Arg Val Thr Ile Ser Leu Asp Met Ser Lys Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270
```

```
His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 174
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Phe Gln Gln Lys Pro Gly Lys Ala Pro Lys Ser Leu Ile
        35                  40                  45

Tyr Thr Ala Ser Ser Leu His Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                  165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 175
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Phe Gln Gln Lys Pro Gly Lys Ala Pro Lys Ser Leu Ile
        35                  40                  45

Tyr Thr Ala Ser Ser Leu His Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 176
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
```

```
                   20                  25                  30

Leu Ala Trp Tyr Gln Gln Lys Pro Gly Lys Ala Pro Lys Leu Leu Ile
            35                  40                  45

Tyr Ala Glu Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 177
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Asp Ile Gln Met Thr Gln Ser Pro Ser Ser Leu Ser Ala Ser Ile Gly
1               5                   10                  15

Asp Lys Val Thr Ile Thr Cys Arg Ala Ser Gln Asp Ile Asn Asn Tyr
            20                  25                  30

Leu Ala Trp Phe Gln Gln Lys Pro Gly Lys Ala Pro Lys Ser Leu Ile
            35                  40                  45

Tyr Thr Ala Ser Ser Leu Gln Ser Gly Val Pro Ser Lys Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 178
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Gly Tyr Asn Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 179
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Asp Ile Val Met Thr Gln Ser Pro Leu Ser Leu Pro Val Thr Pro Gly
1               5                   10                  15
```

```
Glu Pro Ala Ser Ile Ser Cys Lys Ser Ser Gln Ser Leu Leu Tyr Ser
             20                  25                  30

Asn Gly Tyr Asn Tyr Leu Asp Trp Tyr Leu Gln Arg Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Tyr Cys Met Gln Ala
                 85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 180
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Phe Gln Gln Lys Pro Gly Lys Ala Pro Lys Ser Leu Ile
        35                  40                  45

Tyr Thr Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 181
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Ala Ala Trp Phe Gln Gln Lys Pro Gly Lys Ala Pro Lys Ser Leu Ile
        35                  40                  45

Tyr Thr Ala Ser Ser Leu His Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 182
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Gly Ile Asn Asn Tyr
            20                  25                  30

Ala Ala Trp Phe Gln Gln Lys Pro Gly Lys Ala Pro Lys Ser Leu Ile
        35                  40                  45

Tyr Thr Ala Ser Ser Leu His Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 183
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Ala Ala Trp Phe Gln Gln Lys Pro Gly Lys Ala Pro Lys Ser Leu Ile
        35                  40                  45

Tyr Thr Ala Ser Ser Leu His Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
                145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 184
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
                20                  25                  30

Ala Ala Trp Phe Gln Gln Lys Pro Gly Lys Ala Pro Lys Ser Leu Ile
            35                  40                  45

Tyr Thr Ala Ser Ser Leu His Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 185
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Asp Ile Gln Met Thr Gln Ser Pro Ser Ser Leu Ser Ala Ser Val Gly
```

```
                1               5                   10                  15
Asp Arg Val Thr Ile Thr Cys Arg Ala Ser Gln Gly Ile Asn Asn Tyr
                20                  25                  30

Ala Ala Trp Phe Gln Gln Lys Pro Gly Lys Ala Pro Lys Ser Leu Ile
                35                  40                  45

Tyr Thr Ala Ser Ser Leu His Ser Gly Val Pro Ser Lys Phe Ser Gly
                50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Tyr Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
210

<210> SEQ ID NO 186
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
                20                  25                  30

Ala Ala Trp Phe Gln Gln Lys Pro Gly Lys Ala Pro Lys Ser Leu Ile
                35                  40                  45

Tyr Thr Ala Ser Ser Leu His Ser Gly Val Pro Ser Lys Phe Ser Gly
                50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Tyr Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 187
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Ala Ala Trp Phe Gln Gln Lys Pro Gly Lys Ala Pro Lys Ser Leu Ile
        35                  40                  45

Tyr Thr Ala Ser Ser Leu His Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 188
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Ala Ala Trp Phe Gln Gln Lys Pro Gly Lys Ala Pro Lys Ser Leu Ile
            35                  40                  45

Tyr Thr Ala Ser Ser Leu His Ser Gly Val Pro Ser Lys Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Tyr Pro Tyr
            85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 189
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Phe Gln Gln Lys Pro Gly Lys Ala Pro Lys Ser Leu Ile
            35                  40                  45

Tyr Thr Ala Ser Ser Leu His Ser Gly Val Pro Ser Lys Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Tyr Pro Tyr
            85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 190
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Phe Gln Gln Lys Pro Gly Lys Ala Pro Lys Ser Leu Ile
        35                  40                  45

Tyr Thr Ala Ser Ser Leu His Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 191
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Phe Gln Gln Lys Pro Gly Lys Ala Pro Lys Ser Leu Ile
        35                  40                  45

Tyr Thr Ala Ser Ser Leu His Ser Gly Val Pro Ser Lys Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
            210

<210> SEQ ID NO 192
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Phe Gln Gln Lys Pro Gly Lys Ala Pro Lys Ser Leu Ile
        35                  40                  45

Tyr Thr Ala Ser Ser Leu His Ser Gly Val Pro Ser Lys Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
            130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 193
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Phe Gln Gln Lys Pro Gly Lys Ala Pro Lys Ser Leu Ile
        35                  40                  45

Tyr Thr Ala Ser Ser Leu His Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 194
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 194

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Phe Gln Gln Lys Pro Gly Lys Ala Pro Lys Ser Leu Ile
        35                  40                  45

Tyr Thr Ala Ser Ser Leu His Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 195
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 195

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Phe Gln Gln Lys Pro Gly Lys Ala Pro Lys Ser Leu Ile
        35                  40                  45

Tyr Thr Ala Ser Ser Leu His Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 196
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

```
Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Gly Tyr Ala Tyr Leu Asp Trp Tyr Leu Gln Arg Pro Gly Gln Ser
        35                  40                  45

Pro Gln Leu Leu Ile Tyr Gln Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 197
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

```
Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Gly Tyr Ala Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 198
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 198

```
Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Gly Tyr Ala Tyr Leu Asp Trp Tyr Leu Gln Arg Pro Gly Gln Ser
        35                  40                  45

Pro Gln Leu Leu Ile Tyr Gln Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125
```

```
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 199
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
                20                  25                  30

Asn Gly Tyr Ala Tyr Leu Asp Trp Tyr Leu Gln Arg Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 200
<211> LENGTH: 219
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 200

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Gly Tyr Ala Tyr Leu Asp Trp Tyr Leu Gln Arg Pro Gly Gln Ser
        35                  40                  45

Pro Gln Leu Leu Ile Tyr Gln Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 201
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Gly Tyr Ala Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu

```
                  115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 202
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
                20                  25                  30

Asn Gly Tyr Ala Tyr Leu Asp Trp Tyr Leu Gln Arg Pro Gly Gln Ser
            35                  40                  45

Pro Gln Leu Leu Ile Tyr Gln Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Tyr Cys Met Gln Ala
                85                  90                  95

Leu Gln Thr Pro Leu Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 203
<211> LENGTH: 219
<212> TYPE: PRT
<213> ORGANISM: Artificial Sequence
<220> FEATURE:
```

<223> OTHER INFORMATION: Description of Artificial Sequence: Synthetic
       polypeptide

<400> SEQUENCE: 203

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Gly Tyr Ala Tyr Leu Asp Trp Tyr Leu Gln Arg Pro Gly Gln Ser
        35                  40                  45

Pro Gln Leu Leu Ile Tyr Gln Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 204
<211> LENGTH: 219
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 204

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Ala Tyr Asn Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 205
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Gly Tyr Ala Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 206
<211> LENGTH: 219
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 206

Asp Ile Val Met Thr Gln Ser Pro Leu Ser Leu Pro Val Thr Pro Gly
1               5                   10                  15

Glu Pro Ala Ser Ile Ser Cys Lys Ser Gln Ser Leu Leu Tyr Ser
            20                  25                  30

Asn Gly Tyr Ala Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 207
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Asp Ile Val Met Thr Gln Ser Pro Leu Ser Leu Pro Val Thr Pro Gly
1               5                   10                  15

Glu Pro Ala Ser Ile Ser Cys Lys Ser Gln Ser Leu Leu Tyr Ser
            20                  25                  30

Asn Ala Tyr Asn Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110
```

```
Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215
```

<210> SEQ ID NO 208
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

```
Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Gly Tyr Ala Tyr Leu Asp Trp Tyr Leu Gln Arg Pro Gly Gln Ser
        35                  40                  45

Pro Gln Leu Leu Ile Tyr Gln Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215
```

<210> SEQ ID NO 209
<211> LENGTH: 219
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 209

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Ala Tyr Asn Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 210
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 210

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Gly Tyr Ala Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys

```
                    100                 105                 110
Arg Thr Val Ala Ala Pro Ser Val Phe Ile Phe Pro Pro Ser Asp Glu
                115                 120                 125
Gln Leu Lys Ser Gly Thr Ala Ser Val Val Cys Leu Leu Asn Asn Phe
            130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215

<210> SEQ ID NO 211
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Asp Ile Val Met Thr Gln Ser Pro Leu Ser Leu Pro Val Thr Pro Gly
1               5                   10                  15
Glu Pro Ala Ser Ile Ser Cys Lys Ser Ser Gln Ser Leu Leu Tyr Ser
                20                  25                  30
Asn Ala Tyr Asn Tyr Leu Asp Trp Tyr Leu Gln Arg Pro Gly Gln Ser
            35                  40                  45
Pro Gln Leu Leu Ile Tyr Leu Gly Ser Asn Arg Ala Ser Gly Val Pro
        50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Leu Gln Thr Pro Leu Thr Phe Gly Gly Gly Thr Lys Val Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215

<210> SEQ ID NO 212
<211> LENGTH: 219
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Ala Tyr Asn Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 213
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Gly Tyr Ala Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95
```

```
Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 214
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 214

```
Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Gly Tyr Ala Tyr Leu Asp Trp Tyr Leu Gln Arg Pro Gly Gln Ser
        35                  40                  45

Pro Gln Leu Leu Ile Tyr Gln Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 215

<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Ala Tyr Asn Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 216
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
            20                  25                  30

Asn Ala Tyr Asn Tyr Leu Asp Trp Tyr Leu Gln Arg Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

```
Leu Gln Thr Pro Leu Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
    210                 215

<210> SEQ ID NO 217
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Ala Asp Thr Ala Val Tyr Tyr Cys Val
                85                  90                  95

Arg Gly Gly Val Trp Asp Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
```

```
                 225                 230                 235                 240

Phe Pro Pro Lys Pro Lys Asp Thr Leu Met Ile Ser Arg Thr Pro Glu
                       245                 250                 255

Val Thr Cys Val Val Val Asp Val Ser Gln Glu Asp Pro Glu Val Gln
                       260                 265                 270

Phe Asn Trp Tyr Val Asp Gly Val Glu Val His Asn Ala Lys Thr Lys
                       275                 280                 285

Pro Arg Glu Glu Gln Phe Asn Ser Thr Tyr Arg Val Val Ser Val Leu
                       290                 295                 300

Thr Val Leu His Gln Asp Trp Leu Asn Gly Lys Glu Tyr Lys Cys Lys
       305                 310                 315                 320

Val Ser Asn Lys Gly Leu Pro Ser Ser Ile Glu Lys Thr Ile Ser Lys
                       325                 330                 335

Ala Lys Gly Gln Pro Arg Glu Pro Gln Val Tyr Thr Leu Pro Pro Ser
                       340                 345                 350

Gln Glu Glu Met Thr Lys Asn Gln Val Ser Leu Thr Cys Leu Val Lys
                       355                 360                 365

Gly Phe Tyr Pro Ser Asp Ile Ala Val Glu Trp Glu Ser Asn Gly Gln
                       370                 375                 380

Pro Glu Asn Asn Tyr Lys Thr Thr Pro Pro Val Leu Asp Ser Asp Gly
       385                 390                 395                 400

Ser Phe Phe Leu Tyr Ser Arg Leu Thr Val Asp Lys Ser Arg Trp Gln
                       405                 410                 415

Glu Gly Asn Val Phe Ser Cys Ser Val Met His Glu Ala Leu His Asn
                       420                 425                 430

His Tyr Thr Gln Lys Ser Leu Ser Leu Ser Leu Gly
                       435                 440

<210> SEQ ID NO 218
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Asp Ile Gln Met Thr Gln Ser Pro Ser Ser Leu Ser Ala Ser Val Gly
       1               5                   10                  15

Asp Arg Val Thr Ile Thr Cys Arg Ala Ser Gln Asp Ile Asn Asn Tyr
                       20                  25                  30

Leu Ala Trp Phe Gln Gln Lys Pro Gly Lys Ala Pro Lys Ser Leu Ile
                       35                  40                  45

Tyr Thr Ala Ser Ser Leu His Ser Gly Val Pro Ser Lys Phe Ser Gly
                       50                  55                  60

Ser Gly Ser Gly Thr Asp Phe Thr Leu Thr Ile Ser Ser Leu Gln Pro
       65                  70                  75                  80

Glu Asp Phe Ala Thr Tyr Tyr Cys Gln Gln Tyr Val Ser Tyr Pro Tyr
                       85                  90                  95

Thr Phe Gly Gln Gly Thr Lys Leu Glu Ile Lys Arg Thr Val Ala Ala
                       100                 105                 110

Pro Ser Val Phe Ile Phe Pro Pro Ser Asp Glu Gln Leu Lys Ser Gly
                       115                 120                 125

Thr Ala Ser Val Val Cys Leu Leu Asn Asn Phe Tyr Pro Arg Glu Ala
                       130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 219
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 219

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Asp Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Asn Gly Arg Thr Phe Tyr Gln Ser Ser Leu Lys
    50                  55                  60

Ser Arg Val Thr Ile Ser Leu Asp Thr Ser Lys Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285
```

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
                355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly
    450

<210> SEQ ID NO 220
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
                20                  25                  30

Thr Gly Tyr Thr Tyr Leu Asp Trp Tyr Leu Gln Arg Pro Gly Gln Ser
            35                  40                  45

Pro Gln Leu Leu Ile Tyr Gly Gly Ser Ser Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Tyr Cys Gly Gln Ala
                85                  90                  95

Leu Gln Thr Pro Leu Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu

```
                        180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
        210                 215

<210> SEQ ID NO 221
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Asp Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Asn Gly Arg Thr Phe Tyr Gln Ser Ser Leu Lys
    50                  55                  60

Ser Arg Val Thr Ile Ser Leu Asp Thr Ser Lys Asn Gln Phe Ser Leu
65                  70                  75                  80

Lys Met Thr Ser Val Thr Ala Ala Asp Thr Ala Val Tyr Tyr Cys Ala
                85                  90                  95

Arg Val Arg Ala Tyr Ser Gly Ile Gly Leu Asp Gly Thr Asp Val Trp
            100                 105                 110

Gly Gln Gly Thr Thr Val Thr Val Ser Ser
        115                 120

<210> SEQ ID NO 222
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Thr Gly Tyr Thr Tyr Leu Asp Trp Tyr Leu Gln Arg Pro Gly Gln Ser
        35                  40                  45

Pro Gln Leu Leu Ile Tyr Gly Gly Ser Ser Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Tyr Cys Gly Gln Ala
                85                  90                  95

Leu Gln Thr Pro Leu Thr Phe Gly Gln Gly Thr Lys Val Glu Ile Lys
            100                 105                 110

<210> SEQ ID NO 223
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 223

Asp Tyr Tyr Trp Ser
1               5

<210> SEQ ID NO 224
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Phe Ile Tyr Tyr Asn Gly Arg Thr Phe Tyr Gln Ser Ser Leu Lys Ser
1               5                   10                  15

<210> SEQ ID NO 225
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Arg Ser Ser Gln Ser Leu Leu Tyr Ser Thr Gly Tyr Thr Tyr Leu Asp
1               5                   10                  15

<210> SEQ ID NO 226
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gly Gly Ser Ser Arg Ala Ser
1               5

<210> SEQ ID NO 227
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Gly Gln Ala Leu Gln Thr Pro Leu Thr
1               5

<210> SEQ ID NO 228
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N or D
```

```
<400> SEQUENCE: 228

Xaa Tyr Tyr Trp Ser
1               5

<210> SEQ ID NO 229
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Y or D
<220> FEATURE:
<221> NAME/KEY: MOD_RES
<222> LOCATION: (5)..(5)
<223> OTHER INFORMATION: N or T
<220> FEATURE:
<221> NAME/KEY: MOD_RES
<222> LOCATION: (11)..(11)
<223> OTHER INFORMATION: N or Q
<220> FEATURE:
<221> NAME/KEY: MOD_RES
<222> LOCATION: (12)..(12)
<223> OTHER INFORMATION: S or P

<400> SEQUENCE: 229

Phe Ile Tyr Xaa Xaa Gly Arg Thr Phe Tyr Xaa Xaa Ser Leu Lys Ser
1               5                   10                  15

<210> SEQ ID NO 230
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: K or R
<220> FEATURE:
<221> NAME/KEY: MOD_RES
<222> LOCATION: (10)..(10)
<223> OTHER INFORMATION: N or T
<220> FEATURE:
<221> NAME/KEY: MOD_RES
<222> LOCATION: (11)..(11)
<223> OTHER INFORMATION: G or A
<220> FEATURE:
<221> NAME/KEY: MOD_RES
<222> LOCATION: (13)..(13)
<223> OTHER INFORMATION: N, A or T

<400> SEQUENCE: 230

Xaa Ser Ser Gln Ser Leu Leu Tyr Ser Xaa Xaa Tyr Xaa Tyr Leu Asp
1               5                   10                  15

<210> SEQ ID NO 231
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L, Q or G
<220> FEATURE:
<221> NAME/KEY: MOD_RES
```

```
<222> LOCATION: (4)..(4)
<223> OTHER INFORMATION: N or S

<400> SEQUENCE: 231

Xaa Gly Ser Xaa Arg Ala Ser
1               5

<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: M or G

<400> SEQUENCE: 232

Xaa Gln Ala Leu Gln Thr Pro Leu Thr
1               5

<210> SEQ ID NO 233
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: D or G
<220> FEATURE:
<221> NAME/KEY: MOD_RES
<222> LOCATION: (10)..(10)
<223> OTHER INFORMATION: L or A

<400> SEQUENCE: 233

Arg Ala Ser Gln Xaa Ile Asn Asn Tyr Xaa Ala
1               5                   10

<210> SEQ ID NO 234
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110
```

Pro Ala Pro Glu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 235
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 236
<211> LENGTH: 327
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 236

```
Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325
```

<210> SEQ ID NO 237
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

```
<400> SEQUENCE: 237

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 238
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240
```

```
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 239
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 240
<211> LENGTH: 347
<212> TYPE: PRT
<213> ORGANISM: Homo sapiens

<400> SEQUENCE: 240

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110
```

```
Ser Val Arg Ala Lys Pro Ser Ala Pro Val Val Ser Gly Pro Ala Ala
            115                 120                 125

Arg Ala Thr Pro Gln His Thr Val Ser Phe Thr Cys Glu Ser His Gly
130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Leu Thr Arg Glu Asp Val
            180                 185                 190

His Ser Gln Val Ile Cys Glu Val Ala His Val Thr Leu Gln Gly Asp
            195                 200                 205

Pro Leu Arg Gly Thr Ala Asn Leu Ser Glu Thr Ile Arg Val Pro Pro
210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
            275                 280                 285

Asn Val Ser Ala His Arg Asp Asp Val Lys Leu Thr Cys Gln Val Glu
            290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr Gly Gly Ser Gly
            340                 345

<210> SEQ ID NO 241
<211> LENGTH: 346
<212> TYPE: PRT
<213> ORGANISM: Homo sapiens

<400> SEQUENCE: 241

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ala Pro Val Val Ser Gly Pro Ala Ala Arg
        115                 120                 125

Ala Thr Pro Gln His Thr Val Ser Phe Thr Cys Glu Ser His Gly Phe
130                 135                 140
```

Ser Pro Arg Asp Ile Thr Leu Lys Trp Phe Lys Asn Gly Asn Glu Leu
145                 150                 155                 160

Ser Asp Phe Gln Thr Asn Val Asp Pro Val Gly Glu Ser Val Ser Tyr
            165                 170                 175

Ser Ile His Ser Thr Ala Lys Val Val Leu Thr Arg Glu Asp Val His
            180                 185                 190

Ser Gln Val Ile Cys Glu Val Ala His Val Thr Leu Gln Gly Asp Pro
            195                 200                 205

Leu Arg Gly Thr Ala Asn Leu Ser Glu Thr Ile Arg Val Pro Pro Thr
210                 215                 220

Leu Glu Val Thr Gln Gln Pro Val Arg Ala Glu Asn Gln Val Asn Val
225                 230                 235                 240

Thr Cys Gln Val Arg Lys Phe Tyr Pro Gln Arg Leu Gln Leu Thr Trp
                245                 250                 255

Leu Glu Asn Gly Asn Val Ser Arg Thr Glu Thr Ala Ser Thr Val Thr
                260                 265                 270

Glu Asn Lys Asp Gly Thr Tyr Asn Trp Met Ser Trp Leu Leu Val Asn
            275                 280                 285

Val Ser Ala His Arg Asp Asp Val Lys Leu Thr Cys Gln Val Glu His
            290                 295                 300

Asp Gly Gln Pro Ala Val Ser Lys Ser His Asp Leu Lys Val Ser Ala
305                 310                 315                 320

His Pro Lys Glu Gln Gly Ser Asn Thr Ala Ala Glu Asn Thr Gly Ser
                325                 330                 335

Asn Glu Arg Asn Ile Tyr Gly Gly Ser Gly
            340                 345

<210> SEQ ID NO 242
<211> LENGTH: 346
<212> TYPE: PRT
<213> ORGANISM: Homo sapiens

<400> SEQUENCE: 242

Glu Asp Glu Leu Gln Val Ile Gln Pro Glu Lys Ser Val Ser Val Ala
1               5                   10                  15

Ala Gly Glu Ser Ala Thr Leu Arg Cys Ala Met Thr Ser Leu Ile Pro
            20                  25                  30

Val Gly Pro Ile Met Trp Phe Arg Gly Ala Gly Ala Gly Arg Glu Leu
            35                  40                  45

Ile Tyr Asn Gln Lys Glu Gly His Phe Pro Arg Val Thr Thr Val Ser
50                  55                  60

Glu Leu Thr Lys Arg Asn Asn Leu Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Val
            115                 120                 125

Arg Ala Thr Pro Glu His Thr Val Ser Phe Thr Cys Glu Ser His Gly
130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Ala Gly Asp Ser Val Ser

```
                165                 170                 175
Tyr Ser Ile His Ser Thr Ala Arg Val Val Leu Thr Arg Gly Asp Val
            180                 185                 190

His Ser Gln Val Ile Cys Glu Ile Ala His Ile Thr Leu Gln Gly Asp
        195                 200                 205

Pro Leu Arg Gly Thr Ala Asn Leu Ser Glu Ala Ile Arg Val Pro Pro
    210                 215                 220

Thr Leu Glu Val Thr Gln Gln Pro Met Arg Ala Glu Asn Gln Ala Asn
225                 230                 235                 240

Val Thr Cys Gln Val Ser Asn Phe Tyr Pro Arg Gly Leu Gln Leu Thr
                245                 250                 255

Trp Leu Glu Asn Gly Asn Val Ser Arg Thr Glu Thr Ala Ser Thr Leu
            260                 265                 270

Ile Glu Asn Lys Asp Gly Thr Tyr Asn Trp Met Ser Trp Leu Leu Val
        275                 280                 285

Asn Thr Cys Ala His Arg Asp Asp Val Val Leu Thr Cys Gln Val Glu
    290                 295                 300

His Asp Gly Gln Gln Ala Val Ser Lys Ser Tyr Ala Leu Glu Ile Ser
305                 310                 315                 320

Ala His Gln Lys Glu His Gly Ser Asp Ile Thr His Glu Ala Ala Leu
                325                 330                 335

Ala Pro Thr Ala Pro Leu Gly Gly Ser Gly
            340                 345

<210> SEQ ID NO 243
<211> LENGTH: 346
<212> TYPE: PRT
<213> ORGANISM: Homo sapiens

<400> SEQUENCE: 243

Glu Glu Glu Leu Gln Val Ile Gln Pro Asp Lys Ser Ile Ser Val Ala
1               5                   10                  15

Ala Gly Glu Ser Ala Thr Leu His Cys Thr Val Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp His Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
    130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Ala Gly Asp Ser Val Ser
                165                 170                 175

Tyr Ser Ile His Ser Thr Ala Lys Val Val Leu Thr Arg Glu Asp Val
            180                 185                 190
```

His Ser Gln Val Ile Cys Glu Val Ala His Val Thr Leu Gln Gly Asp
                195                 200                 205

Pro Leu Arg Gly Thr Ala Asn Leu Ser Glu Thr Ile Arg Val Pro Pro
        210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Leu
        260                 265                 270

Thr Glu Asn Lys Asp Gly Thr Tyr Asn Trp Met Ser Trp Leu Leu Val
                275                 280                 285

Asn Val Ser Ala His Arg Asp Asp Val Lys Leu Thr Cys Gln Val Glu
        290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Pro Gly Pro Ala Leu
                325                 330                 335

Ala Ser Ala Ala Pro Leu Gly Gly Ser Gly
        340                 345

<210> SEQ ID NO 244
<211> LENGTH: 332
<212> TYPE: PRT
<213> ORGANISM: Homo sapiens

<400> SEQUENCE: 244

Glu Glu Glu Leu Gln Met Ile Gln Pro Glu Lys Leu Leu Leu Val Thr
1               5                   10                  15

Val Gly Lys Thr Ala Thr Leu His Cys Thr Val Thr Ser Leu Leu Pro
                20                  25                  30

Val Gly Pro Val Leu Trp Phe Arg Gly Val Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asn Val Glu Phe Lys Ser Gly Pro Gly Thr Glu Met
                100                 105                 110

Ala Leu Gly Ala Lys Pro Ser Ala Pro Val Val Leu Gly Pro Ala Ala
        115                 120                 125

Arg Thr Thr Pro Glu His Thr Val Ser Phe Thr Cys Glu Ser His Gly
    130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Thr Gly Gln Ser Val Ala
                165                 170                 175

Tyr Ser Ile Arg Ser Thr Ala Arg Val Val Leu Asp Pro Trp Asp Val
            180                 185                 190

Arg Ser Gln Val Ile Cys Glu Val Ala His Val Thr Leu Gln Gly Asp
        195                 200                 205

Pro Leu Arg Gly Thr Ala Asn Leu Ser Glu Ala Ile Arg Val Pro Pro
    210                 215                 220

```
Thr Leu Glu Val Thr Gln Gln Pro Met Arg Val Gly Asn Gln Val Asn
225                 230                 235                 240

Val Thr Cys Gln Val Arg Lys Phe Tyr Pro Gln Ser Leu Gln Leu Thr
            245                 250                 255

Trp Ser Glu Asn Gly Asn Val Cys Gln Arg Glu Thr Ala Ser Thr Leu
        260                 265                 270

Thr Glu Asn Lys Asp Gly Thr Tyr Asn Trp Thr Ser Trp Phe Leu Val
    275                 280                 285

Asn Ile Ser Asp Gln Arg Asp Asp Val Val Leu Thr Cys Gln Val Lys
290                 295                 300

His Asp Gly Gln Leu Ala Val Ser Lys Arg Leu Ala Leu Glu Val Thr
305                 310                 315                 320

Val His Gln Lys Asp Gln Ser Ser Asp Ala Thr Pro
            325                 330

<210> SEQ ID NO 245
<211> LENGTH: 120
<212> TYPE: PRT
<213> ORGANISM: Homo sapiens

<400> SEQUENCE: 245

Trp Gln Pro Pro Leu Leu Phe Asn Lys Thr Lys Ser Val Glu Phe Thr
1               5                   10                  15

Phe Gly Asn Asp Thr Val Val Ile Pro Cys Phe Val Thr Asn Met Glu
            20                  25                  30

Ala Gln Asn Thr Thr Glu Val Tyr Val Lys Trp Lys Phe Lys Gly Arg
        35                  40                  45

Asp Ile Tyr Thr Phe Asp Gly Gln Ala Asn Lys Ser Thr Val Pro Thr
    50                  55                  60

Asp Phe Ser Ser Ala Lys Ile Glu Val Ser Gln Leu Leu Lys Gly Asp
65                  70                  75                  80

Ala Ser Leu Lys Met Asp Lys Ser Asp Ala Val Ser His Thr Gly Asn
                85                  90                  95

Tyr Thr Cys Glu Val Thr Glu Leu Thr Arg Glu Gly Glu Thr Ile Ile
            100                 105                 110

Glu Leu Lys Tyr Arg Val Val Ser
        115                 120

<210> SEQ ID NO 246
<211> LENGTH: 342
<212> TYPE: PRT
<213> ORGANISM: Mus musculus

<400> SEQUENCE: 246

Lys Glu Leu Lys Val Thr Gln Pro Glu Lys Ser Val Ser Val Ala Ala
1               5                   10                  15

Gly Asp Ser Thr Val Leu Asn Cys Thr Leu Thr Ser Leu Leu Pro Val
            20                  25                  30

Gly Pro Ile Lys Trp Tyr Arg Gly Val Gly Gln Ser Arg Leu Leu Ile
        35                  40                  45

Tyr Ser Phe Thr Gly Glu His Phe Pro Arg Val Thr Asn Val Ser Asp
    50                  55                  60

Ala Thr Lys Arg Asn Asn Met Asp Phe Ser Ile Arg Ile Ser Asn Val
65                  70                  75                  80

Thr Pro Glu Asp Ala Gly Thr Tyr Tyr Cys Val Lys Phe Gln Lys Gly
                85                  90                  95
```

Pro Ser Glu Pro Asp Thr Glu Ile Gln Ser Gly Gly Thr Glu Val
            100                 105                 110

Tyr Val Leu Ala Lys Pro Ser Pro Glu Val Ser Gly Pro Ala Asp
            115                 120                 125

Arg Gly Ile Pro Asp Gln Lys Val Asn Phe Thr Cys Lys Ser His Gly
            130                 135                 140

Phe Ser Pro Arg Asn Ile Thr Leu Lys Trp Phe Lys Asp Gly Gln Glu
145                 150                 155                 160

Leu His His Leu Glu Thr Thr Val Asn Pro Ser Gly Lys Asn Val Ser
            165                 170                 175

Tyr Asn Ile Ser Ser Thr Val Arg Val Leu Asn Ser Met Asp Val
            180                 185                 190

His Ser Lys Val Ile Cys Glu Val Ala His Ile Thr Leu Asp Arg Ser
            195                 200                 205

Pro Leu Arg Gly Ile Ala Asn Leu Ser Asn Phe Ile Arg Val Ser Pro
            210                 215                 220

Thr Val Lys Val Thr Gln Gln Ser Pro Thr Ser Met Asn Gln Val Asn
225                 230                 235                 240

Leu Thr Cys Arg Ala Glu Arg Phe Tyr Pro Glu Asp Leu Gln Leu Ile
            245                 250                 255

Trp Leu Glu Asn Gly Asn Val Ser Arg Asn Asp Thr Pro Lys Asn Leu
            260                 265                 270

Thr Lys Asn Thr Asp Gly Thr Tyr Asn Tyr Thr Ser Leu Phe Leu Val
            275                 280                 285

Asn Ser Ser Ala His Arg Glu Asp Val Val Phe Thr Cys Gln Val Lys
            290                 295                 300

His Asp Gln Gln Pro Ala Ile Thr Arg Asn His Thr Val Leu Gly Leu
305                 310                 315                 320

Ala His Ser Ser Asp Gln Gly Ser Met Gln Thr Phe Pro Gly Asn Asn
            325                 330                 335

Ala Thr His Asn Trp Asn
            340

<210> SEQ ID NO 247
<211> LENGTH: 346
<212> TYPE: PRT
<213> ORGANISM: Macaca fascicularis

<400> SEQUENCE: 247

Glu Glu Glu Leu Gln Val Ile Gln Pro Glu Lys Ser Val Ser Val Ala
1               5                   10                  15

Ala Gly Asp Ser Ala Thr Leu Asn Cys Thr Val Ser Ser Leu Ile Pro
            20                  25                  30

Val Gly Pro Ile Gln Trp Phe Arg Gly Ala Gly Pro Gly Arg Glu Leu
            35                  40                  45

Ile Tyr Asn Leu Lys Glu Gly His Phe Pro Arg Val Thr Ala Val Ser
            50                  55                  60

Asp Pro Thr Lys Arg Asn Asn Met Asp Phe Ser Ile Arg Ile Ser Asn
65                  70                  75                  80

Ile Thr Pro Ala Asp Ala Gly Thr Tyr Tyr Cys Val Lys Phe Arg Lys
            85                  90                  95

Gly Ser Pro Asp Val Glu Leu Lys Ser Gly Ala Gly Thr Glu Leu Ser
            100                 105                 110

Val Arg Ala Lys Pro Ser Ala Pro Val Val Ser Gly Pro Ala Val Arg

-continued

```
            115                 120                 125
Ala Thr Ala Glu His Thr Val Ser Phe Thr Cys Glu Ser His Gly Phe
        130                 135                 140

Ser Pro Arg Asp Ile Thr Leu Lys Trp Phe Lys Asn Gly Asn Glu Leu
145                 150                 155                 160

Ser Asp Val Gln Thr Asn Val Asp Pro Ala Gly Lys Ser Val Ser Tyr
                165                 170                 175

Ser Ile Arg Ser Thr Ala Arg Val Leu Leu Thr Arg Arg Asp Val His
            180                 185                 190

Ser Gln Val Ile Cys Glu Val Ala His Val Thr Leu Gln Gly Asp Pro
        195                 200                 205

Leu Arg Gly Thr Ala Asn Leu Ser Glu Ala Ile Arg Val Pro Pro Phe
    210                 215                 220

Leu Glu Val Thr Gln Gln Ser Met Arg Ala Asp Asn Gln Val Asn Val
225                 230                 235                 240

Thr Cys Gln Val Thr Lys Phe Tyr Pro Gln Arg Leu Gln Leu Thr Trp
                245                 250                 255

Leu Glu Asn Gly Asn Val Ser Arg Thr Glu Met Ala Ser Ala Leu Pro
            260                 265                 270

Glu Asn Lys Asp Gly Thr Tyr Asn Trp Thr Ser Trp Leu Leu Val Asn
        275                 280                 285

Val Ser Ala His Arg Asp Asp Val Lys Leu Thr Cys Gln Val Glu His
    290                 295                 300

Asp Gly Gln Pro Ala Val Asn Lys Ser Phe Ser Val Lys Val Ser Ala
305                 310                 315                 320

His Pro Lys Glu Gln Gly Ser Asn Thr Ala Ala Glu Asn Thr Gly Thr
                325                 330                 335

Asn Glu Arg Asn Ile Tyr Gly Gly Ser Gly
            340                 345

<210> SEQ ID NO 248
<211> LENGTH: 346
<212> TYPE: PRT
<213> ORGANISM: Macaca fascicularis

<400> SEQUENCE: 248

Glu Glu Glu Leu Gln Val Ile Gln Pro Glu Lys Ser Val Ser Val Ala
1               5                   10                  15

Ala Gly Glu Ser Ala Thr Leu Asn Cys Thr Ala Thr Ser Leu Ile Pro
            20                  25                  30

Val Gly Pro Ile Gln Trp Phe Arg Gly Val Gly Pro Gly Arg Glu Leu
        35                  40                  45

Ile Tyr His Gln Lys Glu Gly His Phe Pro Arg Val Thr Pro Val Ser
    50                  55                  60

Asp Pro Thr Lys Arg Asn Asn Met Asp Phe Ser Ile Arg Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Val Glu Leu Lys Ser Gly Ala Gly Thr Glu Leu Ser
            100                 105                 110

Val Arg Ala Lys Pro Ser Ala Pro Val Val Ser Gly Pro Ala Val Arg
        115                 120                 125

Ala Thr Ala Glu His Thr Val Ser Phe Thr Cys Glu Ser His Gly Phe
    130                 135                 140
```

Ser Pro Arg Asp Ile Thr Leu Lys Trp Phe Lys Asn Gly Asn Glu Leu
145                 150                 155                 160

Ser Asp Phe Gln Thr Asn Val Asp Pro Ala Gly Lys Ser Val Ser Tyr
            165                 170                 175

Ser Ile Arg Ser Thr Ala Arg Val Val Leu Thr Arg Arg Asp Val His
            180                 185                 190

Ser Gln Val Ile Cys Glu Val Ala His Val Thr Leu Gln Gly Asp Pro
        195                 200                 205

Leu Arg Gly Thr Ala Asn Leu Ser Glu Ala Ile Arg Val Pro Pro Phe
    210                 215                 220

Leu Glu Phe Thr Gln Gln Ser Met Arg Ala Asp Asn Gln Val Asn Val
225                 230                 235                 240

Thr Cys Gln Val Met Lys Phe Tyr Pro Gln Arg Leu Gln Leu Thr Trp
                245                 250                 255

Leu Glu Asn Gly Asn Val Ser Arg Thr Glu Met Ala Ser Ala Leu Pro
            260                 265                 270

Glu Asn Lys Asp Gly Thr Tyr Asn Trp Thr Ser Trp Leu Leu Val Asn
        275                 280                 285

Val Ser Ala His Arg Asp Asp Val Lys Leu Thr Cys Gln Val Glu His
    290                 295                 300

Asp Gly Gln Pro Ala Val Asn Lys Ser Phe Ser Val Lys Val Ser Ala
305                 310                 315                 320

His Pro Lys Glu Gln Gly Ser Asn Thr Ala Ala Glu Asn Thr Gly Thr
                325                 330                 335

Asn Glu Arg Asn Ile Tyr Gly Gly Ser Gly
            340                 345

<210> SEQ ID NO 249
<211> LENGTH: 346
<212> TYPE: PRT
<213> ORGANISM: Macaca fascicularis

<400> SEQUENCE: 249

Glu Glu Glu Leu Gln Val Ile Gln Pro Glu Lys Ser Val Ser Val Ala
1               5                   10                  15

Ala Gly Asp Ser Ala Thr Leu Asn Cys Thr Val Ser Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Leu Lys Glu Gly His Phe Pro Arg Val Thr Pro Val Ser
    50                  55                  60

Asp Pro Thr Lys Arg Asn Asn Met Asp Phe Ser Ile Arg Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Val Glu Leu Lys Ser Gly Ala Gly Thr Glu Leu Ser
            100                 105                 110

Val Arg Ala Lys Pro Ser Ala Pro Val Val Ser Gly Pro Ala Val Arg
        115                 120                 125

Ala Thr Ala Glu His Thr Val Ser Phe Thr Cys Glu Ser His Gly Phe
    130                 135                 140

Ser Pro Arg Asp Ile Thr Leu Lys Trp Phe Lys Asn Gly Asn Glu Leu
145                 150                 155                 160

Ser Asp Phe Gln Thr Asn Val Asp Pro Ala Gly Lys Ser Val Ser Tyr
            165                 170                 175

```
Ser Ile Arg Ser Thr Ala Arg Val Val Leu Thr Arg Arg Asp Val His
            180                 185                 190

Ser Gln Val Ile Cys Glu Val Ala His Val Thr Leu Gln Gly Asp Pro
            195                 200             205

Leu Arg Gly Thr Ala Asn Leu Ser Glu Ala Ile Arg Val Pro Pro Phe
        210                 215                 220

Leu Glu Val Thr Gln Ser Met Arg Ala Asp Asn Gln Val Asn Val
225                 230                 235                 240

Thr Cys Gln Val Thr Lys Phe Tyr Pro Gln Arg Leu Gln Leu Thr Trp
                245                 250                 255

Leu Glu Asn Gly Asn Val Ser Arg Thr Glu Met Ala Ser Ala Leu Pro
            260                 265                 270

Glu Asn Lys Asp Gly Thr Tyr Asn Trp Thr Ser Trp Leu Leu Val Asn
            275                 280                 285

Val Ser Ala His Arg Asp Asp Val Lys Leu Thr Cys Gln Val Glu His
            290                 295                 300

Asp Gly Gln Pro Ala Val Asn Lys Ser Phe Ser Val Lys Val Ser Ala
305                 310                 315                 320

His Pro Lys Glu Gln Gly Ser Asn Thr Ala Ala Glu Asn Thr Gly Thr
                325                 330                 335

Asn Glu Arg Asn Ile Tyr Gly Gly Ser Gly
            340                 345

<210> SEQ ID NO 250
<211> LENGTH: 345
<212> TYPE: PRT
<213> ORGANISM: Macaca fascicularis

<400> SEQUENCE: 250

Glu Glu Glu Leu Gln Val Ile Gln Pro Glu Lys Ser Val Ser Val Thr
1               5                   10                  15

Ala Gly Glu Ser Ala Thr Leu Asn Cys Thr Val Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Leu Lys Glu Gly His Phe Pro Arg Val Thr Thr Val Leu
    50                  55                  60

Asp Pro Thr Lys Arg Asn Asn Met Asp Phe Ser Ile His Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Val Glu Leu Lys Ser Gly Ala Gly Thr Glu Leu Ser
            100                 105                 110

Val Arg Ala Lys Pro Ser Ala Pro Val Val Ser Gly Pro Thr Ala Arg
        115                 120                 125

Ala Thr Pro Glu His Thr Val Ser Phe Thr Cys Glu Ser His Gly Phe
    130                 135                 140

Ser Pro Arg Asp Ile Thr Leu Lys Trp Phe Lys Asn Gly Asn Glu Leu
145                 150                 155                 160

Ser Asp Phe Gln Thr Asn Val Asp Pro Ala Gly Lys Ser Val Ser Tyr
                165                 170                 175

Ser Ile Arg Ser Thr Ala Arg Val Val Leu Thr Arg Arg Asp Val His
            180                 185                 190

Ser Gln Val Ile Cys Glu Val Ala His Val Thr Leu Gln Gly Asp Pro
        195                 200                 205
```

```
            195                 200                 205
Leu Arg Gly Thr Ala Asn Leu Ser Glu Ala Ile Arg Val Pro Pro Thr
210                 215                 220

Leu Glu Val Phe Gln Arg Pro Met Arg Ala Glu Asn Gln Val Asn Val
225                 230                 235                 240

Thr Cys Gln Val Arg Lys Phe Tyr Pro Gln Arg Leu Leu Leu Thr Trp
                    245                 250                 255

Leu Glu Asn Gly Asn Val Ser Gln Thr Glu Thr Ala Ser Thr Leu Thr
                260                 265                 270

Glu Asn Lys Asp Gly Thr Tyr Asn Trp Arg Ser Trp Leu Leu Val Asn
275                 280                 285

Thr Cys Ala His Arg Asp Gly Val Val Leu Thr Cys Gln Val Glu His
290                 295                 300

Asp Gly Gln Pro Ala Val Ser Lys Ser His Ala Leu Glu Val Ser Ala
305                 310                 315                 320

His Gln Lys Glu Gln Cys Ser Asp Thr Thr Ser Gly Pro Val Leu Ala
                325                 330                 335

Pro Thr Ala Pro Leu Gly Gly Ser Gly
            340                 345

<210> SEQ ID NO 251
<211> LENGTH: 345
<212> TYPE: PRT
<213> ORGANISM: Macaca fascicularis

<400> SEQUENCE: 251

Glu Glu Glu Leu Gln Val Ile Gln Pro Glu Lys Ser Ile Ser Val Ala
1               5                   10                  15

Ala Gly Glu Ser Ala Thr Leu Asn Cys Thr Val Thr Ser Leu Ile Pro
                20                  25                  30

Val Gly Pro Ile Gln Trp Phe Arg Gly Val Gly Pro Gly Arg Glu Leu
            35                  40                  45

Ile Phe Asn Leu Gln Glu Gly His Phe Pro Arg Val Thr Pro Val Ser
        50                  55                  60

Asp Pro Thr Lys Arg Asn Asn Met Asp Phe Ser Ile Leu Ile Ser Ser
65                  70                  75                  80

Ile Thr Pro Ala Asp Ala Gly Thr Tyr Tyr Cys Val Lys Phe Arg Lys
                85                  90                  95

Gly Ser Pro Asp Val Glu Leu Lys Ser Gly Ala Gly Thr Glu Leu Ser
            100                 105                 110

Val Arg Ala Lys Pro Ser Ala Pro Val Val Ser Gly Pro Ala Val Arg
        115                 120                 125

Ala Thr Ala Glu His Thr Val Ser Phe Thr Cys Glu Ser His Gly Phe
    130                 135                 140

Ser Pro Arg Asp Ile Thr Leu Lys Trp Phe Lys Asn Gly Asn Glu Leu
145                 150                 155                 160

Ser Asp Phe Gln Thr Ser Val Asp Pro Ala Gly Lys Ser Val Ser Tyr
                165                 170                 175

Ser Ile Arg Ser Thr Ala Arg Val Val Leu Thr Arg Arg Asp Val His
            180                 185                 190

Ser Gln Val Ile Cys Glu Val Ala His Val Thr Leu Gln Gly Asp Pro
        195                 200                 205

Leu Arg Gly Thr Ala Asn Leu Ser Glu Ala Ile Arg Val Pro Pro Phe
210                 215                 220
```

```
Leu Glu Val Thr Gln Gln Ser Met Arg Ala Glu Asn Gln Ala Asn Ile
225                 230                 235                 240

Thr Cys Gln Val Ser Asn Phe Tyr Pro Gln Arg Leu Leu Leu Thr Trp
            245                 250                 255

Leu Glu Asn Gly Asn Val Ser Gln Thr Glu Thr Ala Ser Thr Leu Thr
            260                 265                 270

Glu Asn Lys Asp Gly Thr Tyr Asn Trp Thr Ser Trp Leu Leu Val Asn
        275                 280                 285

Ile Cys Ala His Arg Asp Asp Val Val Leu Thr Cys Gln Val Lys His
290                 295                 300

Asp Gly Gln Pro Ala Val Ser Lys Ser His Thr Leu Glu Ile Ser Ala
305                 310                 315                 320

His Gln Lys Glu Gln Asp Ser Asp Val Thr His Gly Leu Ala Leu Ala
                325                 330                 335

Pro Thr Ala Pro Leu Gly Gly Ser Gly
            340                 345

<210> SEQ ID NO 252
<211> LENGTH: 336
<212> TYPE: PRT
<213> ORGANISM: Macaca fascicularis

<400> SEQUENCE: 252

Glu Glu Glu Leu Gln Met Ile Gln Pro Glu Lys Leu Leu Leu Val Ala
1               5                   10                  15

Val Gly Glu Ser Ala Thr Leu Asn Cys Thr Val Thr Ser Leu Leu Pro
            20                  25                  30

Val Gly Pro Val Leu Trp Phe Arg Gly Val Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Ser Ser
65                  70                  75                  80

Ile Thr Pro Ala Asp Ala Gly Thr Tyr Tyr Cys Val Lys Phe Arg Lys
                85                  90                  95

Gly Ser Pro Glu Asn Val Glu Phe Lys Ser Gly Pro Gly Thr Glu Met
            100                 105                 110

Ala Leu Arg Ala Lys Pro Ser Ala Pro Val Val Ser Gly Pro Ala Ala
        115                 120                 125

Arg Ala Thr Pro Glu His Thr Val Ser Phe Thr Cys Lys Ser His Gly
130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Ala Gly Gln Ser Val Ser
                165                 170                 175

Tyr Ser Ile Arg Ser Thr Ala Arg Val Val Leu Ala Pro Trp Asp Val
            180                 185                 190

Arg Ser Gln Val Thr Cys Glu Val Ala His Val Thr Leu Gln Gly Asp
        195                 200                 205

Pro Leu Arg Gly Thr Ala Asn Leu Ser Glu Ala Ile Arg Val Pro Pro
    210                 215                 220

Thr Leu Glu Val Thr Gln Gln Pro Met Arg Ala Gly Asn Gln Val Asn
225                 230                 235                 240

Ile Thr Tyr Gln Val Arg Asn Phe Tyr Pro Gln Asn Leu Gln Leu Thr
                245                 250                 255
```

-continued

```
Trp Leu Glu Asn Gly Asn Val Cys Arg Thr Glu Thr Ala Ser Thr Leu
            260                 265                 270

Thr Glu Asn Lys Asp Gly Thr Tyr Asn Trp Thr Ser Trp Leu Leu Val
        275                 280                 285

Asn Thr Ser Asp Gln Arg Asp Val Val Leu Thr Cys Gln Val Lys
    290                 295                 300

His Asp Gly Gln Leu Ala Val Asn Lys Ser Leu Val Leu Glu Val Ser
305                 310                 315                 320

Ala His Gln Lys Asp Gln Ser Ser Asp Ala Thr His Gly Gly Ser Gly
                325                 330                 335
```

<210> SEQ ID NO 253
<211> LENGTH: 6
<212> TYPE: PRT
<213> ORGANISM: Homo sapiens

<400> SEQUENCE: 253

```
Leu Ile Pro Val Gly Pro
1               5
```

<210> SEQ ID NO 254
<211> LENGTH: 3
<212> TYPE: PRT
<213> ORGANISM: Homo sapiens

<400> SEQUENCE: 254

```
Gln Lys Glu
1
```

<210> SEQ ID NO 255
<211> LENGTH: 4
<212> TYPE: PRT
<213> ORGANISM: Homo sapiens

<400> SEQUENCE: 255

```
Thr Lys Arg Asn
1
```

<210> SEQ ID NO 256
<211> LENGTH: 5
<212> TYPE: PRT
<213> ORGANISM: Homo sapiens

<400> SEQUENCE: 256

```
Lys Gly Ser Pro Asp
1               5
```

<210> SEQ ID NO 257
<211> LENGTH: 8
<212> TYPE: PRT
<213> ORGANISM: Homo sapiens

<400> SEQUENCE: 257

```
Arg Gly Ala Gly Pro Gly Arg Glu
1               5
```

<210> SEQ ID NO 258
<211> LENGTH: 5
<212> TYPE: PRT
<213> ORGANISM: Homo sapiens

<400> SEQUENCE: 258

```
Ala Gly Thr Tyr Tyr
1               5

<210> SEQ ID NO 259
<211> LENGTH: 10
<212> TYPE: PRT
<213> ORGANISM: Homo sapiens

<400> SEQUENCE: 259

Val Glu Phe Lys Ser Gly Ala Gly Thr Glu
1               5                   10

<210> SEQ ID NO 260
<211> LENGTH: 10
<212> TYPE: PRT
<213> ORGANISM: Homo sapiens

<400> SEQUENCE: 260

Thr Glu Phe Lys Ser Gly Ala Gly Thr Glu
1               5                   10

<210> SEQ ID NO 261
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Gly Gly Ser Ile Arg Asn Tyr
1               5

<210> SEQ ID NO 262
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Ser Phe Asp Met His
1               5

<210> SEQ ID NO 263
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Gly Phe Thr Phe Ser Ser Phe Asp
1               5

<210> SEQ ID NO 264
<211> LENGTH: 4
<212> TYPE: PRT
<213> ORGANISM: Homo sapiens

<400> SEQUENCE: 264

Thr Lys Arg Glu
1
```

```
<210> SEQ ID NO 265
<211> LENGTH: 146
<212> TYPE: PRT
<213> ORGANISM: Homo sapiens

<400> SEQUENCE: 265

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
                20                  25                  30

Glu Leu Gln Val Ile Gln Pro Asp Lys Ser Val Leu Val Ala Ala Gly
            35                  40                  45

Glu Thr Ala Thr Leu Arg Cys Thr Ala Thr Ser Leu Ile Pro Val Gly
        50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala
145

<210> SEQ ID NO 266
<211> LENGTH: 145
<212> TYPE: PRT
<213> ORGANISM: Homo sapiens

<400> SEQUENCE: 266

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
                20                  25                  30

Glu Leu Gln Val Ile Gln Pro Asp Lys Ser Val Ser Val Ala Ala Gly
            35                  40                  45

Glu Ser Ala Ile Leu His Cys Thr Val Thr Ser Leu Ile Pro Val Gly
        50                  55                  60

Pro Ile Gln Trp Phe Arg Gly Ala Gly Pro Ala Arg Glu Leu Ile Tyr
65                  70                  75                  80

Asn Gln Lys Glu Gly His Phe Pro Arg Val Thr Thr Val Ser Glu Ser
                85                  90                  95

Thr Lys Arg Glu Asn Met Asp Phe Ser Ile Ser Ile Ser Asn Ile Thr
            100                 105                 110

Pro Ala Asp Ala Gly Thr Tyr Tyr Cys Val Lys Phe Arg Lys Gly Ser
        115                 120                 125

Pro Asp Thr Glu Phe Lys Ser Gly Ala Gly Thr Glu Leu Ser Val Arg
    130                 135                 140

Ala
145

<210> SEQ ID NO 267
<211> LENGTH: 144
<212> TYPE: PRT
```

<213> ORGANISM: Homo sapiens

<400> SEQUENCE: 267

```
Met Pro Val Pro Ala Ser Trp Pro His Pro Gly Pro Phe Leu Leu
1               5                   10                  15

Leu Thr Leu Leu Leu Gly Leu Thr Glu Val Ala Gly Glu Glu Leu
                20                  25                  30

Gln Met Ile Gln Pro Glu Lys Leu Leu Leu Val Thr Val Gly Lys Thr
                35                  40                  45

Ala Thr Leu His Cys Thr Val Thr Ser Leu Leu Pro Val Gly Pro Val
        50                  55                  60

Leu Trp Phe Arg Gly Val Gly Pro Gly Arg Glu Leu Ile Tyr Asn Gln
65                  70                  75                  80

Lys Glu Gly His Phe Pro Arg Val Thr Thr Val Ser Asp Leu Thr Lys
                85                  90                  95

Arg Asn Asn Met Asp Phe Ser Ile Arg Ile Ser Ser Ile Thr Pro Ala
                100                 105                 110

Asp Val Gly Thr Tyr Tyr Cys Val Lys Phe Arg Lys Gly Ser Pro Glu
                115                 120                 125

Asn Val Glu Phe Lys Ser Gly Pro Gly Thr Glu Met Ala Leu Gly Ala
        130                 135                 140
```

<210> SEQ ID NO 268
<211> LENGTH: 474
<212> TYPE: PRT
<213> ORGANISM: Homo sapiens

<400> SEQUENCE: 268

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
                20                  25                  30

Val Gly Pro Ile Gln Trp Phe Arg Gly Ala Gly Pro Gly Arg Glu Leu
                35                  40                  45

Ile Tyr Asn Gln Lys Glu Gly His Phe Pro Arg Val Thr Thr Val Ser
        50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser Ala Pro Val Val Ser Gly Pro Ala Ala
                115                 120                 125

Arg Ala Thr Pro Gln His Thr Val Ser Phe Thr Cys Glu Ser His Gly
        130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
                180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
```

```
                210                 215                 220
Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
                260                 265                 270

Thr Glu Asn Lys Asp Gly Thr Tyr Asn Trp Met Ser Trp Leu Leu Val
            275                 280                 285

Asn Val Ser Ala His Arg Asp Asp Val Lys Leu Thr Cys Gln Val Glu
        290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr Ile Val Val Gly Val Val Cys Thr Leu
            340                 345                 350

Leu Val Ala Leu Leu Met Ala Ala Leu Tyr Leu Val Arg Ile Arg Gln
        355                 360                 365

Lys Lys Ala Gln Gly Ser Thr Ser Ser Thr Arg Leu His Glu Pro Glu
370                 375                 380

Lys Asn Ala Arg Glu Ile Thr Gln Asp Thr Asn Asp Ile Thr Tyr Ala
385                 390                 395                 400

Asp Leu Asn Leu Pro Lys Gly Lys Lys Pro Ala Pro Gln Ala Ala Glu
                405                 410                 415

Pro Asn Asn His Thr Glu Tyr Ala Ser Ile Gln Thr Ser Pro Gln Pro
            420                 425                 430

Ala Ser Glu Asp Thr Leu Thr Tyr Ala Asp Leu Asp Met Val His Leu
        435                 440                 445

Asn Arg Thr Pro Lys Gln Pro Ala Pro Lys Pro Glu Pro Ser Phe Ser
450                 455                 460

Glu Tyr Ala Ser Val Gln Val Pro Arg Lys
465                 470

<210> SEQ ID NO 269
<211> LENGTH: 474
<212> TYPE: PRT
<213> ORGANISM: Artificial
<220> FEATURE:
<223> OTHER INFORMATION: SIRPaV1 mutant
<220> FEATURE:
<221> NAME/KEY: Site

```
Ile Thr Pro Ala Asp Ala Gly Thr Tyr Tyr Cys Val Lys Phe Arg Lys
                85                  90                  95

Gly Ser Pro Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
            115                 120                 125

Arg Ala Thr Pro Gln His Thr Val Ser Phe Thr Cys Glu Ser His Gly
130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
                180                 185                 190

His Ser Gln Val Ile Cys Glu Val Ala His Val Thr Leu Gln Gly Asp
                195                 200                 205

Pro Leu Arg Gly Thr Ala Asn Leu Ser Glu Thr Ile Arg Val Pro Pro
            210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
            275                 280                 285

Asn Val Ser Ala His Arg Asp Asp Val Lys Leu Thr Cys Gln Val Glu
290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr Ile Val Val Gly Val Val Cys Thr Leu
            340                 345                 350

Leu Val Ala Leu Leu Met Ala Ala Leu Tyr Leu Val Arg Ile Arg Gln
            355                 360                 365

Lys Lys Ala Gln Gly Ser Thr Ser Ser Thr Arg Leu His Glu Pro Glu
370                 375                 380

Lys Asn Ala Arg Glu Ile Thr Gln Asp Thr Asn Asp Ile Thr Tyr Ala
385                 390                 395                 400

Asp Leu Asn Leu Pro Lys Gly Lys Lys Pro Ala Pro Gln Ala Ala Glu
                405                 410                 415

Pro Asn Asn His Thr Glu Tyr Ala Ser Ile Gln Thr Ser Pro Gln Pro
                420                 425                 430

Ala Ser Glu Asp Thr Leu Thr Tyr Ala Asp Leu Asp Met Val His Leu
            435                 440                 445

Asn Arg Thr Pro Lys Gln Pro Ala Pro Lys Pro Glu Pro Ser Phe Ser
450                 455                 460

Glu Tyr Ala Ser Val Gln Val Pro Arg Lys
465                 470

<210> SEQ ID NO 270
<211> LENGTH: 474
<212> TYPE: PRT
```

<213> ORGANISM: Artificial
<220> FEATURE:
<223> OTHER INFORMATION: SIRPaV1 mutant
<220> FEATURE:
<221> NAME/KEY: Site

```
Lys Lys Ala Gln Gly Ser Thr Ser Ser Thr Arg Leu His Glu Pro Glu
370                 375                 380

Lys Asn Ala Arg Glu Ile Thr Gln Asp Thr Asn Asp Ile Thr Tyr Ala
385                 390                 395                 400

Asp Leu Asn Leu Pro Lys Gly Lys Pro Ala Pro Gln Ala Ala Glu
            405                 410                 415

Pro Asn Asn His Thr Glu Tyr Ala Ser Ile Gln Thr Ser Pro Gln Pro
                420                 425                 430

Ala Ser Glu Asp Thr Leu Thr Tyr Ala Asp Leu Asp Met Val His Leu
            435                 440                 445

Asn Arg Thr Pro Lys Gln Pro Ala Pro Lys Pro Glu Pro Ser Phe Ser
450                 455                 460

Glu Tyr Ala Ser Val Gln Val Pro Arg Lys
465                 470

<210> SEQ ID NO 271
<211> LENGTH: 474
<212> TYPE: PRT
<213> ORGANISM: Artificial
<220> FEATURE:
<223> OTHER INFORMATION: SIRPaV1 mutant
<220> FEATURE:
<221> NAME/KEY: Site
<222> LOCATION: (101)..(101)
<223> OTHER INFORMATION: Mutated residue

<400> SEQUENCE: 271

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asn Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
    210                 215                 220

Thr Leu Glu Val Thr Gln Gln Pro Val Arg Ala Glu Asn Gln Val Asn
225                 230                 235                 240
```

```
Val Thr Cys Gln Val Arg Lys Phe Tyr Pro Gln Arg Leu Gln Leu Thr
            245                 250                 255

Trp Leu Glu Asn Gly Asn Val Ser Arg Thr Glu Thr Ala Ser Thr Val
        260                 265                 270

Thr Glu Asn Lys Asp Gly Thr Tyr Asn Trp Met Ser Trp Leu Leu Val
        275                 280                 285

Asn Val Ser Ala His Arg Asp Asp Val Lys Leu Thr Cys Gln Val Glu
        290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr Ile Val Val Gly Val Val Cys Thr Leu
        340                 345                 350

Leu Val Ala Leu Leu Met Ala Ala Leu Tyr Leu Val Arg Ile Arg Gln
        355                 360                 365

Lys Lys Ala Gln Gly Ser Thr Ser Ser Thr Arg Leu His Glu Pro Glu
370                 375                 380

Lys Asn Ala Arg Glu Ile Thr Gln Asp Thr Asn Asp Ile Thr Tyr Ala
385                 390                 395                 400

Asp Leu Asn Leu Pro Lys Gly Lys Lys Pro Ala Pro Gln Ala Ala Glu
                405                 410                 415

Pro Asn Asn His Thr Glu Tyr Ala Ser Ile Gln Thr Ser Pro Gln Pro
                420                 425                 430

Ala Ser Glu Asp Thr Leu Thr Tyr Ala Asp Leu Asp Met Val His Leu
            435                 440                 445

Asn Arg Thr Pro Lys Gln Pro Ala Pro Lys Pro Glu Pro Ser Phe Ser
        450                 455                 460

Glu Tyr Ala Ser Val Gln Val Pro Arg Lys
465                 470

<210> SEQ ID NO 272
<211> LENGTH: 474
<212> TYPE: PRT
<213> ORGANISM: Artificial
<220> FEATURE:
<223> OTHER INFORMATION: SIRPaV1 mutant
<220> FEATURE:
<221> NAME/KEY: Site
<222> LOCATION: (100)..(101)
<223> OTHER INFORMATION: Mutated residue

<400

```
            100             105             110
    Ser Val Arg Ala Lys Pro Ser Ala Pro Val Ser Gly Pro Ala Ala
            115             120             125

Arg Ala Thr Pro Gln His Thr Val Ser Phe Thr Cys Glu Ser His Gly
        130             135             140

Phe Ser Pro Arg Asp Ile Thr Leu Lys Trp Phe Lys Asn Gly Asn Glu
    145             150             155             160

Leu Ser Asp Phe Gln Thr Asn Val Asp Pro Val Gly Glu Ser Val Ser
                    165             170             175

Tyr Ser Ile His Ser Thr Ala Lys Val Val Leu Thr Arg Glu Asp Val
                180             185             190

His Ser Gln Val Ile Cys Glu Val Ala His Val Thr Leu Gln Gly Asp
            195             200             205

Pro Leu Arg Gly Thr Ala Asn Leu Ser Glu Thr Ile Arg Val Pro Pro
        210             215             220

Thr Leu Glu Val Thr Gln Gln Pro Val Arg Ala Glu Asn Gln Val Asn
    225             230             235             240

Val Thr Cys Gln Val Arg Lys Phe Tyr Pro Gln Arg Leu Gln Leu Thr
                    245             250             255

Trp Leu Glu Asn Gly Asn Val Ser Arg Thr Glu Thr Ala Ser Thr Val
                260             265             270

Thr Glu Asn Lys Asp Gly Thr Tyr Asn Trp Met Ser Trp Leu Leu Val
                275             280             285

Asn Val Ser Ala His Arg Asp Asp Val Lys Leu Thr Cys Gln Val Glu
                290             295             300

His Asp Gly Gln Pro Ala Val Ser Lys Ser His Asp Leu Lys Val Ser
    305             310             315             320

Ala His Pro Lys Glu Gln Gly Ser Asn Thr Ala Ala Glu Asn Thr Gly
                    325             330             335

Ser Asn Glu Arg Asn Ile Tyr Ile Val Val Gly Val Val Cys Thr Leu
                340             345             350

Leu Val Ala Leu Leu Met Ala Ala Leu Tyr Leu Val Arg Ile Arg Gln
                355             360             365

Lys Lys Ala Gln Gly Ser Thr Ser Ser Thr Arg Leu His Glu Pro Glu
        370             375             380

Lys Asn Ala Arg Glu Ile Thr Gln Asp Thr Asn Asp Ile Thr Tyr Ala
    385             390             395             400

Asp Leu Asn Leu Pro Lys Gly Lys Lys Pro Ala Pro Gln Ala Ala Glu
                    405             410             415

Pro Asn Asn His Thr Glu Tyr Ala Ser Ile Gln Thr Ser Pro Gln Pro
                420             425             430

Ala Ser Glu Asp Thr Leu Thr Tyr Ala Asp Leu Asp Met Val His Leu
                435             440             445

Asn Arg Thr Pro Lys Gln Pro Ala Pro Lys Pro Glu Pro Ser Phe Ser
    450             455             460

Glu Tyr Ala Ser Val Gln Val Pro Arg Lys
    465             470

<210> SEQ ID NO 273
<211> LENGTH: 473
<212> TYPE: PRT
<213> ORGANISM: Homo sapiens

<400> SEQUENCE: 273
```

-continued

```
Glu Glu Glu Leu Gln Val Ile Gln Pro Asp Lys Ser Val Ser Val Ala
1               5                   10                  15
Ala Gly Glu Ser Ala Ile Leu His Cys Thr Val Thr Ser Leu Ile Pro
            20                  25                  30
Val Gly Pro Ile Gln Trp Phe Arg Gly Ala Gly Pro Ala Arg Glu Leu
        35                  40                  45
Ile Tyr Asn Gln Lys Glu Gly His Phe Pro Arg Val Thr Thr Val Ser
    50                  55                  60
Glu Ser Thr Lys Arg Glu Asn Met Asp Phe Ile Ser Ile Ser Asn
65                  70                  75                  80
Ile Thr Pro Ala Asp Ala Gly Thr Tyr Tyr Cys Val Lys Phe Arg Lys
                85                  90                  95
Gly Ser Pro Asp Thr Glu Phe Lys Ser Gly Ala Gly Thr Glu Leu Ser
            100                 105                 110
Val Arg Ala Lys Pro Ser Ala Pro Val Val Ser Gly Pro Ala Ala Arg
        115                 120                 125
Ala Thr Pro Gln His Thr Val Ser Phe Thr Cys Glu Ser His Gly Phe
    130                 135                 140
Ser Pro Arg Asp Ile Thr Leu Lys Trp Phe Lys Asn Gly Asn Glu Leu
145                 150                 155                 160
Ser Asp Phe Gln Thr Asn Val Asp Pro Val Gly Glu Ser Val Ser Tyr
                165                 170                 175
Ser Ile His Ser Thr Ala Lys Val Val Leu Thr Arg Glu Asp Val His
            180                 185                 190
Ser Gln Val Ile Cys Glu Val Ala His Val Thr Leu Gln Gly Asp Pro
        195                 200                 205
Leu Arg Gly Thr Ala Asn Leu Ser Glu Thr Ile Arg Val Pro Pro Thr
    210                 215                 220
Leu Glu Val Thr Gln Gln Pro Val Arg Ala Glu Asn Gln Val Asn Val
225                 230                 235                 240
Thr Cys Gln Val Arg Lys Phe Tyr Pro Gln Arg Leu Gln Leu Thr Trp
                245                 250                 255
Leu Glu Asn Gly Asn Val Ser Arg Thr Glu Thr Ala Ser Thr Val Thr
            260                 265                 270
Glu Asn Lys Asp Gly Thr Tyr Asn Trp Met Ser Trp Leu Leu Val Asn
        275                 280                 285
Val Ser Ala His Arg Asp Asp Val Lys Leu Thr Cys Gln Val Glu His
    290                 295                 300
Asp Gly Gln Pro Ala Val Ser Lys Ser His Asp Leu Lys Val Ser Ala
305                 310                 315                 320
His Pro Lys Glu Gln Gly Ser Asn Thr Ala Ala Glu Asn Thr Gly Ser
                325                 330                 335
Asn Glu Arg Asn Ile Tyr Ile Val Val Gly Val Val Cys Thr Leu Leu
            340                 345                 350
Val Ala Leu Leu Met Ala Ala Leu Tyr Leu Val Arg Ile Arg Gln Lys
        355                 360                 365
Lys Ala Gln Gly Ser Thr Ser Ser Thr Arg Leu His Glu Pro Glu Lys
    370                 375                 380
Asn Ala Arg Glu Ile Thr Gln Asp Thr Asn Asp Ile Thr Tyr Ala Asp
385                 390                 395                 400
Leu Asn Leu Pro Lys Gly Lys Lys Pro Ala Pro Gln Ala Ala Glu Pro
                405                 410                 415
Asn Asn His Thr Glu Tyr Ala Ser Ile Gln Thr Ser Pro Gln Pro Ala
```

```
                420                 425                 430
Ser Glu Asp Thr Leu Thr Tyr Ala Asp Leu Asp Met Val His Leu Asn
            435                 440                 445

Arg Thr Pro Lys Gln Pro Ala Pro Lys Pro Glu Pro Ser Phe Ser Glu
        450                 455                 460

Tyr Ala Ser Val Gln Val Pro Arg Lys
465                 470

<210> SEQ ID NO 274
<211> LENGTH: 473
<212> TYPE: PRT
<213> ORGANISM: Artificial
<220> FEATURE:
<223> OTHER INFORMATION: SIRPaV2 mutant
<220> FEATURE:
<221> NAME/KEY: Site
<222> LOCATION: (70)..(70)
<223> OTHER INFORMATION: Mutated residue

<400> SEQUENCE: 274

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Asn Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ala Pro Val Val Ser Gly Pro Ala Ala Arg
        115                 120                 125

Ala Thr Pro Gln His Thr Val Ser Phe Thr Cys Glu Ser His Gly Phe
    130                 135                 140

Ser Pro Arg Asp Ile Thr Leu Lys Trp Phe Lys Asn Gly Asn Glu Leu
145                 150                 155                 160

Ser Asp Phe Gln Thr Asn Val Asp Pro Val Gly Glu Ser Val Ser Tyr
                165                 170                 175

Ser Ile His Ser Thr Ala Lys Val Val Leu Thr Arg Glu Asp Val His
            180                 185                 190

Ser Gln Val Ile Cys Glu Val Ala His Val Thr Leu Gln Gly Asp Pro
        195                 200                 205

Leu Arg Gly Thr Ala Asn Leu Ser Glu Thr Ile Arg Val Pro Pro Thr
    210                 215                 220

Leu Glu Val Thr Gln Gln Pro Val Arg Ala Glu Asn Gln Val Asn Val
225                 230                 235                 240

Thr Cys Gln Val Arg Lys Phe Tyr Pro Gln Arg Leu Gln Leu Thr Trp
                245                 250                 255

Leu Glu Asn Gly Asn Val Ser Arg Thr Glu Thr Ala Ser Thr Val Thr
            260                 265                 270

Glu Asn Lys Asp Gly Thr Tyr Asn Trp Met Ser Trp Leu Leu Val Asn
        275                 280                 285
```

```
Val Ser Ala His Arg Asp Asp Val Lys Leu Thr Cys Gln Val Glu His
    290                 295                 300

Asp Gly Gln Pro Ala Val Ser Lys Ser His Asp Leu Lys Val Ser Ala
305                 310                 315                 320

His Pro Lys Glu Gln Gly Ser Asn Thr Ala Ala Glu Asn Thr Gly Ser
                325                 330                 335

Asn Glu Arg Asn Ile Tyr Ile Val Val Gly Val Val Cys Thr Leu Leu
            340                 345                 350

Val Ala Leu Leu Met Ala Ala Leu Tyr Leu Val Arg Ile Arg Gln Lys
                355                 360                 365

Lys Ala Gln Gly Ser Thr Ser Ser Thr Arg Leu His Glu Pro Glu Lys
370                 375                 380

Asn Ala Arg Glu Ile Thr Gln Asp Thr Asn Asp Ile Thr Tyr Ala Asp
385                 390                 395                 400

Leu Asn Leu Pro Lys Gly Lys Lys Pro Ala Pro Gln Ala Ala Glu Pro
                405                 410                 415

Asn Asn His Thr Glu Tyr Ala Ser Ile Gln Thr Ser Pro Gln Pro Ala
                420                 425                 430

Ser Glu Asp Thr Leu Thr Tyr Ala Asp Leu Asp Met Val His Leu Asn
                435                 440                 445

Arg Thr Pro Lys Gln Pro Ala Pro Lys Pro Glu Pro Ser Phe Ser Glu
    450                 455                 460

Tyr Ala Ser Val Gln Val Pro Arg Lys
465                 470

<210> SEQ ID NO 275
<211> LENGTH: 473
<212> TYPE: PRT
<213> ORGANISM: Artificial
<220> FEATURE:
<223> OTHER INFORMATION: SIRPaV2 mutant
<220> FEATURE:
<221> NAME/KEY: Site
<222> LOCATION: (100)..(100)
<223> OTHER INFORMATION: Mutated

```
Ser Asp Phe Gln Thr Asn Val Asp Pro Val Gly Glu Ser Val Ser Tyr
            165                 170                 175

Ser Ile His Ser Thr Ala Lys Val Val Leu Thr Arg Glu Asp Val His
            180                 185                 190

Ser Gln Val Ile Cys Glu Val Ala His Val Thr Leu Gln Gly Asp Pro
            195                 200                 205

Leu Arg Gly Thr Ala Asn Leu Ser Glu Thr Ile Arg Val Pro Pro Thr
        210                 215                 220

Leu Glu Val Thr Gln Gln Pro Val Arg Ala Glu Asn Gln Val Asn Val
225                 230                 235                 240

Thr Cys Gln Val Arg Lys Phe Tyr Pro Gln Arg Leu Gln Leu Thr Trp
            245                 250                 255

Leu Glu Asn Gly Asn Val Ser Arg Thr Glu Thr Ala Ser Thr Val Thr
            260                 265                 270

Glu Asn Lys Asp Gly Thr Tyr Asn Trp Met Ser Trp Leu Leu Val Asn
        275                 280                 285

Val Ser Ala His Arg Asp Asp Val Lys Leu Thr Cys Gln Val Glu His
        290                 295                 300

Asp Gly Gln Pro Ala Val Ser Lys Ser His Asp Leu Lys Val Ser Ala
305                 310                 315                 320

His Pro Lys Glu Gln Gly Ser Asn Thr Ala Ala Glu Asn Thr Gly Ser
            325                 330                 335

Asn Glu Arg Asn Ile Tyr Ile Val Val Gly Val Val Cys Thr Leu Leu
            340                 345                 350

Val Ala Leu Leu Met Ala Ala Leu Tyr Leu Val Arg Ile Arg Gln Lys
            355                 360                 365

Lys Ala Gln Gly Ser Thr Ser Ser Thr Arg Leu His Glu Pro Glu Lys
        370                 375                 380

Asn Ala Arg Glu Ile Thr Gln Asp Thr Asn Asp Ile Thr Tyr Ala Asp
385                 390                 395                 400

Leu Asn Leu Pro Lys Gly Lys Lys Pro Ala Pro Gln Ala Ala Glu Pro
            405                 410                 415

Asn Asn His Thr Glu Tyr Ala Ser Ile Gln Thr Ser Pro Gln Pro Ala
            420                 425                 430

Ser Glu Asp Thr Leu Thr Tyr Ala Asp Leu Asp Met Val His Leu Asn
            435                 440                 445

Arg Thr Pro Lys Gln Pro Ala Pro Lys Pro Glu Pro Ser Phe Ser Glu
        450                 455                 460

Tyr Ala Ser Val Gln Val Pro Arg Lys
465                 470

<210> SEQ ID NO 276
<211> LENGTH: 369
<212> TYPE: PRT
<213> ORGANISM: Homo sapiens

<400> SEQUENCE: 276

Glu Asp Glu Leu Gln Val Ile Gln Pro Glu Lys Ser Val Ser Val Ala
1               5                   10                  15

Ala Gly Glu Ser Ala Thr Leu Arg Cys Ala Met Thr Ser Leu Ile Pro
            20                  25                  30

Val Gly Pro Ile Met Trp Phe Arg Gly Ala Gly Ala Gly Arg Glu Leu
            35                  40                  45

Ile Tyr Asn Gln Lys Glu Gly His Phe Pro Arg Val Thr Thr Val Ser
```

```
                  50                  55                  60

Glu Leu Thr Lys Arg Asn Asn Leu Asp Phe Ser Ile Ser Ile Ser Asn
 65                  70                  75                  80

Ile Thr Pro Ala Asp Ala Gly Thr Tyr Tyr Cys Val Lys Phe Arg Lys
                     85                  90                  95

Gly Ser Pro Asp Asp Val Glu Phe Lys Ser Gly Ala Gly Thr Glu Leu
                    100                 105                 110

Ser Val Arg Ala Lys Pro Ser Ala Pro Val Val Ser Gly Pro Ala Val
                115                 120                 125

Arg Ala Thr Pro Glu His Thr Val Ser Phe Thr Cys Glu Ser His Gly
            130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Ala Gly Asp Ser Val Ser
                    165                 170                 175

Tyr Ser Ile His Ser Thr Ala Arg Val Val Leu Thr Arg Gly Asp Val
                180                 185                 190

His Ser Gln Val Ile Cys Glu Ile Ala His Ile Thr Leu Gln Gly Asp
            195                 200                 205

Pro Leu Arg Gly Thr Ala Asn Leu Ser Glu Ala Ile Arg Val Pro Pro
210                 215                 220

Thr Leu Glu Val Thr Gln Gln Pro Met Arg Ala Glu Asn Gln Ala Asn
225                 230                 235                 240

Val Thr Cys Gln Val Ser Asn Phe Tyr Pro Arg Gly Leu Gln Leu Thr
                    245                 250                 255

Trp Leu Glu Asn Gly Asn Val Ser Arg Thr Glu Thr Ala Ser Thr Leu
                260                 265                 270

Ile Glu Asn Lys Asp Gly Thr Tyr Asn Trp Met Ser Trp Leu Leu Val
            275                 280                 285

Asn Thr Cys Ala His Arg Asp Asp Val Val Leu Thr Cys Gln Val Glu
290                 295                 300

His Asp Gly Gln Gln Ala Val Ser Lys Ser Tyr Ala Leu Glu Ile Ser
305                 310                 315                 320

Ala His Gln Lys Glu His Gly Ser Asp Ile Thr His Glu Ala Ala Leu
                    325                 330                 335

Ala Pro Thr Ala Pro Leu Leu Val Ala Leu Leu Gly Pro Lys Leu
                340                 345                 350

Leu Leu Val Val Gly Val Ser Ala Ile Tyr Ile Cys Trp Lys Gln Lys
            355                 360                 365

Ala

<210> SEQ ID NO 277
<211> LENGTH: 369
<212> TYPE: PRT
<213> ORGANISM: Artificial
<220> FEATURE:
<223> OTHER INFORMATION: SIRPb1 mutant
<220> FEATURE:
<221> NAME/KEY: Site
<222> LOCATION: (101)..(101)
<223> OTHER INFORMATION: Mutated residue

<400> SEQUENCE: 277

Glu Asp Glu Leu Gln Val Ile Gln Pro Glu Lys Ser Val Ser Val Ala
 1               5                  10                  15

Ala Gly Glu Ser Ala Thr Leu Arg Cys Ala Met Thr Ser Leu Ile Pro
```

```
            20                  25                  30
Val Gly Pro Ile Met Trp Phe Arg Gly Ala Gly Ala Gly Arg Glu Leu
        35                  40                  45
Ile Tyr Asn Gln Lys Glu Gly His Phe Pro Arg Val Thr Thr Val Ser
50                  55                  60
Glu Leu Thr Lys Arg Asn Asn Leu Asp Phe Ser Ile Ser Ile Ser Asn
65                  70                  75                  80
Ile Thr Pro Ala Asp Ala Gly Thr Tyr Tyr Cys Val Lys Phe Arg Lys
                85                  90                  95
Gly Ser Pro Asp His Val Glu Phe Lys Ser Gly Ala Gly Thr Glu Leu
            100                 105                 110
Ser Val Arg Ala Lys Pro Ser Ala Pro Val Val Ser Gly Pro Ala Val
            115                 120                 125
Arg Ala Thr Pro Glu His Thr Val Ser Phe Thr Cys Glu Ser His Gly
        130                 135                 140
Phe Ser Pro Arg Asp Ile Thr Leu Lys Trp Phe Lys Asn Gly Asn Glu
145                 150                 155                 160
Leu Ser Asp Phe Gln Thr Asn Val Asp Pro Ala Gly Asp Ser Val Ser
                165                 170                 175
Tyr Ser Ile His Ser Thr Ala Arg Val Val Leu Thr Arg Gly Asp Val
            180                 185                 190
His Ser Gln Val Ile Cys Glu Ile Ala His Ile Thr Leu Gln Gly Asp
            195                 200                 205
Pro Leu Arg Gly Thr Ala Asn Leu Ser Glu Ala Ile Arg Val Pro Pro
        210                 215                 220
Thr Leu Glu Val Thr Gln Gln Pro Met Arg Ala Glu Asn Gln Ala Asn
225                 230                 235                 240
Val Thr Cys Gln Val Ser Asn Phe Tyr Pro Arg Gly Leu Gln Leu Thr
                245                 250                 255
Trp Leu Glu Asn Gly Asn Val Ser Arg Thr Glu Thr Ala Ser Thr Leu
            260                 265                 270
Ile Glu Asn Lys Asp Gly Thr Tyr Asn Trp Met Ser Trp Leu Leu Val
            275                 280                 285
Asn Thr Cys Ala His Arg Asp Asp Val Val Leu Thr Cys Gln Val Glu
        290                 295                 300
His Asp Gly Gln Gln Ala Val Ser Lys Ser Tyr Ala Leu Glu Ile Ser
305                 310                 315                 320
Ala His Gln Lys Glu His Gly Ser Asp Ile Thr His Glu Ala Ala Leu
                325                 330                 335
Ala Pro Thr Ala Pro Leu Leu Val Ala Leu Leu Gly Pro Lys Leu
            340                 345                 350
Leu Leu Val Val Gly Val Ser Ala Ile Tyr Ile Cys Trp Lys Gln Lys
        355                 360                 365
Ala

<210> SEQ ID NO 278
<211> LENGTH: 369
<212> TYPE: PRT
<213> ORGANISM: Homo sapiens

<400> SEQUENCE: 278

Glu Glu Glu Leu Gln Val Ile Gln Pro Asp Lys Ser Ile Ser Val Ala
1               5                   10                  15

Ala Gly Glu Ser Ala Thr Leu His Cys Thr Val Thr Ser Leu Ile Pro
```

```
            20                  25                  30
Val Gly Pro Ile Gln Trp Phe Arg Gly Ala Gly Pro Gly Arg Glu Leu
         35                  40                  45
Ile Tyr Asn Gln Lys Glu Gly His Phe Pro Arg Val Thr Thr Val Ser
 50                  55                  60
Asp Leu Thr Lys Arg Asn Asn Met Asp Phe Ser Ile Arg Ile Ser Asn
 65                  70                  75                  80
Ile Thr Pro Ala Asp Ala Gly Thr Tyr Tyr Cys Val Lys Phe Arg Lys
                 85                  90                  95
Gly Ser Pro Asp His Val Glu Phe Lys Ser Gly Ala Gly Thr Glu Leu
                100                 105                 110
Ser Val Arg Ala Lys Pro Ser Ala Pro Val Val Ser Gly Pro Ala Ala
                115                 120                 125
Arg Ala Thr Pro Gln His Thr Val Ser Phe Thr Cys Glu Ser His Gly
                130                 135                 140
Phe Ser Pro Arg Asp Ile Thr Leu Lys Trp Phe Lys Asn Gly Asn Glu
145                 150                 155                 160
Leu Ser Asp Phe Gln Thr Asn Val Asp Pro Ala Gly Asp Ser Val Ser
                165                 170                 175
Tyr Ser Ile His Ser Thr Ala Lys Val Val Leu Thr Arg Glu Asp Val
                180                 185                 190
His Ser Gln Val Ile Cys Glu Val Ala His Val Thr Leu Gln Gly Asp
                195                 200                 205
Pro Leu Arg Gly Thr Ala Asn Leu Ser Glu Thr Ile Arg Val Pro Pro
                210                 215                 220
Thr Leu Glu Val Thr Gln Gln Pro Val Arg Ala Glu Asn Gln Val Asn
225                 230                 235                 240
Val Thr Cys Gln Val Arg Lys Phe Tyr Pro Gln Arg Leu Gln Leu Thr
                245                 250                 255
Trp Leu Glu Asn Gly Asn Val Ser Arg Thr Glu Thr Ala Ser Thr Leu
                260                 265                 270
Thr Glu Asn Lys Asp Gly Thr Tyr Asn Trp Met Ser Trp Leu Leu Val
                275                 280                 285
Asn Val Ser Ala His Arg Asp Asp Val Lys Leu Thr Cys Gln Val Glu
                290                 295                 300
His Asp Gly Gln Pro Ala Val Ser Lys Ser His Asp Leu Lys Val Ser
305                 310                 315                 320
Ala His Pro Lys Glu Gln Gly Ser Asn Thr Ala Pro Gly Pro Ala Leu
                325                 330                 335
Ala Ser Ala Ala Pro Leu Leu Ile Ala Phe Leu Leu Gly Pro Lys Val
                340                 345                 350
Leu Leu Val Val Gly Val Ser Val Ile Tyr Val Tyr Trp Lys Gln Lys
                355                 360                 365
Ala
```

<210> SEQ ID NO 279
<211> LENGTH: 369
<212> TYPE: PRT
<213> ORGANISM: Artificial
<220> FEATURE:
<223> OTHER INFORMATION: SIRPbL mutant
<220> FEATURE:
<221> NAME/KEY: Site
<222> LOCATION: (101)..(101)
<223> OTHER INFORMATION: Mutated residue

<400> SEQUENCE: 279

```
Glu Glu Glu Leu Gln Val Ile Gln Pro Asp Lys Ser Ile Ser Val Ala
1               5                   10                  15
Ala Gly Glu Ser Ala Thr Leu His Cys Thr Val Thr Ser Leu Ile Pro
            20                  25                  30
Val Gly Pro Ile Gln Trp Phe Arg Gly Ala Gly Pro Gly Arg Glu Leu
        35                  40                  45
Ile Tyr Asn Gln Lys Glu Gly His Phe Pro Arg Val Thr Thr Val Ser
    50                  55                  60
Asp Leu Thr Lys Arg Asn Asn Met Asp Phe Ser Ile Arg Ile Ser Asn
65                  70                  75                  80
Ile Thr Pro Ala Asp Ala Gly Thr Tyr Tyr Cys Val Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Ala Pro Val Val Ser Gly Pro Ala Ala
        115                 120                 125
Arg Ala Thr Pro Gln His Thr Val Ser Phe Thr Cys Glu Ser His Gly
    130                 135                 140
Phe Ser Pro Arg Asp Ile Thr Leu Lys Trp Phe Lys Asn Gly Asn Glu
145                 150                 155                 160
Leu Ser Asp Phe Gln Thr Asn Val Asp Pro Ala Gly Asp Ser Val Ser
                165                 170                 175
Tyr Ser Ile His Ser Thr Ala Lys Val Val Leu Thr Arg Glu Asp Val
            180                 185                 190
His Ser Gln Val Ile Cys Glu Val Ala His Val Thr Leu Gln Gly Asp
        195                 200                 205
Pro Leu Arg Gly Thr Ala Asn Leu Ser Glu Thr Ile Arg Val Pro Pro
    210                 215                 220
Thr Leu Glu Val Thr Gln Gln Pro Val Arg Ala Glu Asn Gln Val Asn
225                 230                 235                 240
Val Thr Cys Gln Val Arg Lys Phe Tyr Pro Gln Arg Leu Gln Leu Thr
                245                 250                 255
Trp Leu Glu Asn Gly Asn Val Ser Arg Thr Glu Thr Ala Ser Thr Leu
            260                 265                 270
Thr Glu Asn Lys Asp Gly Thr Tyr Asn Trp Met Ser Trp Leu Leu Val
        275                 280                 285
Asn Val Ser Ala His Arg Asp Asp Val Lys Leu Thr Cys Gln Val Glu
    290                 295                 300
His Asp Gly Gln Pro Ala Val Ser Lys Ser His Asp Leu Lys Val Ser
305                 310                 315                 320
Ala His Pro Lys Glu Gln Gly Ser Asn Thr Ala Pro Gly Pro Ala Leu
                325                 330                 335
Ala Ser Ala Ala Pro Leu Leu Ile Ala Phe Leu Leu Gly Pro Lys Val
            340                 345                 350
Leu Leu Val Val Gly Val Ser Val Ile Tyr Val Tyr Trp Lys Gln Lys
        355                 360                 365
Ala
```

<210> SEQ ID NO 280
<211> LENGTH: 359
<212> TYPE: PRT
<213> ORGANISM: Homo sapiens

<400> SEQUENCE: 280

```
Glu Glu Glu Leu Gln Met Ile Gln Pro Glu Lys Leu Leu Val Thr
1               5                   10                  15

Val Gly Lys Thr Ala Thr Leu His Cys Thr Val Thr Ser Leu Leu Pro
            20                  25                  30

Val Gly Pro Val Leu Trp Phe Arg Gly Val Gly Pro Gly Arg Glu Leu
            35                  40                  45

Ile Tyr Asn Gln Lys Glu Gly His Phe Pro Arg Val Thr Thr Val Ser
        50                  55                  60

Asp Leu Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asn Val Glu Phe Lys Ser Gly Pro Gly Thr Glu Met
            100                 105                 110

Ala Leu Gly Ala Lys Pro Ser Ala Pro Val Val Leu Gly Pro Ala Ala
            115                 120                 125

Arg Thr Thr Pro Glu His Thr Val Ser Phe Thr Cys Glu Ser His Gly
            130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Thr Gly Gln Ser Val Ala
                165                 170                 175

Tyr Ser Ile Arg Ser Thr Ala Arg Val Val Leu Asp Pro Trp Asp Val
            180                 185                 190

Arg Ser Gln Val Ile Cys Glu Val Ala His Val Thr Leu Gln Gly Asp
            195                 200                 205

Pro Leu Arg Gly Thr Ala Asn Leu Ser Glu Ala Ile Arg Val Pro Pro
210                 215                 220

Thr Leu Glu Val Thr Gln Gln Pro Met Arg Val Gly Asn Gln Val Asn
225                 230                 235                 240

Val Thr Cys Gln Val Arg Lys Phe Tyr Pro Gln Ser Leu Gln Leu Thr
                245                 250                 255

Trp Ser Glu Asn Gly Asn Val Cys Gln Arg Glu Thr Ala Ser Thr Leu
            260                 265                 270

Thr Glu Asn Lys Asp Gly Thr Tyr Asn Trp Thr Ser Trp Phe Leu Val
            275                 280                 285

Asn Ile Ser Asp Gln Arg Asp Asp Val Val Leu Thr Cys Gln Val Lys
        290                 295                 300

His Asp Gly Gln Leu Ala Val Ser Lys Arg Leu Ala Leu Glu Val Thr
305                 310                 315                 320

Val His Gln Lys Asp Gln Ser Ser Asp Ala Thr Pro Gly Pro Ala Ser
                325                 330                 335

Ser Leu Thr Ala Leu Leu Leu Ile Ala Val Leu Leu Gly Pro Ile Tyr
            340                 345                 350

Val Pro Trp Lys Gln Lys Thr
            355
```

<210> SEQ ID NO 281
<211> LENGTH: 359
<212> TYPE: PRT
<213> ORGANISM: Artificial
<220> FEATURE:
<223> OTHER INFORMATION: SIRPg mutant
<220> FEATURE:

<221> NAME/KEY: Site
<222> LOCATION: (100)..(100)
<223> OTHER INFORMATION: Mutated residue

<400> SEQUENCE: 281

```
Glu Glu Glu Leu Gln Met Ile Gln Pro Glu Lys Leu Leu Val Thr
1               5                   10                  15

Val Gly Lys Thr Ala Thr Leu His Cys Thr Val Thr Ser Leu Leu Pro
            20                  25                  30

Val Gly Pro Val Leu Trp Phe Arg Gly Val Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Asp Asn Val Glu Phe Lys Ser Gly Pro Gly Thr Glu Met
                100                 105                 110

Ala Leu Gly Ala Lys Pro Ser Ala Pro Val Val Leu Gly Pro Ala Ala
            115                 120                 125

Arg Thr Thr Pro Glu His Thr Val Ser Phe Thr Cys Glu Ser His Gly
        130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Thr Gly Gln Ser Val Ala
                165                 170                 175

Tyr Ser Ile Arg Ser Thr Ala Arg Val Val Leu Asp Pro Trp Asp Val
            180                 185                 190

Arg Ser Gln Val Ile Cys Glu Val Ala His Val Thr Leu Gln Gly Asp
        195                 200                 205

Pro Leu Arg Gly Thr Ala Asn Leu Ser Glu Ala Ile Arg Val Pro Pro
210                 215                 220

Thr Leu Glu Val Thr Gln Gln Pro Met Arg Val Gly Asn Gln Val Asn
225                 230                 235                 240

Val Thr Cys Gln Val Arg Lys Phe Tyr Pro Gln Ser Leu Gln Leu Thr
                245                 250                 255

Trp Ser Glu Asn Gly Asn Val Cys Gln Arg Glu Thr Ala Ser Thr Leu
            260                 265                 270

Thr Glu Asn Lys Asp Gly Thr Tyr Asn Trp Thr Ser Trp Phe Leu Val
        275                 280                 285

Asn Ile Ser Asp Gln Arg Asp Asp Val Val Leu Thr Cys Gln Val Lys
290                 295                 300

His Asp Gly Gln Leu Ala Val Ser Lys Arg Leu Ala Leu Glu Val Thr
305                 310                 315                 320

Val His Gln Lys Asp Gln Ser Ser Asp Ala Thr Pro Gly Pro Ala Ser
                325                 330                 335

Ser Leu Thr Ala Leu Leu Leu Ile Ala Val Leu Leu Gly Pro Ile Tyr
            340                 345                 350

Val Pro Trp Lys Gln Lys Thr
                355
```

<210> SEQ ID NO 282
<211> LENGTH: 359
<212> TYPE: PRT

```
<213> ORGANISM: Artificial
<220> FEATURE:
<223> OTHER INFORMATION: SIRPg mutant
<220> FEATURE:
<221> NAME/KEY: Site
<222> LOCATION: (101)..(101)
<223> OTHER INFORMATION: Mutated residue

<400> SEQUENCE: 282
```

| | | | | | | | | | | | | | | |
|---|---|---|---|---|---|---|---|---|---|---|---|---|---|---|
| Glu | Glu | Glu | Leu | Gln | Met | Ile | Gln | Pro | Glu | Lys | Leu | Leu | Val | Thr |
| 1 | | | | 5 | | | | | 10 | | | | | 15 |
| Val | Gly | Lys | Thr | Ala | Thr | Leu | His | Cys | Thr | Val | Thr | Ser | Leu | Pro |
| | | | 20 | | | | | 25 | | | | | 30 | |
| Val | Gly | Pro | Val | Leu | Trp | Phe | Arg | Gly | Val | Gly | Pro | Gly | Arg | Glu | Leu |
| | | 35 | | | | | 40 | | | | | 45 | | | |
| Ile | Tyr | Asn | Gln | Lys | Glu | Gly | His | Phe | Pro | Arg | Val | Thr | Thr | Val | Ser |
| | 50 | | | | | 55 | | | | | 60 | | | | |
| Asp | Leu | Thr | Lys | Arg | Asn | Asn | Met | Asp | Phe | Ser | Ile | Arg | Ile | Ser | Ser |
| 65 | | | | | 70 | | | | | 75 | | | | | 80 |
| Ile | Thr | Pro | Ala | Asp | Val | Gly | Thr | Tyr | Tyr | Cys | Val | Lys | Phe | Arg | Lys |
| | | | | 85 | | | | | 90 | | | | | 95 | |
| Gly | Ser | Pro | Glu | Asp | Val | Glu | Phe | Lys | Ser | Gly | Pro | Gly | Thr | Glu | Met |
| | | | 100 | | | | | 105 | | | | | 110 | | |
| Ala | Leu | Gly | Ala | Lys | Pro | Ser | Ala | Pro | Val | Val | Leu | Gly | Pro | Ala | Ala |
| | | | 115 | | | | | 120 | | | | | 125 | | |
| Arg | Thr | Thr | Pro | Glu | His | Thr | Val | Ser | Phe | Thr | Cys | Glu | Ser | His | Gly |
| 130 | | | | | 135 | | | | | 140 | | | | | |
| Phe | Ser | Pro | Arg | Asp | Ile | Thr | Leu | Lys | Trp | Phe | Lys | Asn | Gly | Asn | Glu |
| 145 | | | | | 150 | | | | | 155 | | | | | 160 |
| Leu | Ser | Asp | Phe | Gln | Thr | Asn | Val | Asp | Pro | Thr | Gly | Gln | Ser | Val | Ala |
| | | | | 165 | | | | | 170 | | | | | 175 | |
| Tyr | Ser | Ile | Arg | Ser | Thr | Ala | Arg | Val | Val | Leu | Asp | Pro | Trp | Asp | Val |
| | | | | 180 | | | | | 185 | | | | | 190 | |
| Arg | Ser | Gln | Val | Ile | Cys | Glu | Val | Ala | His | Val | Thr | Leu | Gln | Gly | Asp |
| | | 195 | | | | | 200 | | | | | 205 | | | |
| Pro | Leu | Arg | Gly | Thr | Ala | Asn | Leu | Ser | Glu | Ala | Ile | Arg | Val | Pro | Pro |
| 210 | | | | | 215 | | | | | 220 | | | | | |
| Thr | Leu | Glu | Val | Thr | Gln | Gln | Pro | Met | Arg | Val | Gly | Asn | Gln | Val | Asn |
| 225 | | | | | 230 | | | | | 235 | | | | | 240 |
| Val | Thr | Cys | Gln | Val | Arg | Lys | Phe | Tyr | Pro | Gln | Ser | Leu | Gln | Leu | Thr |
| | | | | 245 | | | | | 250 | | | | | 255 | |
| Trp | Ser | Glu | Asn | Gly | Asn | Val | Cys | Gln | Arg | Glu | Thr | Ala | Ser | Thr | Leu |
| | | | 260 | | | | | 265 | | | | | 270 | | |
| Thr | Glu | Asn | Lys | Asp | Gly | Thr | Tyr | Asn | Trp | Thr | Ser | Trp | Phe | Leu | Val |
| | | | 275 | | | | | 280 | | | | | 285 | | |
| Asn | Ile | Ser | Asp | Gln | Arg | Asp | Asp | Val | Val | Leu | Thr | Cys | Gln | Val | Lys |
| | 290 | | | | | 295 | | | | | 300 | | | | |
| His | Asp | Gly | Gln | Leu | Ala | Val | Ser | Lys | Arg | Leu | Ala | Leu | Glu | Val | Thr |
| 305 | | | | | 310 | | | | | 315 | | | | | 320 |
| Val | His | Gln | Lys | Asp | Gln | Ser | Ser | Asp | Ala | Thr | Pro | Gly | Pro | Ala | Ser |
| | | | | 325 | | | | | 330 | | | | | 335 | |
| Ser | Leu | Thr | Ala | Leu | Leu | Leu | Ile | Ala | Val | Leu | Leu | Gly | Pro | Ile | Tyr |
| | | | 340 | | | | | 345 | | | | | 350 | | |
| Val | Pro | Trp | Lys | Gln | Lys | Thr | | | | | | | | | |
| | | | 355 | | | | | | | | | | | | |

```
<210> SEQ ID NO 283
<211> LENGTH: 359
<212> TYPE: PRT
<213> ORGANISM: Artificial
<220> FEATURE:
<223> OTHER INFORMATION: SIRPg mutant
<220> FEATURE:
<221> NAME/KEY: Site
<222> LOCATION: (100)..(101)
<223> OTHER INFORMATION: Mutated residue

<400> SEQUENCE: 283

Glu Glu Glu Leu Gln Met Ile Gln Pro Glu Lys Leu Leu Leu Val Thr
1               5                   10                  15

Val Gly Lys Thr Ala Thr Leu His Cys Thr Val Thr Ser Leu Leu Pro
            20                  25                  30

Val Gly Pro Val Leu Trp Phe Arg Gly Val Gly Pro Gly Arg Glu Leu
        35                  40                  45

Ile Tyr Asn Gln Lys Glu Gly His Phe Pro Arg Val Thr Thr Val Ser
50                  55                  60

Asp Leu Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Asp Asp Val Glu Phe Lys Ser Gly Pro Gly Thr Glu Met
            100                 105                 110

Ala Leu Gly Ala Lys Pro Ser Ala Pro Val Val Leu Gly Pro Ala Ala
        115                 120                 125

Arg Thr Thr Pro Glu His Thr Val Ser Phe Thr Cys Glu Ser His Gly
130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Thr Gly Gln Ser Val Ala
                165                 170                 175

Tyr Ser Ile Arg Ser Thr Ala Arg Val Val Leu Asp Pro Trp Asp Val
            180                 185                 190

Arg Ser Gln Val Ile Cys Glu Val Ala His Val Thr Leu Gln Gly Asp
        195                 200                 205

Pro Leu Arg Gly Thr Ala Asn Leu Ser Glu Ala Ile Arg Val Pro Pro
210                 215                 220

Thr Leu Glu Val Thr Gln Gln Pro Met Arg Val Gly Asn Gln Val Asn
225                 230                 235                 240

Val Thr Cys Gln Val Arg Lys Phe Tyr Pro Gln Ser Leu Gln Leu Thr
                245                 250                 255

Trp Ser Glu Asn Gly Asn Val Cys Gln Arg Glu Thr Ala Ser Thr Leu
            260                 265                 270

Thr Glu Asn Lys Asp Gly Thr Tyr Asn Trp Thr Ser Trp Phe Leu Val
        275                 280                 285

Asn Ile Ser Asp Gln Arg Asp Asp Val Val Leu Thr Cys Gln Val Lys
290                 295                 300

His Asp Gly Gln Leu Ala Val Ser Lys Arg Leu Ala Leu Glu Val Thr
305                 310                 315                 320

Val His Gln Lys Asp Gln Ser Ser Asp Ala Thr Pro Gly Pro Ala Ser
                325                 330                 335

Ser Leu Thr Ala Leu Leu Leu Ile Ala Val Leu Leu Gly Pro Ile Tyr
            340                 345                 350
```

Val Pro Trp Lys Gln Lys Thr
        355

<210> SEQ ID NO 284
<211> LENGTH: 126
<212> TYPE: PRT
<213> ORGANISM: Artificial
<220> FEATURE:
<223> OTHER INFORMATION: Artificial antibody sequence

<400> SEQUENCE: 284

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Asn Ile Tyr
            20                  25                  30

Trp Ile Asn Trp Val Arg Gln Ala Pro Gly Gln Gly Leu Glu Trp Ile
        35                  40                  45

Gly Asn Ile Tyr Pro Ser Ser Ile Ser Thr Asn Tyr Asn Glu Lys Phe
    50                  55                  60

Lys Thr Arg Ala Thr Leu Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Glu Gly Thr Tyr Tyr Gly Gly Arg Tyr Glu Gly Asp Trp
            100                 105                 110

Phe Gly Tyr Trp Gly Gln Gly Thr Leu Val Thr Val Ser Ser
        115                 120                 125

<210> SEQ ID NO 285
<211> LENGTH: 107
<212> TYPE: PRT
<213> ORGANISM: Artificial
<220> FEATURE:
<223> OTHER INFORMATION: Artificial antibody sequence

<400> SEQUENCE: 285

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Phe Thr Ser Thr Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gly Gly Thr Lys Val Glu Ile Lys
            100                 105

<210> SEQ ID NO 286
<211> LENGTH: 118
<212> TYPE: PRT
<213> ORGANISM: Artificial
<220> FEATURE:
<223> OTHER INFORMATION: Artificial antibody sequence

<400> SEQUENCE: 286

-continued

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Val Met Ser Trp Val Arg Gln Thr Pro Gly Lys Gly Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Thr Leu Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Ser Gln Leu Thr Gly Ser Glu Phe Asp Tyr Trp Gly Gln Gly Thr
            100                 105                 110

Thr Val Thr Val Ser Ser
            115

<210> SEQ ID NO 287
<211> LENGTH: 111
<212> TYPE: PRT
<213> ORGANISM: Artificial
<220> FEATURE:
<223> OTHER INFORMATION: Artificial antibody sequence

<400> SEQUENCE: 287

Asp Ile Val Ile Thr Gln Ser Pro Ala Ser Leu Ala Val Ser Leu Gly
1               5                   10                  15

Glu Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Arg Thr Asp Phe Thr Leu Thr Ile Asn
65                  70                  75                  80

Pro Leu Gln Ala Glu Asp Val Ala Thr Tyr Tyr Cys His Gln Ser Gly
            85                  90                  95

Asp Leu Pro Trp Thr Phe Gly Gly Gly Thr Lys Val Glu Ile Lys
            100                 105                 110

<210> SEQ ID NO 288
<211> LENGTH: 116
<212> TYPE: PRT
<213> ORGANISM: Oryctolagus cuniculus

<400> SEQUENCE: 288

Gln Ser Val Glu Glu Ser Gly Gly Arg Leu Gly Thr Pro Gly Thr Pro
1               5                   10                  15

Leu Thr Leu Thr Cys Thr Val Ser Gly Phe Ser Leu Ser Tyr Val
            20                  25                  30

Met Gly Trp Phe Arg Gln Ala Pro Gly Lys Gly Leu Glu Tyr Ile Gly
        35                  40                  45

Ile Ile Ser Ser Ser Gly Ser Pro Tyr Tyr Ala Ser Trp Val Asn Gly
    50                  55                  60

Arg Phe Thr Ile Ser Lys Thr Ser Thr Thr Met Asp Leu Lys Met Asn
65                  70                  75                  80

Ser Pro Thr Thr Glu Asp Thr Ala Thr Tyr Phe Cys Ala Arg Val Gly

-continued

```
                85                  90                  95

Pro Leu Gly Val Asp Tyr Phe Asn Ile Trp Gly Pro Gly Thr Leu Val
            100                 105                 110

Thr Val Ser Leu
        115

<210> SEQ ID NO 289
<211> LENGTH: 109
<212> TYPE: PRT
<213> ORGANISM: Oryctolagus cuniculus

<400> SEQUENCE: 289

Asp Ile Val Met Thr Gln Thr Pro Ser Ser Val Glu Ala Ala Val Gly
1               5                   10                  15

Gly Thr Val Thr Ile Lys Cys Gln Ala Gly Gln Ser Ile Asn Ser Tyr
            20                  25                  30

Leu Ala Trp Tyr Gln Gln Lys Pro Gly Gln Arg Pro Lys Leu Leu Ile
        35                  40                  45

Tyr Tyr Ala Ser Thr Leu Glu Ser Gly Val Pro Ser Arg Phe Lys Gly
    50                  55                  60

Ser Gly Ser Gly Thr Asp Tyr Thr Leu Thr Ile Ser Asp Leu Glu Ser
65                  70                  75                  80

Ala Asp Ala Ala Thr Tyr Tyr Cys Gln Ser Trp His Tyr Ile Ser Arg
                85                  90                  95

Ser Tyr Ala Phe Gly Gly Gly Thr Glu Val Val Val Lys
            100                 105

<210> SEQ ID NO 290
<211> LENGTH: 115
<212> TYPE: PRT
<213> ORGANISM: Artificial
<220> FEATURE:
<223> OTHER INFORMATION: Artificial antibody sequence

<400> SEQUENCE: 290

Arg Gln Leu Val Glu Ser Gly Gly Leu Val Gln Pro Gly Gly Ser
1               5                   10                  15

Leu Arg Leu Ser Cys Thr Ala Ser Gly Phe Ser Leu Ser Ser His Gly
            20                  25                  30

Ile Ser Trp Val Arg Gln Ala Pro Gly Lys Gly Leu Glu Tyr Ile Gly
        35                  40                  45

Thr Ile Gly Thr Gly Val Ile Thr Tyr Phe Ala Ser Trp Ala Lys Gly
    50                  55                  60

Arg Phe Thr Gly Ser Lys Thr Ser Ser Thr Ala Tyr Met Glu Leu Ser
65                  70                  75                  80

Ser Leu Arg Ser Glu Asp Thr Ala Val Tyr Phe Cys Ala Arg Gly Ser
                85                  90                  95

Ala Trp Asn Asp Pro Phe Asp Pro Trp Gly Gln Gly Thr Leu Val Thr
            100                 105                 110

Val Ser Ser
        115

<210> SEQ ID NO 291
<211> LENGTH: 111
<212> TYPE: PRT
<213> ORGANISM: Artificial
<220> FEATURE:
<223> OTHER INFORMATION: Artificial antibody sequence
```

-continued

```
<400> SEQUENCE: 291

Asp Ile Val Met Thr Gln Ser Pro Ser Leu Ser Ala Ser Val Gly
1               5                   10                  15

Asp Arg Val Thr Ile Thr Cys Gln Ala Ser Gln Ser Val Tyr Gly Asn
            20                  25                  30

Asn Asp Leu Ala Trp Tyr Gln Gln Lys Pro Gly Gln Ala Pro Lys Leu
        35                  40                  45

Leu Ile Tyr Leu Ala Ser Thr Leu Ala Thr Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Gly Asp Asp
                85                  90                  95

Glu Ala Asp Asn Thr Phe Gly Gln Gly Thr Lys Val Glu Ile Lys
                100                 105                 110

<210> SEQ ID NO 292
<211> LENGTH: 115
<212> TYPE: PRT
<213> ORGANISM: Oryctolagus cuniculus

<400> SEQUENCE: 292

Arg Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser His Gly
            20                  25                  30

Ile Ser Trp Val Arg Gln Ala Pro Gly Lys Gly Leu Glu Tyr Ile Gly
        35                  40                  45

Thr Ile Gly Thr Gly Val Ile Thr Tyr Phe Ala Ser Trp Ala Lys Gly
    50                  55                  60

Arg Phe Thr Gly Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Ser
                85                  90                  95

Ala Trp Asn Asp Pro Phe Asp Pro Trp Gly Pro Gly Thr Leu Val Thr
                100                 105                 110

Val Ser Ser
        115

<210> SEQ ID NO 293
<211> LENGTH: 110
<212> TYPE: PRT
<213> ORGANISM: Oryctolagus cuniculus

<400> SEQUENCE: 293

Ala Leu Val Met Thr Gln Thr Pro Ala Ser Val Ser Ala Ala Val Gly
1               5                   10                  15

Gly Thr Val Thr Thr Lys Cys Gln Ala Ser Gln Ser Val Tyr Gly Asn
            20                  25                  30

Asn Asp Leu Ala Trp Tyr Gln His Lys Pro Gly Gln Pro Pro Lys Leu
        35                  40                  45

Leu Ile Tyr Leu Ala Ser Thr Leu Ala Thr Gly Val Pro Ser Arg Phe
    50                  55                  60

Ser Gly Ser Gly Ser Gly Thr Gln Phe Thr Leu Thr Ile Thr Gly Val
65                  70                  75                  80
```

```
Gln Ser Asp Asp Ala Ala Thr Tyr Tyr Cys Leu Gly Gly Asp Asp
                85                  90                  95

Glu Ala Asp Asn Val Phe Gly Gly Gly Thr Glu Val Val Val
            100                 105                 110
```

<210> SEQ ID NO 294
<211> LENGTH: 117
<212> TYPE: PRT
<213> ORGANISM: Artificial
<220> FEATURE:
<223> OTHER INFORMATION: Artificial antibody sequence

<400> SEQUENCE: 294

```
Lys Val Glu Glu Ser Gly Gly Gly Leu Val Gln Pro Gly Gly Ser Leu
1               5                   10                  15

Arg Leu Ser Cys Ala Ala Ser Gly Phe Ser Leu Ser Tyr Val Met
                20                  25                  30

Gly Trp Val Arg Gln Ala Pro Gly Lys Gly Leu Glu Trp Val Ser Ile
            35                  40                  45

Ile Ser Ser Gly Ser Pro Tyr Tyr Ala Ser Trp Val Asn Gly Arg
        50                  55                  60

Phe Thr Ile Ser Lys Asp Asn Ser Glu Gly Met Val Tyr Leu Gln Met
65                  70                  75                  80

Asn Ser Leu Arg Ala Glu Asp Thr Ala Val Tyr Tyr Cys Ala Arg Val
                85                  90                  95

Gly Pro Leu Gly Val Asp Tyr Phe Asn Ile Trp Gly Gln Gly Thr Thr
            100                 105                 110

Val Thr Val Ser Ser
        115
```

<210> SEQ ID NO 295
<211> LENGTH: 109
<212> TYPE: PRT
<213> ORGANISM: Artificial
<220> FEATURE:
<223> OTHER INFORMATION: Artificial antibody sequence

<400> SEQUENCE: 295

```
Asp Ile Val Met Thr Gln Ser Pro Asp Ser Leu Ala Val Ser Leu Gly
1               5                   10                  15

Glu Arg Ala Thr Ile Asn Cys Gln Ala Gly Gln Ser Ile Asn Ser Tyr
                20                  25                  30

Leu Ala Trp Tyr Gln Gln Lys Pro Gly Gln Pro Pro Lys Leu Leu Ile
            35                  40                  45

Tyr Tyr Ala Ser Thr Leu Glu Ser Gly Val Pro Asp Arg Phe Ser Gly
        50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Ser Trp His Tyr Ile Ser Arg
                85                  90                  95

Ser Tyr Ala Phe Gly Gly Gly Thr Lys Leu Glu Ile Lys
            100                 105
```

<210> SEQ ID NO 296
<211> LENGTH: 115
<212> TYPE: PRT
<213> ORGANISM: Artificial
<220> FEATURE:
<223> OTHER INFORMATION: Artificial antibody sequence

```
<400> SEQUENCE: 296

Arg Gln Leu Val Glu Ser Gly Gly Leu Val Gln Pro Gly Gly Ser
1               5                   10                  15

Leu Arg Leu Ser Cys Thr Ala Ser Gly Phe Ser Leu Ser Ser His Gly
            20                  25                  30

Ile Ser Trp Val Arg Gln Ala Pro Gly Lys Gly Leu Glu Tyr Ile Gly
            35                  40                  45

Thr Ile Gly Thr Gly Val Ile Thr Tyr Phe Ala Ser Trp Ala Lys Gly
        50                  55                  60

Arg Phe Thr Gly Ser Lys Thr Ser Ser Thr Ala Tyr Met Glu Leu Ser
65                  70                  75                  80

Ser Leu Arg Ser Glu Asp Thr Ala Val Tyr Phe Cys Ala Arg Gly Ser
                85                  90                  95

Ala Trp Asn Asp Pro Phe Asp Pro Trp Gly Gln Gly Thr Leu Val Thr
            100                 105                 110

Val Ser Ser
        115

<210> SEQ ID NO 297
<211> LENGTH: 111
<212> TYPE: PRT
<213> ORGANISM: Artificial
<220> FEATURE:
<223> OTHER INFORMATION: Artificial antibody sequence

<400> SEQUENCE: 297

Asp Ile Glu Met Thr Gln Ser Pro Ser Ser Val Ser Ala Ser Val Gly
1               5                   10                  15

Asp Arg Val Thr Leu Thr Cys Gln Ala Ser Gln Ser Val Tyr Gly Asn
            20                  25                  30

Asn Asp Leu Ala Trp Tyr Gln Gln Lys Pro Gly Gln Ala Pro Lys Leu
            35                  40                  45

Leu Ile Tyr Leu Ala Ser Thr Leu Ala Thr Gly Val Pro Ser Arg Phe
        50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Gly Gly Asp Asp
                85                  90                  95

Glu Ala Asp Asn Val Phe Gly Gly Gly Thr Lys Val Glu Ile Lys
            100                 105                 110
```

UNITED STATES PATENT AND TRADEMARK OFFICE
CERTIFICATE OF CORRECTION

| | | |
|---|---|---|
| PATENT NO. | : 11,572,412 B2 | |
| APPLICATION NO. | : 17/831245 | |
| DATED | : February 7, 2023 | |
| INVENTOR(S) | : Pankaj Gupta et al. | |

It is certified that error appears in the above-identified patent and that said Letters Patent is hereby corrected as shown below:

On the Title Page

At item (72): Replace "Habte Habtom" with --Habtom Habte--.

Signed and Sealed this
Sixteenth Day of May, 2023

Katherine Kelly Vidal
*Director of the United States Patent and Trademark Office*